(12) United States Patent
Akinsanmi et al.

(10) Patent No.: US 11,542,561 B2
(45) Date of Patent: *Jan. 3, 2023

(54) METHODS OF SCREENING FOR CAUSATIVE AGENTS OF ONYCHODYSTROPHY

(71) Applicant: Bakotic Pathology Associates, LLC, Alpharetta, GA (US)

(72) Inventors: Idowu Akinsanmi, Snellville, GA (US); Lori Bennett, Alpharetta, GA (US); Liquan Yang, Lilburn, GA (US); Marianna Agassandian, Alpharetta, GA (US); Rama Murthy Sakamuri, Cumming, GA (US); Erik Gustafson, Alpharetta, GA (US); Lilly Kong, Covina, CA (US); Kiran Madanahally Divakar, Alpharetta, GA (US)

(73) Assignee: BAKOTIC PATHOLOGY ASSOCIATES, LLC, Alpharetta, GA (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/796,832

(22) Filed: Feb. 20, 2020

(65) Prior Publication Data

US 2020/0270708 A1    Aug. 27, 2020

Related U.S. Application Data

(60) Provisional application No. 62/810,304, filed on Feb. 25, 2019.

(51) Int. Cl.
*C12Q 1/68* (2018.01)
*C12Q 1/6895* (2018.01)
*C12Q 1/686* (2018.01)
*C12Q 1/689* (2018.01)

(52) U.S. Cl.
CPC .......... *C12Q 1/6895* (2013.01); *C12Q 1/686* (2013.01); *C12Q 1/689* (2013.01)

(58) Field of Classification Search
None
See application file for complete search history.

(56) References Cited

U.S. PATENT DOCUMENTS

2003/0050470 A1* 3/2003 An .................. C07H 21/00
                                                    435/6.14
2017/0029906 A1* 2/2017 Divakar ............. C12Q 1/6895

OTHER PUBLICATIONS

Anuj et al., 2009. Identification of Pseudomonas aeruginosa by a duplex real-time polymerase chain reaction assay targeting the ecfX and the gyrB genes. Diagnostic microbiology and infectious disease, 63(2), pp. 127-131. (Year: 2009).*

Arabatzis et al., 2007. Diagnosis of common dermatophyte infections by a novel multiplex real-time polymerase chain reaction detection/identification scheme. British Journal of Dermatology, 157(4), pp. 681-689. (Year: 2007).*
Bergmans et al., 2010. Evaluation of a single-tube real-time PCR for detection and identification of 11 *Dermatophyte* species in clinical material. Clinical microbiology and infection, 16(6), pp. 704-710. (Year: 2010).*
Cafarchia, C., Iatta, R., Latrofa, M.S., Gräser, Y. and Otranto, D., 2013. Molecular epidemiology, phylogeny and evolution of dermatophytes. Infection, Genetics and Evolution, 20, pp. 336-351. (Year: 2013).*
Dalis et al., 2018. Molecular characterization of dermatophytes isolated from cattle in Plateau State, Nigeria. Veterinary microbiology, 219, pp. 212-218. (Year: 2018).*
Deschaght et al., 2009. Comparison of the sensitivity of culture, PCR and quantitative real-time PCR for the detection of Pseudomonas aeruginosain sputum of cystic fibrosis patients. BMC microbiology, 9(1), pp. 1-7. (Year: 2009).*
Ebihara et al., 2009. Molecular detection of dermatophytes and nondermatophytes in onychomycosis by nested polymerase chain reaction based on 28S ribosomal RNA gene sequences. British Journal of Dermatology, 161(5), pp. 1038-1044. (Year: 2009).*
Graser, Y., Czaika, V. and Ohst, T., 2012. Diagnostic PCR of dermatophytes—an overview. JDDG: Journal der Deutschen Dermatologischen Gesellschaft, 10(10), pp. 721-725. (Year: 2012).*
Gupta et al.2007. Fast and sensitive detection of Trichophyton rubrum DNA from the nail samples of patients with onychomycosis by a double-round polymerase chain reaction-based assay. British Journal of Dermatology, 157(4), pp. 698-703. (Year: 2007).*
Gupta, A.K. and Nakrieko, K.A., 2014. Molecular determination of mixed infections of dermatophytes and nondermatophyte molds in individuals with onychomycosis. Journal of the American Podiatric Medical Association, 104(4), pp. 330-336. (Year: 2014).*
Gupta et al., 2016. Genotyping and in vitro antifungal susceptibility testing of Fusarium isolates from onychomycosis in India. Mycopathologia, 181(7), pp. 497-504. (Year: 2016).*
Hafirassou et al., 2017. Usefulness of techniques based on real time PCR for the identification of onychomycosis-causing species. Mycoses, 60(10), pp. 638-644. (Year: 2017).*
Jensen, R.H. and Arendrup, M.C., 2012. Molecular diagnosis of dermatophyte infections. Current opinion in infectious diseases, 25(2), pp. 126-134. (Year: 2012).*
Kim J. Y., Choe Y. B., Ahn K. J., Lee Y. W. 2011; Identification of dermatophytes using multiplex polymerase chain reaction. Ann Dermatol 23:304-312. (Year: 2011).*
Kobylak et al., 2015. Real-time PCR approach in dermatophyte detection and Trichophyton rubrum identification. Acta Biochimica Polonica, 62(1) pp. 119-122. (Year: 2015).*

(Continued)

*Primary Examiner* — Teresa E Strzelecka
*Assistant Examiner* — Olayinka A Oyeyemi
(74) *Attorney, Agent, or Firm* — James S. Keddie; Bozicevic, Field & Francis LLP

(57) ABSTRACT

Provided herein is a real-time PCR-based method of detecting, in a sample, an agent causing onychodystrophy, wherein the agent causing onychodystrophy belongs to a secondary clade member including one or more primary clade members. Also provided are compositions and kits that finds use in implementing the present method.

17 Claims, 49 Drawing Sheets

Specification includes a Sequence Listing.

(56) References Cited

OTHER PUBLICATIONS

Mirhendi, H., Motamedi, M., Makimura, K. and Satoh, K., 2016. Developments diagnostic pan-dermatophyte TaqMan probe real-time PCR assay based on bets tubulin gene. Mycoses, 59(8), pp. 520-527 (Year: 2016).*
Miyajima et al., 2013. Rapid real-time diagnostic PCR for Trichophyton rubrum and Trichophyton mentagrophytes in patients with tinea unguium and tinea pedis using specific fluorescent probes. Journal of dermatological science, 69(3), pp. 229-235. (Year: 2013).*
Mohammadi, A. and Bahramikia, S., 2019. Molecular identification and genetic variation of *Alternaria* species isolated from tomatoes using ITS1 sequencing and inter simple sequence repeat methods. Current Medical Mycology, 5(2), pp. 1-8. (Year: 2019).*
Ninet et al., 2003. Identification of *Dermatophyte* species by 28S ribosomal DNA sequencing with a commercial kit. Journal of clinical microbiology, 41(2), pp. 826-830. (Year: 2003).*
Ohst et al., 2016. Detection of common dermatophytes in clinical specimens using a simple quantitative real-time TaqMan polymerase chain reaction assay. British Journal of Dermatology, 174(3), pp. 602-609. (Year: 2016).*
Sherman et al., 2018. Evaluation of multiplex real-time PCR for identifying dermatophytes in clinical samples—A multicentre study. Mycoses, 61(2), pp. 119-126. (Year: 2018).*
Spiliopoulou et al., 2015. Evaluation of a commercial PCR test for the diagnosis of dermatophyte nail infections. Journal of medical microbiology, 64(1), pp. 25-31. (Year: 2015).*
Vahidnia et al., 2015. High throughput multiplex-PCR for direct detection and diagnosis of *Dermatophyte* species, Candida albicans and Candida parapsilosis in clinical specimen. Journal of microbiological methods, 113, pp. 38-40. (Year: 2015).*
Verrier et al., 2012. Identification of infectious agents in onychomycoses by PCR-terminal restriction fragment length polymorphism. Journal of clinical microbiology, 50(3), pp. 553-561. (Year: 2012).*
Walberg et al., 2006. 18S rDNA polymerase chain reaction and sequencing in onychomycosis diagnostics. Acta dermato-venereologica, 86(3) pp. 223-226. (Year: 2006).*
Walser et al., Epub Dec. 7, 2018. Development and evaluation of a pan-dermatophyte polymerase chain reaction with species-level identification using sloppy molecular beacon probes. British Journal of Dermatology, 2019 180(6), pp. 1489-1497. (Year: 2018).*
Yuksel, T. and Ilkit, M., 2012. Identification of rare macroconidia-producing dermatophytic fungi by real-time PCR. Medical Mycology, 50(4), pp. 346-352. (Year: 2012).*
Ziołkowska et al., 2015. Molecular identification and classification of Trichophyton mentagrophytes complex strains isolated from humans and selected animal species. Mycoses, 58(3), pp. 119-126. (Year: 2015).*

Chiriac, A., Brzezinski, P., Foia, L. and Marincu, I., 2015. Chloronychia: green nail syndrome caused by Pseudomonas aeruginosa in elderly persons. Clinical Interventions in Aging, 10, p. 265-267. (Year: 2015).*
Foongladda, S., Mongkol, N., Petlum, P. and Chayakulkeeree, M., 2014. Multi-probe real-time PCR identification of four common *Candida* species in blood culture broth. Mycopathologia, 177(5), pp. 251-261. (Year: 2014).*
Guiver, M., Levi, K. and Oppenheim, B.A., 2001. Rapid identification of *Candida* species by TaqMan PCR. Journal of clinical pathology, 54(5), pp. 362-366. (Year: 2001).*
Irimie, M., Tataru, A. and Oanta, A., 2011. Evaluation of real time polymerase chain reaction assay for idetification of common *Dermatophyte* species. Bulletin of the Transilvania University of Brasov. Medical Sciences. Series VI, 4(2), p. 65-71. (Year: 2011).*
Romaszkiewicz et al., 2018. Nail dermoscopy (onychoscopy) is useful in diagnosis and treatment follow-up of the nail mixed infection caused by Pseudomonas aeruginosa and Candida albicans. Advances in Dermatology and Allergology/Postpy Dermatologii i Alergologii, 35(3), p. 327-329 (Year: 2018).*
SantaLucia Jr, John. Physical principles and visual-OMP software for optimal PCR design. PCR Primer Design. Humana Press, 2007: pp. 3-33. (Year: 2007).*
Youssef et al., 2018. Onychomycosis: Which fungal species are involved? Experience of the Laboratory of Parasitology-Mycology of the Rabta Hospital of Tunis. Journal de Mycologie Medicale, 28(4), pp. 651-654. (Year: 2018).*
Zhang et al., 2016. Development of Candida-specific real-time PCR assays for the detection and identification of eight medically important *Candida* species. Microbiology insights, 9, MBI-S38517 pp. 21-28. (Year: 2016).*
Chiriac et al., 2015. Chloronychia: green nail syndrome caused by Pseudomonas aeruginosa in elderly persons. Clinical Interventions in Aging, 10, pp. 265-267. (Year: 2015).*
Lavenir, R., Jocktane, D., Laurent, F., Nazaret, S. and Cournoyer, B., 2007. Improved reliability of Pseudomonas aeruginosa PCR detection by the use of the species-specific ecfX gene target. Journal of Microbiological Methods, 70(1), pp. 20-29. (Year: 2007).*
Baskova et al., "The Pan-AC assay: a single-reaction real-time PCR test for quantitative detection of a broad range of *Aspergillus* and *Candida* species", Journal of Medical Microbiology, 2007, 56: 1167-1173.
Ebihara et al., "Molecular detection of dermatophytes and nondermatophytes in onychomycosis by nested polymerase chain reaction based on 28S ribosomal RNA gene sequences", British Journal of Dermatology, 2009, 161: 1038-1044.

* cited by examiner

```
  1        10        20        30        40        50        60        70        80        90       100       110
AAGTAAAAGTCGTAACAAGGTTTCCGTAGTGAACTGCGGAAGGATCATTAAGCGCAGTGCCGTCCCCTTCTCTGAATGCTGAAGCGTGTCGCCGGCCAC 120       130       140       150       160       170       180       190       200       210       220       230
ACGCCCATTCTGTTCTACACTACCGGTTGCCTCGGCGGGCGCCCCCTAGGCTGCTGCAGTGTGCTTCGGCCGTCTCGCAGCGCTTCGGGGATGGAGAAGGATGCCCGGC
                                                                    └──── Epiderm For2 ────┘

240       250       260       270       280       290       300       310       320       330       340
GGGGTTGATGCTCCCCACCCCTGGACAGCAGCGCTGCCGAAGGAGTGATTCTCAGAAATTCTACGAAATTCCATAGGTGGTTCAGTCTGAGGCGTTGGCAAGCAAAAACCAGTCA
            └──── Epiderm2 ────┘                                               └──── Epiderm Rev3 ────┘

350       360       370       380       390       400 402
AAACTTTCAACAACGGATCTCTTGGTTCCGCATGAAGAACGCAGCGAAATGC
```

FIG. 12

```
  1         10        20        30        40        50        60        70        80        90       100       110
  |         |         |         |         |         |         |         |         |         |         |         |
CGCACATTGCGCCCGCCAGTATTCTGGGGCATGCCTGTCTGAGCGTCATTTCAACCCTCAGGACCCGTTCGCGGGGATCAGCTTGCCCCTGGCGGGCT
                                                    |_____Acr For5b_____|
        120       130       140       150       160       170       180       190       200       210       220       230
          |         |         |         |         |         |         |         |         |         |         |         |
GGCCCTGAAATACAGTGGGGTTCCCTCGGCGAACTCCCGTGCAGTAATTAAACCTTCTCGGGCAGGATAGCGGTTGAACCACGCCGTTAAACCACCCCACTTCTCAAGGTTGAC
                                                                           |_____Acr ProbeAR_____|    |Acr Rev5|

240       250       260       270       280 /283
          |         |         |         |         |
CTCAGATCAGGTAGGAATACCCGCTGAACTTAAGCATATCAATAAGCGGAGGA
|Acr Rev5|
```

FIG. 14

```
1         10        20        30        40        50        60        70        80        90        100       110
CGCACATTGCGCCCTTTGGTATTCCAAAGGGCATGCCGTCATTTGTACCCTCAAGCTTTGCTTGGTGTTGGGCGTCTTGTCTCTAGCTTTGCTGGAGACTGCCTTT
         120       130       140       150       160       170       180       190       200       210       220       230
AAAGTAATTGGACAGCCGGCCTACTGGTTTCGGAGCCACAAGTCGCACACTCTATCAGCAAAGGTCTAGACATCCAATTAAGCCTTTTCAACTTTGACCTCGGATCAGTA
         |__Alt For1a__|         |__Alt Probe1__|                                                |__Alt Rev2a__|
         240       250       260       269
GGGATACCCGCTGAACTTAAGCATATATCAATAAGCGGAGG
```

FIG. 15

```
  1         10        20        30        40        50        60        70        80        90       100       110
  CGCACATTGCGCCCTTTGGTATTCCAAAGGGCATGCCGTTCGAGGCGTCATTGTACCCTCAAGCTTTGCTTGGTGTTGTTTTGTCTTTGCCAAAGACTGCCTTT
 120       130       140       150       160       170       180       190       200       210       220       230
 AAAAGGATTGGCCGGCTACTGGTTTTCGGCAGCGGCAACACATTTTTGCGCTTGCAATCAGCAAAAGAGGACGGCAATCCATCAAGACTCCTTCTCACGTTGACTTCGGATCAG
 236
 GTAGGG
```

Curv For2                    Curv Probe2              Curv Rev1

Screen Dermatophytes:

CACTGGCCCAGGGAGGTTGGAAACGACCGCCCAGGGCCGGAAAGTTGGTCAAACTCGGTCATTTAGAGGAAGTA
AAAGTCGTAACAAGGTTTCCGTAGGTGAACCTGCGGAAGG

FIG. 28

Target Sequence for Dermatophytes Screen:

GGAGGTTGGAAACGACCGCCCAGGGCCGGAAAGTTGGTCAAACTCGGTCATTTAGAGGAAGTAAAAGT
CGTAACAAGGTTTCCGTAGGTGAACCTG

FIG. 29

Target Sequence for Saprophyte Screen:
*Alternaria*

CCAGCAGTCGCGGTAAGACAAGGGAGACGAGTGTTATTCATCTTTAACAGGTATATAGGGTACCTAGACGGTGTG
CAATGGCTTAAATAAGTACCTGGTACACTTGAGTTTGATATGTGAGAGGAATATGTCGGAATTGTTGGAGGAAAG
ATGAAATTTGTTAATACCAATAGGACTGATAACGGCGAAGG

FIG. 30

Target Sequence for Saprophyte Screen:
*Curvularia*

CCAGCAGTCGCGGTAAGACAAGGGAGACGAGTGTTATTCATCTTTAACAGGTATATAGGGTACCTAGACGGTGTG
CAATGGCTTAAATAAGTACCTGGTACACTTGAGTTTGATATGTGAGAGGAATTGTCGGAATTGTTGGAGGAAAG
ATGAAATTTGTTAATACCAATAGGACTGATAACGGCGAAGG

FIG. 31

Target Sequence for Saprophyte Screen:
*Fusarium*

CCAGCAGTCGCGGTAATACGTAAGAGACTAGTGTTATTCATCTTAATTAGGTTTAAAGGGTACCCAGACGGTCAAT
ATAGCTTCTAAAATGTTAGTACTTGACTAGAGTTTTATGTAAGAGGGCAGTCTTGAGGAGGAGAGATGAAATTC
CG

FIG. 32

Target Sequence for Saprophyte Screen:
*Scopulariopsis*

CCAGCAGTCGCGGTAATACGTAAGAGACAAGTGTTATTCATCTTAAGTAGGTTTAAAGGGTACCTAGACGGCCAA
CATGACTTTATAAGTAGTATTTGGCTAGAGTTTTATGTAAGAAGTACAGTACTTTAGGTGGAGAGATGAAATTCT
G

FIG. 33

Target Sequence for Saprophyte Screen:
*Acremonium*

CAGCAGTCGCGGTAATACGTAAGAGACTAGTGTTATTCATAAGAATTAGGTTTAAAGGGTACTTAGACGGTTCTA
ATGTCAGTATAGAAGTAACCCTTAATGGTACTTTAGAACTAGAGTTAGATAAAGAGAACAGAACTTGCGGAGGAGA
GATCATATTCATTGATACCAAAGGGACTGGTAATGGCGAAGG

FIG. 34

Target Sequence for Saprophyte Screen:
*Aspergillus*

GATGACTAACACTAGTCTTCTACGTATTACCGCGACTGCTGGCACGTAATTTGGTCAAGACTTATAAATAGGAAAT
TGTCATTATCATTATCCTATTTAGAATTTTATACGAGTTAATCGTTATTGTTTACAATAATACACTTACATTCTTCCA
AGTTACTGGTTCAGCCTTTCGGC

FIG. 35

Target Sequence for Saprophyte Screen:
*Scytalidium*

GGAAGTGGGTGCGGCCTCCCGGCCGCGCTTAAGATATAGTCGGGCCCCAGCGAAAGCTGGGGGGTAAGTCACT
GCGACGAGAGCCG

FIG. 36

Target sequence for Yeast Screen:

*Candida albicans/tropicalis/parapsilosis complex/*

GTCCGAGTTGTAATTTGAAGAAGGTATCTTTGGGCCCGGCTCTTGTCTATGTTCCTTGGAACAGGACGTCACAGAG
GGTGAGAATCCCGTGCGATGAGATGACCCGGGTCTGTGTAAAGTTCCTTCGACGAGTCGAGTTGTTTGGGAATGC
A

FIG. 37

Screen Yeast:

*Candida guilliermodii complex*

GTCCGAGTTGTAATTTGAAGATTGTAACCTTGGGGTTGGCTCTTGTCTATGTTTCTTGGAACAGGACGTCACAGAG
GGTGAGAATCCCGTGCGATGAGATGCCCAATTCTATGTAAGGTGCTTTCGAAGAGTCGAGTTGTTTGGGAATGCA

FIG. 38

Target sequence for Yeast Screen:

*Candida guilliermodii complex*

CCGAGTTGTAATTTGAAGATTGTAACCTTGGGGTTGGCTCTTGTCTATGTTTCTTGGAACAGGACGTCACAGAGGG
TGAGAATCCCGTGCGATGAGATGCCCAATTCTATGTAAGGTGCTTTCGAAGAGTCGAGTTGTTTGGGAATGCA

FIG. 39

Screen Yeast:

*Candida Krusei:*

TGCAGGTTGGAGTCTGTGTGGAAGGCGGTGTCCAAGTCCCTTGGAACAGGGCGCCCAGGAGGGTGAGAGCCCCG
TGGGATGCCGGCGGAAGCAGTGAGGCCCTTCTGACGAGTCGAGTTGTTTGGGAATGCA

FIG. 40

Target sequence for Yeast Screen:

*Candida Krusei:*

CAGGTTGGAGTCTGTGTGGAAGGCGGTGTCCAAGTCCCTTGGAACAGGGCGCCCAGGAGGGTGAGAGCCCCGTG
GGATGCCGGCGGAAGCAGTGAGGCCCTTCTGACGAGTCGAGTTGTTTGGGAATGCA

FIG. 41

Screen Yeast:

*Candida lusitaniae (Clavispora lusitaniae)*
TTTGAAGGTTTCGTGGTCTGAGTCGGCCGCGCCCAAGTCCATTGGAACATGGCGCCTGGGAGGGTGAGAGCCCCG
TATGGCGCACGCCGACTCTTTGCACCGCGGCTCCGACGAGTCGAGTTGTTTGGGAATGCA

FIG. 42

Target sequence for Yeast Screen:

*Candida lusitaniae (Clavispora lusitaniae)*

TGAAGGTTTCGTGGTCTGAGTCGGCCGCGCCCAAGTCCATTGGAACATGGCGCCTGGGAGGGTGAGAGCCCCGT
ATGGCGCACGCCGACTCTTTGCACCGCGGCTCCGACGAGTCGAGTTGTTTGGGAATGCA

FIG. 43

Screen Yeast:

*Malassezia*
TTGTAATCTCGAGACGTGTTTTCCGTGCGGCTCTATGGACAAGTCCCTTGGAATACGGCATCGTAGAGGGTGAGA
ATCCCGTACTTGCATGGAAAACCATGCTTTGCGATACACGCTCTAAGAGTCGAGTTGTTTGGGATTGCA

FIG. 44

Target sequence for Yeast Screen:
*Malassezia*
GTAATCTCGAGACGTGTTTTCCGTGCGGCTCTATGGACAAGTCCCTTGGAATACGGCATCGTAGAGG
GTGAGAATCCCGTACTTGCCATGGAAAACCATGCTTTGCGATACACGCTCTAAGAGTCGAGTTGTTTGGGATTGCA

FIG. 45

Screen Yeast:

*Cryptcoccus / Trichosporon*
GGGGGCATTAGTATTCCGTTGCTAGAGGTGAAATTCTTAGATTTACGGAAGACTAACAACTGCGAAAGCATTTGCC
AAGGACGTTTTCATTGATCAAGAACGAAGGTTAGGGGATCAAAAACGATTAGATACCGTTGTAGTCTTAACA

FIG. 46

Target sequence for Yeast Screen:

*Cryptcoccus / Trichosporon*
GGGCATTAGTATTCCGTTGCTAGAGGTGAAATTCTTAGATTTACGGAAGACTAACAACTGCGAAAGCATTTGCCAA
GGACGTTTTCATTGATCAAGAACGAAGGTTAGGGGATCAAAAACGATTAGATACCGTTGTAGTCTTAA

FIG. 47

*Pseudomonas aeruginosa:*

TTCCACTTCAACGTCCAGCGTGAAGAGGACGGCGTGGGTGTGGAAGTCGCCTTGCAGTGGAACGACAGCTTCAAC
GAGAACCTGCTCTGCTTCACCAACAACATCCCGCAGCGTGATGGCGGCACCCACCTGGCCGGTTTCCGTTCGGCGC
TGACGCGTAACCTGAACAACTACATCGAGCCGAAGGCCTGGCGAAGAAATTCAAGATCGCCACCACCGGCGACGA
TGCCCGCAAGGCCTCACCGCGATCATCTCGGTGAAGGTACCGGACCCGAAGTTCAGCTCGCAGACCAAGGACAA

FIG. 48

Target sequence for *Pseudomonas aeruginosa:*

GGCGTGGGTGTGGAAGTCGCCTTGCAGTGGAACGACAGCTTCAACGAGAACCTGCTCTGCTTCACCAACAACATC
CGCAGCGTGATGGCGGCACCCACCTGGCCGGTTTCCGTTCGGCGCTGACGCGTAACCTGAACAACTACATCGAG
CCGAAGGCCTGGCGAAGAAATTCAAGATCGCCACCA

FIG. 49

Reflex Tests – Dermatophyte – *T. rubrum*

AAGTAAAAGTCGTAACAAGGTTTCCGTAGGTGAACCTGCGGAAGGATCATTAACGCGCAGGCCGGAGGCTGGCC
CCCCACGATAGGGACCGACGTTCCATCAGGGTGAGCAGACGTGCGCCGGCCGTACGCCCCATTCTTGTCTACCTC
ACCCGGTTGCCTCGGCGGGCCGCGCTCCCCCTGCCAGGGAGAGCCGTCCGGCGGGCCCTTCTGGGAGCCTCGAGC
CGGACCGCGCCCGCCGGAGGACAGACACCAAGAAAAAATTCTCTGAAGAGCTGTCAGTCTGAGCGTTTAGCAAGC
ACAATCAGTTAAAACTTTCAACAACGGATCTCTTGGTTCCGGCATCGATGAAGAACGCAGCGAAATGC

FIG. 50

Reflex Tests – Dermatophyte – *T. mentagrophytes*

AGTAAAAGTCGTAACAAGGTTTCCGTAGGTGAACCTGCGGAAGGATCATTAGCGCGCAGGCCGGAGGCTGGCCC
CCCACGATAGGGCCAAACGTCCGTCAGGGGTGAGCAGATGTGCGCCGGCCGTACCGCCCCATTCTTGTCTACATT
ACTCGGTTGCCTCGGCGGGCCGCGCTCTCCCAGGAGAGCCGTTCGGCGAGCCTCTCTTTAGTGGCTAAACGCTGG
ACCGCGCCCGCCGGAGGACAGACGCAAAAAAATTCTTTCAGAAGAGCTGTCAGTCTGAGCGTTAGCAAGCAAAAA
TCAGTTAAAACTTTCAACAACGGATCTCTTGGTTCCGGCATCGATGAAGAACGCAGCGAAATGC

FIG. 51

Reflex Tests – Dermatophyte – *Epidermophyton spp.*

AAGTAAAAGTCGTAACAAGGTTTCCGTAGGTGAACCTGCGGAAGGATCATTAACGCGCAGGCCGCAGTCGGCCC
GTCCCCCTTCTCTCTGAATGCTGGACGGTGTCGCCGGCCACACGCCCATTCTTGTCTACACTACCCGGTTGCCTCGG
CGGGCCGCGCCCCCTAGGCTGCAGTGTCGCTGCAGCGTCTCGGGGGGGCCGTTCGGGGGATGGAGAAGGATGCC
CCGGCGGGGTTGATCGCTCCCCCACCCCTGGACAGCGCTCGCCGAAGGAGTGATTCTCAGAAATTCTACGAAATCT
CCATAGGTGGTTCAGTCTGAGCGTTGGCAAGCAAAAACCAGTCAAAACTTTCAACAACGGATCTCTTGGTTCCGGC
ATCGATGAAGAACGCAGCGAAATGC

FIG. 52

Reflex Tests – Dermatophyte – *Microsporum spp.*

Microsporum
TCCGGCCGCACGCCCATTCTTGTCTACTGACCCGGTTGCCTCGGCGGGCCGCGCCTGCTGTGCTACAGCGGCCGTT
CGGGGGGGACGCCTGAGGGGGACTCTTGTTTCCTAGGCCACGCCCCGGGCAGCGCTCGCCGGAGGATTACTCTG
GAAAACACACTCTTGAAAGAACATACCGTCTGAGCG

FIG. 53

Reflex Tests – Dermatophyte – *Nanissia (Microsporum) gypsia*
GCCGGCCACACGCCCATTCTTGTCTATTTACCCAGTTGCCTCGGCGGGCCGCGCACTCGTGCCGCGCCTCGAGGAG
CCGTCCGGGGACAATCAACTCCCTGGATCGCGCCCGCCGGAGGAGTGATTAAAATCCATGAATACTGTTCCGTCTG
AGCGT

FIG. 54

Reflex Tests – Saprophyte – *Acremonium spp.*

CGCACATTGCGCCCGCCAGTATTCTGGCGGGCATGCCTGTCTGAGCGTCATTTCAACCCTCAGGACCCGTTCGCGG
GACCTGGCGTTGGGGATCAGCCTGCCCCTGGCGGCGGCTGGCCCTGAAATACAGTGGCGGTTCCCTCGCGAACTC
CTCCGTGCAGTAATTAAACCTCTCGCGGCAGGATAGCGGTTGAACCACGCCGTTAAACCCCCACTTCTCAAGGTT
GACCTCAGATCAGGTAGGAATACCCGCTGAACTTAAGCATATCAATAAGCGGAGGA

FIG. 55

Reflex Tests – Saprophyte – *Alternaria spp.*

CGCACATTGCGCCCTTTGGTATTCCAAAGGGCATGCCTGTTCGAGCGTCATTTGTACCCTCAAGCTTTGCTTGGTGT
TGGGCGTCTTGTCTCTAGCTTTGCTGGAGACTCGCCTTAAAGTAATTGGCAGCCGGCCTACTGGTTTCGGAGCGCA
GCACAAGTCGCACTCTCTATCAGCAAAGGTCTAGCATCCATTAAGCCTTTTTTCAACTTTTGACCTCGGATCAGGTA
GGGATACCCGCTGAACTTAAGCATATCAATAAGCGGAGG

FIG. 56

Reflex Tests – Saprophyte – *Aspergillus spp.*

CGCACATTGCGCCCCCTGGTATTCCGGGGGGCATGCCTGTCCGAGCGTCATTGCTGCCCATCAAGCACGGCTTGTG
TGTTGGGTCGTCGTCCCCTCTCCGGGGGGGACGGGCCCCAAAGGCAGCGGCGGCACCGCGTCCGATCCTCGAGC
GTATGGGGCTTTGTCACCCGCTCTGTAGGCCCGGCCGGCGCTTGCCGAACGCAAATCAATCTTTTTCCAGGTTGAC
CTCGGATCAGGTAGGGATACCCGCTGAACTTAAGCATATCAATAAGCGGAGGAAAAGAAACCAACCGGGATTGC
CTCAGTAACGGCGAGTGAAGCGGCAAGAGCTCAAATTTGAAAGCTGGCTCCTTCGGGGTCCGCATTGTAATTTGC
AGAGGATGCTTCGGGTGCGGCCCCTGTCTAAGTGCCCTGGAACGGGCCGTCAGAGAGGGTGAGAATCCCGTCTG
GGATGGGGTGTCCG

FIG. 57

Reflex Tests – Saprophyte – *Curvularia spp.*

CGCACATTGCGCCCTTTGGTATTCCAAAGGGCATGCCTGTTCGAGCGTCATTTGTACCCTCAAGCTTTGCTTGGTGT
TGGGCGTTTTTTGTCTTTGGTTGCCAAAGACTCGCCTTAAAAGGATTGGCAGCCGGCCTACTGGTTTCGCAGCGCA
GCACATTTTTGCGCTTGCAATCAGCAAAAGAGGACGGCAATCCATCAAGACTCCTTCTCACGTTGACCTCGGATCA
GGTAGGG

FIG. 58

Reflex Tests – Saprophyte – *Fusarium spp.*

Fusarium oxyporum
CAGCGGAGGGATCATTACCGAGTTTACAACTCCCAAACCCCTGTGAACATACCACTTGTTGCCTCGGCGGATCAGC
CCGCTCCCGGTAAAACGGGACGGCCCGCCAGAGGACCCCTAAACTCTGTTTCTATATGTAACTTCTGAGTAAAACC
ATAAATAAATCAAAACTTTCAACAACGGATCTCTTGGTTCTGGCATCGATGAAGAACGCAGCAAAATGCGATAAGT

FIG. 59

*Fusarium solani*
CAGCGGAGGGATCATTACCGAGTTATACAACTCATCAACCCTGTGAACATACCTAAAACGTTGCTTCGGCGGGAAC
AGACGGCCCCGTAACAACGGGCCGCCCCCGCCAGAGGACCCCTAACTCTGTTTCTATAATGTTTCTTCTGAGTAAA
CAAGCAAATAAATTAAAACTTTCAACAACGGATCTCTTGGCTCTGGCATCGATGAAGAACGCAGCGAAATGCGAT

FIG. 60

Reflex Tests – Saprophyte – *Scopulariopsis spp.*
CGCACATTGCGCCCGGCAGCAATCTGCCGGGCATGCCTGTCCGAGCGTCATTTCTTCCCTCGAGCGCGGCTAGCCC
TACGGGGCCTGCCGTCGCCCGGTGTTGGGGCTCTACGGGTGGGGCTCGTCCCCCCCGCAGTCCCCGAAATGTAGT
GGCGGTCCAGCCGCGGCGCCCCCTGCGTAGTAGATCCTACATCTCGCATCGGGTCCCGGCGAAGGCCAGCCGTCG
AACCTTTTATTTCATGGTTTGACCTCGGATCAGGTAGGGTTACCCGCTGAACTTAAGCATATCAATAAGCGGAGG

FIG. 61

Reflex Tests – Saprophyte – *Scytalidium spp.*
GGACGATCCGCAGCCAAGCCCCTACGTCCAGCCGGCCTGGATACGGGGAAGGTTCACAGACTAAGTGGAAGTGG
GTGCGGCCTCCCGGCCGCGCTTAAGATATAGTCGGGCCCCAGCGAAAGCTGGGGGGTAAGTCACTGCGACGAG
AGCCGTTCCGTAGGTGAACCTGCGGAAGGATCATTACCGAGTTGATTCGGGCTCCGGCCCGATCCTCCCACCCTTT
GTGTACCCACCTCTGTTGCTTTGGCGGGCCGCGGTCCTCCGCGGCCGCCCTCCGTCCGGGGGGTGGCCAGCGCCC
GCCAGAGGACCATCGAACTCCGGTCAGTGAACGTTGCCGTCTGAAA

FIG. 62

Reflex Assays– Yeast – *Candida albicans*

TTTGAACGCACATTGCGCCCTCTGGTATTCCGGAGGGCATGCCTGTTTGAGCGTCGTTTCTCCCTCAAACCGCTGG
GTTTGGTGTTGAGCAATACGACTTGGGTTTGCTTGAAAGACGGTAGTGGTAAGGCGGGATCGCTTTGACAATGGC
TTAGGTCTACCAAAAACATTGCTTGCGGCGGTAACGTCCACCACGTATATCTTCAAACTTTGACCTCAAATCAGGTA
GGACTACCCGCTGAACTTAAGCATATCAATAAGCGGAGGAAAAGAAACCAACAGGGATTGCCTCAGTAGCGGCG
AGTGAAG

FIG. 63

Reflex Assays – Yeast – *Candida parapsilosis complex*

TTTGAACGCACATTGCGCCCTTTGGTATTCCAAAGGGCATGCCTGTTTGAGCGTCATTTCTCCCTCAAACCCTCGGG
TTTGGTGTTGAGCGATACGCTGGGTTTGCTTGAAAGAAAGGCGGAGTATAAACTAATGGATAGGTTTTTTTCCACTC
ATTGGTACAAACTCCAAAACTTCTTCCAAATTCGACCTCAAATCAGGTAGGACTACCCGCTGAACTTAAGCATATCA
ATAAGCGGAGGAAAAGAAACCAACAGGGATTGCCTTAGTAGCGGCGAGTGAAG

FIG. 64

Reflex Assays – Yeast – *Candida tropicalis*

TTTGAACGCACATTGCGCCCTTTGGTATTCCAAAGGGCATGCCTGTTTGAGCGTCATTTCTCCCTCAAACCCCCGGG
TTTGGTGTTGAGCAATACGCTAGGTTTGTTTGAAAGAATTTAACGTGGAAACTTATTTTAAGCGACTTAGGTTTATC
CAAAACGCTTATTTTGCTAGTGGCCACCACAATTTATTTCATAACTTTGACCTCAAATCAGGTAGGACTACCCGCTG
AACTTAAGCATATCAATAAGCGGAGGAAAAGAAACCAACAGGGATTGCCTTAGTAGCGGCGAGTGAAG

FIG. 65

Reflex Assays – Yeast – *Trichosporon spp.*

*Trichosporon asahii/asteroides/inkin/ovoides*

GAATTCAGTGAATCATCGAATCTTTGAACGCAGCTTGCGCTCTCTGGTATTCCGGAGAGCATGCCTGTTTCAGTGTC
ATGAAATCTCAACCACTAGGGTTTCCTAATGGATTGGATTTGGGCGTCTGCGATTTCTGATCGCTCGCCTTAAAAG
AGTTAGCAAGTTTGACATTAATGTCTGGTGTAATAAGTTTCACTGGGTCCATTGTGTTGAAGCGTGCTTCTAATCGT
CCGCAAGGACAATTACTTTGACTCTGGCCTGAAATCAGGTAGGACTACCCGCTGAACTTAAGCATATCAATAAGCG
GAGGAA

FIG. 66

Reflex Assays – Yeast – *Trichosporon spp.*

*Trichosporon cutaneum/mucoides*

GAATTCAGTGAATCATCGAATCTTTGAACGCAACTTGCGCTCTCTGGTATTCCGGAGAGCATGCCTGTTTGAGTATC
ATGAAATCTCAACCATTAGGGTTTCTTAATGGCTTGGATTTGGGCGCTGCCACTTGCCTGGCTCGCCTTAAAAGAG
TTAGCGTATTAACTTGTCGATCTGGCGTAATAAGTTTCGCTGGTGTAGACTTGAGAAGTGCGCTTCTAATCGTCTTC
GGACAATTCTTGAACTCTGGTCTCAAATCAGGTAGGACTACCCGCTGAACTTAAGCATATCAATAAGCGGAGGAA
A

FIG. 67

Reflex Assays – Yeast – *Candida guilliermondii complex*

TTTGAACGCACATTGCGCCCTCTGGTATTCCAGAGGGCATGCCTGTTTGAGCGTCATTTCTCTCTCAAACCCCCGGG
TTTGGTATTGAGTGATACTCTTAGTCGGACTAGGCGTTGCTTGAAAAGTATTGGCATGGGTAGTACTAGATAGTG
CTGTCGACCTCTCAATGTATTAGGTTTATCCAACTCGTTGAATGGTGTGGCGGGATATTTCTGGTATTGTTGGCCCG
GCCTTACAACAACCAAACAAGTTTGACCTCAAATCAGGTAGGAATACCCGCTGAACTTAAGCATATCAATAAGCGG
AGGAAAAGAAACCAACAGGGATTGCCTTAGTAGCGGCGAGTGAAG

FIG. 68

Reflex Assays – Yeast – *Malassezia spp.*

TACAAGGGAGTGAAAACATCCGTGAAATACCTTGATATATTGAAATGAATGGCTTATTTATTAAAAGACAGTGTCA
GATGGTCAGTTTTACTGGGGCGGTAGCCTCTAAAAAAGTATCAGAGGCCTTCAAAGGTATATTTAAATTGGTCGG
AAACCAATGGAATAATAGTATTCTATCAAAATGTAATGATAAAGTATGCTTTACTGAAAGATTGATAAATCGATCA
GTTACGCAAGTAGGATATAGTGATCCGATGATTCAGAATGGAATGATCATCGCTCAAGAAATAAAAGTTACGCT

FIG. 69

Reflex Assays – Yeast – *Cryptococcus neoformans/gattii*

AACGCAGCGAAATGCGATAAGTAATGTGAATTGCAGAATTCAGTGAATCATCGAGTCTTTGAACGCAACTTGCGC
CCTTTGGTATTCCGAAGGGCATGCCTGTTTGAGAGTCATGAAAATCTCAATCCCTCGGGTTTTATTACCTGTTGGAC
TTGGATTTGGGTGTTTGCCGCGACCTGCAAAGGACGTCGGCTCGCCTTAAATGTGTTAGTGGGAAGGTGATTACCT
GTCAGCCCGGCGTAATAAGTTTCGCTGGGCCTATGGGTAGTCTTCGGCTTGCTGATAACAACCATCTCTTTTTGTT
TGACCTCAAATCAGGTAGGGCTACCCGCTGAACTTAAGCATATCAATAAGCGAAAGAATGA

FIG. 70

**Reflex Assays – Yeast – *Cryptococcus albidus***

AACGCAGCGAAATGCGATAAGTAATGTGAATTGCAGAATTCAGTGAATCATCGAATCTTTGAACGCACCTTGCGCT
CCTTGGTATTCCGAGGAGCATGCCTGTTTGAGTGTCATGAAAACCCTCAACCCTAGATTGGTTAAAACCTTTCTTTG
GTTTGGATTTGGACGTTTGCCGATGATAAGTCGGCTCGTCTTAAAAGTAATAGCTGGATCTGTCTCGCGACATGGT
TTGACTTGGCGTAATAAGTATTTCGCTAAGGACATCTTCGGATGGCCGCGTTGCAGGACTAAAGACCGCTTTCTAA
TCCATTGATCTTCGGATTAATACTCTTGACATCTGGCCTCAAATCAAGTAGGACTACCCGCTGAACTTAAGCATATC
AATAAGCGGAGGAAA

FIG. 71

**Reflex Assays – Yeast – *Cryptococcus laurentii***

AACGCAGCGAAATGCGATAAGTAATGTGAATTGCAGAATTCAGTGAATCATCGAATCTTTGAACGCACCTTGCGCC
TTTTGGTATTCCGAAAGGCATGCCTGTTTGAGTGTCATGAAATCTCAATCCCCCTGGGTTTATGATCTGGGTCGGAC
TTGGAAATGGGCGTCTGCCGGTCACACGGCTCGCCTCAAATGACTTAGTGGATCTCTCTGCATCCGTGACAGACGT
AATAAGTTTCGTCTTGTCCCTTGCTTATGAGTCTGCTCATAACCTGCCATCGCGCACTTTTAGACTCTGACCTCAAAT
CAGGTAGGACTACCCGCTGAACTTAAGCATATCAT

FIG. 72

OIAD Screen Assay Parameters

OIAD Screen Assay Parameters

| Master Mix | Targets | Ct cutoff value | Delta Rn cutoff value |
|---|---|---|---|
| Screen Master Mix 1 | Dermatophyte | 40 | 0.2 |
| | Yeast | 32.5 | 0.2 |
| | EC/IC | 33.5 | 0.4 |
| Screen Master Mix 2 | Saprophyte | 29.5 | 0.4 |
| | *P. aeruginosa* | 40 | 0.05 |
| | EC/IC | 33.5 | 0.4 |

OIAD Reflex Assay Parameters

| Master Mix | Targets | Ct cutoff value | Delta Rn cutoff value |
|---|---|---|---|
| Dermatophyte | Epidermophyton | 30.5 | 0.20 |
| | Microsporum | 40.0 | 0.20 |
| | T. mentagrophytes | 36.5 | 0.40 |
| | T. rubrum | 40.0 | 0.20 |
| Saprophyte Master Mix 1 | Alternaria | 29.0 | 0.50 |
| | Fusarium | 34.5 | 0.20 |
| | Scopulariopsis | 36.0 | 0.30 |
| | Scytalidium | 36.0 | 0.30 |
| Saprophyte Master Mix 2 | Acremonium | 32.0 | 0.50 |
| | Aspergillus | 34.5 | 0.50 |
| | Curvularia | 32.0 | 0.60 |
| Yeast Master Mix 1 | Candida albicans | 33.0 | 1.40 |
| | Candida parapsilosis | 32.2 | 0.40 |
| | Candida tropicalis | 30.5 | 0.40 |
| | Trichosporon spp. | 30.0 | 0.40 |
| Yeast Master Mix 2 | Candida guilliermondii | 31.0 | 0.40 |
| | Cryptococcus spp. | 31.0 | 0.40 |
| | Malassezia spp. | 28.0 | 2.00 |

FIG. 74

OIAD Screen Assay Sensitivity

| OIADScreen Assay-Dermatophyte | Trichophyton mentagrophytes | ng DNA/Extraction | Replicates Tested | No. Detected | % Detected | Mean Ct Value |
|---|---|---|---|---|---|---|
| | | 1 | 6 | 6 | 100 | 19.58 |
| | | 0.1 | 10 | 10 | 100 | 22.49 |
| | | 0.01 | 10 | 10 | 100 | 25.90 |
| | | 0.001 | 10 | 10 | 100 | 29.53 |
| | | 0.0001 | 10 | 10 | 100 | 34.85 |
| | | 0.00001 | 10 | 0 | 0 | 40.00 |
| | Trichophyton rubrum | ng DNA/Extraction | Replicates Tested | No. Detected | % Detected | MeanCt Value |
| | | 1 | 6 | 6 | 100 | 18.74 |
| | | 0.1 | 10 | 10 | 100 | 22.09 |
| | | 0.01 | 10 | 10 | 100 | 25.31 |
| | | 0.001 | 10 | 10 | 100 | 28.69 |
| | | 0.0001 | 10 | 10 | 100 | 33.85 |
| | | 0.00001 | 10 | 0 | 0 | 40.00 |
| | Epidermophyton | ng DNA/Extraction | Replicates Tested | No. Detected | % Detected | MeanCt Value |
| | | 1 | 6 | 6 | 100 | 18.96 |
| | | 0.1 | 10 | 10 | 100 | 22.47 |
| | | 0.01 | 10 | 10 | 100 | 25.83 |
| | | 0.001 | 10 | 10 | 100 | 29.36 |
| | | 0.0001 | 10 | 10 | 100 | 34.06 |
| | | 0.00001 | 10 | 0 | 0 | 40.00 |
| | Microsporum | ng DNA/Extraction | Replicates Tested | No. Detected | % Detected | MeanCt Value |
| | | 1 | 6 | 6 | 100 | 20.72 |
| | | 0.1 | 10 | 10 | 100 | 23.97 |
| | | 0.01 | 10 | 10 | 100 | 27.42 |
| | | 0.001 | 10 | 10 | 100 | 31.36 |
| | | 0.0001 | 10 | 5 | 50 | 38.54 |
| | | 0.00001 | 10 | 0 | 0 | 40.00 |
| OIAD Screen Assay-Saprophytes | Acremonium | ng DNA/Extraction | Replicates Tested | No. Detected | % Detected | MeanCt Value |
| | | 1 | 6 | 6 | 100 | 22.44 |
| | | 0.1 | 10 | 10 | 100 | 25.84 |
| | | 0.01 | 10 | 10 | 100 | 29.14 |
| | | 0.001 | 10 | 10 | 100 | 31.86 |
| | | 0.0001 | 10 | 10 | 100 | 34.46 |
| | | 0.00001 | 10 | 9 | 90 | 37.52 |

FIG. 75

| | | ng DNA/Extraction | Replicates Tested | No. Detected | % Detected | MeanCt Value |
|---|---|---|---|---|---|---|
| | | 1 | 6 | 6 | 100 | 21.13 |
| | | 0.1 | 10 | 10 | 100 | 25.97 |
| | Alternaria | 0.01 | 10 | 10 | 100 | 29.27 |
| | | 0.001 | 10 | 10 | 100 | 30.90 |
| | | 0.0001 | 10 | 9 | 90 | 33.35 |
| | | 0.00001 | 10 | 7 | 70 | 35.18 |
| | | ng DNA/Extraction | Replicates Tested | No. Detected | % Detected | MeanCt Value |
| | | 1 | 6 | 6 | 100 | 19.04 |
| | | 0.1 | 10 | 10 | 100 | 22.78 |
| | Aspergillus | 0.01 | 10 | 10 | 100 | 26.37 |
| | | 0.001 | 10 | 10 | 100 | 29.77 |
| | | 0.0001 | 10 | 10 | 100 | 33.45 |
| | | 0.00001 | 10 | 10 | 100 | 36.48 |
| | | ng DNA/Extraction | Replicates Tested | No. Detected | % Detected | MeanCt Value |
| | | 1 | 6 | 6 | 100 | 18.72 |
| | | 0.1 | 10 | 10 | 100 | 22.10 |
| | Curvularia | 0.01 | 10 | 10 | 100 | 25.60 |
| | | 0.001 | 10 | 10 | 100 | 29.04 |
| | | 0.0001 | 10 | 10 | 100 | 32.53 |
| | | 0.00001 | 10 | 9 | 90 | 36.31 |
| | | ng DNA/Extraction | Replicates Tested | No. Detected | % Detected | MeanCt Value |
| | | 1 | 6 | 6 | 100 | 24.25 |
| | | 0.1 | 10 | 10 | 100 | 27.84 |
| | Fusarium | 0.01 | 10 | 10 | 100 | 31.91 |
| | | 0.001 | 10 | 10 | 100 | 34.33 |
| | | 0.0001 | 10 | 10 | 100 | 37.53 |
| | | 0.00001 | 10 | 3 | 30 | 38.56 |
| | | ng DNA/Extraction | Replicates Tested | No. Detected | % Detected | MeanCt Value |
| | | 1 | N/A | N/A | N/A | N/A |
| | | 0.1 | 10 | 10 | 100 | 22.36 |
| | Scopulariopsis | 0.01 | 10 | 10 | 100 | 24.75 |
| | | 0.001 | 10 | 10 | 100 | 28.31 |
| | | 0.0001 | 10 | 10 | 100 | 32.72 |
| | | 0.00001 | 10 | 9 | 90 | 34.81 |
| | Scytalidium | ng DNA/Extraction | Replicates Tested | No. Detected | % Detected | MeanCt Value |
| | | 1 | N/A | N/A | N/A | N/A |

FIG. 75 (Cont. 1)

| | | 0.1 | 10 | 10 | 100 | 24.60 |
| --- | --- | --- | --- | --- | --- | --- |
| | | 0.01 | 10 | 10 | 100 | 28.57 |
| | | 0.001 | 10 | 10 | 100 | 33.74 |
| | | 0.0001 | 10 | 6 | 60 | 35.37 |
| | | 0.00001 | 10 | 3 | 30 | 39.43 |
| OIAD Screen Assay- Yeasts | | CFU/extraction | Replicates Tested | No. Detected | % Detected | Mean Ct Value |
| | C. albicans | 2400 | 5 | 5 | 100 | 32.34 |
| | | 1200 | 10 | 10 | 100 | 33.41 |
| | | 600 | 10 | 9 | 90 | 35.82 |
| | | 300 | 10 | 5 | 50 | 38.79 |
| | | 150 | 10 | 3 | 30 | 39.87 |
| | | 75 | 10 | 1 | 10 | 39.39 |
| | | 38 | 10 | 0 | 0 | N/A |
| | C. parapsilosis | CFU/extraction | Replicates Tested | No. Detected | % Detected | Mean Ct Value |
| | | 32224 | 12 | 12 | 100 | 28.61 |
| | | 13810 | 12 | 12 | 100 | 29.7 |
| | | 5919 | 11 | 11 | 100 | 32.07 |
| | | 2537 | 12 | 11 | 92 | 33.73 |
| | | 1087 | 12 | 8 | 67 | 33.98 |
| | | 466 | 12 | 8 | 67 | 34.07 |
| | | 200 | 12 | 8 | 67 | 35.73 |
| | | 86 | 12 | 6 | 50 | 36.89 |
| | C. tropicalis | CFU/extraction | Replicates Tested | No. Detected | % Detected | Mean Ct Value |
| | | 800 | 5 | 5 | 100 | 32.98 |
| | | 400 | 10 | 10 | 100 | 34.37 |
| | | 200 | 10 | 6 | 60 | 38.78 |
| | | 100 | 10 | 0 | 0 | N/A |
| | Trichosporon asahii | CFU/extraction | Replicates Tested | No. Detected | % Detected | Mean Ct Value |
| | | 4160 | 5 | 5 | 100 | 29.27 |
| | | 2080 | 9 | 9 | 100 | 31.88 |
| | | 1040 | 9 | 9 | 100 | 33.54 |
| | | 520 | 10 | 10 | 100 | 34.4 |
| | | 260 | 10 | 9 | 90 | 36.72 |
| | | 130 | 10 | 2 | 20 | 39.43 |
| | C. guilliermondii | CFU/extraction | Replicates Tested | No. Detected | % Detected | Mean Ct Value |
| | | 7872 | 5 | 5 | 100 | 32.41 |
| | | 3936 | 10 | 10 | 100 | 35.16 |

FIG. 75 (Cont. 2)

| | | | | | | |
|---|---|---|---|---|---|---|
| | | 1968 | 10 | 5 | 50 | 38.72 |
| | | 984 | 10 | 1 | 10 | 36.65 |
| | | 492 | 10 | 1 | 10 | 39.23 |
| | Cryptococcus neoformans | CFU/extraction | Replicates Tested | No. Detected | % Detected | Mean Ct Value |
| | | 3712 | 5 | 5 | 100 | 32.14 |
| | | 1856 | 10 | 10 | 100 | 34.66 |
| | | 928 | 10 | 6 | 60 | 39.06 |
| | | 464 | 10 | 3 | 30 | 39.5 |
| | | 232 | 10 | 0 | 0 | N/A |
| | Malassezia furfur | CFU/extraction | Replicates Tested | No. Detected | % Detected | Mean Ct Value |
| | | 84000 | 5 | 5 | 100 | 29.67 |
| | | 42000 | 10 | 10 | 100 | 33.21 |
| | | 21000 | 10 | 10 | 100 | 31.84 |
| | | 10500 | 10 | 9 | 90 | 35.17 |
| | | 5250 | 10 | 4 | 40 | 39.17 |
| OIAD Screen Assay-Pseudomonas aeruginosa | Pseudomonas aeruginosa | CFU/extraction | Replicates Tested | No. Detected | % Detected | Mean Ct Value |
| | | 13781 | 12 | 12 | 100 | 34.34 |
| | | 6891 | 12 | 12 | 100 | 35.88 |
| | | 3445 | 11 | 11 | 100 | 37.24 |
| | | 1723 | 12 | 9 | 75 | 38.54 |
| | | 861 | 12 | 3 | 25 | 38.84 |
| | | 431 | 12 | 0 | 0 | N/A |

FIG. 75 (Cont. 3)

OIAD Reflex Assays Sensitivity

| | | ng DNA/Extraction | Replicates Tested | No. Detected | % Detected | Mean Ct Value |
|---|---|---|---|---|---|---|
| OIAD Reflex Assays-Dermatophyte Rxn | Trichophyton mentagrophytes | 1 | 6 | 6 | 100 | 20.04 |
| | | 0.1 | 10 | 10 | 100 | 23.29 |
| | | 0.01 | 10 | 10 | 100 | 26.75 |
| | | 0.001 | 10 | 10 | 100 | 30.32 |
| | | 0.0001 | 10 | 10 | 100 | 32.93 |
| | | 0.00001 | 10 | 10 | 100 | 36.39 |
| | | ng DNA/Extraction | Replicates Tested | No. Detected | % Detected | Mean Ct Value |
| | Trichophyton rubrum | 1 | 6 | 6 | 100 | 21.17 |
| | | 0.1 | 10 | 10 | 100 | 24.62 |
| | | 0.01 | 10 | 10 | 100 | 28.02 |
| | | 0.001 | 10 | 10 | 100 | 31.57 |
| | | 0.0001 | 10 | 10 | 100 | 35.24 |
| | | 0.00001 | 10 | 100 | 100 | 38.15 |
| | | ng DNA/Extraction | Replicates Tested | No. Detected | % Detected | Mean Ct Value |
| | Epidermo-phyton | 1 | 6 | 6 | 100 | 18.76 |
| | | 0.1 | 10 | 10 | 100 | 22.28 |
| | | 0.01 | 10 | 10 | 100 | 25.90 |
| | | 0.001 | 10 | 10 | 100 | 29.29 |
| | | 0.0001 | 10 | 10 | 100 | 32.53 |
| | | 0.00001 | 10 | 10 | 100 | 36.01 |
| | | ng DNA/Extraction | Replicates Tested | No. Detected | % Detected | Mean Ct Value |
| | Microsporum | 1 | 6 | 6 | 100 | 21.66 |
| | | 0.1 | 10 | 10 | 100 | 24.93 |
| | | 0.01 | 10 | 10 | 100 | 28.98 |
| | | 0.001 | 10 | 10 | 100 | 32.31 |
| | | 0.0001 | 10 | 10 | 100 | 36.04 |
| | | 0.00001 | 10 | 7 | 70 | 38.25 |
| OIAD Reflex Assays-Saprophytes Rxn 1and 2 | | ng DNA/Extraction | Replicates Tested | No. Detected | % Detected | Mean Ct Value |
| | Acremonium | 1 | 6 | 6 | 100 | 21.40 |
| | | 0.1 | 10 | 10 | 100 | 23.77 |
| | | 0.01 | 10 | 10 | 100 | 27.22 |
| | | 0.001 | 10 | 10 | 100 | 32.23 |
| | | 0.0001 | 10 | 2 | 20 | 34.70 |
| | | 0.00001 | 10 | 0 | 0 | 37.80 |

FIG. 76

| | | ng DNA/Extraction | Replicates Tested | No. Detected | % Detected | Mean Ct Value |
|---|---|---|---|---|---|---|
| | Alternaria | 1 | 6 | 6 | 100 | 18.02 |
| | | 0.1 | 10 | 10 | 100 | 20.22 |
| | | 0.01 | 10 | 10 | 100 | 23.96 |
| | | 0.001 | 10 | 10 | 100 | 27.18 |
| | | 0.0001 | 10 | 10 | 100 | 31.97 |
| | | 0.00001 | 10 | 5 | 50 | 35.42 |
| | Aspergillus | ng DNA/Extraction | Replicates Tested | No. Detected | % Detected | Mean Ct Value |
| | | 1 | 6 | 6 | 100 | 23.76 |
| | | 0.1 | 10 | 10 | 100 | 28.58 |
| | | 0.01 | 10 | 10 | 100 | 34.24 |
| | | 0.001 | 10 | 10 | 100 | 37.22 |
| | | 0.0001 | 10 | 1 | 10 | 39.26 |
| | | 0.00001 | 10 | 0 | 0 | 40.00 |
| | Curvularia | ng DNA/Extraction | Replicates Tested | No. Detected | % Detected | Mean Ct Value |
| | | 1 | 6 | 6 | 100 | 22.97 |
| | | 0.1 | 10 | 10 | 100 | 26.71 |
| | | 0.01 | 10 | 10 | 100 | 30.51 |
| | | 0.001 | 10 | 10 | 100 | 33.97 |
| | | 0.0001 | 10 | 10 | 100 | 37.85 |
| | | 0.00001 | 10 | 1 | 10 | 39.46 |
| | Fusarium | ng DNA/Extraction | Replicates Tested | No. Detected | % Detected | Mean Ct Value |
| | | 1 | 6 | 6 | 100 | 26.42 |
| | | 0.1 | 10 | 10 | 100 | 29.03 |
| | | 0.01 | 10 | 10 | 100 | 32.69 |
| | | 0.001 | 10 | 10 | 100 | 36.15 |
| | | 0.0001 | 10 | 9 | 90 | 39.19 |
| | | 0.00001 | 10 | 7 | 70 | 40.00 |
| | Scopulariopsis | ng DNA/Extraction | Replicates Tested | No. Detected | % Detected | Mean Ct Value |
| | | 1 | N/A | N/A | N/A | N/A |
| | | 0.1 | 10 | 10 | 100 | 22.08 |
| | | 0.01 | 10 | 10 | 100 | 26.31 |
| | | 0.001 | 10 | 10 | 100 | 30.62 |
| | | 0.0001 | 10 | 8 | 80 | 35.42 |
| | | 0.00001 | 10 | 3 | 30 | 37.56 |
| | Scytalidium | ng DNA/Extraction | Replicates Tested | No. Detected | % Detected | Mean Ct Value |
| | | 1 | N/A | N/A | N/A | N/A |

FIG. 76 (Cont. 1)

| | | 0.1 | 10 | 10 | 100 | 23.02 |
|---|---|---|---|---|---|---|
| | | 0.01 | 10 | 10 | 100 | 27.47 |
| | | 0.001 | 10 | 10 | 100 | 32.83 |
| | | 0.0001 | 10 | 7 | 70 | 36.23 |
| | | 0.00001 | 10 | 0 | 0 | 40.00 |
| OIAD Reflex Assays- Yeasts Rxn 1 and 2 | C. albicans | CFU/extraction | Replicates Tested | No. Detected | % Detected | Mean Ct Value |
| | | 1200 | 10 | 10 | 100 | 30.78 |
| | | 600 | 10 | 10 | 100 | 31.89 |
| | | 300 | 10 | 10 | 100 | 32.88 |
| | | 150 | 10 | 10 | 100 | 33.98 |
| | | 75 | 10 | 10 | 100 | 35.19 |
| | | 38 | 10 | 9 | 90 | 36.65 |
| | | 19 | 10 | 8 | 80 | 36.89 |
| | C. parapsilosis | CFU/extraction | Replicates Tested | No. Detected | % Detected | Mean Ct Value |
| | | 13810 | 12 | 12 | 100 | 29.37 |
| | | 5919 | 12 | 12 | 100 | 31.32 |
| | | 2537 | 12 | 12 | 100 | 32.67 |
| | | 1087 | 12 | 12 | 100 | 33.77 |
| | | 466 | 12 | 12 | 100 | 34.66 |
| | | 200 | 12 | 11 | 92 | 35.76 |
| | | 86 | 12 | 10 | 83 | 37.05 |
| | C. tropicalis | CFU/extraction | Replicates Tested | No. Detected | % Detected | Mean Ct Value |
| | | 400 | 10 | 10 | 100 | 31.06 |
| | | 200 | 10 | 10 | 100 | 32.66 |
| | | 100 | 10 | 10 | 100 | 34.11 |
| | | 50 | 10 | 10 | 100 | 35.08 |
| | | 25 | 10 | 9 | 90 | 36.04 |
| | | 13 | 10 | 9 | 90 | 37.36 |
| | | 6 | 10 | 3 | 30 | 39.23 |
| | Trichosporon asahii | CFU/extraction | Replicates Tested | No. Detected | % Detected | Mean Ct Value |
| | | 520 | 10 | 10 | 100 | 29.33 |
| | | 260 | 10 | 10 | 100 | 30.7 |
| | | 130 | 10 | 10 | 100 | 31.73 |
| | | 65 | 10 | 10 | 100 | 32.85 |
| | | 33 | 10 | 10 | 100 | 33.82 |
| | | 16 | 10 | 9 | 90 | 36.36 |
| | | 8 | 10 | 3 | 30 | 38.72 |

FIG. 76 (Cont. 2)

| | | CFU/extraction | Replicates Tested | No. Detected | % Detected | Mean Ct Value |
|---|---|---|---|---|---|---|
| | *C. guilliermondii* | 3936 | 10 | 10 | 100 | 31.66 |
| | | 1968 | 10 | 10 | 100 | 33.04 |
| | | 984 | 10 | 10 | 100 | 33.76 |
| | | 492 | 10 | 10 | 100 | 34.56 |
| | | 246 | 10 | 9 | 90 | 36.23 |
| | | 123 | 10 | 5 | 50 | 38.31 |
| | | 62 | 10 | 4 | 40 | 38.68 |
| | *Cryptococcus neoformans* | CFU/extraction | Replicates Tested | No. Detected | % Detected | Mean Ct Value |
| | | 1856 | 10 | 10 | 100 | 32.93 |
| | | 928 | 10 | 10 | 100 | 34.09 |
| | | 464 | 10 | 10 | 100 | 35.62 |
| | | 232 | 10 | 10 | 100 | 36.38 |
| | | 116 | 10 | 9 | 90 | 37.09 |
| | | 58 | 10 | 6 | 60 | 38.5 |
| | | 29 | 10 | 7 | 70 | 38.66 |
| | *Malassezia furfur* | CFU/extraction | Replicates Tested | No. Detected | % Detected | Mean Ct Value |
| | | 840 | 10 | 10 | 100 | 32.42 |
| | | 420 | 10 | 10 | 100 | 33.91 |
| | | 210 | 10 | 10 | 100 | 35.36 |
| | | 105 | 10 | 8 | 80 | 37.25 |
| | | 53 | 10 | 8 | 80 | 37.44 |

FIG. 76 (Cont. 3)

SEQUENCE LISTING

```
<160> NUMBER OF SEQ ID NOS: 246

<210> SEQ ID NO 1
<211> LENGTH: 18
<212> TYPE: DNA
<213> ORGANISM: Artificial sequence
<220> FEATURE:
<223> OTHER INFORMATION: synthetic sequence

<400> SEQUENCE: 1
ggaggttgga aacgaccg                                                    18

<210> SEQ ID NO 2
<211> LENGTH: 20
<212> TYPE: DNA
<213> ORGANISM: Artificial sequence
<220> FEATURE:
<223> OTHER INFORMATION: synthetic sequence

<400> SEQUENCE: 2
caggttcacc tacggaaacc                                                  20

<210> SEQ ID NO 3
<211> LENGTH: 23
<212> TYPE: DNA
<213> ORGANISM: Artificial sequence
<220> FEATURE:
<223> OTHER INFORMATION: synthetic sequence

<400> SEQUENCE: 3
cccagggccg gaaagttggt caa                                              23

<210> SEQ ID NO 4
<211> LENGTH: 27
<212> TYPE: DNA
<213> ORGANISM: Artificial sequence
<220> FEATURE:
<223> OTHER INFORMATION: synthetic sequence

<400> SEQUENCE: 4
gtccgagttg taatttgaag aaggtat                                          27

<210> SEQ ID NO 5
<211> LENGTH: 28
<212> TYPE: DNA
<213> ORGANISM: Artificial sequence
<220> FEATURE:
<223> OTHER INFORMATION: synthetic sequence

<400> SEQUENCE: 5
ccgagttgta atttgaagat tgtaacct                                         28
```

```
<210> SEQ ID NO 6
<211> LENGTH: 23
<212> TYPE: DNA
<213> ORGANISM: Artificial sequence
<220> FEATURE:
<223> OTHER INFORMATION: synthetic sequence

<400> SEQUENCE: 6
gtaatctcga gacgtgtttt ccg                                           23

<210> SEQ ID NO 7
<211> LENGTH: 22
<212> TYPE: DNA
<213> ORGANISM: Artificial sequence
<220> FEATURE:
<223> OTHER INFORMATION: synthetic sequence

<400> SEQUENCE: 7
caggttggag tctgtgtgga ag                                            22

<210> SEQ ID NO 8
<211> LENGTH: 22
<212> TYPE: DNA
<213> ORGANISM: Artificial sequence
<220> FEATURE:
<223> OTHER INFORMATION: synthetic sequence

<400> SEQUENCE: 8
tgaaggtttc gtggtctgag tc                                            22

<210> SEQ ID NO 9
<211> LENGTH: 23
<212> TYPE: DNA
<213> ORGANISM: Artificial sequence
<220> FEATURE:
<223> OTHER INFORMATION: synthetic sequence

<400> SEQUENCE: 9
tgcattccca acaactcga ctc                                            23

<210> SEQ ID NO 10
<211> LENGTH: 23
<212> TYPE: DNA
<213> ORGANISM: Artificial sequence
<220> FEATURE:
<223> OTHER INFORMATION: synthetic sequence

<400> SEQUENCE: 10
tgagaatccc gtgcgatgag atg                                           23

<210> SEQ ID NO 11
<211> LENGTH: 25
<212> TYPE: DNA
<213> ORGANISM: Artificial sequence
<220> FEATURE:
<223> OTHER INFORMATION: synthetic sequence

<400> SEQUENCE: 11
agggtgagaa tcccgtactt gccat                                         25

<210> SEQ ID NO 12
<211> LENGTH: 19
<212> TYPE: DNA
<213> ORGANISM: Artificial sequence
<220> FEATURE:
<223> OTHER INFORMATION: synthetic sequence
```

```
<400> SEQUENCE: 12
cttccgccgg catcccacg                                               19

<210> SEQ ID NO 13
<211> LENGTH: 20
<212> TYPE: DNA
<213> ORGANISM: Artificial sequence
<220> FEATURE:
<223> OTHER INFORMATION: synthetic sequence

<400> SEQUENCE: 13
acgccgactc tttgcaccgc                                              20

<210> SEQ ID NO 14
<211> LENGTH: 24
<212> TYPE: DNA
<213> ORGANISM: Artificial sequence
<220> FEATURE:
<223> OTHER INFORMATION: synthetic sequence

<400> SEQUENCE: 14
gggcattrgt attccgttgc taga                                         24

<210> SEQ ID NO 15
<211> LENGTH: 30
<212> TYPE: DNA
<213> ORGANISM: Artificial sequence
<220> FEATURE:
<223> OTHER INFORMATION: synthetic sequence

<400> SEQUENCE: 15
ttaagactac aacggtatct aatcgttttt                                   30

<210> SEQ ID NO 16
<211> LENGTH: 31
<212> TYPE: DNA
<213> ORGANISM: Artificial sequence
<220> FEATURE:
<223> OTHER INFORMATION: synthetic sequence

<400> SEQUENCE: 16
aaggacgttt tcattgatca agaacgaagg t                                 31

<210> SEQ ID NO 17
<211> LENGTH: 20
<212> TYPE: DNA
<213> ORGANISM: Artificial sequence
<220> FEATURE:
<223> OTHER INFORMATION: synthetic sequence

<400> SEQUENCE: 17
catccatgct gaccacgaag                                              20

<210> SEQ ID NO 18
<211> LENGTH: 20
<212> TYPE: DNA
<213> ORGANISM: Artificial sequence
<220> FEATURE:
<223> OTHER INFORMATION: synthetic sequence

<400> SEQUENCE: 18
tccatttaag gaggcagcca                                              20
```

```
<210> SEQ ID NO 19
<211> LENGTH: 23
<212> TYPE: DNA
<213> ORGANISM: Artificial sequence
<220> FEATURE:
<223> OTHER INFORMATION: synthetic sequence

<400> SEQUENCE: 19
tctgctcaca ccggtcattt ggt                                             23

<210> SEQ ID NO 20
<211> LENGTH: 19
<212> TYPE: DNA
<213> ORGANISM: Artificial sequence
<220> FEATURE:
<223> OTHER INFORMATION: synthetic sequence

<400> SEQUENCE: 20
ccagcagtcg cggtaatac                                                  19

<210> SEQ ID NO 21
<211> LENGTH: 19
<212> TYPE: DNA
<213> ORGANISM: Artificial sequence
<220> FEATURE:
<223> OTHER INFORMATION: synthetic sequence

<400> SEQUENCE: 21
ccttcgccgt tatcagtcc                                                  19

<210> SEQ ID NO 22
<211> LENGTH: 21
<212> TYPE: DNA
<213> ORGANISM: Artificial sequence
<220> FEATURE:
<223> OTHER INFORMATION: synthetic sequence

<400> SEQUENCE: 22
cagaatttca tctctccacc t                                               21

<210> SEQ ID NO 23
<211> LENGTH: 23
<212> TYPE: DNA
<213> ORGANISM: Artificial sequence
<220> FEATURE:
<223> OTHER INFORMATION: synthetic sequence

<400> SEQUENCE: 23
gatgactaac actagtcttc tac                                             23

<210> SEQ ID NO 24
<211> LENGTH: 22
<212> TYPE: DNA
<213> ORGANISM: Artificial sequence
<220> FEATURE:
<223> OTHER INFORMATION: synthetic sequence

<400> SEQUENCE: 24
gaaaggctga accagtaact tg                                              22

<210> SEQ ID NO 25
<211> LENGTH: 16
<212> TYPE: DNA
<213> ORGANISM: Artificial sequence
<220> FEATURE:
<223> OTHER INFORMATION: synthetic sequence
```

<400> SEQUENCE: 25
ggaagtgggt gcggcc                                                        16

<210> SEQ ID NO 26
<211> LENGTH: 17
<212> TYPE: DNA
<213> ORGANISM: Artificial sequence
<220> FEATURE:
<223> OTHER INFORMATION: synthetic sequence

<400> SEQUENCE: 26
cggctctcgt cgcagtg                                                       17

<210> SEQ ID NO 27
<211> LENGTH: 24
<212> TYPE: DNA
<213> ORGANISM: Artificial sequence
<220> FEATURE:
<223> OTHER INFORMATION: synthetic sequence

<400> SEQUENCE: 27
cggccgcgct taagatatag tcgg                                               24

<210> SEQ ID NO 28
<211> LENGTH: 33
<212> TYPE: DNA
<213> ORGANISM: Artificial sequence
<220> FEATURE:
<223> OTHER INFORMATION: synthetic sequence

<400> SEQUENCE: 28
cataagaatt aggtttaaag ggtacttaga cgg                                     33

<210> SEQ ID NO 29
<211> LENGTH: 36
<212> TYPE: DNA
<213> ORGANISM: Artificial sequence
<220> FEATURE:
<223> OTHER INFORMATION: synthetic sequence

<400> SEQUENCE: 29
caagtgttat tcatcttaag taggtttaaa gggtac                                  36

<210> SEQ ID NO 30
<211> LENGTH: 24
<212> TYPE: DNA
<213> ORGANISM: Artificial sequence
<220> FEATURE:
<223> OTHER INFORMATION: synthetic sequence

<400> SEQUENCE: 30
cgactgctgg cacgtaattt ggtc                                               24

<210> SEQ ID NO 31
<211> LENGTH: 32
<212> TYPE: DNA
<213> ORGANISM: Artificial sequence
<220> FEATURE:
<223> OTHER INFORMATION: synthetic sequence

<400> SEQUENCE: 31
ccgacatatt cctctcacat atcaaactca ag                                      32

```
<210> SEQ ID NO 32
<211> LENGTH: 18
<212> TYPE: DNA
<213> ORGANISM: Artificial sequence
<220> FEATURE:
<223> OTHER INFORMATION: synthetic sequence

<400> SEQUENCE: 32
ggcgtgggtg tggaagtc                                                 18

<210> SEQ ID NO 33
<211> LENGTH: 22
<212> TYPE: DNA
<213> ORGANISM: Artificial sequence
<220> FEATURE:
<223> OTHER INFORMATION: synthetic sequence

<400> SEQUENCE: 33
tggtggcgat cttgaatttc tt                                            22

<210> SEQ ID NO 34
<211> LENGTH: 27
<212> TYPE: DNA
<213> ORGANISM: Artificial sequence
<220> FEATURE:
<223> OTHER INFORMATION: synthetic sequence

<400> SEQUENCE: 34
ccttgcagtg gaacgacagc ttcaacg                                       27

<210> SEQ ID NO 35
<211> LENGTH: 22
<212> TYPE: DNA
<213> ORGANISM: Artificial sequence
<220> FEATURE:
<223> OTHER INFORMATION: synthetic sequence

<400> SEQUENCE: 35
cgcccattct tgtctactga cc                                            22

<210> SEQ ID NO 36
<211> LENGTH: 18
<212> TYPE: DNA
<213> ORGANISM: Artificial sequence
<220> FEATURE:
<223> OTHER INFORMATION: synthetic sequence

<400> SEQUENCE: 36
gggcgtggcc taggaaac                                                 18

<210> SEQ ID NO 37
<211> LENGTH: 24
<212> TYPE: DNA
<213> ORGANISM: Artificial sequence
<220> FEATURE:
<223> OTHER INFORMATION: synthetic sequence

<400> SEQUENCE: 37
acgcccattc ttgtctatttt accc                                         24

<210> SEQ ID NO 38
<211> LENGTH: 29
<212> TYPE: DNA
<213> ORGANISM: Artificial sequence
<220> FEATURE:
<223> OTHER INFORMATION: synthetic sequence
```

```
<400> SEQUENCE: 38
ggaacagtat tcatggattt taatcactc                                29

<210> SEQ ID NO 39
<211> LENGTH: 19
<212> TYPE: DNA
<213> ORGANISM: Artificial sequence
<220> FEATURE:
<223> OTHER INFORMATION: synthetic sequence

<400> SEQUENCE: 39
ccccgaacgg ccgctgtag                                           19

<210> SEQ ID NO 40
<211> LENGTH: 24
<212> TYPE: DNA
<213> ORGANISM: Artificial sequence
<220> FEATURE:
<223> OTHER INFORMATION: synthetic sequence

<400> SEQUENCE: 40
cgcgatccag ggagttgatt gtcc                                     24

<210> SEQ ID NO 41
<211> LENGTH: 18
<212> TYPE: DNA
<213> ORGANISM: Artificial sequence
<220> FEATURE:
<223> OTHER INFORMATION: synthetic sequence

<400> SEQUENCE: 41
cctaggctgc agtgtcgc                                            18

<210> SEQ ID NO 42
<211> LENGTH: 20
<212> TYPE: DNA
<213> ORGANISM: Artificial sequence
<220> FEATURE:
<223> OTHER INFORMATION: synthetic sequence

<400> SEQUENCE: 42
aacgctcaga ctgaaccacc                                          20

<210> SEQ ID NO 43
<211> LENGTH: 18
<212> TYPE: DNA
<213> ORGANISM: Artificial sequence
<220> FEATURE:
<223> OTHER INFORMATION: synthetic sequence

<400> SEQUENCE: 43
cccacccctg gacagcgc                                            18

<210> SEQ ID NO 44
<211> LENGTH: 16
<212> TYPE: DNA
<213> ORGANISM: Artificial sequence
<220> FEATURE:
<223> OTHER INFORMATION: synthetic sequence

<400> SEQUENCE: 44
gccgcgctct cccagg                                              16

<210> SEQ ID NO 45
<211> LENGTH: 21
```

```
<212> TYPE: DNA
<213> ORGANISM: Artificial sequence
<220> FEATURE:
<223> OTHER INFORMATION: synthetic sequence

<400> SEQUENCE: 45
gctcagactg acagctcttc t                                          21

<210> SEQ ID NO 46
<211> LENGTH: 20
<212> TYPE: DNA
<213> ORGANISM: Artificial sequence
<220> FEATURE:
<223> OTHER INFORMATION: synthetic sequence

<400> SEQUENCE: 46
tggctaaacg ctggaccgcg                                            20

<210> SEQ ID NO 47
<211> LENGTH: 17
<212> TYPE: DNA
<213> ORGANISM: Artificial sequence
<220> FEATURE:
<223> OTHER INFORMATION: synthetic sequence

<400> SEQUENCE: 47
gcgggccctt ctgggag                                               17

<210> SEQ ID NO 48
<211> LENGTH: 22
<212> TYPE: DNA
<213> ORGANISM: Artificial sequence
<220> FEATURE:
<223> OTHER INFORMATION: synthetic sequence

<400> SEQUENCE: 48
aactgattgt gcttgctaaa cg                                         22

<210> SEQ ID NO 49
<211> LENGTH: 35
<212> TYPE: DNA
<213> ORGANISM: Artificial sequence
<220> FEATURE:
<223> OTHER INFORMATION: synthetic sequence

<400> SEQUENCE: 49
cggaggacag acaccaagaa aaaattctct gaaga                           35

<210> SEQ ID NO 50
<211> LENGTH: 17
<212> TYPE: DNA
<213> ORGANISM: Artificial sequence
<220> FEATURE:
<223> OTHER INFORMATION: synthetic sequence

<400> SEQUENCE: 50
cggcctactg gtttcgg                                               17

<210> SEQ ID NO 51
<211> LENGTH: 24
<212> TYPE: DNA
<213> ORGANISM: Artificial sequence
<220> FEATURE:
<223> OTHER INFORMATION: synthetic sequence

<400> SEQUENCE: 51
```

```
ccgaggtcaa aagttgaaaa aagg                                          24

<210> SEQ ID NO 52
<211> LENGTH: 22
<212> TYPE: DNA
<213> ORGANISM: Artificial sequence
<220> FEATURE:
<223> OTHER INFORMATION: synthetic sequence

<400> SEQUENCE: 52
cgcagcacaa gtcgcactct ct                                            22

<210> SEQ ID NO 53
<211> LENGTH: 26
<212> TYPE: DNA
<213> ORGANISM: Artificial sequence
<220> FEATURE:
<223> OTHER INFORMATION: synthetic sequence

<400> SEQUENCE: 53
ggagggatca ttaccgagtt tacaac                                        26

<210> SEQ ID NO 54
<211> LENGTH: 23
<212> TYPE: DNA
<213> ORGANISM: Artificial sequence
<220> FEATURE:
<223> OTHER INFORMATION: synthetic sequence

<400> SEQUENCE: 54
ctcatcaacc ctgtgaacgt acc                                           23

<210> SEQ ID NO 55
<211> LENGTH: 36
<212> TYPE: DNA
<213> ORGANISM: Artificial sequence
<220> FEATURE:
<223> OTHER INFORMATION: synthetic sequence

<400> SEQUENCE: 55
tgaaagtttt gatttattta tggttttact cagaag                             36

<210> SEQ ID NO 56
<211> LENGTH: 17
<212> TYPE: DNA
<213> ORGANISM: Artificial sequence
<220> FEATURE:
<223> OTHER INFORMATION: synthetic sequence

<400> SEQUENCE: 56
cccccgccag aggaccc                                                  17

<210> SEQ ID NO 57
<211> LENGTH: 21
<212> TYPE: DNA
<213> ORGANISM: Artificial sequence
<220> FEATURE:
<223> OTHER INFORMATION: synthetic sequence

<400> SEQUENCE: 57
ctgtccgagc gtcatttctt c                                             21

<210> SEQ ID NO 58
<211> LENGTH: 20
<212> TYPE: DNA
<213> ORGANISM: Artificial sequence
```

```
<220> FEATURE:
<223> OTHER INFORMATION: synthetic sequence

<400> SEQUENCE: 58
gacccgatgc gagatgtagg                                                  20

<210> SEQ ID NO 59
<211> LENGTH: 19
<212> TYPE: DNA
<213> ORGANISM: Artificial sequence
<220> FEATURE:
<223> OTHER INFORMATION: synthetic sequence

<400> SEQUENCE: 59
ctcgtccccc ccgcagtcc                                                   19

<210> SEQ ID NO 60
<211> LENGTH: 18
<212> TYPE: DNA
<213> ORGANISM: Artificial sequence
<220> FEATURE:
<223> OTHER INFORMATION: synthetic sequence

<400> SEQUENCE: 60
ccggcctact ggtttcgc                                                    18

<210> SEQ ID NO 61
<211> LENGTH: 22
<212> TYPE: DNA
<213> ORGANISM: Artificial sequence
<220> FEATURE:
<223> OTHER INFORMATION: synthetic sequence

<400> SEQUENCE: 61
gaggtcaacg tgagaaggag tc                                               22

<210> SEQ ID NO 62
<211> LENGTH: 26
<212> TYPE: DNA
<213> ORGANISM: Artificial sequence
<220> FEATURE:
<223> OTHER INFORMATION: synthetic sequence

<400> SEQUENCE: 62
tgcgcttgca atcagcaaaa gaggac                                           26

<210> SEQ ID NO 63
<211> LENGTH: 21
<212> TYPE: DNA
<213> ORGANISM: Artificial sequence
<220> FEATURE:
<223> OTHER INFORMATION: synthetic sequence

<400> SEQUENCE: 63
cgtcatttca accctcagga c                                                21

<210> SEQ ID NO 64
<211> LENGTH: 21
<212> TYPE: DNA
<213> ORGANISM: Artificial sequence
<220> FEATURE:
<223> OTHER INFORMATION: synthetic sequence

<400> SEQUENCE: 64
ctacctgatc cgaggtcaac c                                                21
```

<210> SEQ ID NO 65
<211> LENGTH: 20
<212> TYPE: DNA
<213> ORGANISM: Artificial sequence
<220> FEATURE:
<223> OTHER INFORMATION: synthetic sequence

<400> SEQUENCE: 65 tgggggttt aacggcgtgg                    20

<210> SEQ ID NO 66
<211> LENGTH: 19
<212> TYPE: DNA
<213> ORGANISM: Artificial sequence
<220> FEATURE:
<223> OTHER INFORMATION: synthetic sequence

<400> SEQUENCE: 66
aaccaaccgg gattgcctc                    19

<210> SEQ ID NO 67
<211> LENGTH: 19
<212> TYPE: DNA
<213> ORGANISM: Artificial sequence
<220> FEATURE:
<223> OTHER INFORMATION: synthetic sequence

<400> SEQUENCE: 67
cgttccaggg cacttagac                    19

<210> SEQ ID NO 68
<211> LENGTH: 19
<212> TYPE: DNA
<213> ORGANISM: Artificial sequence
<220> FEATURE:
<223> OTHER INFORMATION: synthetic sequence

<400> SEQUENCE: 68
ctggctcctt cggggtccg                    19

<210> SEQ ID NO 69
<211> LENGTH: 24
<212> TYPE: DNA
<213> ORGANISM: Artificial sequence
<220> FEATURE:
<223> OTHER INFORMATION: synthetic sequence

<400> SEQUENCE: 69
gctgggtttg gtgttgagca atac              24

<210> SEQ ID NO 70
<211> LENGTH: 22
<212> TYPE: DNA
<213> ORGANISM: Artificial sequence
<220> FEATURE:
<223> OTHER INFORMATION: synthetic sequence

<400> SEQUENCE: 70
gcgggtagtc ctacctgatt tg                22

<210> SEQ ID NO 71
<211> LENGTH: 25
<212> TYPE: DNA
<213> ORGANISM: Artificial sequence
<220> FEATURE:
<223> OTHER INFORMATION: synthetic sequence

<400> SEQUENCE: 71
gcttgaaaag tattggcatg ggtag                                     25

<210> SEQ ID NO 72
<211> LENGTH: 27
<212> TYPE: DNA
<213> ORGANISM: Artificial sequence
<220> FEATURE:
<223> OTHER INFORMATION: synthetic sequence

<400> SEQUENCE: 72
tcgctttgac aatggcttag gtctacc                                   27

<210> SEQ ID NO 73
<211> LENGTH: 36
<212> TYPE: DNA
<213> ORGANISM: Artificial sequence
<220> FEATURE:
<223> OTHER INFORMATION: synthetic sequence

<400> SEQUENCE: 73
cctatccatt agtttatact ccgcctttct ttcaag                         36

<210> SEQ ID NO 74
<211> LENGTH: 26
<212> TYPE: DNA
<213> ORGANISM: Artificial sequence
<220> FEATURE:
<223> OTHER INFORMATION: synthetic sequence

<400> SEQUENCE: 74
aaacgcttat tttgctagtg gccacc                                    26

<210> SEQ ID NO 75
<211> LENGTH: 21
<212> TYPE: DNA
<213> ORGANISM: Artificial sequence
<220> FEATURE:
<223> OTHER INFORMATION: synthetic sequence

<400> SEQUENCE: 75
agtgtcatga aatctcaacc a                                         21

<210> SEQ ID NO 76
<211> LENGTH: 20
<212> TYPE: DNA
<213> ORGANISM: Artificial sequence
<220> FEATURE:
<223> OTHER INFORMATION: synthetic sequence

<400> SEQUENCE: 76
ccttgcggac gattagaagc                                           20

<210> SEQ ID NO 77
<211> LENGTH: 20
<212> TYPE: DNA
<213> ORGANISM: Artificial sequence
<220> FEATURE:
<223> OTHER INFORMATION: synthetic sequence

<400> SEQUENCE: 77
taatggattg gatttgggcg                                           20

<210> SEQ ID NO 78

```
<211> LENGTH: 23
<212> TYPE: DNA
<213> ORGANISM: Artificial sequence
<220> FEATURE:
<223> OTHER INFORMATION: synthetic sequence

<400> SEQUENCE: 78
taatggcttg gatttgggcg ctg                                          23

<210> SEQ ID NO 79
<211> LENGTH: 19
<212> TYPE: DNA
<213> ORGANISM: Artificial sequence
<220> FEATURE:
<223> OTHER INFORMATION: synthetic sequence

<400> SEQUENCE: 79
gcgccctttg gtattccga                                               19

<210> SEQ ID NO 80
<211> LENGTH: 24
<212> TYPE: DNA
<213> ORGANISM: Artificial sequence
<220> FEATURE:
<223> OTHER INFORMATION: synthetic sequence

<400> SEQUENCE: 80
tgtttggttg ttgtaaggcc gggc                                         24

<210> SEQ ID NO 81
<211> LENGTH: 27
<212> TYPE: DNA
<213> ORGANISM: Artificial sequence
<220> FEATURE:
<223> OTHER INFORMATION: synthetic sequence

<400> SEQUENCE: 81
ttgttatcag caagccgaag actaccc                                      27

<210> SEQ ID NO 82
<211> LENGTH: 27
<212> TYPE: DNA
<213> ORGANISM: Artificial sequence
<220> FEATURE:
<223> OTHER INFORMATION: synthetic sequence

<400> SEQUENCE: 82
agcagactca taagcaaggg acaagac                                      27

<210> SEQ ID NO 83
<211> LENGTH: 24
<212> TYPE: DNA
<213> ORGANISM: Artificial sequence
<220> FEATURE:
<223> OTHER INFORMATION: synthetic sequence

<400> SEQUENCE: 83
aagcggtctt tagtcctgca acgc                                         24

<210> SEQ ID NO 84
<211> LENGTH: 18
<212> TYPE: DNA
<213> ORGANISM: Artificial sequence
<220> FEATURE:
<223> OTHER INFORMATION: synthetic sequence

<400> SEQUENCE: 84
```

```
ggtcagtttt actggggc                                                   18

<210> SEQ ID NO 85
<211> LENGTH: 22
<212> TYPE: DNA
<213> ORGANISM: Artificial sequence
<220> FEATURE:
<223> OTHER INFORMATION: synthetic sequence

<400> SEQUENCE: 85
gtcctacttg cgtagctgat cg                                              22

<210> SEQ ID NO 86
<211> LENGTH: 26
<212> TYPE: DNA
<213> ORGANISM: Artificial sequence
<220> FEATURE:
<223> OTHER INFORMATION: synthetic sequence

<400> SEQUENCE: 86
ctatatccta cttgcgtaac tgatcg                                          26

<210> SEQ ID NO 87
<211> LENGTH: 27
<212> TYPE: DNA
<213> ORGANISM: Artificial sequence
<220> FEATURE:
<223> OTHER INFORMATION: synthetic sequence

<400> SEQUENCE: 87 tataccttttg aaggcctctg atacttt                                        27

<210> SEQ ID NO 88
<211> LENGTH: 168
<212> TYPE: DNA
<213> ORGANISM: Artificial sequence
<220> FEATURE:
<223> OTHER INFORMATION: synthetic sequence

<400> SEQUENCE: 88
gctgggtttg gtgttgagca atacgacttg ggtttgcttg aaagacggta gtggtaaggc     60
gggatcgctt tgacaatggc ttaggtctac caaaaacatt gcttgcggcg gtaacgtcca    120
ccacgtatat cttcaaactt tgacctcaaa tcaggtagga ctacccgc                 168

<210> SEQ ID NO 89
<211> LENGTH: 142
<212> TYPE: DNA
<213> ORGANISM: Artificial sequence
<220> FEATURE:
<223> OTHER INFORMATION: synthetic sequence

<400> SEQUENCE: 89
ctcgggtttg gtgttgagcg atacgctggg tttgcttgaa agaaaggcgg agtataaact     60
aatggatagg ttttttccac tcattggtac aaactccaaa acttcttcca aattcgacct    120
caaatcaggt aggactaccc gc                                             142

<210> SEQ ID NO 90
<211> LENGTH: 230
<212> TYPE: DNA
<213> ORGANISM: Artificial sequence
<220> FEATURE:
<223> OTHER INFORMATION: synthetic sequence
<220> FEATURE:
```

```
<221> NAME/KEY: misc_feature
<222> LOCATION: (112)..(112)
<223> OTHER INFORMATION: n is a, c, g, or t

<400> SEQUENCE: 90
gcgggccctt ctgggagcct cgagccggac cgcgcccgcc ggaggacaga caccaagaaa      60
aaattctctg aagagctgtc agtctgagcg tttagcaagc acaatcagtt andgccgcgc    120
tctcccagga gagccgttcg gcgagcctct ctttagtggc taaacgctgg accgcgcccg   180
ccggaggaca gacgcaaaaa aattctttca gaagagctgt cagtctgagc               230

<210> SEQ ID NO 91
<211> LENGTH: 163
<212> TYPE: DNA
<213> ORGANISM: Artificial sequence
<220> FEATURE:
<223> OTHER INFORMATION: synthetic sequence

<400> SEQUENCE: 91
cctaggctgc agtgtcgctg cagcgtctcg gggggccgt tcggggatg gagaaggatg       60 ccccggcggg gttgatcgct cccccacccc tggacagcgc tcgccgaagg agtgattctc   120
agaaattcta cgaaatctcc ataggtggtt cagtctgagc gtt                      163

<210> SEQ ID NO 92
<211> LENGTH: 252
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (113)..(113)
<223> OTHER INFORMATION: n is a, c, g, or t

<400> SEQUENCE: 92
cgcccattct tgtctactga cccggttgcc tcggcgggcc gcgcctgctg tgctacagcg     60
gccgttcggg ggggacgcct gaggggggact cttgtttcct aggccacgcc candacgccc  120
attcttgtct atttacccag ttgcctcggc gggccgcgca ctcgtgccgc gcctcgagga   180
gccgtccggg gacaatcaac tccctggatc gcgcccgccg gaggagtgat taaaatccat   240
gaatactgtt cc                                                        252

<210> SEQ ID NO 93
<211> LENGTH: 199
<212> TYPE: DNA
<213> ORGANISM: Artificial sequence
<220> FEATURE:
<223> OTHER INFORMATION: synthetic sequence

<400> SEQUENCE: 93
cgtcatttca accctcagga cccgttcgcg ggacctggcg ttggggatca gcctgcccct     60
ggcggcggct ggccctgaaa tacagtggcg gttccctcgc gaactcctcc gtgcagtaat   120
taaacctctc gcggcaggat agcggttgaa ccacgccgtt aaaccccca cttctcaagg    180 ttgacctcag atcaggtag                                                 199

<210> SEQ ID NO 94
<211> LENGTH: 199
<212> TYPE: DNA
<213> ORGANISM: Artificial sequence
<220> FEATURE:
<223> OTHER INFORMATION: synthetic sequence
```

```
<400> SEQUENCE: 94
cgtcatttca accctcagga cccgttcgcg ggacctggcg ttggggatca gcctgcccct      60
ggcggcggct ggccctgaaa tacagtggcg gttccctcgc gaactcctcc gtgcagtaat     120
taaacctctc gcggcaggat agcggttgaa ccacgccgtt aaaccccca cttctcaagg      180 ttgacctcag atcaggtag                                                   199

<210> SEQ ID NO 95
<211> LENGTH: 92
<212> TYPE: DNA
<213> ORGANISM: Artificial sequence
<220> FEATURE:
<223> OTHER INFORMATION: synthetic sequence

<400> SEQUENCE: 95
cggcctactg gtttcggagc gcagcacaag tcgcactctc tatcagcaaa ggtctagcat      60
ccattaagcc ttttttcaac ttttgacctc gg                                    92

<210> SEQ ID NO 96
<211> LENGTH: 92
<212> TYPE: DNA
<213> ORGANISM: Artificial sequence
<220> FEATURE:
<223> OTHER INFORMATION: synthetic sequence

<400> SEQUENCE: 96
cggcctactg gtttcggagc gcagcacaag tcgcactctc tatcagcaaa ggtctagcat      60
ccattaagcc ttttttcaac ttttgacctc gg                                    92

<210> SEQ ID NO 97
<211> LENGTH: 94
<212> TYPE: DNA
<213> ORGANISM: Artificial sequence
<220> FEATURE:
<223> OTHER INFORMATION: synthetic sequence

<400> SEQUENCE: 97
ccggcctact ggtttcgcag cgcagcacat ttttgcgctt gcaatcagca aaagaggacg      60
gcaatccatc aagactcctt ctcacgttga cctc                                  94

<210> SEQ ID NO 98
<211> LENGTH: 94
<212> TYPE: DNA
<213> ORGANISM: Artificial sequence
<220> FEATURE:
<223> OTHER INFORMATION: synthetic sequence

<400> SEQUENCE: 98
ccggcctact ggtttcgcag cgcagcacat ttttgcgctt gcaatcagca aaagaggacg      60
gcaatccatc aagactcctt ctcacgttga cctc                                  94

<210> SEQ ID NO 99
<211> LENGTH: 87
<212> TYPE: DNA
<213> ORGANISM: Artificial sequence
<220> FEATURE:
<223> OTHER INFORMATION: synthetic sequence

<400> SEQUENCE: 99
ggaagtgggt gcggcctccc ggccgcgctt aagatatagt cgggccccca gcgaaagctg      60
```

```
gggggtaagt cactgcgacg agagccg                                              87
```

<210> SEQ ID NO 100
<211> LENGTH: 87
<212> TYPE: DNA
<213> ORGANISM: Artificial sequence
<220> FEATURE:
<223> OTHER INFORMATION: synthetic sequence

<400> SEQUENCE: 100

```
ggaagtgggt gcggcctccc ggccgcgctt aagatatagt cgggccccca gcgaaagctg          60
gggggtaagt cactgcgacg agagccg                                              87
```

<210> SEQ ID NO 101
<211> LENGTH: 135
<212> TYPE: DNA
<213> ORGANISM: Artificial sequence
<220> FEATURE:
<223> OTHER INFORMATION: synthetic sequence

<400> SEQUENCE: 101

```
aaccaaccgg gattgcctca gtaacggcga gtgaagcggc aagagctcaa atttgaaagc          60
tggctccttc ggggtccgca ttgtaatttg cagaggatgc ttcgggtgcg gcccctgtct         120
aagtgccctg gaacg                                                          135
```

<210> SEQ ID NO 102
<211> LENGTH: 135
<212> TYPE: DNA
<213> ORGANISM: Artificial sequence
<220> FEATURE:
<223> OTHER INFORMATION: synthetic sequence

<400> SEQUENCE: 102

```
aaccaaccgg gattgcctca gtaacggcga gtgaagcggc aagagctcaa atttgaaagc          60
tggctccttc ggggtccgca ttgtaatttg cagaggatgc ttcgggtgcg gcccctgtct         120
aagtgccctg gaacg                                                          135
```

<210> SEQ ID NO 103
<211> LENGTH: 169
<212> TYPE: DNA
<213> ORGANISM: Artificial sequence
<220> FEATURE:
<223> OTHER INFORMATION: synthetic sequence

<400> SEQUENCE: 103

```
ggagggatca ttaccgagtt tacaactccc aaaccctgt gaacatacca cttgttgcct           60
cggcggatca gcccgctccc ggtaaaacgg gacggcccgc cagaggaccc ctaaactctg         120
tttctatatg taacttctga gtaaaaccat aaataaatca aactttca                     169
```

<210> SEQ ID NO 104
<211> LENGTH: 146
<212> TYPE: DNA
<213> ORGANISM: Artificial sequence
<220> FEATURE:
<223> OTHER INFORMATION: synthetic sequence

<400> SEQUENCE: 104

```
ctcatcaacc ctgtgaacat acctaaaacg ttgcttcggc gggaacagac ggccccgtaa          60
caacgggccg cccccgccag aggacccta actctgtttc tataatgttt cttctgagta         120
aacaagcaaa taaattaaaa ctttca                                              146
```

<210> SEQ ID NO 105
<211> LENGTH: 169
<212> TYPE: DNA
<213> ORGANISM: Artificial sequence
<220> FEATURE:
<223> OTHER INFORMATION: synthetic sequence

<400> SEQUENCE: 105

```
ggagggatca ttaccgagtt tacaactccc aaacccctgt gaacatacca cttgttgcct      60
cggcggatca gcccgctccc ggtaaaacgg gacggcccgc cagaggaccc ctaaactctg     120
tttctatatg taacttctga gtaaaaccat aaataaatca aaactttca                 169
```

<210> SEQ ID NO 106
<211> LENGTH: 146
<212> TYPE: DNA
<213> ORGANISM: Artificial sequence
<220> FEATURE:
<223> OTHER INFORMATION: synthetic sequence

<400> SEQUENCE: 106

```
ctcatcaacc ctgtgaacat acctaaaacg ttgcttcggc gggaacagac ggccccgtaa      60
caacgggccg cccccgccag aggacccta actctgtttc tataatgttt cttctgagta     120
aacaagcaaa taaattaaaa ctttca                                          146
```

<210> SEQ ID NO 107
<211> LENGTH: 170
<212> TYPE: DNA
<213> ORGANISM: Artificial sequence
<220> FEATURE:
<223> OTHER INFORMATION: synthetic sequence

<400> SEQUENCE: 107

```
ctgtccgagc gtcatttctt ccctcgagcg cggctagccc tacggggcct gccgtcgccc      60
ggtgttgggg ctctacgggt ggggctcgtc ccccccgcag tccccgaaat gtagtggcgg     120
tccagccgcg gcgcccctg cgtagtagat cctacatctc gcatcgggtc                170
```

<210> SEQ ID NO 108
<211> LENGTH: 170
<212> TYPE: DNA
<213> ORGANISM: Artificial sequence
<220> FEATURE:
<223> OTHER INFORMATION: synthetic sequence

<400> SEQUENCE: 108

```
ctgtccgagc gtcatttctt ccctcgagcg cggctagccc tacggggcct gccgtcgccc      60
ggtgttgggg ctctacgggt ggggctcgtc ccccccgcag tccccgaaat gtagtggcgg     120
tccagccgcg gcgcccctg cgtagtagat cctacatctc gcatcgggtc                170
```

<210> SEQ ID NO 109
<211> LENGTH: 79
<212> TYPE: DNA
<213> ORGANISM: Artificial sequence
<220> FEATURE:
<223> OTHER INFORMATION: synthetic sequence

<400> SEQUENCE: 109

```
acccttaaa cctaataaag atgattaaca ctagtcttct acgtattacc gcgactgctg       60
gcacgtaatt tggtcaaga                                                   79
```

<210> SEQ ID NO 110
<211> LENGTH: 79
<212> TYPE: DNA
<213> ORGANISM: Aspergillus versicolor

<400> SEQUENCE: 110 acccttttaaa cctaataaag atgattaaca ctagtcttct acgtattacc gcgactgctg    60
gcacgtagtt tggtcaaga    79

<210> SEQ ID NO 111
<211> LENGTH: 79
<212> TYPE: DNA
<213> ORGANISM: Aspergillus flavus

<400> SEQUENCE: 111 acccttttaaa cctaataaag atgactaaca ctagtcttct acgtattacc gcgactgctg    60
gcacgtaatt tggtcaaga    79

<210> SEQ ID NO 112
<211> LENGTH: 79
<212> TYPE: DNA
<213> ORGANISM: Aspergillus ochraceus

<400> SEQUENCE: 112 acccttttaaa cctaataaag atgattaaca ctagtcttct acgtattacc gcgactgctg    60
gcacgtaatt tggtcaaga    79

<210> SEQ ID NO 113
<211> LENGTH: 78
<212> TYPE: DNA
<213> ORGANISM: Artificial sequence
<220> FEATURE:
<223> OTHER INFORMATION: synthetic sequence

<400> SEQUENCE: 113
gaattttata cgagttaatc gttattgtat tattataata cactttcatt cttccaagtt    60
actggttcag cctttcgg    78

<210> SEQ ID NO 114
<211> LENGTH: 78
<212> TYPE: DNA
<213> ORGANISM: Aspergillus versicolor

<400> SEQUENCE: 114
gaattttata cgacttaatc gttattgtat tattataata cactttcatt cttccaagtt    60
actggttcag cctttcgg    78

<210> SEQ ID NO 115
<211> LENGTH: 78
<212> TYPE: DNA
<213> ORGANISM: Aspergillus flavus

<400> SEQUENCE: 115
gaattttata cgagttaatc gttattgtat tacaataata cacttacatt cttccaagtt    60
actggttcag cctttcgg    78

<210> SEQ ID NO 116
<211> LENGTH: 78
<212> TYPE: DNA
<213> ORGANISM: Aspergillus ochraceus

<400> SEQUENCE: 116
gaactttata cgagttaatc gttattgtat tattacaata cattttcatt cttccaagtt    60
actggttcag cctttcgg    78

<210> SEQ ID NO 117
<211> LENGTH: 73
<212> TYPE: DNA
<213> ORGANISM: Artificial sequence
<220> FEATURE:
<223> OTHER INFORMATION: synthetic sequence

<400> SEQUENCE: 117
tgccagcagt cgcggtaata cgtaagagac kagtgttatt catcttaawt aggtttaaag    60
ggtacctaga cgg    73

<210> SEQ ID NO 118
<211> LENGTH: 73
<212> TYPE: DNA
<213> ORGANISM: Alternaria alternata

<400> SEQUENCE: 118
tgccagcagt cgcggtaaga caagggagac gagtgttatt catctttaac aggtatatag    60
ggtacctaga cgg    73

<210> SEQ ID NO 119
<211> LENGTH: 73
<212> TYPE: DNA
<213> ORGANISM: Artificial sequence
<220> FEATURE:
<223> OTHER INFORMATION: synthetic sequence

<400> SEQUENCE: 119
tgccagcagt cgcggtaaga caagggagac gagtgttatt catctttaac aggtatatag    60
ggtacctaga cgg    73

<210> SEQ ID NO 120
<211> LENGTH: 73
<212> TYPE: DNA
<213> ORGANISM: Artificial sequence
<220> FEATURE:
<223> OTHER INFORMATION: synthetic sequence

<400> SEQUENCE: 120
tgccagcagt cgcggtaata cgtaagagac aagtgttatt catcttaagt aggtttaaag    60
ggtacctaga cgg    73

<210> SEQ ID NO 121
<211> LENGTH: 73
<212> TYPE: DNA
<213> ORGANISM: Fuarium solani

<400> SEQUENCE: 121
tgccagcagt cgcggtaata cgtaagagac tagtgttatt catcttaatt aggtttaaag    60
ggtacccaga cgg    73

<210> SEQ ID NO 122
<211> LENGTH: 73
<212> TYPE: DNA
<213> ORGANISM: Artificial sequence
<220> FEATURE:

<223> OTHER INFORMATION: synthetic sequence

<400> SEQUENCE: 122
tgccagcagt cgcggtaata cgtaagagac tagtgttatt cataagaatt aggtttaaag    60
ggtacttaga cgg    73

<210> SEQ ID NO 123
<211> LENGTH: 76
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (15)..(17)
<223> OTHER INFORMATION: n is a, c, g, or t

<400> SEQUENCE: 123
atgtaagagg aayannncgg aattgtwgga ggagagatga aattcgttga taccaaaggg    60
actggtaamg gcgaag    76

<210> SEQ ID NO 124
<211> LENGTH: 76
<212> TYPE: DNA
<213> ORGANISM: Alternaria alternata

<400> SEQUENCE: 124
atgtgagagg aatatgtcgg aattgttgga ggaaagatga aatttgttaa taccaatagg    60
actgataacg gcgaag    76

<210> SEQ ID NO 125
<211> LENGTH: 76
<212> TYPE: DNA
<213> ORGANISM: Artificial sequence
<220> FEATURE:
<223> OTHER INFORMATION: synthetic sequence

<400> SEQUENCE: 125
atgtgagagg aatatgtcgg aattgttgga ggaaagatga aatttgttaa taccaatagg    60
actgataacg gcgaag    76

<210> SEQ ID NO 126
<211> LENGTH: 72
<212> TYPE: DNA
<213> ORGANISM: Artificial sequence
<220> FEATURE:
<223> OTHER INFORMATION: synthetic sequence

<400> SEQUENCE: 126
atgtaagaag tacagtactt ttaggtggag agatgaaatt ctgtgatact ctagggactg    60
gtaaaggcga ag    72

<210> SEQ ID NO 127
<211> LENGTH: 71
<212> TYPE: DNA
<213> ORGANISM: Fuarium solani

<400> SEQUENCE: 127
atgtaagagg gcagtacttg aggaggagag atgaaattcc gtgatactaa agggactctg    60
taaaggcgaa g    71

-continued

```
<210> SEQ ID NO 128
<211> LENGTH: 76
<212> TYPE: DNA
<213> ORGANISM: Artificial sequence
<220> FEATURE:
<223> OTHER INFORMATION: synthetic sequence

<400> SEQUENCE: 128
agttagatac aagagaacag aacttgcgga ggagagatca tattcattga taccaaaggg      60
actggtaatg gcgaag                                                     76

<210> SEQ ID NO 129
<211> LENGTH: 93
<212> TYPE: DNA
<213> ORGANISM: Artificial sequence
<220> FEATURE:
<223> OTHER INFORMATION: synthetic sequence

<400> SEQUENCE: 129
agtggaagtg ggtgcggcct cccggccgcg cttaagatat agtcgggccc ccagcgaaag      60 ctgggggta agtcactgcg acgagagccg ttc                                   93

<210> SEQ ID NO 130
<211> LENGTH: 93
<212> TYPE: DNA
<213> ORGANISM: Scytidium dimidiatum

<400> SEQUENCE: 130
agtggaagtg ggtgcggcct cccggccgcg cttaagatat agtcgggccc ccagcgaaag      60 ctgggggta agtcactgcg acgagagccg ttc                                   93

<210> SEQ ID NO 131
<211> LENGTH: 114
<212> TYPE: DNA
<213> ORGANISM: Artificial sequence
<220> FEATURE:
<223> OTHER INFORMATION: synthetic sequence

<400> SEQUENCE: 131
cactggccca gggaggttgg aaacgaccgc ccagggccgg aaagttggtc aaactcggtc      60
atttagagga agtaaaagtc gtaacaaggt ttccgtaggt gaacctgcgg aagg           114

<210> SEQ ID NO 132
<211> LENGTH: 158
<212> TYPE: DNA
<213> ORGANISM: Candida parapsilosis
<220> FEATURE:
<221> NAME/KEY: misc_feature
<222> LOCATION: (42)..(42)
<223> OTHER INFORMATION: n is a, c, g, or t

<400> SEQUENCE: 132
gtgtccgagt tgtaatttga agaaggtatc tttgggtctg gntcttgtct aygttdcttg      60
gaacagaacg tcacagaggg tgagaatccc gtgcgatgag atgtcccaga cctatgtaaa     120
gttccttcga agagtcgagt tgtttgggaa tgcagctc                             158

<210> SEQ ID NO 133
<211> LENGTH: 154
<212> TYPE: DNA
<213> ORGANISM: Candida albicans

<400> SEQUENCE: 133
```

```
gcgtccgagt tgtaatttga agaaggtatc tttgggcccg gctcttgtct atgttccttg      60
gaacaggacg tcacagaggg tgagaatccc gtgcgatgag atgacccggg tctgtgtaaa     120
gttccttcga cgagtcgagt tgtttgggaa tgca                                 154

<210> SEQ ID NO 134
<211> LENGTH: 158
<212> TYPE: DNA
<213> ORGANISM: Candida tropicalis

<400> SEQUENCE: 134
gagtccgagt tgtaatttga agaaggtatc tttgggtctg gctcttgtct atgtttcttg      60
gaacagaacg tcacagaggg tgagaatccc gtgcgatgag atgatccagg cctatgtaaa    120
gttccttcga agagtcgagt tgtttgggaa tgcagctc                             158

<210> SEQ ID NO 135
<211> LENGTH: 114
<212> TYPE: DNA
<213> ORGANISM: Candida orthopsilosis

<400> SEQUENCE: 135
gtgtccgagt tgtaatttga agaaggtatc tttgggtctg gctcttgtct atgtttcttg      60
gaacagaacg tcacagaggg tgagaatccc gtgcgatgag atgtccccga ccta          114

<210> SEQ ID NO 136
<211> LENGTH: 158
<212> TYPE: DNA
<213> ORGANISM: Candida metapsilosis

<400> SEQUENCE: 136
gtgtccgagt tgtaatttga agaaggtatc tttgggtctg gctcttgtct atgtttcttg      60
gaacagaacg tcacagaggg tgagaatccc gtgcgatgag atgacccaga cctatgtaaa    120
gttccttcga agagtcgagt tgtttgggaa tgcagctc                             158

<210> SEQ ID NO 137
<211> LENGTH: 157
<212> TYPE: DNA
<213> ORGANISM: Candida fermentati

<400> SEQUENCE: 137
gtgtccgagt tgtaatttga agattgtaac cttggggttg gctcttgtct atgtttcttg      60
gaacaggacg tcacagaggg tgagaatccc gtgcgatgag atgcccaatc ctatgtaagg    120
tgctttcgaa gagtcgagtt gtttgggaat gcagctc                              157

<210> SEQ ID NO 138
<211> LENGTH: 157
<212> TYPE: DNA
<213> ORGANISM: Candida carpophila

<400> SEQUENCE: 138
gtgtccgagt tgtaatttga agattgtaac cttggggttg gctcttgtct atgtttcttg      60
gaacaggacg tcacagaggg tgagaatccc gtgcgatgag atgcccaatc ctatgtaagg    120
tgctttcgaa gagtcgagtt gtttgggaat gcagctc                              157

<210> SEQ ID NO 139
<211> LENGTH: 157
<212> TYPE: DNA
<213> ORGANISM: Candida guilliermondii
```

```
<400> SEQUENCE: 139
gtgtccgagt tgtaatttga agattgtaac cttggggttg gctcttgtct atgtttcttg      60
gaacaggacg tcacagaggg tgagaatccc gtgcgatgag atgcccaatt ctatgtaagg     120
tgctttcgaa gagtcgagtt gtttgggaat gcagctc                              157

<210> SEQ ID NO 140
<211> LENGTH: 153
<212> TYPE: DNA
<213> ORGANISM: Candida krusei

<400> SEQUENCE: 140
cggcacgagt tgtagattgc aggttggagt ctgtgtggaa ggcggtgtcc aagtcccttg      60
gaacagggcg cccaggaggg tgagagcccc gtgggatgcc ggcggaagca gtgaggccct     120
tctgacgagt cgagttgttt gggaatgcag ctc                                  153

<210> SEQ ID NO 141
<211> LENGTH: 151
<212> TYPE: DNA
<213> ORGANISM: CIavispora lusitaniae
<220> FEATURE:
<221> NAME/KEY: misc_feature
<222> LOCATION: (6)..(6)
<223> OTHER INFORMATION: n is a, c, g, or t

<400> SEQUENCE: 141
gggaanttgt aatttgcagg tttcgtggtc tgagtcggcc gcgcccaagt ccattggaac      60
atggcgcctg ggagggtgag agccccgtat ggcgcacgcc gactctttgc accgcggctc     120
cgacgagtcg agttgtttgg gaatgcagct c                                    151

<210> SEQ ID NO 142
<211> LENGTH: 157
<212> TYPE: DNA
<213> ORGANISM: Malassezia globosa

<400> SEQUENCE: 142
gtgtccgcgt tgtaatctcg agacgtgttt ccgtgcggc tctatggaca agtcccttgg       60
aatacggcat cgtagagggt gagaatcccg tacttgccat ggaaaaccat gctttccgat     120
acacgctcta agagtcgagt tgtttgggat tgcactc                              157

<210> SEQ ID NO 143
<211> LENGTH: 159
<212> TYPE: DNA
<213> ORGANISM: Malassezia  obtusa

<400> SEQUENCE: 143
gtgtccgcgt tgtaatctcg agacgtgttt ccgtgcggc gctatggaca agttccttgg       60
aacagggcat cgtagagggt gaaaatcccg tacttgccat ggacgtaccg tgctttcgca     120
tacacgctct aagagtcgag ttgtttggga ttgcagctc                            159

<210> SEQ ID NO 144
<211> LENGTH: 159
<212> TYPE: DNA
<213> ORGANISM: Malassezia sympodialis

<400> SEQUENCE: 144
gtgtccgcgt tgtaatctcg agacgtgttt ccgtgcggc tctatggaca agtcccttgg       60
```

```
aacagggcat cgtagagggt gaaaatcccg tacttgccat ggatgtaccg tgctttgtga      120
tacacgctct aagagtcgag ttgtttggga ttgcagctc                             159

<210> SEQ ID NO 145
<211> LENGTH: 159
<212> TYPE: DNA
<213> ORGANISM: Malassezia furfur

<400> SEQUENCE: 145
gtatccgcgt tgtaacctcg agacacgttt tccgtgcggc gctatggaca agttccttgg      60
aacaggacat cgtagagggt gaaaatcccg tacttgccat ggatgtaccg cgctttgcga      120
tacgtgctct aagagtcgag ttgtttggga ttgcagctc                             159

<210> SEQ ID NO 146
<211> LENGTH: 159
<212> TYPE: DNA
<213> ORGANISM: Malassezia slooffiae

<400> SEQUENCE: 146
gtgtccgcgt tgtaatttcg agacgtgttt tccgcgtggc gccatggaca agttccctgg      60
aatgggacat cgtagagggt gaaaatcccg tacttgccat ggacgtacca tgctttgcga      120
tacacgctcc aagagtcgag tagtttggga ttgctgctc                             159

<210> SEQ ID NO 147
<211> LENGTH: 159
<212> TYPE: DNA
<213> ORGANISM: Malassezia japonica

<400> SEQUENCE: 147
gtgcccgcgt tgtaatctcg agacgcgttt tccgcgcggc gctatggaca agttccttgg      60
aacaggacat cgtagagggt gaaaatcccg tacttgccat ggatgcaccg tgctttgtga      120
tacgtgctca aagagtcgag ttgtttggga ttgcagctc                             159

<210> SEQ ID NO 148
<211> LENGTH: 149
<212> TYPE: DNA
<213> ORGANISM: Trichosporon asahii

<400> SEQUENCE: 148
gggggcatta gtattccgtt gctagaggtg aaattcttag atttacggaa gactaacaac      60
tgcgaaagca tttgccaagg acgttttcat tgatcaagaa cgaaggttag gggatcaaaa      120
acgattagat accgttgtag tcttaacag                                        149

<210> SEQ ID NO 149
<211> LENGTH: 159
<212> TYPE: DNA
<213> ORGANISM: Trichosporon asteroides

<400> SEQUENCE: 149
gggggcatta gtattccgtt gctagaggtg aaattcttag atttacggaa gactaacaac      60
tgcgaaagca tttgccaagg acgttttcat tgatcaagaa cgaaggttag gggatcaaaa      120
acgattagat accgttgtag tcttaacagg ggggcatta                             159

<210> SEQ ID NO 150
<211> LENGTH: 139
<212> TYPE: DNA
<213> ORGANISM: Trichosporon inkin
```

<400> SEQUENCE: 150
gtattccgtt gctagaggtg aaattcttag atttacggaa gactaacaac tgcgaaagca    60
tttgccaagg acgttttcat tgatcaagaa cgaaggttag gggatcaaaa acgattagat   120
accgttgtag tcttaacag                                                139

<210> SEQ ID NO 151
<211> LENGTH: 149
<212> TYPE: DNA
<213> ORGANISM: Trichosporon ovoides

<400> SEQUENCE: 151
gggggcatta gtattccgtt gctagaggtg aaattcttag atttacggaa gactaacaac    60
tgcgaaagca tttgccaagg acgttttcat tgatcaagaa cgaaggttag gggatcaaaa   120
acgattagat accgttgtag tcttaacag                                     149

<210> SEQ ID NO 152
<211> LENGTH: 149
<212> TYPE: DNA
<213> ORGANISM: Trichosporon cutaneum

<400> SEQUENCE: 152
gggggcatta gtattccgtt gctagaggtg aaattcttag atttacggaa gactaacaac    60
tgcgaaagca tttgccaagg acgttttcat tgatcaagaa cgaaggttag gggatcaaaa   120
acgattagat accgttgtag tcttaacag                                     149

<210> SEQ ID NO 153
<211> LENGTH: 149
<212> TYPE: DNA
<213> ORGANISM: Cryptococcus albidus

<400> SEQUENCE: 153
gggggcatta gtattcagtt gctagaggtg aaattcttag atttactgaa gactaactac    60
tgcgaaagca tttgccaagg acgttttcat taatcaagaa cgaaggttag gggatcaaaa   120
atgattagat accgttgtag tcctaacag                                     149

<210> SEQ ID NO 154
<211> LENGTH: 149
<212> TYPE: DNA
<213> ORGANISM: Cryptococcus laurentii

<400> SEQUENCE: 154
gggggcatta gtattccgtt gctagaggtg aaattcttag atttacggaa gactaacttc    60
tgcgaaagca tttgccaagg acgttttcat tgatcaagaa cgaaggttag gggatcaaaa   120
acgattagat accgttgtag tcttaacag                                     149

<210> SEQ ID NO 155
<211> LENGTH: 149
<212> TYPE: DNA
<213> ORGANISM: Cryptococcus aureus

<400> SEQUENCE: 155
gggggcatta gtattcagtt gctagaggtg aaattcttag atttactgaa gactaacttc    60
tgcgaaagca tttgccaagg acgttttcat tgatcaagaa cgaaggttag gggatcaaaa   120
acgattagat accgttgtag tcttaacag                                     149

<210> SEQ ID NO 156
<211> LENGTH: 149
<212> TYPE: DNA
<213> ORGANISM: Cryptococcus neoformans

<400> SEQUENCE: 156
gggggcattg gtattccgtt gctagaggtg aaattcttag attgacggaa gaccaacaac    60
tgcgaaagca tttgccaagg acgttttcat tgatcaagaa cgaaggttag gggatcaaaa   120
acgattagat accgttgtag tcttaacag                                     149

<210> SEQ ID NO 157
<211> LENGTH: 149
<212> TYPE: DNA
<213> ORGANISM: Cryptococcus gattii

<400> SEQUENCE: 157
gggggcattg gtattccgtt gctagaggtg aaattcttag attgacggaa gaccaacaac    60
tgcgaaagca tttgccaagg acgttttcat tgatcaagaa cgaaggttag gggatcaaaa   120
acgattagat accgttgtag tcttaacag                                     149

<210> SEQ ID NO 158
<211> LENGTH: 149
<212> TYPE: DNA
<213> ORGANISM: Trichosporon mucoides

<400> SEQUENCE: 158
gggggcatta gtattccatt gctagaggtg aaattcttag atttatggaa gactaacaac    60
tgcgaaagca tttgccaagg acgttttcat tgatcaagaa cgaaggttag gggatcaaaa   120
acgattagat accgttgtag tcttaacag                                     149

<210> SEQ ID NO 159
<211> LENGTH: 360
<212> TYPE: DNA
<213> ORGANISM: Pseudomonas aeruginosa

<400> SEQUENCE: 159
ttccacttca acgtccagcg tgaagaggac ggcgtgggtg tggaagtcgc cttgcagtgg    60
aacgacagct tcaacgagaa cctgctctgc ttcaccaaca acatcccgca gcgtgatggc   120
ggcacccacc tggccggttt ccgttcggcg ctgacgcgta acctgaacaa ctacatcgag   180
cgaaggcctg gcgaagaaat tcaagatcgc caccaccggc gacgatgccc gcgaaggcct   240
caccgcgatc atctcggtga aggtaccgga cccgaagttc agctcgcaga ccaaggacaa   300
gctggtctcc tccgaggtga agaccgcggt ggaacaggag atgggcaagt acttcgccga   360

<210> SEQ ID NO 160
<211> LENGTH: 368
<212> TYPE: DNA
<213> ORGANISM: Trichophyton rubrum

<400> SEQUENCE: 160
aagtaaaagt cgtaacaagg tttccgtagg tgaacctgcg aaggatcat taacgcgcag     60 gccggaggct ggccccccac gatagggacc gacgttccat cagggtgagc agacgtgcgc   120
cggccgtacg ccccccattct tgtctacctc accggttgc ctcggcgggc gcgctcccc    180 ctgccaggga gagccgtccg gcgggccctt ctggagcct cgagcggac cgcgcccgcc    240 ggaggacaga caccaagaaa aaattctctg aagagctgtc agtctgagcg tttagcaagc   300

```
acaatcagtt aaaactttca acaacggatc tcttggttcc ggcatcgatg aagaacgcag    360
cgaaatgc                                                             368
```

<210> SEQ ID NO 161
<211> LENGTH: 364
<212> TYPE: DNA
<213> ORGANISM: Trichophyton mentagrophytes

<400> SEQUENCE: 161

```
aagtaaaagt cgtaacaagg tttccgtagg tgaacctgcg aaggatcat tagcgcgcag     60 gccggaggct ggcccccac gatagggcca aacgtccgtc aggggtgagc agatgtgcgc    120
cggccgtacc gccccattct tgtctacatt actcggttgc ctcggcgggc cgcgctctcc   180
caggagagcc gttcggcgag cctctcttta gtggctaaac gctggaccgc gcccgccgga   240
ggacagacgc aaaaaaattc tttcagaaga gctgtcagtc tgagcgttag caagcaaaaa   300
tcagttaaaa ctttcaacaa cggatctctt ggttccggca tcgatgaaga acgcagcgaa   360
atgc                                                                364
```

<210> SEQ ID NO 162
<211> LENGTH: 402
<212> TYPE: DNA
<213> ORGANISM: Unknown
<220> FEATURE:
<223> OTHER INFORMATION: genus Epidermophyton

<400> SEQUENCE: 162

```
aagtaaaagt cgtaacaagg tttccgtagg tgaacctgcg aaggatcat taacgcgcag     60 gccgcagtcg gccgtcccc cttctctctg aatgctggac ggtgtcgccg gccacacgcc    120
cattcttgtc tacactaccc ggttgcctcg gcgggccgcg cccctaggc tgcagtgtcg    180 ctgcagcgtc tcgggggggc cgttcgggg atggagaagg atgccccggc ggggttgatc    240
gctcccccac ccctggacag cgctcgccga aggagtgatt ctcagaaatt ctacgaaatc    300
tccataggtg gttcagtctg agcgttggca agcaaaaacc agtcaaaact ttcaacaacg    360
gatctcttgg ttccggcatc gatgaagaac gcagcgaaat gc                       402
```

<210> SEQ ID NO 163
<211> LENGTH: 187
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (64)..(66)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (82)..(85)
<223> OTHER INFORMATION: n is a, c, g, or t
<220> FEATURE:

```
<221> NAME/KEY: misc_feature
<222> LOCATION: (100)..(110)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (150)..(151)
<223> OTHER INFORMATION: n is a, c, g, or t
<220> FEATURE:
<221> NAME/KEY: misc_feature
<222> LOCATION: (160)..(163)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 163
kccggccrca cgcccattct tgtctaytka cccrgttgcc tcggcgggcc gcgcmykcng        60
tgcnnnmgcg nccnntcgrg gnnnnmgcck kmsggggacn nnnnnnnnnn arkcmackcc       120
cyggrymgcg cycgccggag gaktrmtntn naaaaymcan nnntgnaaka myrtwccgtc       180 tgagcgn                                                                187

<210> SEQ ID NO 164
<211> LENGTH: 186
<212> TYPE: DNA
<213> ORGANISM: Unknown
<220> FEATURE:
<223> OTHER INFORMATION: genus Microsporum

<400> SEQUENCE: 164
tccggccgca cgcccattct tgtctactga cccggttgcc tcggcgggcc gcgcctgctg        60
tgctacagcg gccgttcggg ggggacgcct gaggggggact cttgtttcct aggccacgcc      120
ccgggcagcg ctcgccggag gattactctg gaaaacacac tcttgaaaga acataccgtc      180
tgagcg                                                                 186

<210> SEQ ID NO 165
<211> LENGTH: 156
<212> TYPE: DNA
<213> ORGANISM: Nanissia gypsia

<400> SEQUENCE: 165
gccggccaca cgcccattct tgtctattta cccagttgcc tcggcgggcc gcgcactcgt        60
gccgcgcctc gaggagccgt ccggggacaa tcaactccct ggatcgcgcc cgccggagga      120
gtgattaaaa tccatgaata ctgttccgtc tgagcg                                156

<210> SEQ ID NO 166
<211> LENGTH: 283
<212> TYPE: DNA
<213> ORGANISM: Unknown
<220> FEATURE:
<223> OTHER INFORMATION: genus Acremonium

<400> SEQUENCE: 166
cgcacattgc gcccgccagt attctggcgg gcatgcctgt ctgagcgtca tttcaaccct        60
caggacccgt tcgcgggacc tggcgttggg gatcagcctg cccctggcgg cggctggccc      120
```

-continued

```
tgaaatacag tggcggttcc ctcgcgaact cctccgtgca gtaattaaac ctctcgcggc    180
aggatagcgg ttgaaccacg ccgttaaacc ccccacttct caaggttgac ctcagatcag    240
gtaggaatac ccgctgaact taagcatatc aataagcgga gga                      283
```

<210> SEQ ID NO 167
<211> LENGTH: 269
<212> TYPE: DNA
<213> ORGANISM: Unknown
<220> FEATURE:
<223> OTHER INFORMATION: genus Alternaria

<400> SEQUENCE: 167

```
cgcacattgc gcccttTggt attccaaagg gcatgcctgt tcgagcgtca tttgtaccct    60
caagctttgc ttggtgttgg gcgtcttgtc tctagctttg ctggagactc gccttaaagt    120
aattggcagc cggcctactg gtttcggagc gcagcacaag tcgcactctc tatcagcaaa    180
ggtctagcat ccattaagcc ttttttcaac ttttgacctc ggatcaggta gggatacccg    240
ctgaacttaa gcatatcaat aagcggagg                                     269
```

<210> SEQ ID NO 168
<211> LENGTH: 463
<212> TYPE: DNA
<213> ORGANISM: Unknown
<220> FEATURE:
<223> OTHER INFORMATION: genus Aspergillus

<400> SEQUENCE: 168

```
cgcacattgc gcccctggt attccggggg gcatgcctgt ccgagcgtca ttgctgccca     60
tcaagcacgg cttgtgtgtt gggtcgtcgt cccctctccg gggggacgg gccccaaagg     120 cagcggcggc accgcgtccg atcctcgagc gtatggggct ttgtcacccg ctctgtaggc    180
ccggccggcg cttgccgaac gcaaatcaat cttttttccag gttgacctcg gatcaggtag    240
ggatacccgc tgaacttaag catatcaata agcggaggaa aagaaaccaa ccgggattgc    300
ctcagtaacg gcgagtgaag cggcaagagc tcaaatttga agctggctc cttcggggtc     360 cgcattgtaa tttgcagagg atgcttcggg tgcggcccct gtctaagtgc cctggaacgg    420
gccgtcagag agggtgagaa tcccgtctgg gatgggtgt ccg                       463
```

<210> SEQ ID NO 169
<211> LENGTH: 236
<212> TYPE: DNA
<213> ORGANISM: Unknown
<220> FEATURE:
<223> OTHER INFORMATION: genus Curvularia

<400> SEQUENCE: 169

```
cgcacattgc gcccttTggt attccaaagg gcatgcctgt tcgagcgtca tttgtaccct    60
caagctttgc ttggtgttgg gcgttttttg tctttggttg ccaaagactc gccttaaaag    120
gattggcagc cggcctactg gtttcgcagc gcagcacatt tttgcgcttg caatcagcaa    180
aagaggacgg caatccatca agactccttc tcacgttgac ctcggatcag gtaggg         236
```

<210> SEQ ID NO 170
<211> LENGTH: 183
<212> TYPE: DNA
<213> ORGANISM: Artificial sequence
<220> FEATURE:
<223> OTHER INFORMATION: synthetic sequence
<220> FEATURE:

```
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t

<400> SEQUENCE: 170
cagcggaggg atcattaccg agttntacaa ctcmymaacc nctgtgaaca taccnnamny      60
gttgcytcgg cnggawcagm csgcncccgk wamaacgggm cgnscccgcc agaggacccc     120
taanctctgt ttctatantg twwcttctga gtaaammnry aaataaatya aaactttcaa     180
caa                                                                  183

<210> SEQ ID NO 171
<211> LENGTH: 177
<212> TYPE: DNA
<213> ORGANISM: Fusarium oxyporum

<400> SEQUENCE: 171
cagcggaggg atcattaccg agtttacaac tcccaaaccc ctgtgaacat accacttgtt      60
gcctcggcgg atcagcccgc tcccggtaaa acgggacggc cgccagagg accccctaaac    120 tctgttttcta tatgtaactt ctgagtaaaa ccataaataa atcaaaactt tcaacaa       177

<210> SEQ ID NO 172
<211> LENGTH: 180
<212> TYPE: DNA
<213> ORGANISM: Fusarium solani

<400> SEQUENCE: 172
cagcggaggg atcattaccg agttatacaa ctcatcaacc ctgtgaacat acctaaaacg      60
ttgcttcggc gggaacagac ggccccctaa caacgggccg ccccgccag aggacccta      120 actctgtttc tataatgttt cttctgagta aacaagcaaa taaattaaaa ctttcaacaa    180
```

```
<210> SEQ ID NO 173
<211> LENGTH: 301
<212> TYPE: DNA
<213> ORGANISM: Unknown
<220> FEATURE:
<223> OTHER INFORMATION: genus Scopulariopsis

<400> SEQUENCE: 173
cgcacattgc gcccggcagc aatctgccgg gcatgcctgt ccgagcgtca tttcttccct        60
cgagcgcggc tagccctacg gggcctgccg tcgcccggtg ttggggctct acgggtgggg       120
ctcgtccccc ccgcagtccc cgaaatgtag tggcggtcca gccgcggcgc ccctgcgta       180 gtagatccta catctcgcat cgggtccggg cgaaggccag ccgtcgaacc ttttatttca       240
tggtttgacc tcggatcagg tagggttacc cgctgaactt aagcatatca ataagcggag       300
g                                                                       301

<210> SEQ ID NO 174
<211> LENGTH: 345
<212> TYPE: DNA
<213> ORGANISM: Unknown
<220> FEATURE:
<223> OTHER INFORMATION: genus Scytalidium

<400> SEQUENCE: 174
ggacgatccg cagccaagcc cctacgtcca gccggcctgg atacggggaa ggttcacaga        60
ctaagtggaa gtgggtgcgg cctcccggcc gcgcttaaga tatagtcggg cccccagcga       120
aagctggggg gtaagtcact gcgacgagag ccgttccgta ggtgaacctg cggaaggatc       180
attaccgagt tgattcgggc tccggcccga tcctcccacc ctttgtgtac ccacctctgt       240
tgctttggcg ggccgcggtc ctccgcggcc gccctccgtc cgggggggtgg ccagcgcccg      300 ccagaggacc atcgaactcc ggtcagtgaa cgttgccgtc tgaaa                       345

<210> SEQ ID NO 175
<211> LENGTH: 439
<212> TYPE: DNA
<213> ORGANISM: Candida albicans

<400> SEQUENCE: 175
ggcccagcct gccgccagag gtctaaactt acaaccaatt ttttattaac ttgtcacacc        60
agattattac ttaatagtca aaactttcaa caacggatct cttggttctc gcatcgatga       120
agaacgcagc gaaatgcgat acgtaatatg aattgcagat attcgtgaat catcgaatct       180
ttgaacgcac attgcgccct ctggtattcc ggagggcatg cctgtttgag cgtcgtttct       240
ccctcaaacc gctgggtttg gtgttgagca atacgacttg ggtttgcttg aaagacggta       300
gtggtaaggc gggatcgctt tgacaatggc ttaggtctaa ccaaaaacat tgcttgcggc       360
ggtaacgtct accacgtata tcttcaaact ttgacctcaa atcaggtagg actacccgct       420
gaacttaagc atatcaaaa                                                    439

<210> SEQ ID NO 176
<211> LENGTH: 434
<212> TYPE: DNA
<213> ORGANISM: Candida parapsilosis

<400> SEQUENCE: 176
aaactttgct ttggtaggcc ttctatatgg ggcctgccag agattaaact caaccaaatt        60
ttatttaatg tcaaccgatt atttaatagt caaaactttc aacaacggat ctcttggttc       120
```

```
tcgcatcgat gaagaacgca gcgaaatgcg ataagtaata tgaattgcag atattcgtga    180
atcatcgaat ctttgaacgc acattgcgcc ctttggtatt ccaaagggca tgcctgtttg    240
agcgtcattt ctccctcaaa ccctcgggtt tggtgttgag cgatacgctg ggtttgcttg    300
aaagaaaggc ggagtataaa ctaatggata ggttttttcc actcattggt acaaactcca    360
aaacttcttc caaattcgac ctcaaatcag gtaggactac ccgctgaact taagcatatc    420
attaagcgga ggaa                                                      434
```

<210> SEQ ID NO 177
<211> LENGTH: 414
<212> TYPE: DNA
<213> ORGANISM: Candida tropicalis

<400> SEQUENCE: 177

```
ataactaaac caaactttttt atttacagtc aaacttgatt tattattaca atagtcaaaa     60
ctttcaacaa cggatctctt ggttctcgca tcgatgaaga acgcagcgaa atgcgatacg    120
taatatgaat tgcagatatt cgtgaatcat cgaatctttg aacgcacatt gcgcccnttg    180
gtattccaaa gggcatgcct gtttgagcgt catttctccc tcaaaccccc gggtttggtg    240
ttgagcaata cgctaggttt gtttgaaaga atttaacgtg gaaacttatt ttaagcgact    300
taggtttatc caaaaacgct tattttgcta gtggccacca caatttattt cataactttg    360
acctcaaatc aggtaggact acccgctgaa cttaagcata tcaataagcg gagg          414
```

<210> SEQ ID NO 178
<211> LENGTH: 174
<212> TYPE: DNA
<213> ORGANISM: Artificial sequence
<220> FEATURE:
<223> OTHER INFORMATION: synthetic sequence

<400> SEQUENCE: 178

```
ttcagtgtca tgaaatctca accactaggg tttcctaatg gattggattt gggcgtctgc     60
gatctctgat cgctcgcctt aaaagagtta gcaagtttga cattaatgtc tggtgtaata    120
agtttcactg gtccattgt gttgaagcgt gcttctaatc gtccgcaagg acaa           174
```

<210> SEQ ID NO 179
<211> LENGTH: 168
<212> TYPE: DNA
<213> ORGANISM: Trichosporon cutaneum

<400> SEQUENCE: 179

```
ttgagtatca tgaaatctca accattaggg tttcttaatg gcttggattt gggcgctgcc     60
acttgcctgg ctcgccttaa aagagttagc gtattaactt gtcgatctgg cgtaataagt    120
ttcgctggtg tagacttgag aagtgcgctt ctaatcgtct tcggacaa                 168
```

<210> SEQ ID NO 180
<211> LENGTH: 168
<212> TYPE: DNA
<213> ORGANISM: Trichosporon mucoides

<400> SEQUENCE: 180

```
ttgagtatca tgaaatctca accattaggg tttcttaatg gcttggattt gggcgctgcc     60
acttgcctgg ctcgccttaa aggagttagc gtattaactt gtcgatctgg cgtaataagt    120
ttcgctggtg tagacttgag aagtgcgctt ctaatcgtcc tcggacaa                 168
```

```
<210> SEQ ID NO 181
<211> LENGTH: 174
<212> TYPE: DNA
<213> ORGANISM: Trichosporon asahii

<400> SEQUENCE: 181
ttcagtgtca tgaaatctca accactaggg tttcctaatg gattggattt gggcgtctgc    60
gatttctgat cgctcgcctt aaaagagtta gcaagtttga cattaatgtc tggtgtaata   120
agtttcactg ggtccattgt gttgaagcgt gcttctaatc gtccgcaagg acaa         174

<210> SEQ ID NO 182
<211> LENGTH: 174
<212> TYPE: DNA
<213> ORGANISM: Trichosporon asteroides

<400> SEQUENCE: 182
ttcagtgtca tgaaatctca accactaggg tttcctaatg gattggattt gggcgtctgc    60
gatctctgat cgctcgcctt aaaagagtta gcaagtttga cattaatgtc tggtgtaata   120
agtttcactg ggtccattgt gttgaagcgt gcttctaatc gtccgcaagg acaa         174

<210> SEQ ID NO 183
<211> LENGTH: 174
<212> TYPE: DNA
<213> ORGANISM: Trichosporon inkin

<400> SEQUENCE: 183
ttcagtgtca tgaaatctca accactaggg tttcctaatg gattggattt gggcgtctgc    60
gatctctgat cgctcgcctt aaaagagtta gcaagtttga cattcatgtc tggtgtaata   120
agtttcactg ggtccatggt gttgaagcgt gcttctaatc gtccgcaagg acaa         174

<210> SEQ ID NO 184
<211> LENGTH: 174
<212> TYPE: DNA
<213> ORGANISM: Trichosporon ovoides

<400> SEQUENCE: 184
ttcagtgtca tgaaatctca accactaggg tttcctaatg gattggattt gggcgtctgc    60
gatctctgat cgctcgcctt aaaagagtta gcaagtttga cattaatgtc tggtgtaata   120
agtttcactg ggtccattgt gttgaagcgt gcttctaatc gtccgcaagg acaa         174

<210> SEQ ID NO 185
<211> LENGTH: 448
<212> TYPE: DNA
<213> ORGANISM: Candida guilliermodii

<400> SEQUENCE: 185 ttattttttac agttagtcaa attttgaatt aatcttcaaa actttcaaca acggatctct    60
tggttctcgc atcgatgaag aacgcagcga atgcgataa gtaatatgaa ttgcagattt    120
tcgtgaatca tcgaatcttt gaacgcacat tgcgccctct ggtattccag agggcatgcc   180
tgtttgagcg tcatttctct ctcaaacccc cgggtttggt attgagtgat actcttagtc   240
ggactaggcg tttgcttgaa aagtattggc atgggtagta ctggatagtg ctgtcgacct   300
ctcaatgtat taggtttatc caactcgttg aatggtgtgg cgggatattt ctggtattgt   360
tggcccggcc ttcaacaac caaacaagtt tgacctcaaa tcaggtagga atacccgctg    420
aacttaagca tatcaataag ccggagaa                                      448
```

<210> SEQ ID NO 186
<211> LENGTH: 560
<212> TYPE: DNA
<213> ORGANISM: Unknown
<220> FEATURE:
<223> OTHER INFORMATION: genus Malassezia

<400> SEQUENCE: 186

| | | | | | |
|---|---|---|---|---|---|
| tcagtgaaat | tgaattagcc | gtgcagatgc | ggtttgcctt | ccggaggacg | cgaagaccct | 60 |
| atgcagcttt | actgtattct | gatattgccg | tttgtgatat | atagtgtaga | atacaaggga | 120 |
| gtgaaaacat | ccgtgaaata | ccttgatata | ttgaaatgaa | tggcttattt | attaaaagac | 180 |
| agtgtcagat | ggtcagtttt | actggggcgg | tagcctctaa | aaagtatca | gaggccttca | 240 |
| aaggtatatt | taaattggtc | ggaaaccaat | ggaataatag | tattctatca | aaatgtaatg | 300 |
| ataaagtatg | ctttactgaa | agattgataa | atcgatcagt | tacgcaagta | ggatatagtg | 360 |
| atccgatgat | tcagaatgga | atgatcatcg | ctcaagaaat | aaaagttacg | ctagggataa | 420 |
| caggtttatc | gtttgcgaga | gttcatattg | tccaaacggt | ttgacacctc | gatgtcgact | 480 |
| cttctcatcc | tccaggtgta | gtcgcttgga | agggttcagc | tgttcgctga | gtaaagagga | 540 |
| acgtgagttg | ggtttaatac | | | | | 560 |

<210> SEQ ID NO 187
<211> LENGTH: 172
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (131)..(139)
<223> OTHER INFORMATION: n is a, c, g, or t
<220> FEATURE:
<221> NAME/KEY: misc_feature
<222> LOCATION: (169)..(170)
<223> OTHER INFORMATION: n is a, c, g, or t

<400> SEQUENCE: 187

| | | | | | |
|---|---|---|---|---|---|
| atcatcgart | ctttgaacgc | amcttgcgcc | ctttggtatt | ccgaagggca | tgcctgtttg | 60 |
| agwgtcatga | aaatctcaat | ccctcgggtt | ttattacctg | ttggacttgg | atttgggygt | 120 |
| ttgccgygac | nnnnnnnnna | cgtcggctcg | ccttaaatgt | gttagtggnn | ak | 172 |

<210> SEQ ID NO 188
<211> LENGTH: 166
<212> TYPE: DNA
<213> ORGANISM: Cryptococcus albidus

<400> SEQUENCE: 188

| | | | | | |
|---|---|---|---|---|---|
| atcatcgaat | ctttgaacgc | accttgcgct | ccttggtatt | ccgaggagca | tgcctgtttg | 60 |
| agtgtcatga | aaaccctcaa | ccctagattg | gttaaaacct | ttctttggtt | tggatttgga | 120 |
| cgtttgccga | tgataagtcg | gctcgtctta | aaagtaatag | ctggat | | 166 |

<210> SEQ ID NO 189
<211> LENGTH: 160
<212> TYPE: DNA
<213> ORGANISM: Cryptococcus laurentii

<400> SEQUENCE: 189

| | | | | | |
|---|---|---|---|---|---|
| atcatcgaat | ctttgaacgc | accttgcgcc | ttttggtatt | ccgaaaggca | tgcctgtttg | 60 |
| agtgtcatga | aatctcaatc | cccctgggtt | tatgatctgg | gtcggacttg | gaaatgggcg | 120 |

```
tctgccggtc acacggctcg cctcaaatga cttagtggat                              160
```

<210> SEQ ID NO 190
<211> LENGTH: 172
<212> TYPE: DNA
<213> ORGANISM: Cryptococcus gattii

<400> SEQUENCE: 190

```
atcatcgagt ctttgaacgc aacttgcgcc ctttggtatt ccgaagggca tgcctgtttg        60
agagtcatga aaatctcaat ccctcgggtt ttattacctg ttggacttgg atttgggtgt       120
ttgccgcgac ctgcaaagga cgtcggctcg ccttaaatgt gttagtggga ag               172
```

<210> SEQ ID NO 191
<211> LENGTH: 172
<212> TYPE: DNA
<213> ORGANISM: Cryptococcus neoformans

<400> SEQUENCE: 191

```
atcatcgagt ctttgaacgc aacttgcgcc ctttggtatt ccgaagggca tgcctgtttg        60
agagtcatga aaatctcaat ccctcgggtt ttattacctg ttggacttgg atttgggtgt       120
ttgccgcgac ctgcaaagga cgtcggctcg ccttaaatgt gttagtggga ag               172
```

<210> SEQ ID NO 192
<211> LENGTH: 145
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 192

```
kstgwytacc tgtcagmccg gcgtaataag tttcgctggg cctwtggngg tagtcttcgg        60
cttgctgata acaccatck cnnactttn gactctgacc tcaaatcagg taggactacc       120
cgctgaactt aagcatatca ataag                                             145
```

<210> SEQ ID NO 193
<211> LENGTH: 178
<212> TYPE: DNA
<213> ORGANISM: Cryptococcus albidus

<400> SEQUENCE: 193

```
tctgtctcgc gacatggttt gacttggcgt aataagtatt tcgctaagga catcttccgg        60
atggccgcgt tgcaggacta aagaccgctt tctaatccat tgatcttcgg attaatactc      120
ttgacatctg gcctcaaatc aagtaggact acccgctgaa cttaagcata tcaataag        178
```

<210> SEQ ID NO 194
<211> LENGTH: 137
<212> TYPE: DNA
<213> ORGANISM: Cryptococcus laurentii

<400> SEQUENCE: 194

```
tctctctgca tccgtgacag acgtaataag tttcgtcttg tcccttgctt atgagtctgc    60
tcataacctg ccatcgcgca cttttagact ctgacctcaa atcaggtagg actacccgct   120
gaacttaagc atatcat                                                  137
```

<210> SEQ ID NO 195
<211> LENGTH: 80
<212> TYPE: DNA
<213> ORGANISM: Cryptococcus gattii

<400> SEQUENCE: 195

```
ggtgattacc tgtcagcccg gcgtaataag tttcgctggg cctatggggt agtcttcggc    60
ttgctgataa caaccatctc                                                80
```

<210> SEQ ID NO 196
<211> LENGTH: 138
<212> TYPE: DNA
<213> ORGANISM: Cryptococcus neoformans

<400> SEQUENCE: 196

```
ggtgattacc tgtcagcccg gcgtaataag tttcgctggg cctatggggt agtcttcggc    60
ttgctgataa caaccatctc tttttgtttg acctcaaatc aggtagggct acccgctgaa   120
cttaagcata tcaataag                                                 138
```

<210> SEQ ID NO 197
<211> LENGTH: 145
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (82)..(83)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t

<400> SEQUENCE: 197

```
kstgwytacc tgtcagmccg gcgtaataag tttcgctggg cctwtggngg tagtcttcgg    60
cttgctgata acaaccatck cnnacttttn gactctgacc tcaaatcagg taggactacc   120
cgctgaactt aagcatatca ataag                                         145
```

<210> SEQ ID NO 198
<211> LENGTH: 178
<212> TYPE: DNA
<213> ORGANISM: Cryptococcus albidus

<400> SEQUENCE: 198

```
tctgtctcgc gacatggttt gacttggcgt aataagtatt tcgctaagga catcttccgg    60
atggccgcgt tgcaggacta aagaccgctt tctaatccat tgatcttcgg attaatactc   120
ttgacatctg gcctcaaatc aagtaggact acccgctgaa cttaagcata tcaataag    178
```

<210> SEQ ID NO 199
<211> LENGTH: 137

```
<212> TYPE: DNA
<213> ORGANISM: Cryptococcus laurentii

<400> SEQUENCE: 199
tctctctgca tccgtgacag acgtaataag tttcgtcttg tcccttgctt atgagtctgc    60
tcataacctg ccatcgcgca cttttagact ctgacctcaa atcaggtagg actacccgct   120
gaacttaagc atatcat                                                  137

<210> SEQ ID NO 200
<211> LENGTH: 80
<212> TYPE: DNA
<213> ORGANISM: Cryptococcus gattii

<400> SEQUENCE: 200
ggtgattacc tgtcagcccg gcgtaataag tttcgctggg cctatggggt agtcttcggc    60
ttgctgataa caaccatctc                                                80

<210> SEQ ID NO 201
<211> LENGTH: 138
<212> TYPE: DNA
<213> ORGANISM: Cryptococcus neoformans

<400> SEQUENCE: 201
ggtgattacc tgtcagcccg gcgtaataag tttcgctggg cctatggggt agtcttcggc    60
ttgctgataa caaccatctc ttttgtttg acctcaaatc aggtagggct acccgctgaa   120
cttaagcata tcaataag                                                 138

<210> SEQ ID NO 202
<211> LENGTH: 114
<212> TYPE: DNA
<213> ORGANISM: Unknown
<220> FEATURE:
<223> OTHER INFORMATION: Dermatophyte

<400> SEQUENCE: 202
cactggccca gggaggttgg aaacgaccgc ccagggccgg aaagttggtc aaactcggtc    60
atttagagga agtaaaagtc gtaacaaggt ttccgtaggt gaacctgcgg aagg         114

<210> SEQ ID NO 203
<211> LENGTH: 96
<212> TYPE: DNA
<213> ORGANISM: Unknown
<220> FEATURE:
<223> OTHER INFORMATION: Dermatophyte

<400> SEQUENCE: 203
ggaggttgga aacgaccgcc cagggccgga aagttggtca aactcggtca tttagaggaa    60
gtaaaagtcg taacaaggtt tccgtaggtg aacctg                              96

<210> SEQ ID NO 204
<211> LENGTH: 191
<212> TYPE: DNA
<213> ORGANISM: Unknown
<220> FEATURE:
<223> OTHER INFORMATION: genus Alternaria

<400> SEQUENCE: 204
ccagcagtcg cggtaagaca agggagacga gtgttattca tctttaacag gtatataggg    60
tacctagacg gtgtgcaatg gcttaaataa gtacctggta cacttgagtt tgatatgtga   120
```

```
gaggaatatg tcggaattgt tggaggaaag atgaaatttg ttaataccaa taggactgat    180
aacggcgaag g                                                        191

<210> SEQ ID NO 205
<211> LENGTH: 190
<212> TYPE: DNA
<213> ORGANISM: Unknown
<220> FEATURE:
<223> OTHER INFORMATION: genus Curvularia

<400> SEQUENCE: 205
ccagcagtcg cggtaagaca agggagacga gtgttattca tctttaacag gtatataggg    60
tacctagacg gtgtgcaatg gcttaaataa gtacctggta cacttgagtt tgatatgtga   120
gaggaattgt cggaattgtt ggaggaaaga tgaaatttgt taataccaat aggactgata   180
acggcgaagg                                                          190

<210> SEQ ID NO 206
<211> LENGTH: 150
<212> TYPE: DNA
<213> ORGANISM: Unknown
<220> FEATURE:
<223> OTHER INFORMATION: genus Fusarium

<400> SEQUENCE: 206
ccagcagtcg cggtaatacg taagagacta gtgttattca tcttaattag gtttaaaggg    60
tacccagacg gtcaatatag cttctaaaat gttagtactt gactagagtt ttatgtaaga   120
gggcagtctt gaggaggaga gatgaaattc                                    150

<210> SEQ ID NO 207
<211> LENGTH: 150
<212> TYPE: DNA
<213> ORGANISM: Unknown
<220> FEATURE:
<223> OTHER INFORMATION: genus Scopulariopsis

<400> SEQUENCE: 207
ccagcagtcg cggtaatacg taagagacaa gtgttattca tcttaagtag gtttaaaggg    60
tacctagacg gccaacatga ctttataagt agtatttggc tagagttttta tgtaagaagt   120 acagtacttt aggtggagag atgaaattct                                    150

<210> SEQ ID NO 208
<211> LENGTH: 193
<212> TYPE: DNA
<213> ORGANISM: Unknown
<220> FEATURE:
<223> OTHER INFORMATION: genus Acremonium

<400> SEQUENCE: 208
cagcagtcgc ggtaatacgt aagagactag tgttattcat aagaattagg tttaagggt     60 acttagacgg ttctaatgtc agtatagaag taacccttaa tggtacttta gaactagagt   120
tagataaaga gaacagaact tgcggaggag agatcatatt cattgatacc aaagggactg   180
gtaatggcga agg                                                      193

<210> SEQ ID NO 209
<211> LENGTH: 177
<212> TYPE: DNA
<213> ORGANISM: Unknown
<220> FEATURE:
<223> OTHER INFORMATION: genus Aspergillus
```

<400> SEQUENCE: 209

```
gatgactaac actagtcttc tacgtattac cgcgactgct ggcacgtaat ttggtcaaga      60
cttataaata ggaaattgtc attatcatta tcctatttag aattttatac gagttaatcg     120
ttattgttta caataataca cttacattct tccaagttac tggttcagcc tttcggc       177
```

<210> SEQ ID NO 210
<211> LENGTH: 87
<212> TYPE: DNA
<213> ORGANISM: Unknown
<220> FEATURE:
<223> OTHER INFORMATION: genus Scytalidium

<400> SEQUENCE: 210

```
ggaagtgggt gcggcctccc ggccgcgctt aagatatagt cgggccccca gcgaaagctg      60
gggggtaagt cactgcgacg agagccg                                         87
```

<210> SEQ ID NO 211
<211> LENGTH: 152
<212> TYPE: DNA
<213> ORGANISM: Unknown
<220> FEATURE:
<223> OTHER INFORMATION: genus Candida

<400> SEQUENCE: 211

```
gtccgagttg taatttgaag aaggtatctt tgggcccggc tcttgtctat gttccttgga      60
acaggacgtc acagagggtg agaatcccgt gcgatgagat gacccgggtc tgtgtaaagt     120
tccttcgacg agtcgagttg tttgggaatg ca                                   152
```

<210> SEQ ID NO 212
<211> LENGTH: 151
<212> TYPE: DNA
<213> ORGANISM: Candida guilliermodii

<400> SEQUENCE: 212

```
gtccgagttg taatttgaag attgtaacct tggggttggc tcttgtctat gtttcttgga      60
acaggacgtc acagagggtg agaatcccgt gcgatgagat gcccaattct atgtaaggtg     120
ctttcgaaga gtcgagttgt ttgggaatgc a                                   151
```

<210> SEQ ID NO 213
<211> LENGTH: 149
<212> TYPE: DNA
<213> ORGANISM: Candida guilliermodii

<400> SEQUENCE: 213

```
ccgagttgta atttgaagat tgtaaccttg gggttggctc ttgtctatgt tcttggaac       60 aggacgtcac agagggtgag aatcccgtgc gatgagatgc caattctat gtaaggtgct     120 ttcgaagagt cgagttgttt gggaatgca                                     149
```

<210> SEQ ID NO 214
<211> LENGTH: 132
<212> TYPE: DNA
<213> ORGANISM: Candida krusei

<400> SEQUENCE: 214

```
tgcaggttgg agtctgtgtg gaaggcggtg tccaagtccc ttggaacagg gcgcccagga      60
gggtgagagc cccgtgggat gccggcggaa gcagtgaggc ccttctgacg agtcgagttg     120
```

```
tttgggaatg ca                                                   132

<210> SEQ ID NO 215
<211> LENGTH: 130
<212> TYPE: DNA
<213> ORGANISM: Candida krusei

<400> SEQUENCE: 215
caggttggag tctgtgtgga aggcggtgtc caagtccctt ggaacagggc gcccaggagg   60
gtgagagccc cgtgggatgc cggcggaagc agtgaggccc ttctgacgag tcgagttgtt  120
tgggaatgca                                                        130

<210> SEQ ID NO 216
<211> LENGTH: 135
<212> TYPE: DNA
<213> ORGANISM: Candida lusitaniae

<400> SEQUENCE: 216
tttgaaggtt tcgtggtctg agtcggccgc gcccaagtcc attggaacat ggcgcctggg   60
agggtgagag ccccgtatgg cgcacgccga ctctttgcac cgcggctccg acgagtcgag  120
ttgtttggga atgca                                                  135

<210> SEQ ID NO 217
<211> LENGTH: 133
<212> TYPE: DNA
<213> ORGANISM: Candida lusitaniae

<400> SEQUENCE: 217
tgaaggtttc gtggtctgag tcggccgcgc ccaagtccat tggaacatgg cgcctgggag   60
ggtgagagcc ccgtatggcg cacgccgact ctttgcaccg cggctccgac gagtcgagtt  120
gtttgggaat gca                                                    133

<210> SEQ ID NO 218
<211> LENGTH: 144
<212> TYPE: DNA
<213> ORGANISM: Unknown
<220> FEATURE:
<223> OTHER INFORMATION: genus Malassezia

<400> SEQUENCE: 218
ttgtaatctc gagacgtgtt ttccgtgcgg ctctatggac aagtcccttg gaatacggca   60
tcgtagaggg tgagaatccc gtacttgcat ggaaaaccat gctttgcgat acacgctcta  120
agagtcgagt tgtttgggat tgca                                        144

<210> SEQ ID NO 219
<211> LENGTH: 143
<212> TYPE: DNA
<213> ORGANISM: Unknown
<220> FEATURE:
<223> OTHER INFORMATION: genus Malassezia

<400> SEQUENCE: 219
gtaatctcga gacgtgtttt ccgtgcggct ctatggacaa gtcccttgga atacggcatc   60
gtagagggtg agaatcccgt acttgccatg gaaaaccatg ctttgcgata cacgctctaa  120
gagtcgagtt gtttgggatt gca                                         143

<210> SEQ ID NO 220
<211> LENGTH: 148
```

```
<212> TYPE: DNA
<213> ORGANISM: Unknown
<220> FEATURE:
<223> OTHER INFORMATION: genus Cryptococcus, genus Trichosporon

<400> SEQUENCE: 220
gggggcatta gtattccgtt gctagaggtg aaattcttag atttacggaa gactaacaac      60
tgcgaaagca tttgccaagg acgttttcat tgatcaagaa cgaaggttag gggatcaaaa     120
acgattagat accgttgtag tcttaaca                                        148

<210> SEQ ID NO 221
<211> LENGTH: 144
<212> TYPE: DNA
<213> ORGANISM: Unknown
<220> FEATURE:
<223> OTHER INFORMATION: genus Cryptococcus, genus Trichosporon

<400> SEQUENCE: 221
gggcattagt attccgttgc tagaggtgaa attcttagat ttacggaaga ctaacaactg      60
cgaaagcatt tgccaaggac gttttcattg atcaagaacg aaggttaggg gatcaaaaac     120
gattagatac cgttgtagtc ttaa                                            144

<210> SEQ ID NO 222
<211> LENGTH: 301
<212> TYPE: DNA
<213> ORGANISM: Pseudomonas aeruginosa

<400> SEQUENCE: 222
ttccacttca acgtccagcg tgaagaggac ggcgtgggtg tggaagtcgc cttgcagtgg      60
aacgacagct tcaacgagaa cctgctctgc ttcaccaaca acatcccgca gcgtgatggc     120
ggcacccacc tggccggttt ccgttcggcg ctgacgcgta acctgaacaa ctacatcgag     180
ccgaaggcct ggcgaagaaa ttcaagatcg ccaccaccgg cgacgatgcc cgcgaaggcc     240
tcaccgcgat catctcggtg aaggtaccgg acccgaagtt cagctcgcag accaaggaca     300
a                                                                     301

<210> SEQ ID NO 223
<211> LENGTH: 186
<212> TYPE: DNA
<213> ORGANISM: Pseudomonas aeruginosa

<400> SEQUENCE: 223
ggcgtgggtg tggaagtcgc cttgcagtgg aacgacagct tcaacgagaa cctgctctgc      60
ttcaccaaca acatcccgca gcgtgatggc ggcacccacc tggccggttt ccgttcggcg     120
ctgacgcgta acctgaacaa ctacatcgag ccgaaggcct ggcgaagaaa ttcaagatcg     180
ccacca                                                                186

<210> SEQ ID NO 224
<211> LENGTH: 368
<212> TYPE: DNA
<213> ORGANISM: Trichophyton rubrum

<400> SEQUENCE: 224
aagtaaaagt cgtaacaagg tttccgtagg tgaacctgcg gaaggatcat taacgcgcag      60
gccggaggct ggccccccac gatagggacc gacgttccat cagggtgagc agacgtgcgc     120
cggccgtacg cccccattct tgtctacctc accggttgc ctcggcgggc cgcgctcccc     180
```

```
ctgccaggga gagccgtccg gcgggcccct ctgggagcct cgagccggac cgcgcccgcc    240
ggaggacaga caccaagaaa aaattctctg aagagctgtc agtctgagcg tttagcaagc    300
acaatcagtt aaaactttca acaacggatc tcttggttcc ggcatcgatg aagaacgcag    360
cgaaatgc                                                             368

<210> SEQ ID NO 225
<211> LENGTH: 363
<212> TYPE: DNA
<213> ORGANISM: Trichophyton mentagrophytes

<400> SEQUENCE: 225
agtaaaagtc gtaacaaggt ttccgtaggt gaacctgcgg aaggatcatt agcgcgcagg    60
ccggaggctg ccccccacg atagggccaa acgtccgtca ggggtgagca gatgtgcgcc    120
ggccgtaccg ccccattctt gtctacatta ctcggttgcc tcggcgggcc gcgctctccc    180
aggagagccg ttcggcgagc ctctctttag tggctaaacg ctggaccgcg cccgccggag    240
gacagacgca aaaaaattct ttcagaagag ctgtcagtct gagcgttagc aagcaaaaat    300
cagttaaaac tttcaacaac ggatctcttg gttccggcat cgatgaagaa cgcagcgaaa    360
tgc                                                                  363

<210> SEQ ID NO 226
<211> LENGTH: 402
<212> TYPE: DNA
<213> ORGANISM: Unknown
<220> FEATURE:
<223> OTHER INFORMATION: genus Epidermophyton

<400> SEQUENCE: 226
aagtaaaagt cgtaacaagg tttccgtagg tgaacctgcg gaaggatcat taacgcgcag    60
gccgcagtcg gcccgtcccc cttctctctg aatgctggac ggtgtcgccg ccacacgcc    120 cattcttgtc tacactaccc ggttgcctcg gcgggccgcg cccccctaggc tgcagtgtcg    180 ctgcagcgtc tcggggggc cgttcggggg atggagaagg atgccccggc ggggttgatc    240
gctcccccac ccctggacag cgctcgccga aggagtgatt ctcagaaatt ctacgaaatc    300
tccataggtg gttcagtctg agcgttggca agcaaaaacc agtcaaaact ttcaacaacg    360
gatctcttgg ttccggcatc gatgaagaac gcagcgaaat gc                       402

<210> SEQ ID NO 227
<211> LENGTH: 186
<212> TYPE: DNA
<213> ORGANISM: Unknown
<220> FEATURE:
<223> OTHER INFORMATION: genus Microsporum

<400> SEQUENCE: 227
tccggccgca cgcccattct tgtctactga cccggttgcc tcggcgggcc gcgcctgctg    60
tgctacagcg gccgttcggg ggggacgcct gagggggact cttgtttcct aggccacgcc    120
ccgggcagcg ctcgccggag gattactctg gaaaacacac tcttgaaaga acataccgtc    180
tgagcg                                                               186

<210> SEQ ID NO 228
<211> LENGTH: 157
<212> TYPE: DNA
<213> ORGANISM: Nanissia gypsia

<400> SEQUENCE: 228
```

```
gccggccaca cgcccattct tgtctattta cccagttgcc tcggcgggcc gcgcactcgt    60
gccgcgcctc gaggagccgt ccggggacaa tcaactccct ggatcgcgcc cgccggagga   120
gtgattaaaa tccatgaata ctgttccgtc tgagcgt                            157
```

<210> SEQ ID NO 229
<211> LENGTH: 283
<212> TYPE: DNA
<213> ORGANISM: Unknown
<220> FEATURE:
<223> OTHER INFORMATION: genus Acremonium

<400> SEQUENCE: 229

```
cgcacattgc gcccgccagt attctggcgg gcatgcctgt ctgagcgtca tttcaaccct    60
caggacccgt tcgcgggacc tggcgttggg gatcagcctg ccctggcgg cggctggccc    120 tgaaatacag tggcggttcc ctcgcgaact cctccgtgca gtaattaaac ctctcgcggc   180
aggatagcgg ttgaaccacg ccgttaaacc ccccacttct caaggttgac ctcagatcag   240
gtaggaatac ccgctgaact taagcatatc aataagcgga gga                     283
```

<210> SEQ ID NO 230
<211> LENGTH: 269
<212> TYPE: DNA
<213> ORGANISM: Unknown
<220> FEATURE:
<223> OTHER INFORMATION: genus Alternaria

<400> SEQUENCE: 230

```
cgcacattgc gcccttggt attccaaagg gcatgcctgt tcgagcgtca tttgtaccct    60
caagctttgc ttggtgttgg gcgtcttgtc tctagctttg ctggagactc gccttaaagt   120
aattggcagc cggcctactg gtttcggagc gcagcacaag tcgcactctc tatcagcaaa   180
ggtctagcat ccattaagcc tttttttcaac ttttgacctc ggatcaggta gggataccccg   240 ctgaacttaa gcatatcaat aagcggagg                                     269
```

<210> SEQ ID NO 231
<211> LENGTH: 463
<212> TYPE: DNA
<213> ORGANISM: Unknown
<220> FEATURE:
<223> OTHER INFORMATION: genus Aspergillus

<400> SEQUENCE: 231

```
cgcacattgc gcccctggt attccggggg gcatgcctgt ccgagcgtca ttgctgccca    60
tcaagcacgg cttgtgtgtt gggtcgtcgt ccctctccg gggggacgg gccccaaagg   120 cagcggcggc accgcgtccg atcctcgagc gtatgggct ttgtcacccg ctctgtaggc   180
ccggccggcg cttgccgaac gcaaatcaat cttttttccag gttgacctcg gatcaggtag   240
ggatacccgc tgaacttaag catatcaata agcggaggaa aagaaaccaa ccgggattgc   300
ctcagtaacg gcgagtgaag cggcaagagc tcaaatttga agctggctc cttcggggtc   360 cgcattgtaa tttgcagagg atgcttcggg tgcggcccct gtctaagtgc cctggaacgg   420
gccgtcagag agggtgagaa tcccgtctgg gatgggtgt ccg                      463
```

<210> SEQ ID NO 232
<211> LENGTH: 236
<212> TYPE: DNA
<213> ORGANISM: Unknown
<220> FEATURE:

<223> OTHER INFORMATION: genus Curvularia

<400> SEQUENCE: 232

```
cgcacattgc gcccttttggt attccaaagg gcatgcctgt tcgagcgtca tttgtaccct      60
caagctttgc ttggtgttgg gcgttttttg tctttggttg ccaaagactc gccttaaaag     120
gattggcagc cggcctactg gtttcgcagc gcagcacatt tttgcgcttg caatcagcaa     180
aagaggacgg caatccatca agactccttc tcacgttgac ctcggatcag gtaggg         236
```

<210> SEQ ID NO 233
<211> LENGTH: 228
<212> TYPE: DNA
<213> ORGANISM: Fusarium oxyporum

<400> SEQUENCE: 233

```
cagcggaggg atcattaccg agtttacaac tcccaaaccc ctgtgaacat accacttgtt      60
gcctcggcgg atcagcccgc tcccggtaaa acgggacggc ccgccagagg acccctaaac     120
tctgtttcta tatgtaactt ctgagtaaaa ccataaataa atcaaaactt tcaacaacgg     180
atctcttggt tctggcatcg atgaagaacg cagcaaaatg cgataagt                  228
```

<210> SEQ ID NO 234
<211> LENGTH: 227
<212> TYPE: DNA
<213> ORGANISM: Fusarium solani

<400> SEQUENCE: 234

```
cagcggaggg atcattaccg agttatacaa ctcatcaacc ctgtgaacat acctaaaacg      60
ttgcttcggc gggaacagac ggccccgtaa caacgggccg ccccgccag aggacccta      120
actctgtttc tataatgttt cttctgagta aacaagcaaa taaattaaaa ctttcaacaa     180
cggatctctt ggctctggca tcgatgaaga acgcagcgaa atgcgat                   227
```

<210> SEQ ID NO 235
<211> LENGTH: 301
<212> TYPE: DNA
<213> ORGANISM: Unknown
<220> FEATURE:
<223> OTHER INFORMATION: genus Scopulariopsis

<400> SEQUENCE: 235

```
cgcacattgc gcccggcagc aatctgccgg gcatgcctgt ccgagcgtca tttcttccct      60
cgagcgcggc tagccctacg gggcctgccg tcgcccggtg ttggggctct acgggtgggg     120
ctcgtccccc ccgcagtccc cgaaatgtag tggcggtcca gccgcggcgc ccctgcgta     180
gtagatccta catctcgcat cgggtcccgg cgaaggccag ccgtcgaacc ttttatttca     240
tggtttgacc tcggatcagg tagggttacc cgctgaactt aagcatatca ataagcggag     300
g                                                                     301
```

<210> SEQ ID NO 236
<211> LENGTH: 345
<212> TYPE: DNA
<213> ORGANISM: Unknown
<220> FEATURE:
<223> OTHER INFORMATION: genus Scytalidium

<400> SEQUENCE: 236

```
ggacgatccg cagccaagcc cctacgtcca gccggcctgg atacggggaa ggttcacaga      60
ctaagtggaa gtgggtgcgg cctccggcc gcgcttaaga tatagtcggg ccccagcga      120
```

```
aagctggggg gtaagtcact gcgacgagag ccgttccgta ggtgaacctg cggaaggatc    180
attaccgagt tgattcgggc tccggcccga tcctcccacc ctttgtgtac ccacctctgt    240
tgctttggcg ggccgcggtc ctccgcggcc gccctccgtc cggggggtgg ccagcgcccg    300
ccagaggacc atcgaactcc ggtcagtgaa cgttgccgtc tgaaa                    345
```

<210> SEQ ID NO 237
<211> LENGTH: 309
<212> TYPE: DNA
<213> ORGANISM: Candida albicans

<400> SEQUENCE: 237

```
tttgaacgca cattgcgccc tctggtattc cggagggcat gcctgtttga gcgtcgtttc     60
tccctcaaac cgctgggttt ggtgttgagc aatacgactt gggtttgctt gaaagacggt    120
agtggtaagg cgggatcgct ttgacaatgg cttaggtcta ccaaaaacat tgcttgcggc    180
ggtaacgtcc accacgtata tcttcaaact ttgacctcaa atcaggtagg actacccgct    240
gaacttaagc atatcaataa gcggaggaaa agaaaccaac agggattgcc tcagtagcgg    300
cgagtgaag                                                            309
```

<210> SEQ ID NO 238
<211> LENGTH: 283
<212> TYPE: DNA
<213> ORGANISM: Candida parapsilosis

<400> SEQUENCE: 238

```
tttgaacgca cattgcgccc tttggtattc caaagggcat gcctgtttga gcgtcatttc     60
tccctcaaac cctcgggttt ggtgttgagc gatacgctgg gtttgcttga agaaaggcg    120 gagtataaac taatggatag gttttttcca ctcattggta caaactccaa aacttcttcc    180
aaattcgacc tcaaatcagg taggactacc cgctgaactt aagcatatca ataagcggag    240
gaaaagaaac caacagggat tgccttagta gcggcgagtg aag                      283
```

<210> SEQ ID NO 239
<211> LENGTH: 299
<212> TYPE: DNA
<213> ORGANISM: Candida tropicalis

<400> SEQUENCE: 239

```
tttgaacgca cattgcgccc tttggtattc caaagggcat gcctgtttga gcgtcatttc     60
tccctcaaac ccccgggttt ggtgttgagc aatacgctag gtttgtttga aagaatttaa    120
cgtggaaact tattttaagc gacttaggtt tatccaaaac gcttattttg ctagtggcca    180
ccacaattta tttcataact ttgacctcaa atcaggtagg actacccgct gaacttaagc    240
atatcaataa gcggaggaaa agaaaccaac agggattgcc ttagtagcgg cgagtgaag    299
```

<210> SEQ ID NO 240
<211> LENGTH: 312
<212> TYPE: DNA
<213> ORGANISM: Unknown
<220> FEATURE:
<223> OTHER INFORMATION: genus Trichosporon

<400> SEQUENCE: 240

```
gaattcagtg aatcatcgaa tctttgaacg cagcttgcgc tctctggtat tccggagagc     60
atgcctgttt cagtgtcatg aaatctcaac cactagggtt tcctaatgga ttggatttgg    120
```

```
gcgtctgcga tttctgatcg ctcgccttaa aagagttagc aagtttgaca ttaatgtctg      180
gtgtaataag tttcactggg tccattgtgt tgaagcgtgc ttctaatcgt ccgcaaggac      240
aattactttg actctggcct gaaatcaggt aggactaccc gctgaactta agcatatcaa      300
taagcggagg aa                                                          312

<210> SEQ ID NO 241
<211> LENGTH: 306
<212> TYPE: DNA
<213> ORGANISM: Unknown
<220> FEATURE:
<223> OTHER INFORMATION: genus Trichosporon

<400> SEQUENCE: 241
gaattcagtg aatcatcgaa tctttgaacg caacttgcgc tctctggtat tccggagagc       60
atgcctgttt gagtatcatg aaatctcaac cattagggtt tcttaatggc ttggatttgg      120
gcgctgccac ttgcctggct cgccttaaaa gagttagcgt attaacttgt cgatctggcg      180
taataagttt cgctggtgta gacttgagaa gtgcgcttct aatcgtcttc ggacaattct      240
tgaactctgg tctcaaatca ggtaggacta cccgctgaac ttaagcatat caataagcgg      300
aggaaa                                                                 306

<210> SEQ ID NO 242
<211> LENGTH: 350
<212> TYPE: DNA
<213> ORGANISM: Candida guilliermondii

<400> SEQUENCE: 242
tttgaacgca cattgcgccc tctggtattc cagagggcat gcctgtttga gcgtcatttc       60
tctctcaaac ccccgggttt ggtattgagt gatactctta gtcggactag gcgttgcttg      120
aaaagtattg gcatgggtag tactagatag tgctgtcgac ctctcaatgt attaggttta      180
tccaactcgt tgaatggtgt ggcgggatat ttctggtatt gttggcccgg ccttacaaca      240
accaaacaag tttgacctca aatcaggtag gaatacccgc tgaacttaag catatcaata      300
agcggaggaa aagaaaccaa cagggattgc cttagtagcg gcgagtgaag                 350

<210> SEQ ID NO 243
<211> LENGTH: 301
<212> TYPE: DNA
<213> ORGANISM: Unknown
<220> FEATURE:
<223> OTHER INFORMATION: genus Malassezia

<400> SEQUENCE: 243
tacaagggag tgaaaacatc cgtgaaatac cttgatatat tgaaatgaat ggcttattta       60
ttaaaagaca gtgtcagatg gtcagtttta ctggggcggt agcctctaaa aaagtatcag      120
aggccttcaa aggtatattt aaattggtcg gaaccaatg gaataatagt attctatcaa       180
aatgtaatga taaagtatgc tttactgaaa gattgataaa tcgatcagtt acgcaagtag      240
gatatagtga tccgatgatt cagaatggaa tgatcatcgc tcaagaaata aaagttacgc      300
t                                                                      301

<210> SEQ ID NO 244
<211> LENGTH: 366
<212> TYPE: DNA
<213> ORGANISM: Unknown
<220> FEATURE:
<223> OTHER INFORMATION: Cryptococcus neoformans, Cryptococcus gatti
```

```
<400> SEQUENCE: 244
aacgcagcga aatgcgataa gtaatgtgaa ttgcagaatt cagtgaatca tcgagtcttt      60
gaacgcaact tgcgcccttt ggtattccga agggcatgcc tgtttgagag tcatgaaaat     120
ctcaatccct cgggttttat tacctgttgg acttggattt gggtgtttgc cgcgacctgc     180
aaaggacgtc ggctcgcctt aaatgtgtta gtgggaaggt gattacctgt cagcccggcg     240
taataagttt cgctgggcct atggggtagt cttcggcttg ctgataacaa ccatctcttt     300
ttgtttgacc tcaaatcagg tagggctacc cgctgaactt aagcatatca ataagcgaaa     360
gaatga                                                                366

<210> SEQ ID NO 245
<211> LENGTH: 397
<212> TYPE: DNA
<213> ORGANISM: Cryptococcus albidus

<400> SEQUENCE: 245
aacgcagcga aatgcgataa gtaatgtgaa ttgcagaatt cagtgaatca tcgaatcttt      60
gaacgcacct tgcgctcctt ggtattccga ggagcatgcc tgtttgagtg tcatgaaaac     120
cctcaaccct agattggtta aaacctttct ttggtttgga tttggacgtt tgccgatgat     180
aagtcggctc gtcttaaaag taatagctgg atctgtctcg cgacatggtt tgacttggcg     240
taataagtat ttcgctaagg acatcttcgg atggccgcgt tgcaggacta aagaccgctt     300
tctaatccat tgatcttcgg attaatactc ttgacatctg gcctcaaatc aagtaggact     360
acccgctgaa cttaagcata tcaataagcg gaggaaa                              397

<210> SEQ ID NO 246
<211> LENGTH: 342
<212> TYPE: DNA
<213> ORGANISM: Cryptococcus laurentii

<400> SEQUENCE: 246
aacgcagcga aatgcgataa gtaatgtgaa ttgcagaatt cagtgaatca tcgaatcttt      60
gaacgcacct tgcgcctttt ggtattccga aaggcatgcc tgtttgagtg tcatgaaatc     120
tcaatccccc tgggtttatg atctgggtcg gacttggaaa tgggcgtctg ccggtcacac     180
ggctcgcctc aaatgactta gtggatctct ctgcatccgt gacagacgta ataagtttcg     240
tcttgtccct tgcttatgag tctgctcata acctgccatc gcgcacttttt agactctgac   300 ctcaaatcag gtaggactac ccgctgaact taagcatatc at                        342
```

METHODS OF SCREENING FOR CAUSATIVE AGENTS OF ONYCHODYSTROPHY

CROSS-REFERENCING

This application claims the benefit of U.S. provisional application Ser. No. 62/810,304, filed on Feb. 25, 2019, which application is incporated by reference herein.

INTRODUCTION

Onychomycosis is the clinical term for a fungal infection of the nail. It constitutes an important public health problem due to its high incidence, increasing prevalence (10% and rising in the U.S. population and has been shown to be more widespread in older individuals.) and associated complications. Persons with onychomycosis have shown to be at increased risk to develop cellulitis, skin ulcerations, both of which may lead to loss of digits or limb. Contributing to the risk of associated complications related to this infection is the fact that it is most prevalent among persons who are most susceptible to serious bacterial infections, to wit, elderly individuals, type 1 and type 2 diabetics, and persons who are otherwise immunocompromised. In addition to advanced age, and immunological deficiencies, additional predisposing factors are chronic microtrauma to the nail apparatus, onycholysis, onychoschezia, and genetic predispositions. The pathogens most commonly associated with onychomycosis belong to three genera designated as the dermatophytes, saprophytic molds, and yeasts. The identification of a dermatophyte, among which *Trichophyton rubrum* and *Trichophyton interdigitale/mentagrophytes* are commonly isolated species, in keratin is always indicative of infection. To a lesser extent, saprophytic molds such as *Aspergillus*, *Acremonium* and *Alternaria*, and yeasts including *Candida* species, may infect the nail unit, and may be seen either as a primary cause of infection, or as a surface contaminant. Yeasts, including *Candidas, Malassezia, Trichosporon*, and *Cryptococcus* are more likely to be associated with fingernail infections, and their incidence is rising in North America.

SUMMARY

Provided herein is a method of detecting, in a sample, an agent causing onychodystrophy, wherein the agent causing onychodystrophy belongs to a secondary clade member including one or more primary clade members. The method includes i) screening a sample using at least a first and second set of secondary clade-specific primers to determine whether a secondary clade member among a plurality of secondary clade members is present or absent in the sample, wherein the plurality of secondary clade members includes a dermatophyte, a yeast, and a saprophyte, wherein the screening includes: performing a first real time polymerase chain reaction (PCR) in a first reaction mixture using the first set of secondary clade-specific primers and a first hydrolysis probe specific for a DNA region amplified by the first set of secondary clade-specific primers, the first hydrolysis probe including a fluorescent reporter dye and a quencher; and performing a second real time PCR in a second reaction mixture using the second set of secondary clade-specific primers and a second hydrolysis probe specific for a DNA region amplified by the second set of secondary clade-specific primers, the second hydrolysis probe including a fluorescent reporter dye and a quencher; and ii) if the secondary clade member is determined to be present in the sample, performing a second screen of the sample to determine whether an agent causing onychodystrophy is present or absent in the sample using primary clade-specific primers that are specific to a primary clade member that belongs to the secondary clade member, wherein the second screen includes performing at least a third real time PCR in a third reaction mixture using the primary clade-specific primers and a third hydrolysis probe specific for a DNA region amplified by the primary clade-specific primers, the third hydrolysis probe including a fluorescent reporter dye and a quencher.

Also provided herein, is a method of detecting a yeast and/or a dermatophyte in a sample, the method including i) screening a sample using at least a first set of yeast-specific primers and at least first set of dermatophyte-specific primers to determine whether a yeast and/or dermatophyte is present or absent in the sample, wherein the screening includes: performing a first real time polymerase chain reaction (PCR) in a first reaction mixture using the first set of yeast-specific primers and a first hydrolysis probe specific for a DNA region amplified by the first set of yeast-specific primers, the first hydrolysis probe including a fluorescent reporter dye and a quencher; and performing a second real time PCR in a second reaction mixture using the first set of dermatophyte-specific primers and a second hydrolysis probe specific for a DNA region amplified by the first set of dermatophyte-specific primers, the second hydrolysis probe including a fluorescent reporter dye and a quencher; and ii) if the yeast and/or dermatophyte is determined to be present in the sample, performing a second screen of the sample to determine whether a genus and/or species of the yeast and/or dermatophyte is present or absent in the sample using yeast and/or dermatophyte genus and/or species-specific primers, wherein the second screen includes performing at least a third real time PCR in a third reaction mixture using the yeast and/or dermatophyte genus and/or species-specific primers and a third hydrolysis probe specific for a DNA region amplified by the yeast and/or dermatophyte genus and/or species-specific primers, the third hydrolysis probe including a fluorescent reporter dye and a quencher.

Also provided herein, is a method of detecting a saprophyte and/or *Pseudomonas aeruginosa* in a sample, the method including: i) screening a sample using at least a first set of saprophyte-specific primers and at least first set of *Pseudomonas aeruginosa*-specific primers to determine whether a saprophyte and/or *Pseudomonas aeruginosa* is present or absent in the sample, wherein the screening includes: performing a first real time polymerase chain reaction (PCR) in a first reaction mixture using the first set of saprophyte-specific primers and a first hydrolysis probe specific for a DNA region amplified by the first set of saprophyte-specific primers, the first hydrolysis probe including a fluorescent reporter dye and a quencher; and performing a second real time PCR in a second reaction mixture using the first set of *Pseudomonas aeruginosa*-specific primers and a second hydrolysis probe specific for a DNA region amplified by the first set of *Pseudomonas aeruginosa*-specific primers, the second hydrolysis probe including a fluorescent reporter dye and a quencher; and ii) if the saprophyte is determined to be present in the sample, performing a second screen of the sample to determine whether a genus and/or species of the saprophyte is present or absent in the sample using saprophyte genus and/or species-specific primers, wherein the second screen includes performing at least a third real time PCR in a third reaction mixture using the saprophyte genus and/or species-specific primers and a third hydrolysis probe specific for a DNA region amplified by the saprophyte genus and/or species-specific primers, the third hydrolysis probe including a fluorescent reporter dye and a quencher.

Kits and compositions including the primers and hydrolysis probes utilized in the methods described herein are also provided.

BRIEF DESCRIPTION OF THE DRAWINGS

Figure 7:
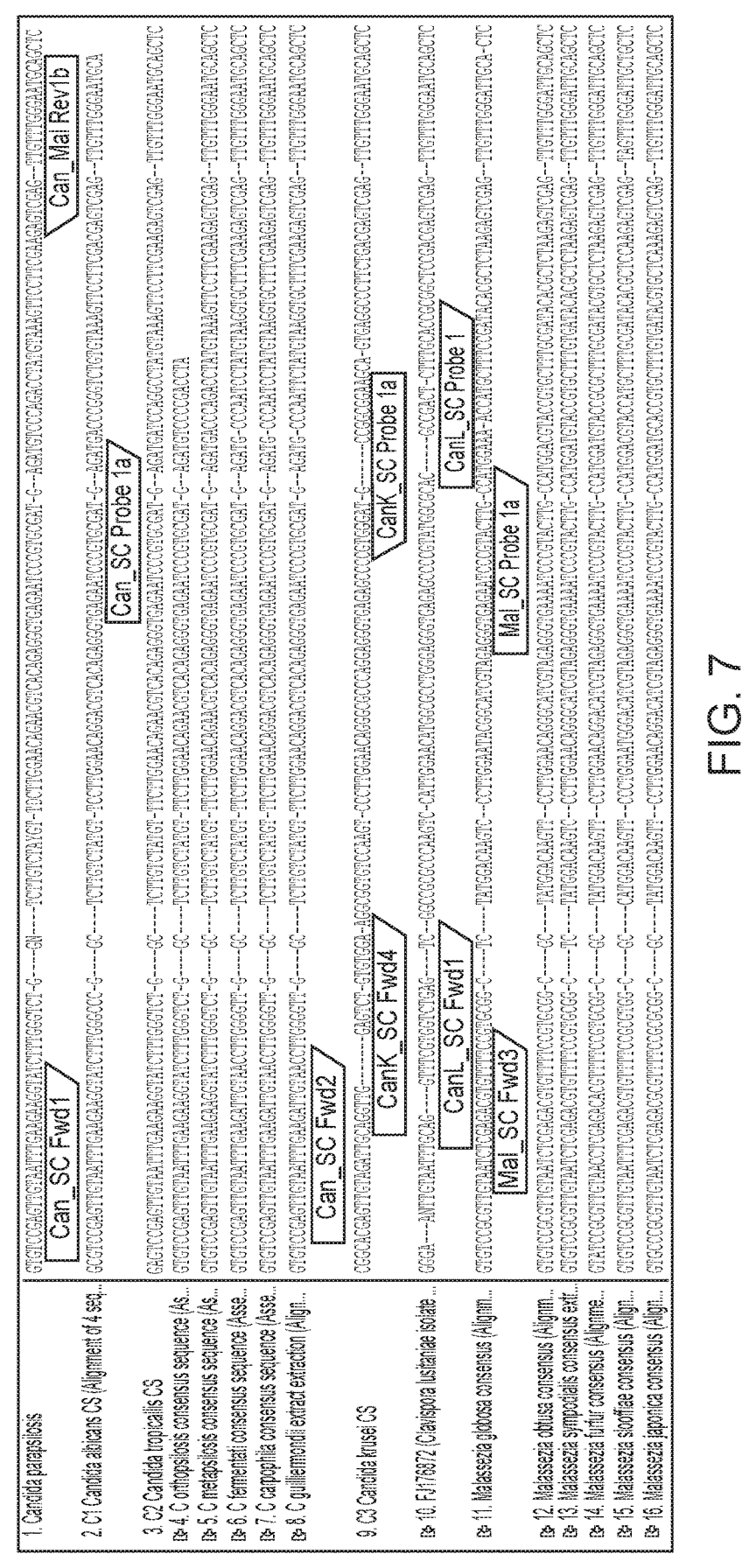

FIG. 7 shows alignments to genomic regions of primers and probes targeting the 28SrRNA gene in *Candida* spp. and *Malassezia* spp. In addition to the forward primers and probes, a universal reverse primer was designed for both *Candida* and *Malassezia*, according to embodiments of the present disclosure. The sequences are set forth from top to bottom as SEQ ID NOs: 132-147.

Figure 8:
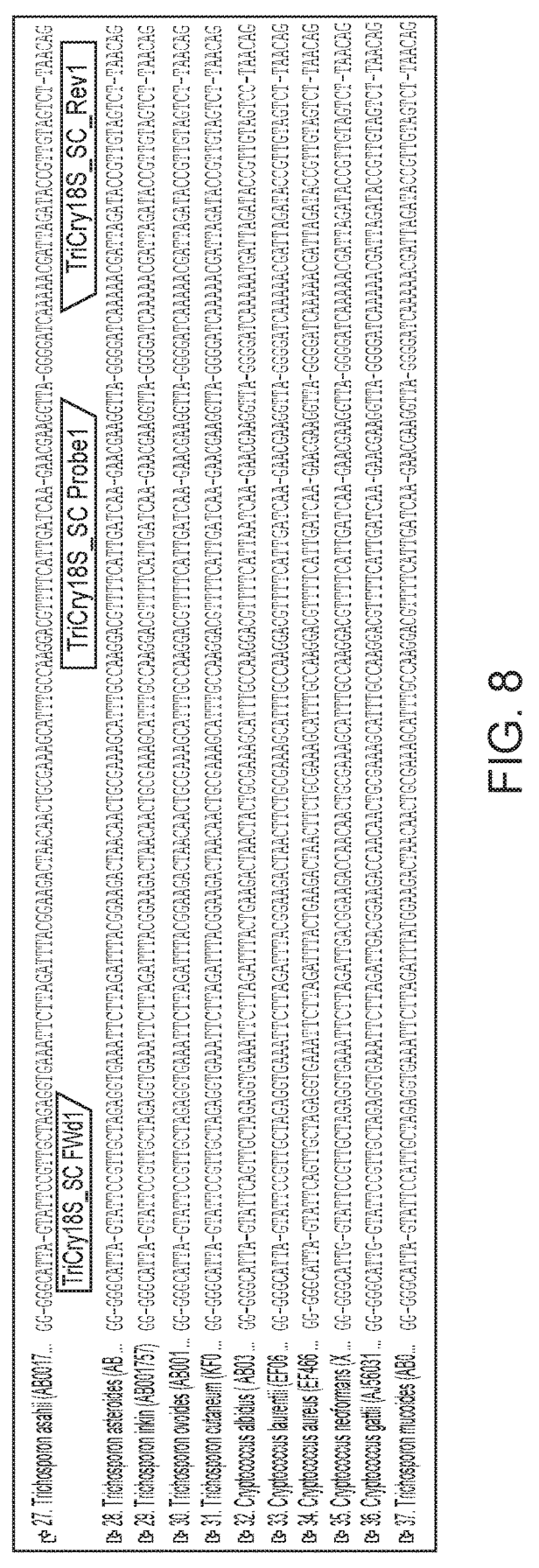

FIG. 8 shows alignments to genomic regions of primers and a probe targeting the 28S rRNA gene for *Trichosporon* and *Cryptcoccus* in *Trichosporon* spp. and *Cryptcoccus* spp. A set of universal primers and probe were designed for the detection of both *Trichosporon* and *Cryptcoccus*, according to embodiments of the present disclosure. The sequences are set forth from top to bottom as SEQ ID NOs: 148-158.

FIG. 12 shows alignments to genomic regions of primers and probes targeting *Epidermophyton*, according to embodiments of the present disclosure. The sequence is set forth as SEQ ID NO: 162.

FIG. 14 shows alignments to genomic regions of primers and probes targeting *Acremonium*, according to embodiments of the present disclosure. The sequence is set forth as SEQ ID NO: 166.

FIG. 15 shows alignments to genomic regions of primers and probes targeting *Alternaria*, according to embodiments of the present disclosure. The sequence is set forth as SEQ ID NO: 167.

FIG. 17 shows alignments to genomic regions of primers and probes targeting *Curvularia*, according to embodiments of the present disclosure. The sequence is set forth as SEQ ID NO: 169.

Figure 25:
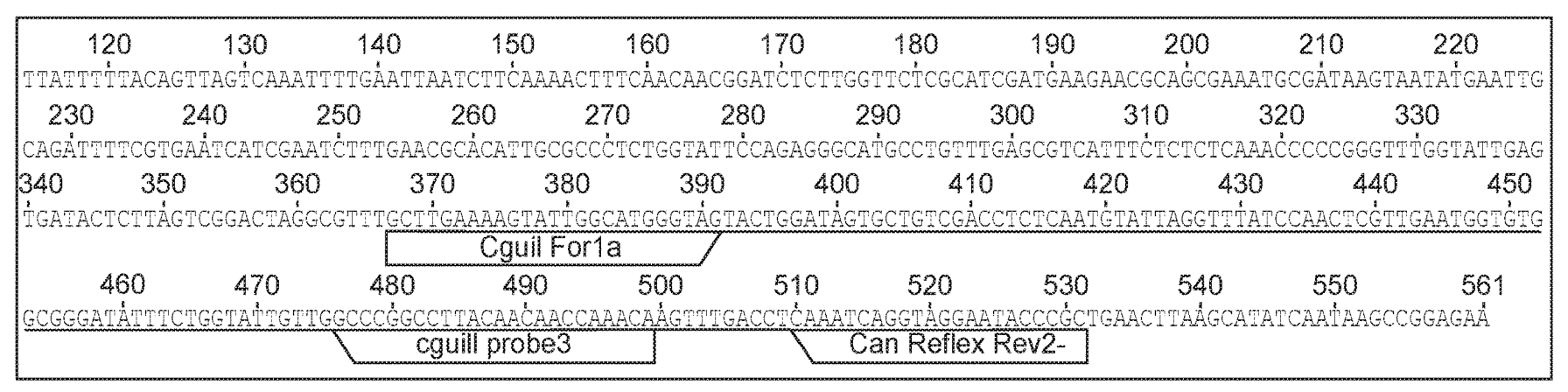

FIG. 25 shows alignments to genomic regions of primers and probes targeting the ITS2 gene in *Candida guilliermodii*, according to embodiments of the present disclosure. The sequence is set forth as SEQ ID NO: 185.

FIG. 28 shows primer (underlined) and probe (wavy underlined) binding sites for a Dermatophyte screen according to embodiments of the present disclosure. The sequence is set forth as SEQ ID NO: 202.

FIG. 29 shows a target sequence, including primer (underlined) and probe (wavy underlined) binding sites for a Dermatophyte screen according to embodiments of the present disclosure. The sequence is set forth as SEQ ID NO: 203.

FIG. 30 shows a target sequence, including primer (underlined) and probe (wavy underlined) binding sites for a Saprophyte screen according to embodiments of the present disclosure. The sequence is set forth as SEQ ID NO: 204.

FIG. 31 shows a target sequence, including primer (underlined) and probe (wavy underlined) binding sites for a Saprophyte screen according to embodiments of the present disclosure. The sequence is set forth as SEQ ID NO: 205.

FIG. 32 shows a target sequence, including primer (underlined) and probe (wavy underlined) binding sites for a Saprophyte screen according to embodiments of the present disclosure. The sequence is set forth as SEQ ID NO: 206.

FIG. 33 shows a target sequence, including primer (underlined) and probe (wavy underlined) binding sites for a Saprophyte screen according to embodiments of the present disclosure. The sequence is set forth as SEQ ID NO: 207.

FIG. 34 shows a target sequence, including primer (underlined) and probe (wavy underlined) binding sites for a Saprophyte screen according to embodiments of the present disclosure. The sequence is set forth as SEQ ID NO: 208.

FIG. 35 shows a target sequence, including primer (underlined) and probe (wavy underlined) binding sites for a Saprophyte screen according to embodiments of the present disclosure. The sequence is set forth as SEQ ID NO: 209.

FIG. 36 shows a target sequence, including primer (underlined) and probe (wavy underlined) binding sites for a Saprophyte screen according to embodiments of the present disclosure. The sequence is set forth as SEQ ID NO: 210.

FIG. 37 shows a target sequence, including primer (underlined) and probe (wavy underlined) binding sites for a Yeast screen according to embodiments of the present disclosure. The sequence is set forth as SEQ ID NO: 211.

FIG. 38 shows primer (underlined) and probe (wavy underlined) binding sites for a Yeast screen according to embodiments of the present disclosure. The sequence is set forth as SEQ ID NO: 212.

FIG. 39 shows a target sequence, including primer (underlined) and probe (wavy underlined) binding sites for a Yeast screen according to embodiments of the present disclosure. The sequence is set forth as SEQ ID NO: 213.

FIG. 40 shows primer (underlined) and probe (wavy underlined) binding sites for a Yeast screen according to embodiments of the present disclosure. The sequence is set forth as SEQ ID NO: 214.

FIG. 41 shows a target sequence, including primer (underlined) and probe (wavy underlined) binding sites for a Yeast screen according to embodiments of the present disclosure. The sequence is set forth as SEQ ID NO: 215.

FIG. 42 shows primer (underlined) and probe (wavy underlined) binding sites for a Yeast screen according to embodiments of the present disclosure. The sequence is set forth as SEQ ID NO: 216.

FIG. 43 shows a target sequence, including primer (underlined) and probe (wavy underlined) binding sites for a Yeast screen according to embodiments of the present disclosure. The sequence is set forth as SEQ ID NO: 217.

FIG. 44 shows primer (underlined) and probe (wavy underlined) binding sites for a Yeast screen according to embodiments of the present disclosure. The sequence is set forth as SEQ ID NO: 218.

FIG. 45 shows a target sequence, including primer (underlined) and probe (wavy underlined) binding sites for a Yeast screen according to embodiments of the present disclosure. The sequence is set forth as SEQ ID NO: 219.

FIG. 46 shows primer (underlined) and probe (wavy underlined) binding sites for a Yeast screen according to embodiments of the present disclosure. The sequence is set forth as SEQ ID NO: 220.

FIG. 47 shows a target sequence, including primer (underlined) and probe (wavy underlined) binding sites for a Yeast screen according to embodiments of the present disclosure. The sequence is set forth as SEQ ID NO: 221.

FIG. 48 shows primer (underlined) and probe (wavy underlined) binding sites for a *Pseudomonas aeruginosa* screen according to embodiments of the present disclosure. The sequence is set forth as SEQ ID NO: 222.

FIG. 49 shows a target sequence, including primer (underlined) and probe (wavy underlined) binding sites for a *Pseudomonas aeruginosa* screen according to embodiments of the present disclosure. The sequence is set forth as SEQ ID NO: 223.

FIG. 50 shows primer (underlined) and probe (wavy underlined) binding sites for a Dermatophyte reflex test according to embodiments of the present disclosure. The sequence is set forth as SEQ ID NO: 224.

FIG. 51 shows primer (underlined) and probe (wavy underlined) binding sites for a Dermatophyte reflex test according to embodiments of the present disclosure. The sequence is set forth as SEQ ID NO: 225.

FIG. 52 shows primer (underlined) and probe (wavy underlined) binding sites for a Dermatophyte reflex test according to embodiments of the present disclosure. The sequence is set forth as SEQ ID NO: 226.

FIG. 53 shows primer (underlined) and probe (wavy underlined) binding sites for a Dermatophyte reflex test according to embodiments of the present disclosure. The sequence is set forth as SEQ ID NO: 227.

FIG. 54 shows primer (underlined) and probe (wavy underlined) binding sites for a Dermatophyte reflex test according to embodiments of the present disclosure. The sequence is set forth as SEQ ID NO: 228.

FIG. 55 shows primer (underlined) and probe (wavy underlined) binding sites for a Saprophyte reflex test according to embodiments of the present disclosure. The sequence is set forth as SEQ ID NO: 229.

FIG. 56 shows primer (underlined) and probe (wavy underlined) binding sites for a Saprophyte reflex test according to embodiments of the present disclosure. The sequence is set forth as SEQ ID NO: 230.

FIG. 57 shows primer (underlined) and probe (wavy underlined) binding sites for a Saprophyte reflex test according to embodiments of the present disclosure. The sequence is set forth as SEQ ID NO: 231.

FIG. 58 shows primer (underlined) and probe (wavy underlined) binding sites for a Saprophyte reflex test according to embodiments of the present disclosure. The sequence is set forth as SEQ ID NO: 232.

FIG. 59 shows primer (underlined) and probe (wavy underlined) binding sites for a Saprophyte reflex test according to embodiments of the present disclosure. The sequence is set forth as SEQ ID NO: 233.

FIG. 60 shows primer (underlined) and probe (wavy underlined) binding sites for a Saprophyte reflex test according to embodiments of the present disclosure. The sequence is set forth as SEQ ID NO: 234.

FIG. 61 shows primer (underlined) and probe (wavy underlined) binding sites for a Saprophyte reflex test according to embodiments of the present disclosure. The sequence is set forth as SEQ ID NO: 235.

FIG. 62 shows primer (underlined) and probe (wavy underlined) binding sites for a Saprophyte reflex test according to embodiments of the present disclosure. The sequence is set forth as SEQ ID NO: 236.

FIG. 63 shows primer (underlined) and probe (wavy underlined) binding sites for a Yeast reflex test according to embodiments of the present disclosure. The sequence is set forth as SEQ ID NO: 237.

FIG. 64 shows primer (underlined) and probe (wavy underlined) binding sites for a Yeast reflex test according to embodiments of the present disclosure. The sequence is set forth as SEQ ID NO: 238.

FIG. 65 shows primer (underlined) and probe (wavy underlined) binding sites for a Yeast reflex test according to embodiments of the present disclosure. The sequence is set forth as SEQ ID NO: 239.

FIG. 66 shows primer (underlined) and probe (wavy underlined) binding sites for a Yeast reflex test according to embodiments of the present disclosure. The sequence is set forth as SEQ ID NO: 240.

FIG. 67 shows primer (underlined) and probe (wavy underlined) binding sites for a Yeast reflex test according to embodiments of the present disclosure. The sequence is set forth as SEQ ID NO: 241.

FIG. 68 shows primer (underlined) and probe (wavy underlined) binding sites for a Yeast reflex test according to embodiments of the present disclosure. The sequence is set forth as SEQ ID NO: 242.

FIG. 69 shows primer (underlined) and probe (wavy underlined) binding sites for a Yeast reflex test according to embodiments of the present disclosure. The sequence is set forth as SEQ ID NO: 243.

FIG. 70 shows primer (underlined) and probe (wavy underlined) binding sites for a Yeast reflex test according to embodiments of the present disclosure. The sequence is set forth as SEQ ID NO: 244.

FIG. 71 shows primer (underlined) and probe (wavy underlined) binding sites for a Yeast reflex test according to embodiments of the present disclosure. The sequence is set forth as SEQ ID NO: 245.

FIG. 72 shows primer (underlined) and probe (wavy underlined) binding sites for a Yeast reflex test according to embodiments of the present disclosure. The sequence is set forth as SEQ ID NO: 246.

FIG. 74 provides tables showing example OIAD Screen Assay Paramaters and OIAD Reflex Assay Parameters according to embodiments of the present disclosure.

FIG. 75 provides a table showing detailed results for OIAD Screen Assay Sensitivity.

FIG. 76 provides a table showing detailed results for OIAD Reflex Assays Sensitivity.

DEFINITIONS

Figure 1:
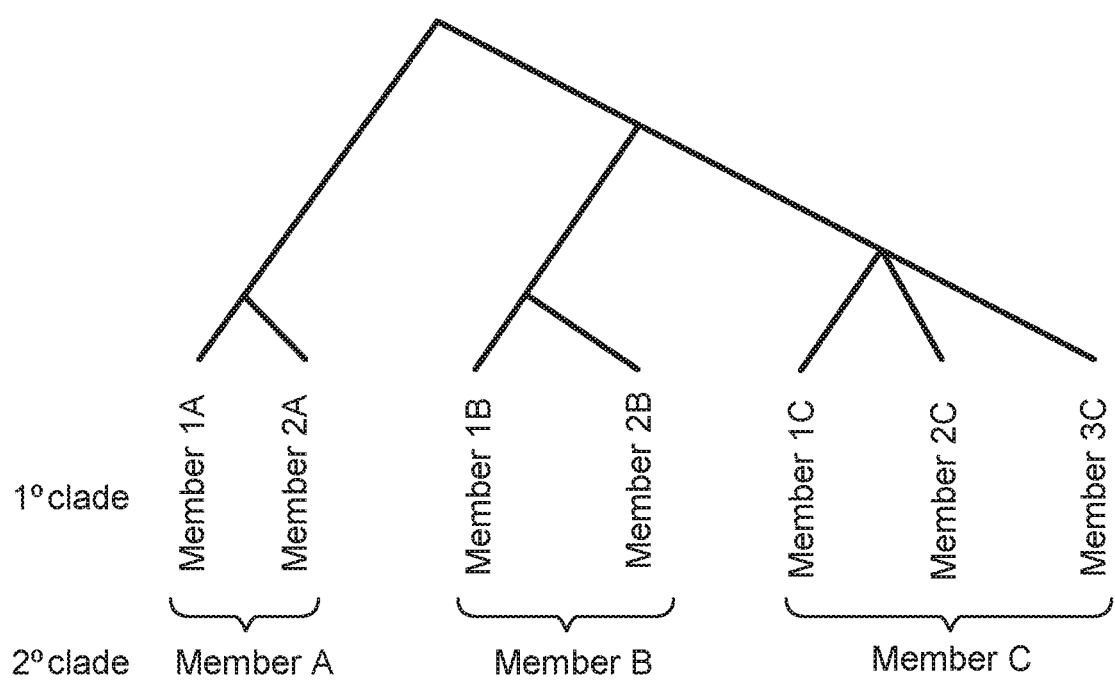
FIG. 1 schematically depicts an example of a relationship between primary and secondary clade members, according to embodiments of the present disclosure.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

Nucleotides, may be referred to by their commonly accepted single-letter codes, as defined in conformity with the IUPAC-IUBMB standards described in *Nucleic Acids Res.* 13:3021-3030 (1985) and in the *Biochemical J.* 219(2): 345-373 (1984) which are herein incorporated by reference. Nucleotide or nucleic acid sequences defined herein are represented by one-letter symbols for the bases as follows:

A (adenine);
C (cytosine);
G (guanine);
T (thymine);
U (uracil);
M (A or C);
R (A or G);
W (A or T/U);
S (C or G);
Y (C or T/U);
K (G or T/U);
V (A or C or G; not T/U);
H (A or C or T/U; not G);
D (A or G or T/U; not C);
B (C or G or T/U; not A);
N (A or C or G or T/U) or (unknown).

As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection.

As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Any suitable methods of alignment of sequences for comparison may be employed. Thus, the determination of percent identity between any two sequences can be accomplished using a mathematical algorithm. Preferred, non-limiting examples of such mathematical algorithms are the algorithm of Myers and Miller, CABIOS, 4:11 (1988), which is hereby incorporated by reference in its entirety; the local homology algorithm of Smith et al, Adv. Appl. Math., 2:482 (1981), which is hereby incorporated by reference in its entirety; the homology alignment algorithm of Needleman and Wunsch, J M B, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karhn and Altschul, Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST®, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al., CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST® programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST® analyses is publicly available through the National Center for Biotechnology Information (NCBI; www(dot)ncbi(dot)nlm(dot)nih(dot)gov).

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product," depending on the context.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

As used herein, the term "portion," when used in reference to a nucleotide sequence, refers to fragments of that sequence. The fragments may range in size from ten nucleotides to the entire nucleotide sequence minus one nucleotide (e.g., 10 nucleotides or more, 20 nucleotides or more, 50 nucleotides or more, 100 nucleotides or more, 1000 nucleotides or more, etc., up to the entire nucleotide sequence minus one nucleotide).

A "nuclear-encoded ribosomal RNA gene" as used herein, may refer to a nucleotide sequence of a nuclear genome of a cell, where the nucleotide sequence corresponds to a transcriptional unit of one or more ribosomal RNA (rRNA) coding regions. Where the transcriptional unit includes multiple rRNAs, the nucleotide sequence may include a nucleotide sequence of the internal transcribed spacer (ITS) region that is interposed between consecutive rRNA coding regions. In some embodiments, the nuclear-encoded rRNA gene includes an 18S rRNA, 5.8S rRNA, 28S rRNA and two ITS regions (ITS1 and ITS2). The nuclear-encoded rRNA gene may have a structure respresented by the formula: 5'-(18S)-(ITS1)-(5.8S)-(ITS2)-(28S)-3', where 18S is the 18S rRNA, 5.8S is the 5.8S rRNA, 28S is the 28S rRNA, ITS1 is the first ITS region, and ITS2 is the second ITS region.

As used herein, a "subject" refers to any animal, such as a mammal like a dog, cat, bird, livestock, and including a human.

A "set" may contain one or more elements that constitute the set.

"Within," as used in reference to a number being within a range of numbers, is meant to be inclusive of the values defining the upper and lower limits of the range.

"Onychomycosis" refers to a superficial fungal infection involving keratin of the nail unit of an animal, e.g., a human subject. An "Onychomycotic fungus" is the etiological agent for onychomycosis, and may include dermatophytes, *Candida* spp., and saprophytic molds.

As used herein, the term "agent causing onychodystrophy" refers to an infectious causative agent of onychodystrophy or an infectious agent associated with onychodystrophy, including, but not limited to an onychomycotic fungus, and certain bacteria, such as *Pseudomonas aereuginosa*.

"Onychodystrophy" generally refers to any alteration of nail morphology. Nail dystrophy may manifest as a misshapen, damaged, infected or discolored nail unit that may affect the toenails, fingernails or both.

A "dermatophyte" refers to a group of onychomycotic etiological agents that includes the genera *Trichophyton*, *Epidermophyton*, and *Microsporum*. Species within *Trichophyton* include, but are not limited to, *T. interdigitale/mentagrophytes* (which are allomorphs of the same species) and *T. rubrum*.

As used herein the term "yeast" includes organisms of the following genera: *Candida*, *Malassezia*, *Cryptococcus*, and *Trichosporon*.

"Saprophyte," and "saprophytic mold" are used interchangeably to refer to a group of onychomycotic etiological agents that is not a dermatophyte or a candida. A saprophyte may include, but is not limited to, the genera *Aspergillus*, *Acremonium*, *Alternaria*, *Penicillium*, *Paecilomyces*, *Fusarium*, *Scopulariopsis*, *Chaetomium*, *Curvularia*, *Mucor*, *Scytalidium* and *Rhizopus*.

A "clade," as used herein, refers to a group of organisms which share one or more feature(s) of a nucleic acid molecule(s) associated with an organism of the group. The nucleic acid molecule may be a DNA molecule, e.g., genomic DNA, mitochondrial DNA, etc., or a portion thereof, of the organism, or may be a RNA molecule, e.g., a transcribed RNA molecule, in the organism. The feature of the nucleic acid molecule shared by organisms in a clade may include structural features, such as sequence identity of a homologous nucleotide sequence contained in the nucleic acid molecule, or functional features, such as the melting temperature of an amplification product containing a homologous nucleotide sequence amplified from the nucleic acid molecule, or the melting temperature of a hybridization between an amplification product containing a homologous nucleotide sequence amplified from the nucleic acid molecule and a clade-specific hybridization probe. An organism that belongs to a specific clade will in general share all the features of the nucleic acid containing the nucleotide sequence that defines the clade with all other organisms in the same clade. Clades may be categorized by a level, where a clade of higher-numbered level (e.g., secondary clade) requires fewer shared nucleic acid features than a clade of lower-numbered level (e.g., primary clade). For example, a "primary" clade requires an organism share more nucleic acid features than required by a "secondary" clade. Thus, a primary clade will encompass fewer organisms than a secondary clade. In some cases, the clade of lowest-numbered level corresponds to a phylogenetic species. The features of the nucleic acids containing a nucleotide sequence defining a clade may include, but are not limited to, sequence identity, annealing/melting temperature with a selected nucleic acid, rate of PCR amplification by primers that amplify the nucleotide sequence, and/or combinations thereof.

A "clade member," as used herein, refers to a clade defined by a predetermined set of feature(s) (e.g., the sequence identity of a homologous nucleotide sequence, the melting temperature of an amplification product containing a homologous nucleotide sequence, etc., as described above) of a nucleic acid molecule associated with organisms belonging to the clade. A first clade member "contains" or "comprises" a second clade member, and conversely, the second clade member "belongs to" or "is within" the first clade member, when all the defining features of the first clade member is shared with the second clade member, but when defining features of the second clade member that are different from the defining features of the first clade member are not all shared by other clade members having all the defining features of the first clade member.

"Clade-specific," as used in reference to a clade-specific reagent, refers to a reagent (e.g., primer or probe) having the necessary structural properties to provide an empirical measurement, obtained by using the reagent, of one or more feature(s) of the nucleic acid defining the clade member, by which measurement the clade member can be differentiated from another clade members defined by different feature(s) of a nucleic acid defining the second clade member. In certain cases, a reagent specific to a first clade member does not provide information about the presence or absence of a second clade member that belongs to the first clade member and is at a level lower than the level of the first clade member. Thus, a secondary clade-specific detection reagent used to determine the presence of a secondary clade member may not allow determination of the presence or absence of a primary clade member that belongs to the secondary clade member.

"Hydrolysis probe," as used herein refers to an oligonucleotide labelled with a fluorescent reporter molecule on its 5' end and a quencher molecule on its 3' end. Hydrolysis probes take advantage of the 5' exonuclease activity of some polymerases. During the extension or elongation phase of a PCR reaction, a polymerase, such as Taq polymerase, uses an upstream primer as a binding site and then extends. The hydrolysis probe is then cleaved during polymerase extension at its 5' end by the 5'-exonuclease activity of the polymerase.

Before embodiments of the present disclosure are further described, it is to be understood that these embodiments of the present disclosure are not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges, and are also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of embodiments of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an onychomycotic fungus" includes a plurality of such onychomycotic fungi and reference to "the primer pair" includes reference to one or more primer pairs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the present disclosure, which are, for clarity, described in the context of separate embodiments, may also be provided in combination in a single embodiment. Conversely, various features of the present disclosure, which are, for brevity, described in the context of a single embodiment, may also be provided separately or in any suitable sub-combination. All combinations of the embodiments pertaining to the present disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

DETAILED DESCRIPTION

As summarized above, a method of detecting, in a sample, an agent causing onychodystrophy, wherein the agent causing onychodystrophy belongs to a secondary clade member including one or more primary clade members, is provided. The method includes i) screening a sample using at least a first and second set of secondary clade-specific primers to determine whether a secondary clade member among a plurality of secondary clade members is present or absent in the sample, wherein the plurality of secondary clade members includes a dermatophyte, a yeast, and a saprophyte, wherein the screening includes: performing a first real time polymerase chain reaction (PCR) in a first reaction mixture using the first set of secondary clade-specific primers and a first hydrolysis probe specific for a DNA region amplified by the first set of secondary clade-specific primers, the first hydrolysis probe including a fluorescent reporter dye and a quencher; and performing a second real time PCR in a second reaction mixture using the second set of secondary clade-specific primers and a second hydrolysis probe specific for a DNA region amplified by the second set of secondary clade-specific primers, the second hydrolysis probe including a fluorescent reporter dye and a quencher; and ii) if the secondary clade member is determined to be present in the sample, performing a second screen of the sample to determine whether an agent causing onychodystrophy is present or absent in the sample using primary clade-specific primers that are specific to a primary clade member that belongs to the secondary clade member, wherein the second screen includes performing at least a third real time PCR in a third reaction mixture using the primary clade-specific primers and a third hydrolysis probe specific for a DNA region amplified by the primary clade-specific primers, the third hydrolysis probe including a fluorescent reporter dye and a quencher.

The present disclosure also provides a method of detecting a yeast and/or a dermatophyte in a sample, the method including i) screening a sample using at least a first set of yeast-specific primers and at least first set of dermatophyte-specific primers to determine whether a yeast and/or dermatophyte is present or absent in the sample, wherein the screening includes: performing a first real time polymerase chain reaction (PCR) in a first reaction mixture using the first set of yeast-specific primers and a first hydrolysis probe specific for a DNA region amplified by the first set of yeast-specific primers, the first hydrolysis probe including a fluorescent reporter dye and a quencher; and performing a second real time PCR in a second reaction mixture using the first set of dermatophyte-specific primers and a second hydrolysis probe specific for a DNA region amplified by the first set of dermatophyte-specific primers, the second hydrolysis probe including a fluorescent reporter dye and a quencher; and ii) if the yeast and/or dermatophyte is determined to be present in the sample, performing a second screen of the sample to determine whether a genus and/or species of the yeast and/or dermatophyte is present or absent in the sample using yeast and/or dermatophyte genus and/or species-specific primers, wherein the second screen includes performing at least a third real time PCR in a third reaction mixture using the yeast and/or dermatophyte genus and/or species-specific primers and a third hydrolysis probe specific for a DNA region amplified by the yeast and/or dermatophyte genus and/or species-specific primers, the third hydrolysis probe including a fluorescent reporter dye and a quencher.

The present disclosure also provides a method of detecting a saprophyte and/or *Pseudomonas aeruginosa* in a sample, the method including: i) screening a sample using at least a first set of saprophyte-specific primers and at least first set of *Pseudomonas aeruginosa*-specific primers to determine whether a saprophyte and/or *Pseudomonas aeruginosa* is present or absent in the sample, wherein the screening includes: performing a first real time polymerase chain reaction (PCR) in a first reaction mixture using the first set of saprophyte-specific primers and a first hydrolysis probe specific for a DNA region amplified by the first set of saprophyte-specific primers, the first hydrolysis probe including a fluorescent reporter dye and a quencher; and performing a second real time PCR in a second reaction mixture using the first set of *Pseudomonas aeruginosa*-specific primers and a second hydrolysis probe specific for a DNA region amplified by the first set of *Pseudomonas aeruginosa*-specific primers, the second hydrolysis probe including a fluorescent reporter dye and a quencher; and ii) if the saprophyte is determined to be present in the sample, performing a second screen of the sample to determine whether a genus and/or species of the saprophyte is present or absent in the sample using saprophyte genus and/or species-specific primers, wherein the second screen includes performing at least a third real time PCR in a third reaction mixture using the saprophyte genus and/or species-specific primers and a third hydrolysis probe specific for a DNA region amplified by the saprophyte genus and/or species-specific primers, the third hydrolysis probe including a fluorescent reporter dye and a quencher.

Further aspects of the present disclosure are described now, with reference to the figures.

FIG. 1 shows a schematic diagram, showing an example of a relationship between individual members of a primary (1°) clade, which may correspond to, e.g., individual species or genera of fungi. The primary clade members may in turn be grouped into members of different secondary (2°) clades. Secondary clades are defined such that a primary clade member belongs to only one secondary clade. In some embodiments, where the primary clade member corresponds to a species, the secondary clade to which the primary clade member belongs may correspond to a genus, family, order, etc., or a subset thereof, e.g., of fungi. According to embodiments of the present disclosure, the relationship between members of the primary and secondary clades may be defined by features of nucleic acid molecules containing nucleotide sequences associated with organisms that belong to the respective clades, where the features are detectable by clade-specific detection reagents, such as clade-specific primers designed to amplify clade-specific nucleic acid products.

Figure 2:
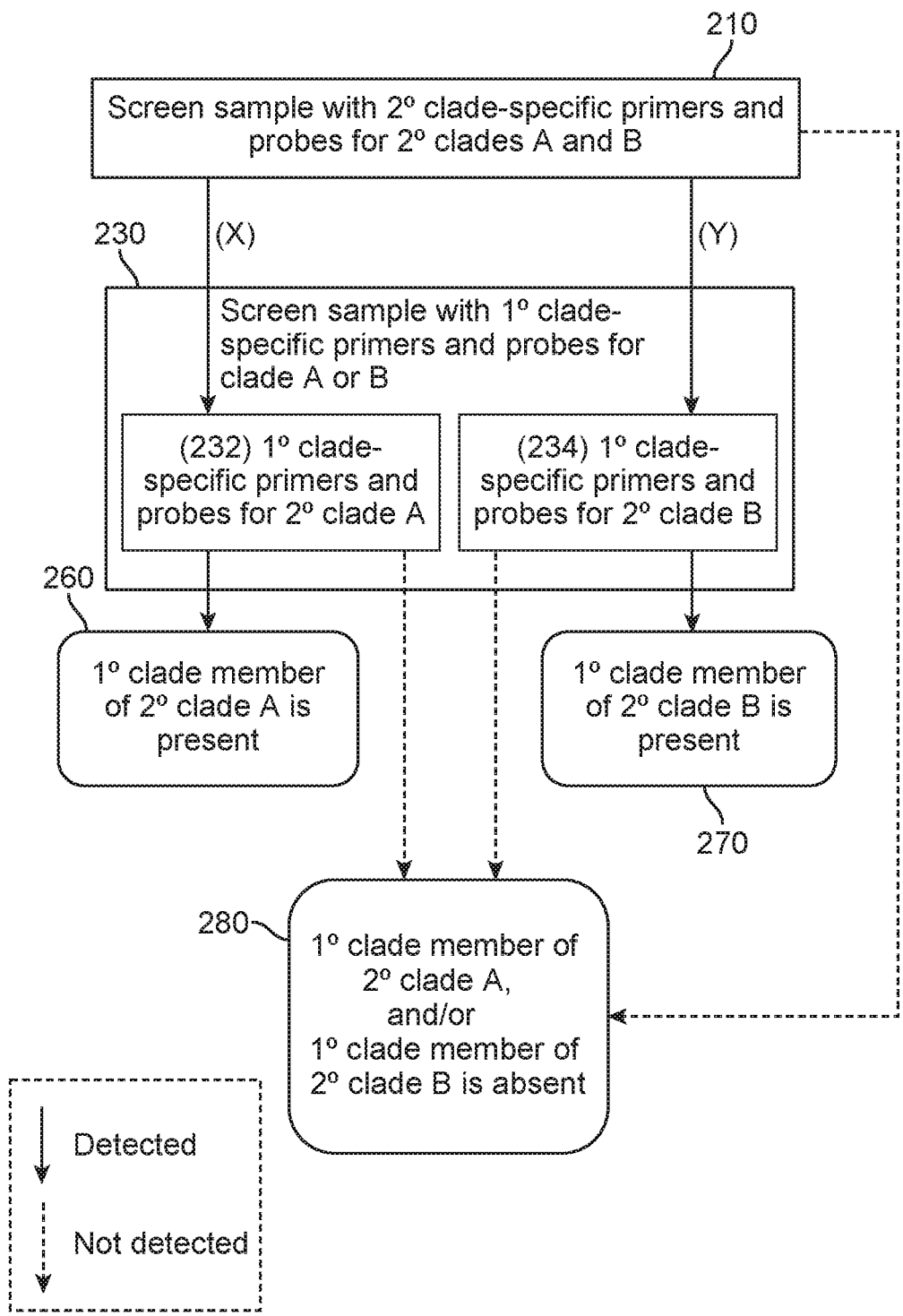
FIG. 2 shows a flow chart representing embodiments of the present disclosure.

With reference to FIG. 2, aspects of the present disclosure include a method including i) screening 210 a sample for a target organism that belongs to a primary clade member by using secondary clade-specific detection reagents, e.g., secondary clade-specific primers and probes, to determine the presence or absence of a secondary clade member to which the primary clade member belongs, and ii) screening 230 the sample to determine the presence or absence of the target organism by using detection reagents specific to primary clades that belong to the secondary clade member, e.g., primary clade-specific primers and probes 232/234, in samples for which the presence of the secondary clade member has been determined. Detection of a primary clade member by the primary clade-specific detection reagents allows for the determination 260/270 that the organism that belongs to the primary clade member is present in the sample. The determination 280 that the organism that belongs to the primary clade member is not present in the sample is made when the secondary clade member to which the organism belongs is not detected in the sample using secondary clade-specific detection reagents, or when the primary clade member to which the organism belongs is not detected in the sample using primary clade-specific detection reagents.

Figure 3:
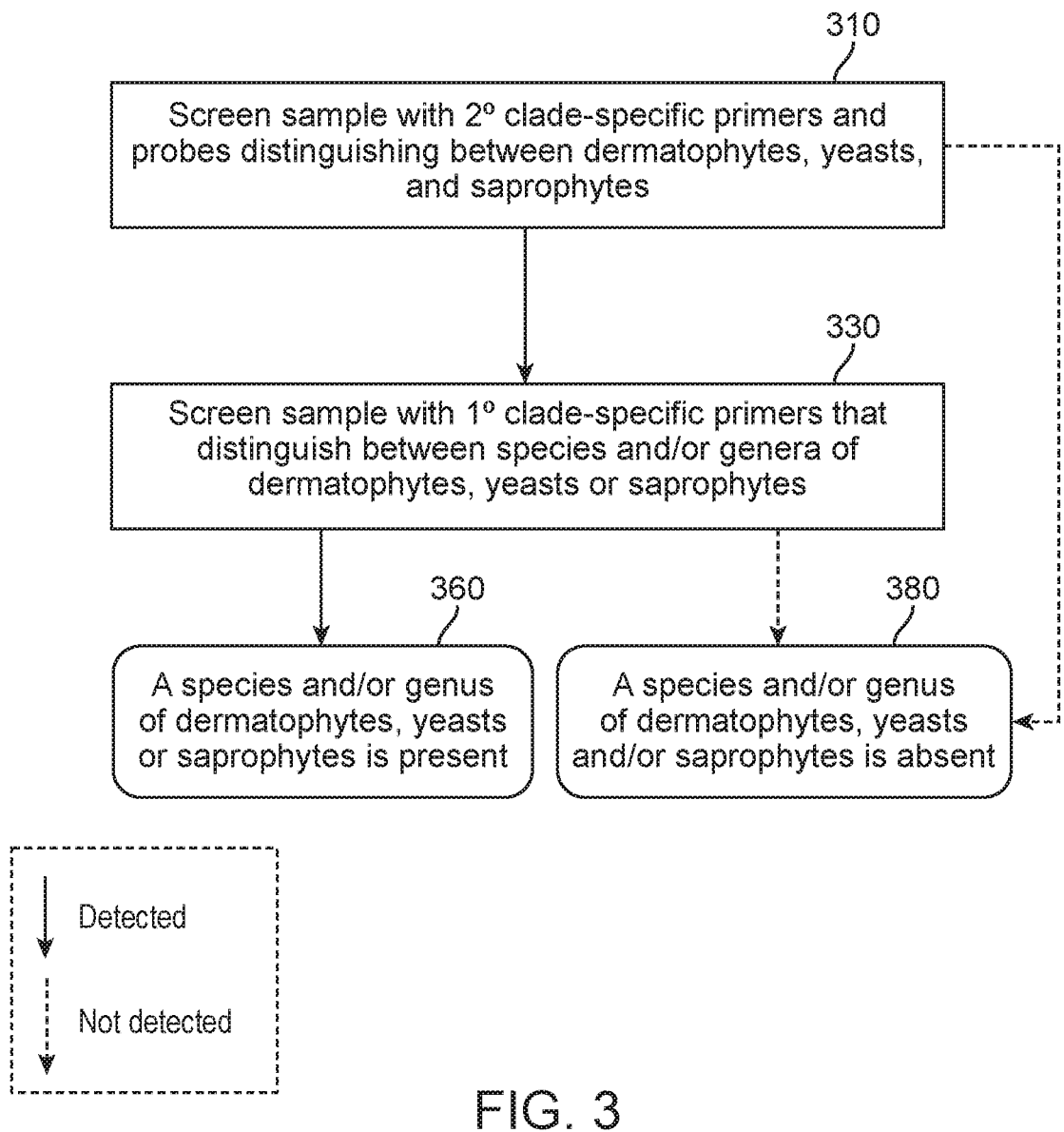
FIG. 3 shows a flow chart representing embodiments of the present disclosure.

FIG. 3 shows an embodiment of the present method for detecting, in a sample, an agent causing onychodystrophy. The first round of screening 310 may be performed using the secondary clade-specific primers and probes that distinguish between different secondary clades of onychomycotic fungi. The secondary clade-specific primers and probes may be used to run a real-time polymerase chain reaction (PCR), using the nucleic acids present in the sample as template. In certain embodiments, the onychomycotic fungi are divided into the secondary clade members: dermatophytes, yeasts, and saprophytes.

Upon determining the presence of one or more secondary clade members, in the sample, the sample may be screened 330 using primary clade-specific primers and probes that distinguish between different primary clade members of dermatophytes, yeasts, or saprophytes to determine the presence or absence of a primary clade member, e.g., a particular species or genus of yeast, a particular species or genus of dermatophytes, or a particular species or genus of saprophytes. The primary clade-specific primers may be used to run a real-time PCR, using the nucleic acids present in the sample as template. Detection of a primary clade member by the primary clade-specific primers and probes allows for the determination 360 that an agent causing onychodystrophy species or genus that belongs to the detected primary clade member is present in the sample. The determination 380 that the agent causing onychodystrophy species or genus that belongs to the primary clade member is not present in the sample is made when the secondary clade member to which the agent causing onychodystrophy species or genus belongs is not detected in the sample using the secondary clade-specific primers, or when the primary clade member to which the agent causing onychodystrophy species or genus belongs is not detected in the sample using the primary clade-specific primers.

Figure 4:
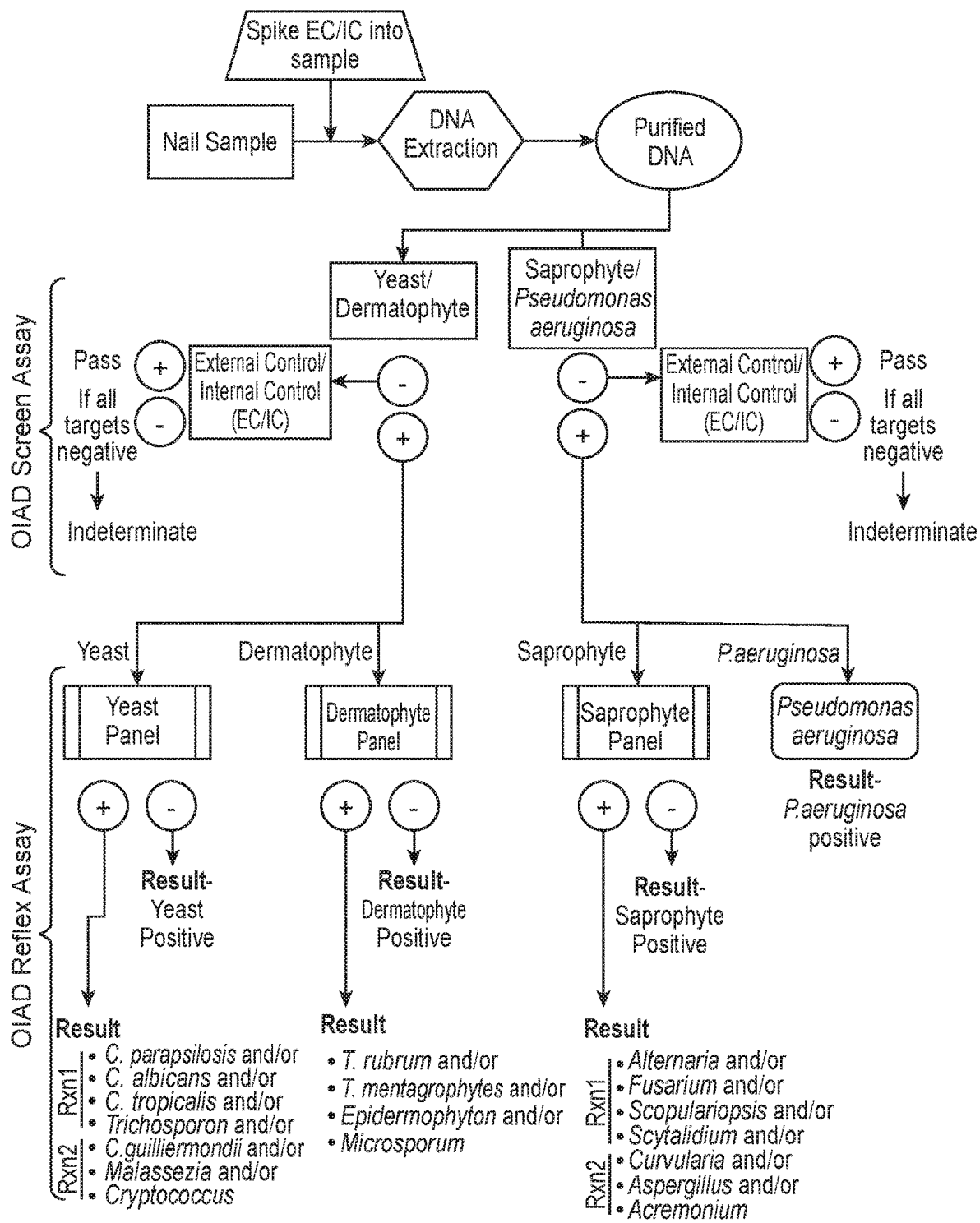
FIG. 4 shows a flow chart representing embodiments of the present disclosure.
Figure 5:
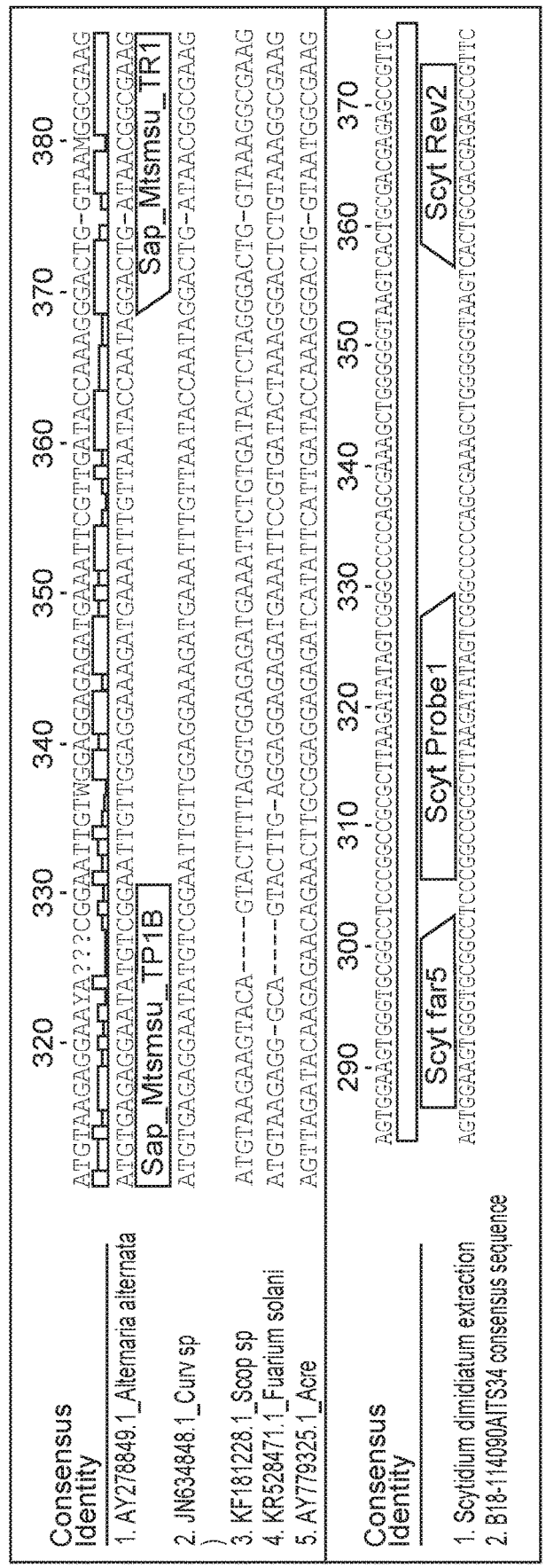
FIG. 5 shows alignments to genomic regions of primers designed to amplify Saprophyte-specific target sequences, according to embodiments of the present disclosure. The sequences are set forth from top to bottom as SEQ ID NOs: 109-130.
Figure 6:
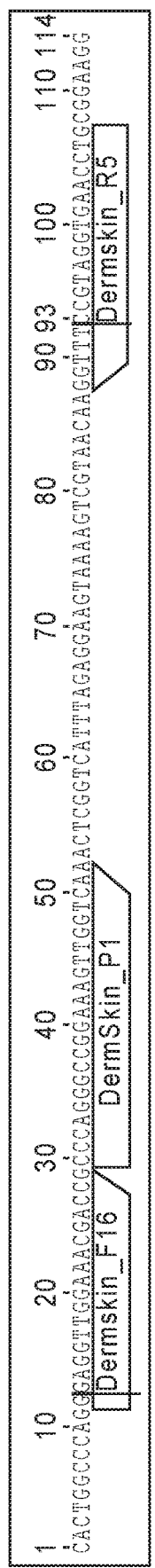
FIG. 6 shows alignments to genomic regions of primers designed to amplify dermatophyte-specific target sequences, according to embodiments of the present disclosure. The sequence is set forth as SEQ ID NO: 131.
Figure 9:
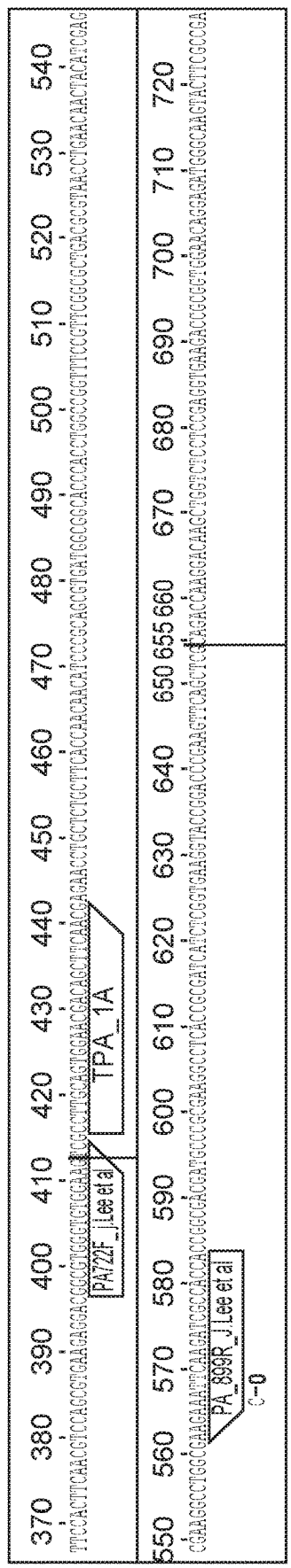
FIG. 9 shows alignments to genomic regions of primers and probes targeting the gyrase gene in *P. aeruginosa*, according to embodiments of the present disclosure. The sequence is set forth as SEQ ID NO: 159.
Figure 10:
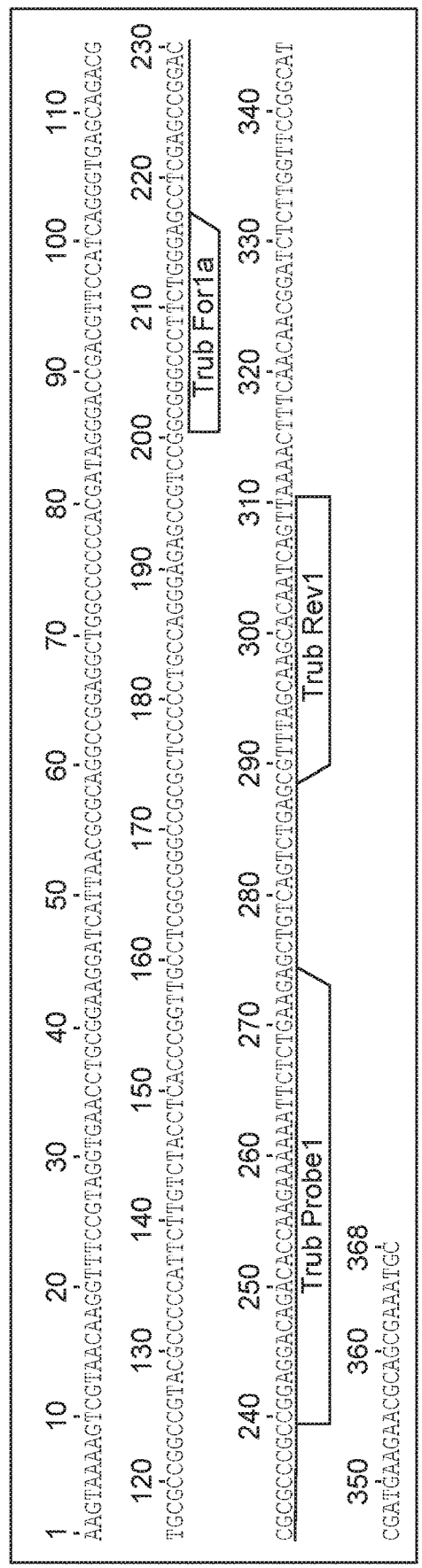
FIG. 10 shows alignments to genomic regions of primers and probes targeting *Trichophyton rubrum*, according to embodiments of the present disclosure. The sequence is set forth as SEQ ID NO:160.
Figure 11:
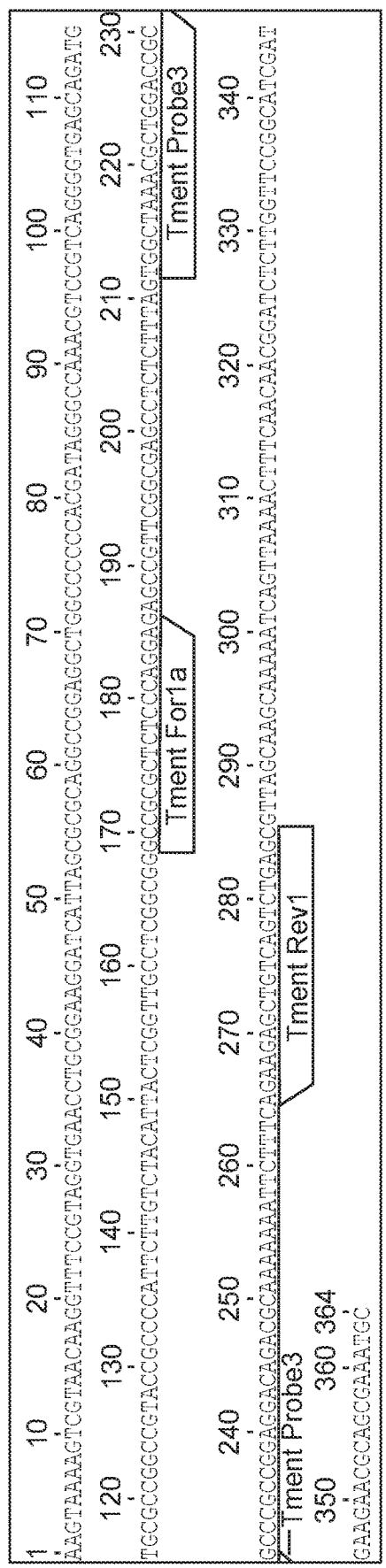
FIG. 11 shows alignments to genomic regions of primers and probes targeting *Trichophyton mentagrophytes*, according to embodiments of the present disclosure. The sequence is set forth as SEQ ID NO: 161.
Figure 13:
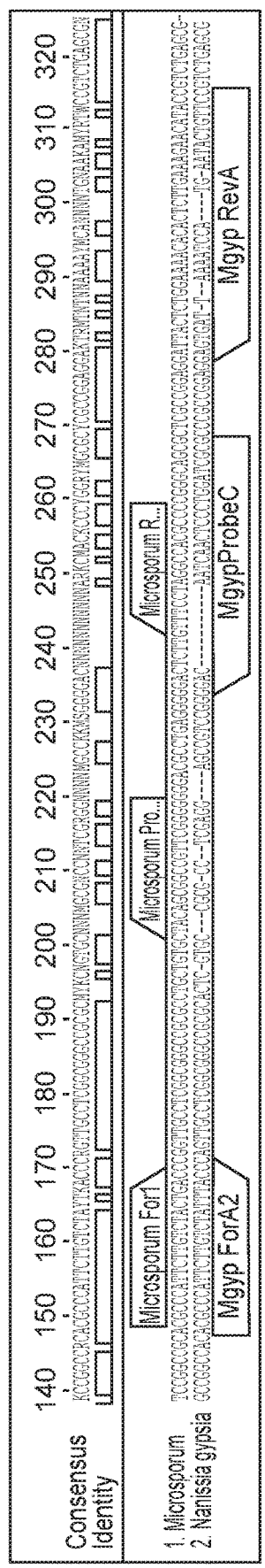
FIG. 13 shows alignments to genomic regions of primers and probes targeting *Microsporum*, according to embodiments of the present disclosure. The sequences are set forth as SEQ ID NOs: 163-165.
Figure 16:
FIG. 16 shows alignments to genomic regions of primers and probes targeting *Aspergillus*, according to embodiments of the present disclosure. The sequence is set forth as SEQ ID NO: 168.
Figure 18:
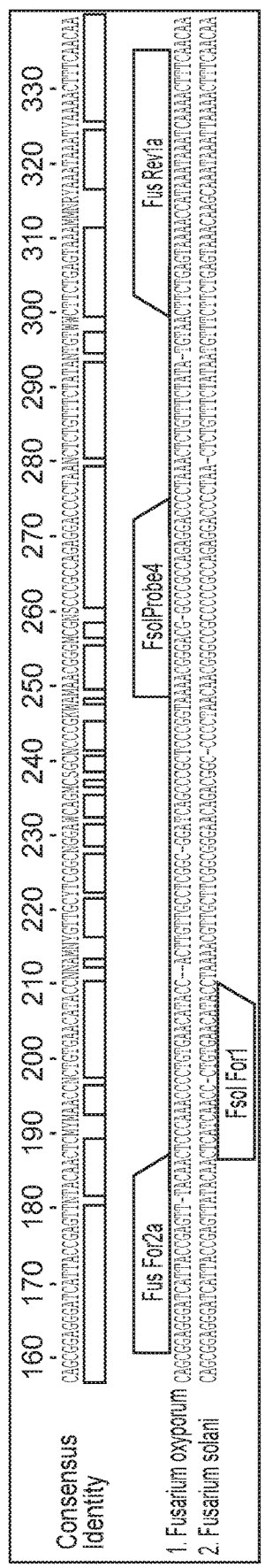
FIG. 18 shows alignments to genomic regions of primers and probes targeting *Fusarium*, according to embodiments of the present disclosure. The sequences are set forth from top to bottom as SEQ ID NOs: 170-172.
Figure 19:
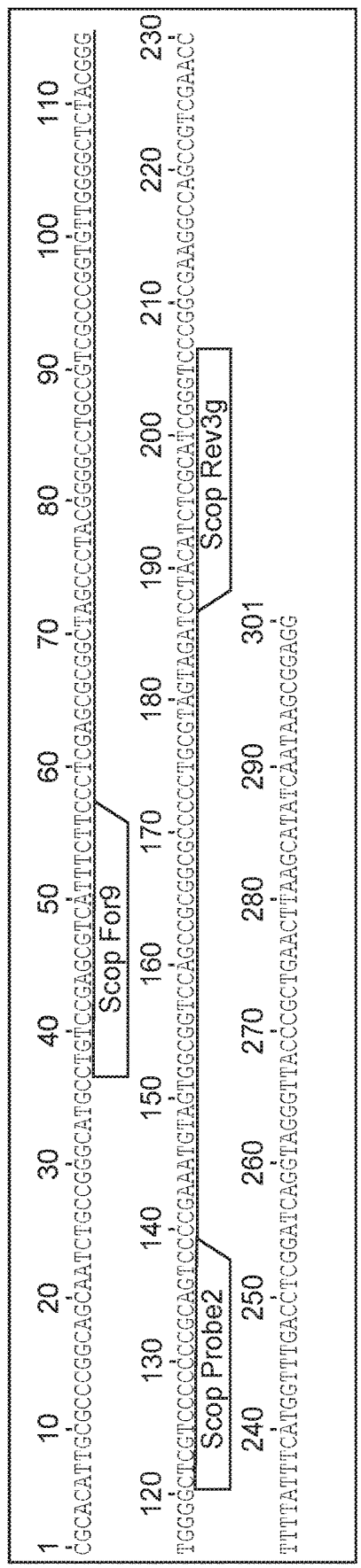
FIG. 19 shows alignments to genomic regions of primers and probes targeting *Scopulariopsis*, according to embodiments of the present disclosure. The sequence is set forth as SEQ ID NO: 173.
Figure 20:
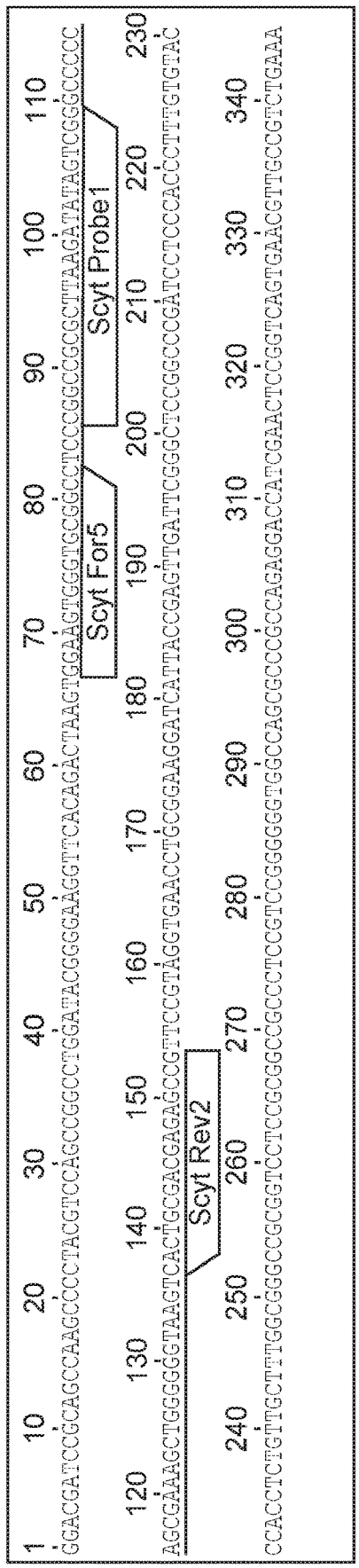
FIG. 20 shows alignments to genomic regions of primers and probes targeting *Scytalidium*, according to embodiments of the present disclosure. The sequence is set forth as SEQ ID NO: 174.
Figure 21:
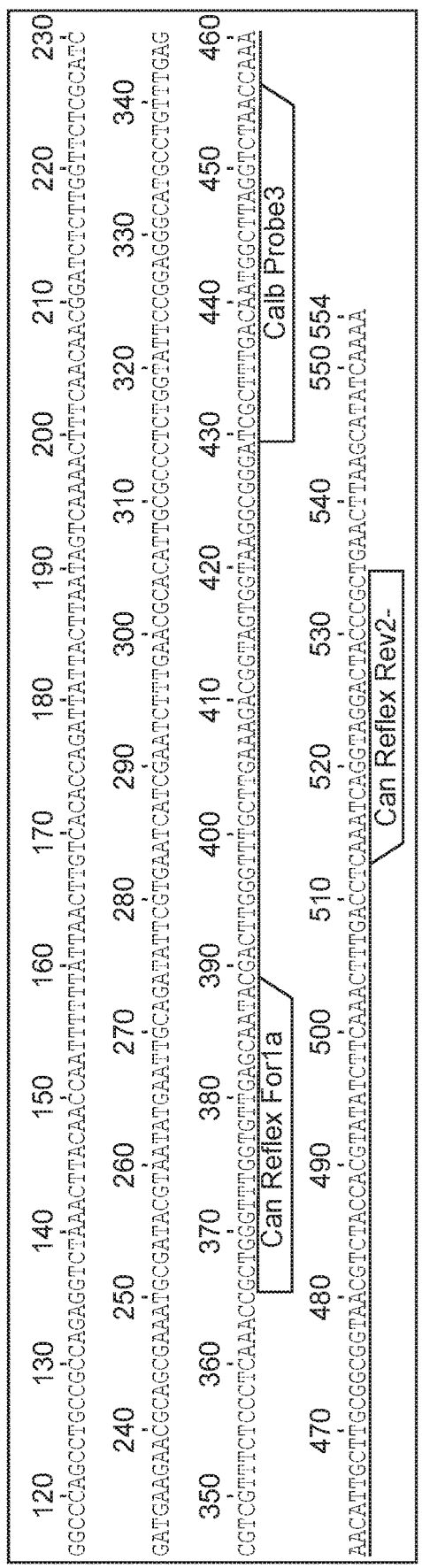
FIG. 21 shows alignments to genomic regions of primers and probes targeting the ITS2 gene in *Candida albicans*, according to embodiments of the present disclosure. The sequence is set forth as SEQ ID NO: 175.
Figure 22:
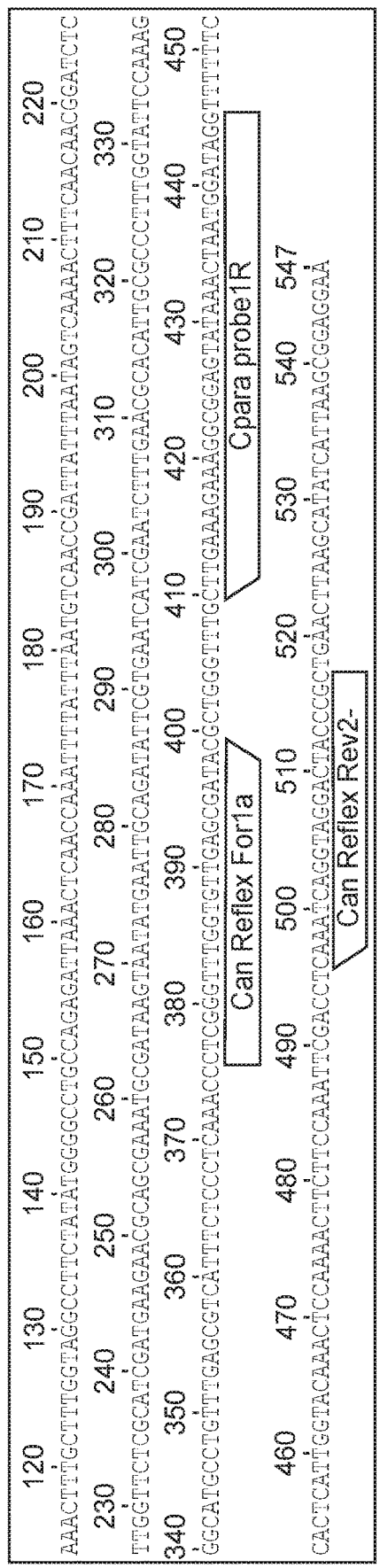
FIG. 22 shows alignments to genomic regions of primers and probes targeting the ITS2 gene in *Candida parapsilosis*, according to embodiments of the present disclosure. The sequence is set forth as SEQ ID NO: 176.
Figure 23:
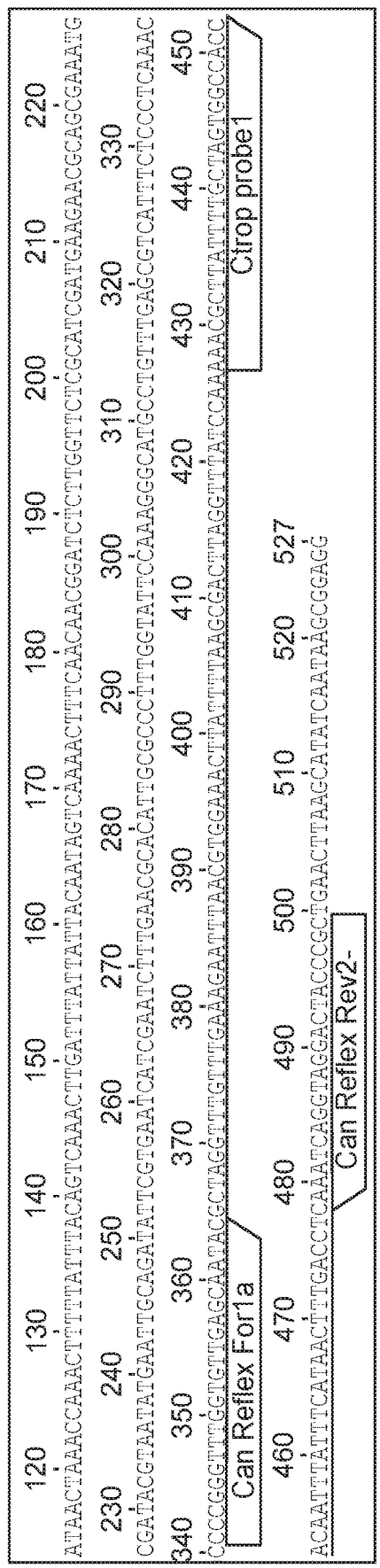
FIG. 23 shows alignments to genomic regions of primers and probes targeting the ITS2 gene in *Candida tropicalis*, according to embodiments of the present disclosure. The sequence is set forth as SEQ ID NO: 177.
Figure 24:
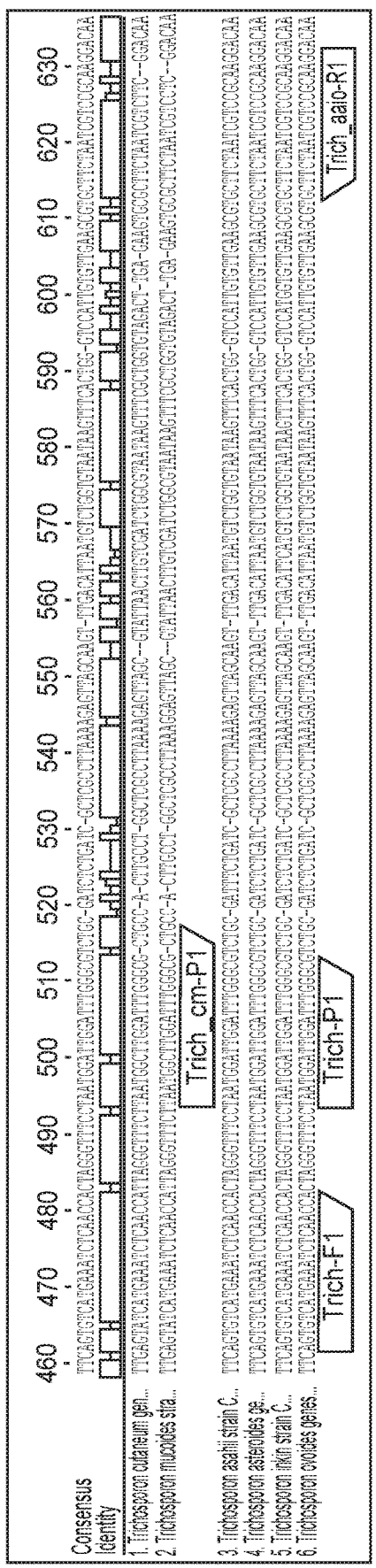
FIG. 24 shows alignments to genomic regions of primers and probes targeting the ITS2 gene in *Trichosporon* spp., according to embodiments of the present disclosure. The sequences are set forth as SEQ ID NOs: 178-184.
Figure 26:
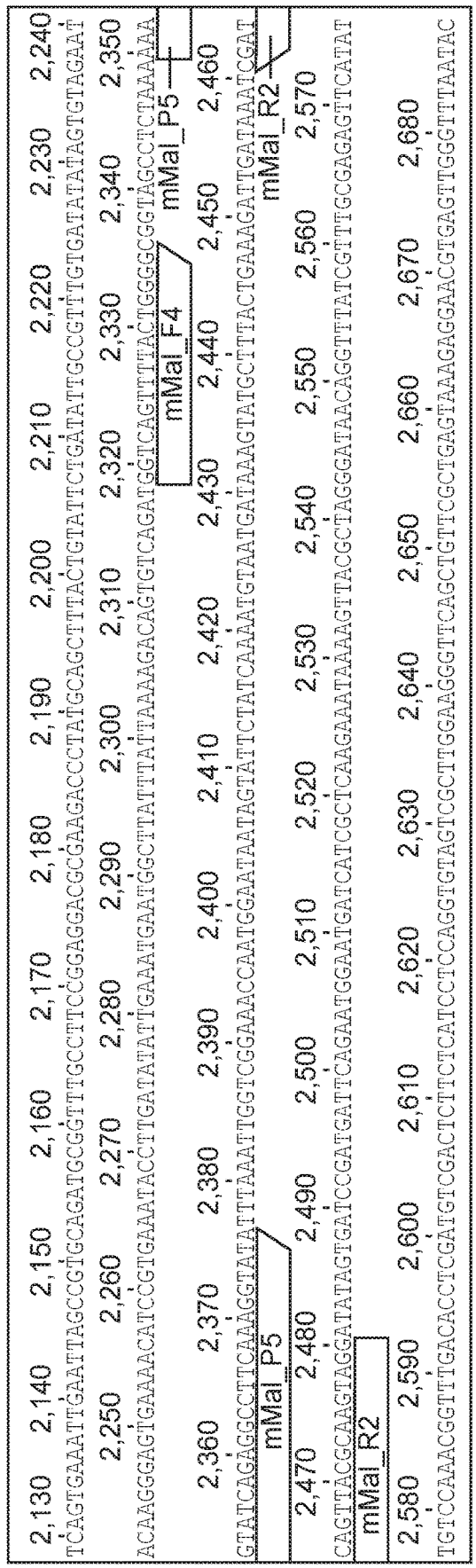
FIG. 26 shows alignments to genomic regions of primers and probes targeting the mitochondrion rnl gene in *Malassezia* spp., according to embodiments of the present disclosure. The sequence is set forth as SEQ ID NO: 186.
Figure 27:
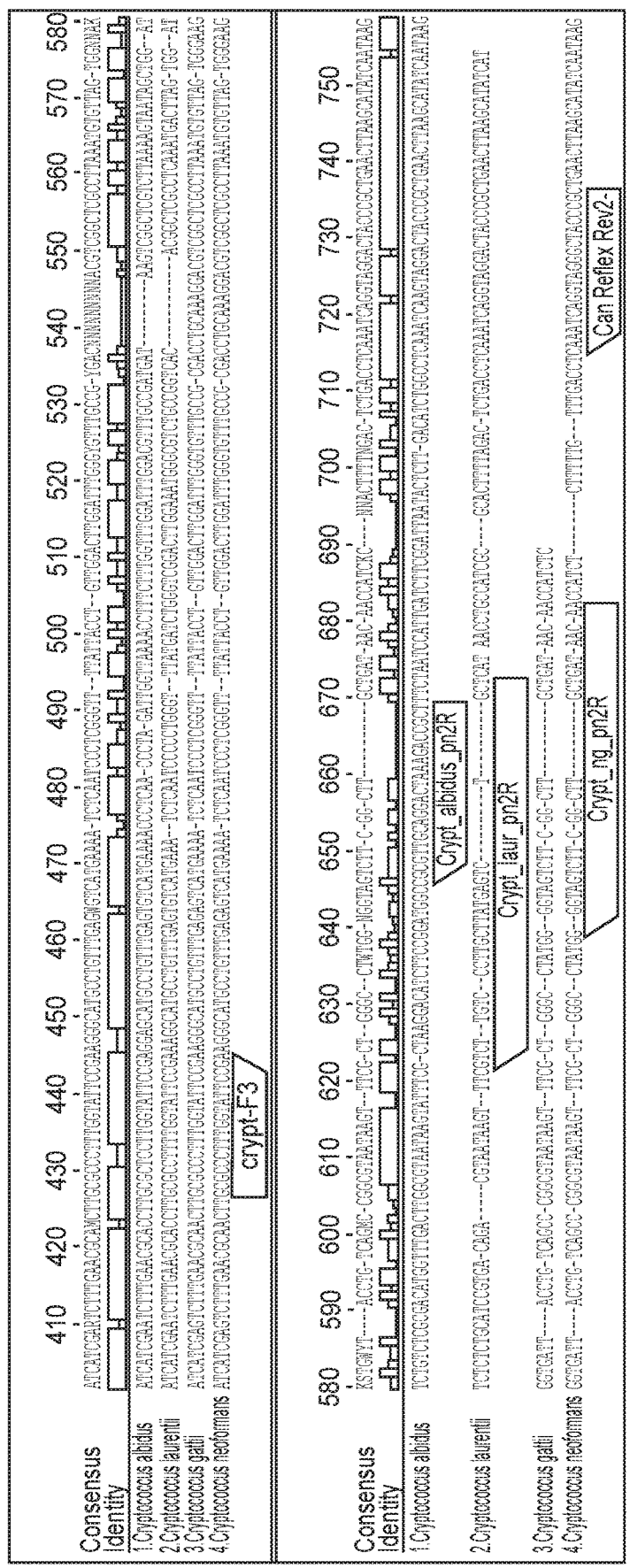
FIG. 27 shows alignments to genomic regions of primers and probes targeting the ITS2 gene in *Cryptococcus* spp., according to embodiments of the present disclosure. The sequences are set forth as SEQ ID NO: 187-201.
Figure 73:
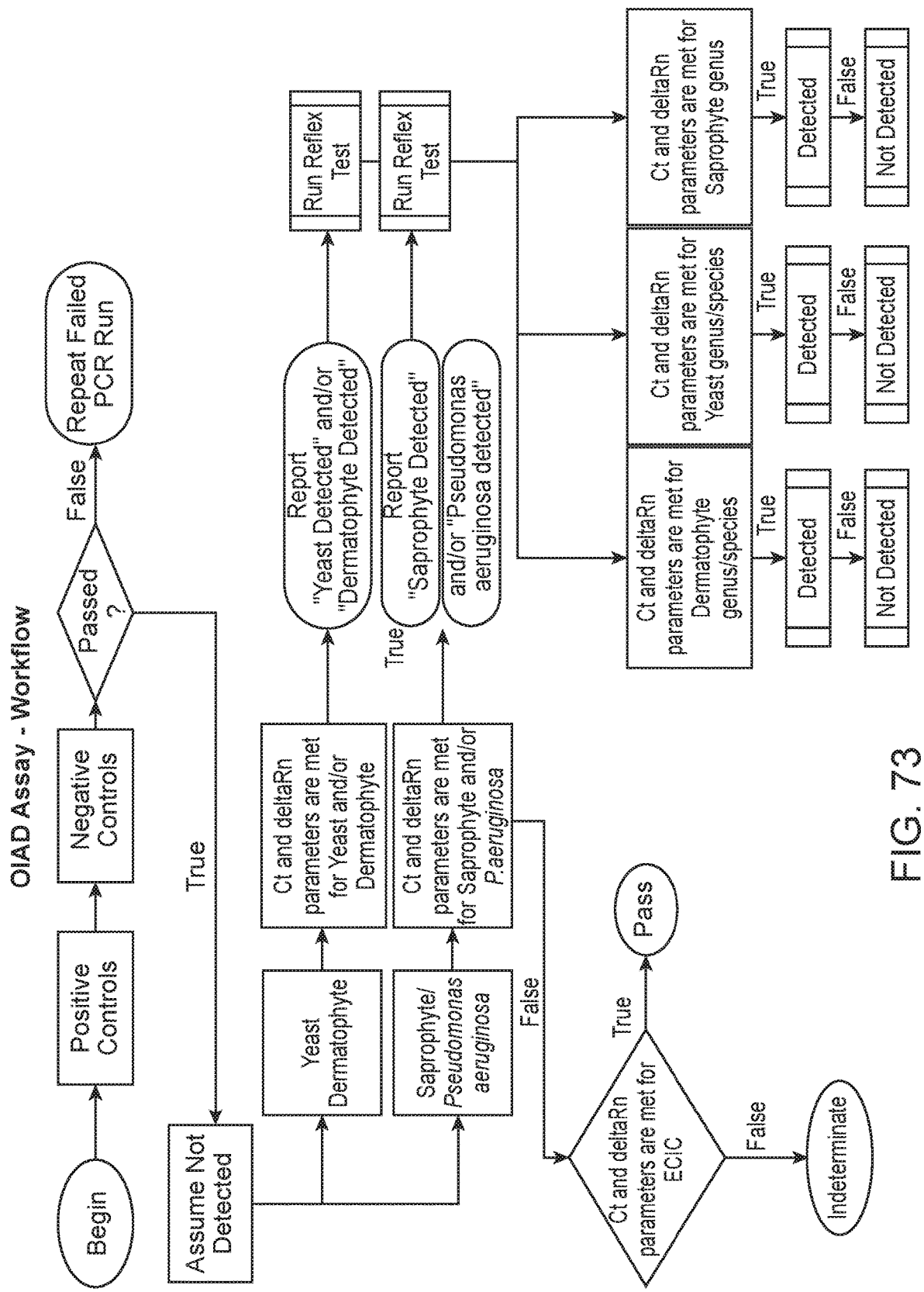
FIG. 73 provides a schematic of an OIAD Assay workflow according to embodiments of the present disclosure.

FIG. 4 shows embodiments of Onychodystrophy Infectious Agent Detection (OIAD) Screen Assays and OIAD Relex Assays according to embodiments of the present disclosure. An exemplary and non-limiting OIAD Assay process flow is shown in FIG. 4. As indicated, the OIAD Screen Assaycan test for the presence of three classes of fungi and one bacterium: dermatophytes, yeasts, saprophytes and *Pseudomonas aeruginosa*. The OIAD Screen Assay provides a variety of advantages over prior methods. In addition to reducing the cost, it enables identification of potentially at-risk individuals. If the OIAD Screen Assay is positive, the result will be confirmed by the OIAD Reflex Assays. The results of the OIAD Screen Assay are used to determine which of three, or if any, OIAD Reflex Assays will be performed. The OIAD Reflex Assays together can identify seven yeast, at least four dermatophyte and seven saprophyte fungi down to the genus and/or species level. Genus or species level identification is often necessary for initiating appropriate treatment options. Utilizing the OIAD Screen Assay reduces unnecessary medical testing and cost, as OIAD Reflex testing is not performed when the OIAD Screen Assay results are negative.

An additional advantage of the presently disclosed OIAD Screen and Reflex assay design is that the same PCR run parameters can be used across Screen and Reflex assays, whereas prior methods required different run parameters between assays. Example PCR run conditions are shown in Table 1A below.

TABLE 1A

| | Holding Stage | Cycling Stage-40 Cycles | |
|---|---|---|---|
| | | Denaturation | Anneal/Amplify |
| Ramp Rate | 1.9° C./s | 1.9° C./s | 1.6° C./s |
| Temperature | 94.0° C. | 95.0 | 60.0 |

TABLE 1A-continued

| | Holding Stage | Cycling Stage-40 Cycles | |
|---|---|---|---|
| | | Denaturation | Anneal/Amplify |
| Time | 2:00 | 0:15 | 0:30 |
| Collect Data | No | No | Yes |

In addition, in embodiments, the OIAD Screen Assays described herein are configured to use the same PCR reagents regardless of target sequence, with the exception of the target-specific primers and probes. Similarly, in embodiments, the OIAD Reflex Assays described herein are configured to use the same PCR reagents regardless of target sequence, with the exception of the target-specific primers and probes. Furthermore, the Screen and Reflex Assays can be designed such that they both use the same enzyme system.

In addition, the primers and probes of the disclosed methods, compositions, and kits described herein may be specifically designed for compatibility with a common PCR run protocol. For example, in embodiments of the present disclosure primers may be designed with a Tm in the range of 58-60° C., while probes may be designed with a Tm in the range of 64-66° C.

These design choices allow for significant increases in efficiency and throughput relative to prior assays.

The prevalence range of causative agents of onychodystrophy is provided below in Table 1B.

TABLE 1B

| Class | % Positive Reported Range* |
|---|---|
| Dermatophytes | 18.8 to 100 |
| Saprophytes | 0 to 51.6 |
| Yeasts | 2.7 to 64.1 |
| Pseudomonas aeruginosa | 4-7 |

*% positive of culture confirmed cases

Several genes in the fungal ribosomal DNA 18S and 28S genes, including the ITS1 and ITS2 regions, and regions in the mitochondrial genome may be targeted for the design of primers and probes for the OIAD Screen Assay and OIAD Reflex Assays. For *Pseudomonas aeruginosa* detection in the OIAD Screen Assay, the gyrase gene may be utilized as the target for primer and probe design. Target regions for primer sequences may be identified by selecting highly homologous regions among similar targets that are dissimilar to non-targeted species. Regions of the rRNA genes are highly conserved among target organisms, allowing for amplification of multiple species or genera by each primer pair, with the ITS region utilized for additional specificity.

The OIAD Assay includes the OIAD Screen Assays and OIAD Reflex Assays. In example embodiments, the OIAD Screen Assay includes two PCR master mixes (OIAD Screen Rxn 1 and OIAD Screen Rxn 2). An extracted DNA sample can be tested in one or both reactions. The OIAD Screen Rxn 1 can include primers and probes for dermatophyte and yeast organisms, e.g., as shown in FIG. 4 and Table 2. Optionally, the OIAD Screen Rxn 1 can include primer and probes for an extraction control and inhibition control (ECIC).

TABLE 2

Example primer/probe sequences and target regions employed in the Dermatophyte and Yeast OIAD Screen Rxn1 (D = Dermatophyte, Y = Yeast, ECIC = extraction control and inhibition control)

| | Primer Name | Sequences (5'-3') | SEQ ID NO: | Target regions | Probe Label | Primer/Probe Details |
|---|---|---|---|---|---|---|
| D | YD_1 | GGAGGTTGGAAACGACCG | 1 | 18S rDNA | | Dermatophyte Forward |
| | YD_2 | CAGGTTCACCTACGGAAACC | 2 | 18S rDNA | | Dermatophyte Reverse |
| | YD_Probe_2 | CCCAGGGCCGGAAAGTTGGTCAA | 3 | | ATTO550 | Dermatophyte Probe |
| Y | YD_3 | GTCCGAGTTGTAATTTGAAGAAGGTAT | 4 | 28S rDNA | | *Candida* Forward1 |
| | YD_4 | CCGAGTTGTAATTTGAAGATTGTAACCT | 5 | 28S rDNA | | *Candida* Forward2 |
| | YD_5 | GTAATCTCGAGACGTGTTTTCCG | 6 | 28S rDNA | | *Malassezia* Forward1 |
| | YD_6 | CAGGTTGGAGTCTGTGTGGAAG | 7 | 28S rDNA | | *Candida* Forward3 |
| | YD_7 | TGAAGGTTTCGTGGTCTGAGTC | 8 | 28S rDNA | | *Candida* Forward4 |
| | YD_8 | TGCATTCCCAAACAACTCGACTC | 9 | 28S rDNA | | *Candida* & *Malassezia* common Reverse |
| | YD_Probe_3 | TGAGAATCCCGTGCGATGAGATG | 10 | | FAM | *Candida* Probe1 |
| | YD_Probe_4 | AGGGTGAGAATCCCGTACTTGCCAT | 11 | | FAM | *Malassezia* Probe |
| | YD_Probe_5 | CTTCCGCCGGCATCCCACG | 12 | | FAM | *Candida* Probe2 |
| | YD_Probe_6 | ACGCCGACTCTTTGCACCGC | 13 | | FAM | *Candida* Probe3 |
| | YD_9 | GGGCATTRGTATTCCGTTGCTAGA | 14 | 18S rDNA | | *Trichosporon* & *Cryptococcus* Forward |
| | YD_10 | TTAAGACTACAACGGTATCTAATCGTTTTT | 15 | 18S rDNA | | *Trichosporon* & *Cryptococcus* Reverse |
| | YD_Probe_7 | AAGGACGTTTTCATTGATCAAGAACGAAGGT | 16 | | FAM | *Trichosporon* & *Cryptococcus* Probe |
| ECIC | ECIC_F | CATCCATGCTGACCACGAAG | 17 | cit1 | | ECIC Forward |
| | ECIC_R | TCCATTTAAGGAGGCAGCCA | 18 | cit1 | | ECIC Reverse |
| | YD_Probe_1 | TCTGCTCACACCGGTCATTTGGT | 19 | | ATTO647 | ECIC Probe |

TABLE 2(A)

Example PCR Run Chemistry per PCR reaction

Yeasts/Dermatophytes

| | |
|---|---|
| Rox | 75 nM |
| Enzyme | Platinum II 1U |
| MgCl2 | 2 mM |
| Primers | |
| DermSkin-F16 (YD_1) | 250 nM |
| DermSkin-R5 (YD_2) | 250 nM |
| Can_SC FWd 1 (YD_3) | 300 nM |
| Can_SC FWd 2 (YD_4) | 300 nM |
| Mal_SC FWd 3 (YD_5) | 50 nM |
| CanK_SC FWd 4 (YD_6) | 300 nM |
| CanL_SC FWd 1 (YD_7) | 300 nM |
| Can_Mal Rev 1b (YD_8) | 300 nM |
| TriCry18S_SC FWD1 (YD_9) | 200 nM |
| TriCry18S_SC Rev1 (YD_10) | 200 nM |
| ECIC 2F (ECIC_F) | 50 nM |
| ECIC 2R (ECIC-R) | 50 nM |
| Probes | |
| DermSkin Tinea Probe P1 (YD_Probe_2) | 50 nM |
| Can_SC Probe 1a (YD_Probe_3) | 200 nM |
| Mal_SC Probe 1a (YD_Probe_4) | 80 nM |
| CanK_SC Probe 1a (YD_Probe_5) | 60 nM |
| CanL_SC Probe 1 (YD_Probe_6) | 60 nM |
| TriCry18S_SC Probe 1 (YD_Probe_7) | 80 nM |

The OIAD Screen Rxn2 can include primers and probes for saprophytes and *Pseudomonas aeruginosa*, e.g., as shown in FIG. 4 and Table 3. Positive samples can be further identified for genus and/or species using OIAD Reflex Assays, which can include OIAD Reflex Dermatophyte Rxn, OIAD Reflex Saprophyte Rxn1 and Rxn2, and OIAD Reflex Yeast Rxn1 and Rxn2 (see FIG. 4). Optionally, the OIAD Screen Rxn 2 can include primer and probes for an extraction control and inhibition control (ECIC).

TABLE 3

Example primer/probe sequences and target regions employed in the Saprophyte and
*Pseudomonas aeruginosa* OIAD Screen Rxn2 (S = Saprophytes, Pa = *Pseudomonas aeruginosa*, ECIC = extraction control and inhibition control)

| | Primer Name | Sequences (5'-3') | SEQ ID NO: | Target Regions | Probe Label | Primer/Probe Details |
|---|---|---|---|---|---|---|
| S | SP_1 | CCAGCAGTCGCGGTAATAC | 20 | mt-SSU | | Saprophyte Forward1 |
| | SP_2 | CCTTCGCCGTTATCAGTCC | 21 | mt-SSU | | Saprophyte Reverse1 |
| | SP_3 | CAGAATTTCATCTCTCCACCT | 22 | mt-SSU | | Saprophyte Reverse2 |
| | SP_4 | GATGACTAACACTAGTCTTCTAC | 23 | mt-SSU | | Saprophyte Forward2 |
| | SP_5 | GAAAGGCTGAACCAGTAACTTG | 24 | mt-SSU | | Saprophyte Reverse3 |
| | SP_6 | GGAAGTGGGTGCGGCC | 25 | rRNA | | Saprophyte Forward3 |
| | SP_7 | CGGCTCTCGTCGCAGTG | 26 | rRNA | | Saprophyte Reverse4 |
| | SP_Probe_3 | CGGCCGCGCTTAAGATATAGTCGG | 27 | | FAM | Saprophyte Probe1 |
| | SP_Probe_4 | CATAAGAATTAGGTTTAAAGGGTACTTAGACGG | 28 | | FAM | Saprophyte Probe2 |
| | SP_Probe_5 | CAAGTGTTATTCATCTTAAGTAGGTTTAAAGGGTAC | 29 | | FAM | Saprophyte Probe3 |
| | SP_Probe_6 | CGACTGCTGGCACGTAATTTGGTC | 30 | | FAM | Saprophyte Probe4 |
| | SP_Probe_7 | CCGACATATTCCTCTCACATATCAAACTCAAG | 31 | | FAM | Saprophyte Probe5 |
| Pa | SP_8 | GGCGTGGGTGTGGAAGTC | 32 | gyrA | | *Pseudomonas* Forward |
| | SP_9 | TGGTGGCGATCTTGAATTTCTT | 33 | gyrA | | *Pseudomonas* Reverse |
| | SP_Probe_1 | CCTTGCAGTGGAACGACAGCTTCAACG | 34 | | Atto550 | *Pseudomonas* Probe |
| ECIC | ECIC_F | CATCCATGCTGACCACGAAG | 17 | cit1 | | ECIC Forward |
| | ECIC_R | TCCATTTAAGGAGGCAGCCA | 18 | cit1 | | ECIC Reverse |
| | SP_Probe_2 | TCTGCTCACACCGGTCATTTGGT | 19 | | ATTO647 | ECIC Probe |

TABLE 3(A)

Example PCR Run Chemistry per PCR reaction

Saprophyted/Pseudomonas Screen Assay

| | |
|---|---|
| Rox | 75 nM |
| Enzyme | Platinum II 1U |
| MgCl2 | 2 mM |
| Primers | |
| TF2 (SP_1) | 200 nM |
| TR2 | 200 nM |
| TR1 (SP_2) | 200 nM |
| TF8 (SP_4) | 200 nM |
| TR8 (SP_5) | 200 nM |
| Scyt For5 (SP_6) | 200 nM |
| Scyt Rev2 (SP_7) | 200 nM |
| PA_F | 100 nM |
| PA_R | 100 nM |
| ECIC 2F | 50 nM |
| ECIC 2R | 50 nM |
| Probes | |
| Probe_PA | 50 nM |
| Probe ECIC | 200 nM |
| Probe_TP2D (SP_Probe_4) | 80 nM |
| Probe TP2D_7 (SP_Probe_5) | 60 nM |
| Probe_TP1B (SP_Probe_7) | 60 nM |
| Probe_TPED (SP_Probe_6) | 250 nM |
| Probe_Scyt (SP_Probe_3) | 100 nM |

The OIAD Reflex Dermatophyte Rxn can include primers and probes for one or more of *Trichophyton rubrum* (T.r) complex, *Trichophyton mentagrophytes* complex (T.m), *Epidermophyton* spp. (E.) and *Microsporum* spp. (M.) (FIG. 4, Table 4).

TABLE 4

Example primer/probe sequences and target regions employed in the Dermatophyte OIAD Reflex Rxn

| | Primer Name | Sequences (5'-3') | SEQ ID NO: | Target Regions | Probe Label | Primer/Probe Details |
|---|---|---|---|---|---|---|
| M. | D_1 | CGCCCATTCTTGTCTACTGACC | 35 | ITS | | *Microsporum* Forward1 |

TABLE 4-continued

Example primer/probe sequences and target regions employed in the Dermatophyte OIAD Reflex Rxn

| | Primer Name | Sequences (5'-3') | SEQ ID NO: | Target Regions | Probe Label | Primer/Probe Details |
|---|---|---|---|---|---|---|
| | D_2 | GGGCGTGGCCTAGGAAAC | 36 | ITS | | *Microsporum* Reverse1 |
| | D_3 | ACGCCCATTCTTGTCTATTTACCC | 37 | ITS | | *Microsporum* Forward2 |
| | D_4 | GGAACAGTATTCATGGATTTTAATCACTC | 38 | ITS | | *Microsporum* Reverse2 |
| | D_Probe_3 | CCCCGAACGGCCGCTGTAG | 39 | | FAM | *Microsporum* Probe1 |
| | D_Probe_4 | CGCGATCCAGGGAGTTGATTGTCC | 40 | | FAM | *Microsporum* Probe2 |
| E. | D_5 | CCTAGGCTGCAGTGTCGC | 41 | ITS | | *Epidermophyton* Forward |
| | D_6 | AACGCTCAGACTGAACCACC | 42 | ITS | | *Epidermophyton* Reverse |
| | D_Probe_2 | CCCACCCCTGGACAGCGC | 43 | | ATT647 | *Epidermophyton* Probe |
| T.m | D_7 | GCCGCGCTCTCCCAGG | 44 | ITS | | *T mentagrophytes* Forward |
| | D_8 | GCTCAGACTGACAGCTCTTCT | 45 | ITS | | *T mentagrophytes* Reverse |
| | D_Probe_5 | TGGCTAAACGCTGGACCGCG | 46 | | ATTO550 | *T mentagrophytes* Probe |
| T.r | D_9 | GCGGGCCCTTCTGGGAG | 47 | ITS | | *T rubrum* Forward |
| | D-10 | AACTGATTGTGCTTGCTAAACG | 48 | ITS | | *T rubrum* Reverse |
| | D_Probe_1 | CGGAGGACAGACACCAAGAAAAAATTCTCTGAAGA | 49 | | MAX | *T rubrum* Probe |

TABLE 4(A)

Example PCR Run Chemistry per PCR reaction:

Saprophyted/Pseudomonas Screen Assay

| Rox | 37.5 nM |
|---|---|
| Enzyme | Platinum II 1U |
| MgCl2 | 2.5 mM |

Primers

| Microsporum For1 (D_1) | 250 nM |
|---|---|
| Microsporum Rev3 (D_2) | 250 nM |
| Mgyp ForA2 (D_3) | 300 nM |
| MgypRevA (D_4) | 300 nM |
| Epiderm For2 (D_5) | 250 nM |
| Epiderm Rev3 (D_6) | 250 nM |
| Tment For1a (D_7) | 250 nM |
| Tment Rev1 (D_8) | 250 nM |
| Trub For1a (D_9) | 300 nM |
| Trub Rev1 (D_10) | 300 nM |

TABLE 4(A)-continued

Example PCR Run Chemistry per PCR reaction:

Saprophyted/Pseudomonas Screen Assay

Probes

| Trub Probe1 (D_Probe_1) | 120 nM |
|---|---|
| Epiderm2 (D_Probe_2) | 60 nM |
| Microsporum Probe2 (D_Probe_3) | 90 nM |
| Mgyp ProbeC (D_Probe_4) | 120 nM |
| Tment Probe3 (D_Probe_5) | 100 nM |

The OIAD Reflex Saprophyte Rxn1 can include primers and probes for one or more of *Alternaria* spp (A.), *Fusarium* spp. (F.), *Scopulariopsis* spp. (Sco.) and *Scytalidium* spp (Scy.) (FIG. 4, Table 5).

TABLE 5

Example primer/probe sequences and target regions employed in the Saprophyte OIAD Reflex Rxn1

| | Primer Name | Sequences (5'-3') | SEQ ID NO: | Target Regions | Probe Label | Primer/Probe Details |
|---|---|---|---|---|---|---|
| A. | S1_1 | CGGCCTACTGGTTTCGG | 50 | ITS | | *Alternaria* Forward |
| | S1_2 | CCGAGGTCAAAAGTTGAAAAAAGG | 51 | ITS | | *Alternaria* Reverse |
| | S1_Probe_2 | CGCAGCACAAGTCGCACTCTCT | 52 | | FAM | *Alternaria* Probe |

TABLE 5-continued

Example primer/probe sequences and target regions employed in the Saprophyte OIAD Reflex Rxn1

| | Primer Name | Sequences (5'-3') | SEQ ID NO: | Target Regions | Probe Label | Primer/Probe Details |
|---|---|---|---|---|---|---|
| F. | S1_3 | GGAGGGATCATTACCGAGTTTACAAC | 53 | ITS | | *Fusarium* Forward1 |
| | S1_4 | CTCATCAACCCTGTGAACGTACC | 54 | ITS | | *Fusarium* Forward2 |
| | S1_5 | TGAAAGTTTTGATTTATTTATGGTTTTACTCAGAAG | 55 | ITS | | *Fusarium* Reverse1 |
| | S1_Probe_3 | CCCCCGCCAGAGGACCC | 56 | | ATTO550 | *Fusarium* Probe |
| Sco. | S1_6 | CTGTCCGAGCGTCATTTCTTC | 57 | ITS | | *Scopulariopsis* Forward |
| | S1_7 | GACCCGATGCGAGATGTAGG | 58 | ITS | | *Scopulariopsis* Reverse |
| | S1_Probe_4 | CTCGTCCCCCCCGCAGTCC | 59 | | MAX | *Scopulariopsis* Probe |
| Scy. | S1_8 | GGAAGTGGGTGCGGCC | 25 | ITS | | *Scytalidium* Forward |
| | S1_9 | CGGCTCTCGTCGCAGTG | 26 | ITS | | *Scytalidium* Reverse |
| | S1_Probe_1 | CGGCCGCGCTTAAGATATAGTCGG | 27 | | ATT647 | *Scytalidium* Probe |

The OIAD Reflex Saprophyte Rxn2 can include primers and probes for one or more of *Curvularia* spp. (C.), *Acremonium* spp. (Acr.) and *Aspergillus* spp (Asp.) (FIG. 4, Table 6).

TABLE 6

Example primer/probe sequences and target regions employed in the Saprophyte OIAD Reflex Rxn2

| | Primer Name | Sequences (5'-3') | SEQ ID NO: | Target Regions | Probe Label | Primer/Probe Details |
|---|---|---|---|---|---|---|
| C. | S2_1 | CCGGCCTACTGGTTTCGC | 60 | ITS | | *Curvularia* Forward |
| | S2_2 | GAGGTCAACGTGAGAAGGAGTC | 61 | ITS | | *Curvularia* Reverse |
| | S2_Probe_1 | TGCGCTTGCAATCAGCAAAAGAGGAC | 62 | | MAX | *Curvularia* Probe |
| Acr. | S2_3 | CGTCATTTCAACCCTCAGGAC | 63 | ITS | | *Acremonium* Forward |
| | S2_4 | CTACCTGATCCGAGGTCAACC | 64 | ITS | | *Acremonium* Reverse |
| | S2_Probe_2 | TGGGGGGTTTAACGGCGTGG | 65 | | ATTO550 | *Acremonium* Probe |
| Asp. | S2_5 | AACCAACCGGGATTGCCTC | 66 | ITS | | *Aspergillus* Forward |
| | S2_6 | CGTTCCAGGGCACTTAGAC | 67 | ITS | | *Aspergillus* Reverse |
| | S2_Probe_3 | CTGGCTCCTTCGGGGTCCG | 68 | | FAM | *Aspergillus* Probe |

TABLE 6(A)

Example PCR Run Chemistry for each PCR reaction

Reaction 1 (Alternaria, Fusarium, Scopulariopsis, and Scytalidium)

| Rox | 37.5 nM |
|---|---|
| Enzyme | Platinum II 1U |
| MgCl2 | 2.5 mM |

TABLE 6(A)-continued

Example PCR Run Chemistry for each PCR reaction

Reaction 1 (Alternaria, Fusarium, Scopulariopsis, and Scytalidium)

Primers

| Alt For1a (S1_1) | 300 nM |
|---|---|
| Alt Rev2a (S1_2) | 300 nM |

TABLE 6(A)-continued

Example PCR Run Chemistry for each PCR reaction

Reaction 1 (Alternaria, Fusarium, Scopulariopsis, and Scytalidium)

| | |
|---|---|
| Fus For2a (S1_3) | 250 nM |
| Fsol For1 (S1_4) | 250 nM |
| Fus Rev1a (S1_5) | 250 nM |
| Scop For9 (S1_6) | 200 nM |
| Scop Rev3g (S1_7) | 200 nM |
| Scyt For5 (S1_8) | 300 nM |
| Scyt Rev2 (S1_9) | 300 nM |

Probes

| | |
|---|---|
| Scyt Probe1 (S1_Probe_1) | 60 nM |
| Alt Probe1 (S1_Probe_2) | 120 nM |
| FsolProbe4 (S1_probe_3) | 100 nM |
| Scop Probe2 (S1_Probe_4) | 80 nM |

Reaction 2 (Acremonium, Aspergillus, and Curvularia)

| | |
|---|---|
| Rox | 37.5 nM |
| Enzyme | Platinum II 1U |
| MgCl2 | 2.5 mM |

Primers

| | |
|---|---|
| Cury For2 (S2_1) | 250 nM |
| Cury Rev1 (S2_2) | 250 nM |
| Acr For5b (S2_3) | 300 nM |
| Acr Rev5 (S2_4) | 300 nM |
| Asp For2 (S2_5) | 200 nM |
| Asp Rev5b (S2_6) | 200 nM |

Probes

| | |
|---|---|
| Cury Probe2 (S2_Probe_1) | 80 nM |
| Acr ProbeAR (S2_Probe_2) | 60 nM |
| Asp Probe7 (S2_Probe_3) | 100 nM |

The OIAD Reflex Yeast Rxn1 can include primers and probes for one or more of *Candida albicans* (C.a.), *Candida parapsilosis* (C.p.), *Candida tropicalis* (C.t.) and *Trichosporon* spp. (Tr.) (FIG. 4, Table 7).

TABLE 7

Example primer/probe sequences and target regions employed in the Yeast OIAD Reflex Rxn1

| | Primer Name | Sequences (5'-3') | SEQ ID NO: | Target Regions | Probe Label | Primer/Probe Details |
|---|---|---|---|---|---|---|
| C.a., C.p., C.t. | Y1_1 | GCTGGGTTTGGTGTTGAGCAATAC | 69 | ITS2 | | *Candida* Common Forward1 |
| | Y1_2 | GCGGGTAGTCCTACCTGATTTG | 70 | ITS2 | | *Candida* Common Reverse |
| | Y1_3 | GCTTGAAAAGTATTGGCATGGGTAG | 71 | ITS2 | | *Candida* Common Forward2 |
| | Y1_Probe_1 | TCGCTTTGACAATGGCTTAGGTCTACC | 72 | | FAM | *C albicans* Probe |
| | Y1_Probe_2 | CCTATCCATTAGTTTATACTCCGCCTTTCTTTCAAG | 73 | | Cy5 | *C parasilosis* Probe |
| | Y1_Probe_3 | AAACGCTTATTTTGCTAGTGGCCACC | 74 | | ATTO550 | *C tropicalis* Probe |
| Tr. | Y1_4 | AGTGTCATGAAATCTCAACCA | 75 | ITS2 | | *Trichosporon* Forward |
| | Y1_5 | CCTTGCGGACGATTAGAAGC | 76 | ITS2 | | *Trichosporon* Reverse |
| | Y1_Probe_4 | TAATGGATTGGATTTGGGCG | 77 | | MAX | *Trichosporon* Probe1 |
| | Y1_Probe_5 | TAATGGCTTGGATTTGGGCGCTG | 78 | | MAX | *Trichosporon* Probe2 |

The OIAD Reflex Yeast Rxn2 can include primers and probes for one or more of *Candida guilliermondii* (C.g.), *Malassezia* spp. (M.) and *Cryptococcus* spp. (Cryp.) (FIG. 1, Table 8).

TABLE 8

Example primer/probe sequences and target regions employed in the Yeast OIAD Reflex_Rxn2

| | Primer Name | Sequences (5'-3') | SEQ ID NO: | Target Regions | Probe Label | Primer/Probe Details |
|---|---|---|---|---|---|---|
| C.g. & Cryp. | Y2_1 | GCTTGAAAAGTATTGGCATGGGTAG | 71 | ITS2 | | Candida Common Forward |
| | Y2_2 | GCGCCCTTTGGTATTCCGA | 79 | ITS2 | | Cryptococcus Forward |
| | Y2_3 | GCGGGTAGTCCTACCTGATTTG | 70 | ITS2 | | Candida Common Reverse |
| | Y2_Probe_1 | TGTTTGGTTGTTGTAAGGCCGGGC | 80 | | FAM | C guillermondii Probe |
| | Y2_Probe_2 | TTGTTATCAGCAAGCCGAAGACTACCC | 81 | | Cy5 | Cryptococcus Probe1 |
| | Y2_Probe_3 | AGCAGACTCATAAGCAAGGGACAAGAC | 82 | | Cy5 | Cryptococcus Probe2 |
| | Y2_Probe_4 | AAGCGGTCTTTAGTCCTGCAACGC | 83 | | Cy5 | Cryptococcus Probe3 |
| M. | Y2_4 | GGTCAGTTTTACTGGGGC | 84 | Mitochondrion rnl | | Malassezia Forward |
| | Y2_5 | GTCCTACTTGCGTAGCTGATCG | 85 | Mitochondrion rnl | | Malassezia Reverse1 |
| | Y2_6 | CTATATCCTACTTGCGTAACTGATCG | 86 | Mitochondrion rnl | | Malassezia Reverse2 |
| | Y2_Probe_5 | TATACCTTTGAAGGCCTCTGATACTTT | 87 | | MAX | Malassezia Probe |

TABLE (8a)

Example PCR Run Chemistry per PCR reaction:

| Reaction 1 (C. albicans, C. parapsilosis, C. tropicalis, Trichosporon) | | Reaction 2 (C. guilliermondii, Cryptococcus, Malassezia) | |
|---|---|---|---|
| Rox | 37.5 nM | Rox | 37.5 nM |
| Enzyme | Platinum II 1U | Enzyme | Platinum II 1U |
| MgCl2 | 2.5 mM | MgCl2 | 2.5 mM |
| Primers | | Primers | |
| Can Reflex For1a (Y1_1) | 350 nM | Cguill For1a (Y2_1) | 250 nM |
| Can Reflex Rev2 (Y1_2) | 250 nM | Cypt-F3 (Y2_2) | 300 nM |
| Cguill For1a (Y1_3) | 125 nM | Can Reflex Rev2 (Y2_3) | 250 nM |
| Trich-F1 (Y1_4) | 250 nM | Mal-F4 (Y2_4) | 300 nM |
| Trich_aaio-R1 (Y1_5) | 250 nM | Mal-R2a (Y2_5) | 300 nM |
| | | Mal-R2b (Y2_6) | 300 nM |
| Probes | | Probes | |
| Calb Probe3_FAM (Y1_Probe_1) | 200 nM | Cguill Probe3_FAM (Y2_Probe_1) | 120 nM |
| Cpara Probe1Ra_Cy5 (Y1_Probe_2) | 80 nM | Crypt_ng_p2R_Cy5 (Y2_Probe_2) | 120 nM |
| Ctrop probe1_Atto550 (Y1_Probe_3) | 40 nM | Crypt_laur_p2R_Cy5 (Y2_Probe_3) | 120 nM |
| Trich-P1_MAX (Y1_Probe_4) | 120 nM | Crypt_alb_p2R_Cy5 (Y2_Probe_4) | 120 nM |
| Trich_cm-P1_MAX (Y1_Probe_5) | 120 nM | Mal-P5R_MAX (Y2_Probe_5) | 160 nM |

Hydrolysis Probes

Aspects of the present disclosure employ hydrolysis probes for the detection of nucleic acids. Hydrolysis probes take advantage of the 5' exonuclease activity of some polymerases. During the extension or elongation phase of a PCR reaction, a polymerase, such as Taq polymerase, uses an upstream primer as a binding site and then extends. The hydrolysis probe is then cleaved during polymerase extension at its 5' end by the 5'-exonuclease activity of the polymerase.

The TaqMan® assay (see, e.g., U.S. Pat. No. 5,210,015, incorporated herein by reference) is an example of a hydrolysis-probe based assay. In the TaqMan® assay, hydrolysis probes are typically labeled with a reporter on the 5' end and a quencher on the 3' end. When the reporter and quencher are fixed onto the same probe, they are forced to remain in close proximity. This proximity effectively quenches the reporter signal, even when the probe is hybridized to the target sequence. The hydrolysis probes are cleaved during polymerase extension at their 5' end by the 5'-exonuclease activity of Taq. When this occurs, the reporter fluorophore is released from the probe, and subsequently, is no longer in close proximity to the quencher. This produces a perpetual increase in reporter signal with each extension phase as the PCR reaction continues cycling. In order to achieve maximal signal with each cycle, hydrolysis probes are often designed with a Tm that is roughly 10° C. higher than the primers in the reaction. Uses of the real-time hydrolysis probe reaction are also described in U.S. Pat. Nos. 5,538,848; 7,205,105; and 9,970,050, which are incorporated by reference herein. Any suitable reporter-quencher pair known in the art may be utilized in connection with the disclosed hydrolysis probes, e.g., a suitable fluorophore-quencher pair. TaqMan® probes are available commercials from ThermoFisher Scientific. Suitable dyes for use with the hydrolysis probes described herein include, e.g., ATTO550, FAM, ATTO647, Atto550, MAX, Cy5. Suitable quenchers for use with the hydrolysis probes described herein may include BHQ-1™, BHQ-2™, BHQ-3™, DABCYL™, QSY-7&9® or other dark quencher.

Clade-Specific Primers and Probes

Aspects of the present disclosure include clade-specific primers and probes, e.g., secondary and primary clade-specific primers and probes, that are designed to amplify (e.g., when combined with a polymerase, a template and a source of nucleotides under suitable conditions, such as a PCR condition) and detect target sequences within the genomes of clade members to produce nucleic acid products that distinguish one clade member from another clade member. The genomic locus targeted by clade-specific primers and and probes specific for a first clade member may be the same or a different genomic locus targeted by clade-specific primers and probes specific for a second, different clade member.

In certain embodiments, clade-specific primers and probes are designed to amplify and detect a nucleic acid product when the primers are used to perform PCR with template nucleic acids obtained from an organism that belongs to a clade member present in a sample, and are designed not to amplify a nucleic acid product when the clade member is not present in the sample assayed. In certain embodiments, clade-specific primers and probes are designed to amplify and detect a nucleic acid product when the primers are used to perform PCR with template nucleic acids in a sample containing a target clade member, and are designed not to amplify a nucleic acid product in a sample containing a non-target clade member but not the target clade member. Thus, clade-specific primers and probes that specifically amplify and detect a nucleic acid product in target clade members may be designed to amplify homologous nucleotide sequences that have a high percentage of sequence identity among organisms each of which belong to a target clade member, but do not amplify a homologous nucleotide sequence that have a low percentage of sequence identity in organisms which belong to a non-target clade member. In certain embodiments, the clade-specific primers may be designed to amplify in a sample containing a target clade member a target nucleotide sequence that is 70% or more, e.g., 80% or more, 85% or more, 90% or more, including 95% or more, and that is 100% or less, e.g., 95% or less, 90% or less, 85% or less, including 80% or less identical to a homologous nucleotide sequence in one or more other organisms, each of which belongs to a target clade member. In some cases, the clade-specific primers may be designed to amplify in a sample containing a target clade member a target nucleotide sequence that is 70% to 100%, e.g., 80% to 100%, including 85% to 100% identical to a homologous nucleotide sequence in one or more other organisms, each of which belongs to a target clade member.

In some embodiments, clade-specific primers and probes are configured to amplify and detect a nucleic acid product when nucleic acids containing the target nucleotide sequence from the target clade member as well as non-fungal nucleic acids are present in the sample, and not to amplify a nucleic acid product when the non-fungal nucleic acids are present but the nucleic acids from the target clade member is absent from the sample. In certain embodiments, the non-fungal nucleic acids include human genomic DNA and/or bacterial DNA. In certain embodiments, the clade-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences. Bacteria from which bacterial genomic sequences may be derived include, but are not limited to, *Pseudomonas aeruginosa, Proteus mirabilis, Staphylococcus aureus, Serratia marcescens*, and *Streptococcus pyogenes*.

Clade-specific primers, e.g., a pair of clade-specific primers, may be associated with a reference, or expected, $C_t$ (cycle threshold) range for real-time PCR reactions in which a clade-specific nucleic acid product is amplified by the clade-specific primers. The clade-specific reference $C_t$ range may provide one indication that a clade member is present in a sample when a $C_t$ value obtained for the real-time PCR reaction using the clade-specific primers in the sample is within the clade-specific reference $C_t$ range. In some embodiments, the clade-specific reference $C_t$ range for a first clade member covers a distinct range of $C_t$ values than the clade-specific reference $C_t$ range for a second clade member.

In some cases, clade-specific primers and probes are designed to amplify and detect a first nucleic acid product when the primers are used to perform PCR with template nucleic acids in a sample containing a first clade member, and are designed to amplify a second nucleic acid product when the primers are used to perform PCR with template nucleic acids in a sample containing a second clade member that is different from the first clade member, where the first and second nucleic acid products are distinguishable. In some cases, a pair of clade-specific primers is designed to amplify a first nucleic acid product when the pair is used to perform PCR with template nucleic acids obtained from a first clade member present in a sample, and the same pair of primers are designed to amplify a second nucleic acid product when the pair is used to perform PCR with template nucleic acids obtained from a second clade member present in a sample, where the first and second nucleic acid products are distinguishable. In some cases, a first set of clade-specific primers are designed to amplify a first nucleic acid product when the primers are used to perform PCR with template nucleic acids in a sample containing a first clade member, and a second set of clade-specific primers are designed to amplify a second nucleic acid product when the primers are used to perform PCR with template nucleic acids in a sample containing a second clade member, where the first and second nucleic acid products are distinguishable.

The clade-specific primers may be designed to target any suitable nucleotide sequence that has sufficient sequence identity among sequences associated with organisms that belong to a clade member and that is divergent in organisms that do not belong to the clade member.

Clade-specific primers may be designed to be used in the present method in a single reaction mixture that includes any convenient number of clade-specific primers. In certain embodiments, a pair (e.g., forward and reverse primer pair) of clade-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of clade-specific primers, each pair in the reaction mixture being configured to amplify a different clade-specific nucleotide sequence. In certain embodiments, a pair (e.g., forward and reverse primer pair) of clade-specific primers is designed to be used in a single reaction mixture that includes 1 to 10 pairs, e.g. 1 to 8 pairs, 1 to 6 pairs, 1 to 5 pairs, including 1 to 4 pairs of clade-specific primers, each pair in the reaction mixture being configured to amplify a different clade-specific nucleotide sequence.

Secondary Clade-Specific Primers and Probes

Aspects of the present disclosure include secondary clade-specific primers and probes that are designed to amplify and detect target sequences within the genomes of organisms that belong to a secondary clade member to produce nucleic acid products that distinguish one secondary clade member from another secondary clade member. In some instances, a secondary clade member contains a plurality of (e.g., 2 or more, 3 or more, 4 or more, or 5 or more) primary clade members. As the secondary clade-specific primers are designed to be specific to a secondary clade member, the secondary clade-specific primers, when used to perform PCR on a sample, may not provide information that distinguishes between the presence or absence of a first primary clade member that belongs to the secondary clade member from the presence or absence of a second primary clade member that belongs to the same secondary clade member as the first primary clade member, when the primers are used to determine that the secondary clade member is present in the sample.

In certain embodiments, secondary clade-specific primers are designed to amplify a nucleic acid product when the primers are used to perform PCR with template nucleic acids obtained from an organism that belongs to a secondary clade member present in a sample, and designed not to amplify a nucleic acid product when the secondary clade member is not present in the sample assayed. In certain embodiments, secondary clade-specific primers are designed to amplify a nucleic acid product when the primers are used to perform PCR with template nucleic acids in a sample containing a target secondary clade member, and designed not to amplify a nucleic acid product in a sample containing a non-target secondary clade member but not the target secondary clade member. Thus, secondary clade-specific primers that specifically amplify a nucleic acid product in a target secondary clade member may be designed to amplify homologous nucleotide sequences that have a high percentage of sequence identity among organisms each of which belong to a target secondary clade member, but do not amplify a homologous nucleotide sequence that have a low percentage of sequence identity in organisms which belong to a non-target secondary clade member. In certain embodiments, the secondary clade-specific primers may be designed to amplify in a sample containing a target secondary clade member a target nucleotide sequence that is 70% or more, e.g., 80% or more, 85% or more, 90% or more, including 95% or more, and that is 100% or less, e.g., 95% or less, 90% or less, 85% or less, including 80% or less identical to a homologous nucleotide sequence in one or more other organisms, each of which belongs to a target secondary clade member. In some cases, the secondary clade-specific primers may be designed to amplify in a sample containing a target secondary clade member a target nucleotide sequence that is 70% to 100%, e.g., 80% to 100%, including 85% to 100% identical to a homologous nucleotide sequence in one or more other organisms, each of which belongs to a target secondary clade member.

Secondary clade-specific primers may be designed to be used in the present method in a single reaction mixture that includes any convenient number of secondary clade-specific primers. In certain embodiments, a pair (e.g., forward and reverse primer pair) of secondary clade-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair in the reaction mixture being configured to amplify a different secondary clade-specific nucleotide sequence. In certain embodiments, a pair of secondary clade-specific primers is designed to be used in a single reaction mixture that includes 1 to 10 pairs, e.g. 1 to 8 pairs, 1 to 6 pairs, 1 to 5 pairs, including 1 to 4 pairs of secondary clade-specific primers, each pair in the reaction mixture being configured to amplify a different secondary clade-specific nucleotide sequence.

The secondary clade-specific primers may be designed to target any suitable nucleotide sequence that has a high percentage of sequence identity among organisms that belong to a secondary clade member and that is divergent in organisms that do not belong to the secondary clade member. In certain embodiments, the secondary clade-specific primers are configured to amplify a secondary clade-specific nucleotide sequence within a nuclear-encoded ribosomal RNA gene. In certain embodiments, the secondary clade-specific primers are configured to amplify a secondary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the secondary clade-specific primers are configured to amplify a secondary clade-specific nucleotide sequence encoding an 18S ribosomal RNA, or a portion thereof, and/or an internal transcribed spacer, or a portion thereof, adjacent the nucleotide sequence encoding the 18S ribosomal RNA.

The secondary clade member may be any suitable group of organisms that can be defined by one or more feature(s) of a nucleic acid containing nucleotide sequence(s) associated with organisms that belong to the group. The group of organisms may include a group of fungi, bacteria, archaea, protists, plants, animals, etc.

Yeast

In some instances, the secondary clade member is yeast. The yeast secondary clade member may include a plurality of species of the *Candida* genus *Malassezia* genus, *Trichosporon* genus, and *Cryptococcus* genus. In some instances, the plurality of primary clade members that belong to yeast include, without limitation, the species *C. albicans, C. parapsilosis, C. glabrata, C. tropicalis, C. guilliermondii, C. krusei,* and *Malassezia pachydermatis*. Thus, in certain embodiments, yeast-specific primers include primers that are designed to amplify target sequences within the genome of a yeast to produce nucleic acid products that distinguish a yeast from a non-yeast (e.g., dermatophyte, or other non-yeast saprophyte). As the yeast-specific primers are designed to be specific to yeast, the yeast-specific primers, when used to perform PCR on a sample, may not provide information that is sufficient to identify individual species of yeast, when the primers are used to determine that a yeast is present in the sample.

In certain embodiments, yeast-specific primers and probes are designed to amplify and detect a nucleic acid product when the primers are used to perform PCR with template nucleic acids obtained from a yeast present in a sample, and designed not to amplify a nucleic acid product when a yeast is not present in the sample assayed. In certain embodiments, yeast-specific primers are designed to amplify a nucleic acid product when the primers are used to perform PCR with template nucleic acids in a sample containing a yeast, and designed not to amplify a nucleic acid product in a sample containing a non-yeast but not containing a yeast. Thus, yeast-specific primers that specifically amplify a nucleic acid product in yeast may be designed to amplify homologous nucleotide sequences that have a high percentage of sequence identity among yeast, but have lower percentage of sequence identity in non-yeast organisms (e.g., dermatophytes and saprophytes). In certain embodiments, the yeast-specific primers are designed to amplify in a sample containing a first yeast a target nucleotide sequence that is 70% or more, e.g., 80% or more, 85% or more, 90% or more, including 95% or more, and that is 100% or less, e.g., 95% or less, 90% or less, 85% or less, including 80% or less identical to a homologous nucleotide sequence in one or more other yeasts. In some cases, the yeast-specific primers may be designed to amplify in a sample containing a first yeast a target nucleotide sequence that is 70% to 100%, e.g., 80% to 100%, including 85% to 100% identical to a homologous nucleotide sequence in one or more other yeasts.

In some embodiments, yeast-specific primers are configured to amplify a nucleic acid product when nucleic acids containing the target nucleotide sequence from the yeast as well as non-fungal nucleic acids are present in the sample, and not to amplify a nucleic acid product when the nucleic acids from the yeast is absent from the sample and non-fungal nucleic acids are present in the sample. The non-fungal nucleic acids may include human genomic DNA and/or bacterial DNA. In certain embodiments, the yeast-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In some cases, yeast-specific primers are designed to amplify a first nucleic acid product when the yeast-specific primers are used to perform PCR with template nucleic acids in a sample containing a yeast, and non-yeast-specific primers are designed to amplify a second nucleic acid product when the non-yeast-specific primers are used to perform PCR with template nucleic acids in a sample containing the non-yeast organism targeted by the non-yeast-specific primers, where the first and second nucleic acid products are distinguishable.

Yeast secondary clade-specific primers may be designed to be used in the present method in a single reaction mixture that includes any convenient number of secondary clade-specific primers. In certain embodiments, a pair of yeast-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair being configured to amplify a different secondary clade-specific nucleotide sequence. In certain embodiments, a pair of yeast-specific primers is designed to be used in a single reaction mixture that includes 1 to 10 pairs, e.g. 1 to 5 pairs, including 1 to 4 pairs of secondary clade-specific primers, each pair being configured to amplify a different secondary clade-specific nucleotide sequence. In certain embodiments, the pair of yeast-specific primers is designed to be used in a single reaction mixture that includes a pair of dermatophyte- and/or one or more pairs of saprophyte secondary clade-specific primers.

The yeast-specific primers may be designed to target any suitable nucleotide sequence that has a high percentage of sequence identity among yeasts and is divergent in non-yeasts. In certain embodiments, the yeast-specific primers are configured to amplify a yeast-specific nucleotide sequence within a nuclear-encoded ribosomal RNA gene. In certain embodiments, the yeast-specific primers are configured to amplify a yeast-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the yeast-specific primers are configured to amplify a yeast-specific nucleotide sequence encoding an 18S ribosomal RNA, or a portion thereof, and/or an internal transcribed spacer, or a portion thereof, adjacent the nucleotide sequence encoding the 18S ribosomal RNA.

In certain embodiments, the yeast-specific primers are configured to amplify a nucleotide sequence that includes a sequence 70% or more, e.g., 80% or more, 90% or more, 95% or more, 97% or more, and up to 100% identical to the sequence set forth in one of FIGS. 37, 39, 41, 43, 45, and 47. In certain embodiments, the yeast-specific primers are configured to amplify a nucleotide sequence 70% or more, e.g., 80% or more, 90% or more, 95% or more, including 97% or more identical to the sequence set forth in one of FIGS. 37, 39, 41, 43, 45, and 47. In certain embodiments, the yeast-specific primers include a primer containing a nucleotide sequence 85% or more, e.g., 90% or more, 95% or more, 98% or more, 99% or more, and up to 100% identical to the sequence set forth in one of SEQ ID NOs:4-9 and 14-15, or the primer sequence identified in one of FIGS. 37, 39, 41, 43, 45, and 47. In certain embodiments, the yeast-specific primers are 85% or more, e.g., 90% or more, 95% or more, 98% or more, 99% or more, and up to 100% identical to the sequence set forth in one of SEQ ID NOs: 4-9 and 14-15, or the primer sequence identified in one of FIGS. 37, 39, 41, 43, 45, and 47.

Dermatophyte

In some instances, the secondary clade member is a dermatophyte. The dermatophyte secondary clade may include a plurality of primary clade members. In some instances, the plurality of primary clade members that belong to dermatophytes include, without limitation, the genera/species *Trichophyton rubrum, T. mentagrophytes, Epidermophyton*, and *Microsporum*. Thus, in certain embodiments, dermatophyte-specific primers include primers that are designed to amplify target sequences within the genome of a dermatophyte to produce nucleic acid products that distinguish a dermatophyte from a non-dermatophyte (e.g., candida, or other non-dermatophyte saprophyte). As the dermatophyte-specific primers are designed to be specific to dermatophytes, the dermatophyte-specific primers, when used to perform PCR on a sample, may not provide information that distinguishes the presence or absence of a first primary clade member that belongs to dermatophytes from a second primary clade member that belongs to dermatophytes. Thus, the dermatophyte-specific primers may not provide information that is sufficient to identify individual species of dermatophytes, when the primers are used to determine that a dermatophyte is present in the sample. In some embodiments, the dermatophyte-specific primers may not provide information that is sufficient to identify a genus, e.g., a *Trichophyton, Epidermophyton*, and *Microsporum*, or species within dermatophytes, when the primers are used to determine that a dermatophyte is present in the sample.

In certain embodiments, dermatophyte-specific primers are designed to amplify a nucleic acid product when the primers are used to perform PCR with template nucleic acids obtained from a dermatophyte present in a sample, and designed not to amplify a nucleic acid product when a dermatophyte is not present in the sample assayed. In certain embodiments, dermatophyte-specific primers are designed to amplify a nucleic acid product when the primers are used to perform PCR with template nucleic acids in a sample containing a dermatophyte, and designed not to amplify a nucleic acid product in a sample containing a non-dermatophyte but not a dermatophyte. Thus, dermatophyte-specific primers that specifically amplify a nucleic acid product in dermatophytes may be designed to amplify homologous nucleotide sequences that have a high percentage of sequence identity among dermatophytes, but have lower percentage of sequence identity in non-dermatophytes (e.g., candida and saprophytes). In certain embodiments, the dermatophyte-specific primers are designed to amplify in a sample containing a first dermatophyte a target nucleotide sequence that is 70% or more, e.g., 80% or more, 85% or more, 90% or more, including 95% or more, and that may be 100% or less, e.g., 95% or less, 90% or less, 85% or less, including 80% or less identical to a homologous nucleotide sequence in one or more other dermatophytes. In some cases, the dermatophyte-specific primers may be designed to amplify in a sample containing a first dermatophyte a target nucleotide sequence that is 70% to 100%, e.g., 80% to 100%, including 85% to 100% identical to a homologous nucleotide sequence in one or more other dermatophytes.

In some embodiments, dermatophyte-specific primers and probes are configured to amplify and detect a nucleic acid product when nucleic acids containing the target nucleotide sequence from the dermatophyte as well as non-fungal nucleic acids are present in the sample, and not to amplify a nucleic acid product when the nucleic acids from the dermatophyte is absent from the sample and non-fungal nucleic acids are present in the sample. The non-fungal nucleic acids may include human genomic DNA and/or bacterial DNA. In certain embodiments, the dermatophyte-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In some cases, dermatophyte-specific primers are designed to amplify a first nucleic acid product when the dermatophyte-specific primers are used to perform PCR with template nucleic acids in a sample containing a dermatophyte, and non-dermatophyte-specific primers are designed to amplify a second nucleic acid product when the non-dermatophyte-specific primers are used to perform PCR with template nucleic acids in a sample containing the non-dermatophyte targeted by the non-dermatophyte-specific primers, where the first and second nucleic acid products are distinguishable.

Dermatophyte secondary clade-specific primers may be designed to be used in the present method in a single reaction mixture that includes any convenient number of secondary clade-specific primers. In certain embodiments, a pair (e.g., forward and reverse primer pair) of dermatophyte-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair being configured to amplify a different secondary clade-specific nucleotide sequence. In certain embodiments, a pair (e.g., forward and reverse primer pair) of dermatophyte-specific primers is designed to be used in a single reaction mixture that includes 1 to 10 pairs, e.g. 1 to 8 pairs, 1 to 6 pairs, 1 to 5 pairs, including 1 to 4 pairs of secondary clade-specific primers, each pair being configured to amplify a different secondary clade-specific nucleotide sequence. In certain embodiments, the pair of dermatophyte-specific primers is designed to be used in a single reaction mixture that includes a pair of yeast- and/or one or more pairs of saprophyte secondary clade-specific primers.

The dermatophyte-specific primers may be designed to target any suitable nucleotide sequence that has a high percentage of sequence identity among dermatophytes and is divergent in non-dermatophytes. In certain embodiments, the dermatophyte-specific primers are configured to amplify a dermatophyte-specific nucleotide sequence within a nuclear-encoded ribosomal RNA gene. In certain embodiments, the dermatophyte-specific primers are configured to amplify a dermatophyte-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the dermatophyte-specific primers are configured to amplify a dermatophyte-specific nucleotide sequence encoding an 18S ribosomal RNA, or a portion thereof, and/or an internal transcribed spacer, or a portion thereof, adjacent the nucleotide sequence encoding the 18S ribosomal RNA.

In certain embodiments, the dermatophyte-specific primers are configured to amplify a nucleotide sequence that includes a sequence 70% or more, e.g., 80% or more, 90% or more, 95% or more, including 97% or more identical to the sequence set forth in FIG. 29. In certain embodiments, the dermatophyte-specific primers are configured to amplify a nucleotide sequence 70% or more, e.g., 80% or more, 90% or more, 95% or more, including 97% or more identical to the sequence set forth in FIG. 29. In certain embodiments, the dermatophyte-specific primers include a primer containing a nucleotide sequence 85% or more, e.g., 90% or more, 95% or more, 98% or more, including 99% or more identical to the sequence set forth as SEQ ID NOs:3 or 4, or a primer sequence identified in FIG. 28 or 29. In certain embodiments, the dermatophyte-specific primers are 85% or more, e.g., 90% or more, 95% or more, 98% or more, including 99% or more identical to the sequence set forth as SEQ ID NOs:1 or 2.

Saprophyte

In some instances, the secondary clade member is a saprophyte (e.g., a non-dermatophyte, non-yeast onychomycotic fungus). The saprophyte secondary clade may include a plurality of primary clade members. In some instances, the plurality of primary clade members that belong to saprophytes include, without limitation, the genera *Aspergillus, Penicillium, Paecilomyces, Fusarium, Acremonium, Scopulariopsis, Chaetomium, Curvularia, Alternaria, Mucor, Scytalidium* and *Rhizopus*. Thus, in certain embodiments, saprophyte-specific primers include primers that are designed to amplify target sequences within the genome of a saprophyte to produce nucleic acid products that distinguish a saprophyte from a non-saprophyte (e.g., candida, or dermatophyte). As the saprophyte-specific primers are designed to be specific to saprophytes, the saprophyte-specific primers, when used to perform PCR on a sample, may not provide information that is sufficient to identify a saprophyte genus or species, when the primers are used to determine that a saprophyte is present in the sample.

In certain embodiments, saprophyte-specific primers are designed to amplify a nucleic acid product when the primers are used to perform PCR with template nucleic acids obtained from a saprophyte present in a sample, and designed not to amplify a nucleic acid product when a saprophyte is not present in the sample assayed. In certain embodiments, saprophyte-specific primers are designed to amplify a nucleic acid product when the primers are used to perform PCR with template nucleic acids in a sample containing a saprophyte, and designed not to amplify a nucleic acid product in a sample containing a non-saprophyte but not a saprophyte. Thus, saprophyte-specific primers that specifically amplify a nucleic acid product in saprophytes may be designed to amplify homologous nucleotide sequences that have a high percentage of sequence identity among saprophytes, but have lower percentage of sequence identity in non-saprophytes (e.g., candida and dermatophytes). In certain embodiments, the saprophyte-specific primers are designed to amplify in a sample containing a first saprophyte a target nucleotide sequence that is 70% or more, e.g., 80% or more, 85% or more, 90% or more, including 95% or more, and that may be 100% or less, e.g., 95% or less, 90% or less, 85% or less, including 80% or less identical to a homologous nucleotide sequence in one or more other saprophytes. In some cases, the saprophyte-specific primers may be designed to amplify in a sample containing a first saprophyte a target nucleotide sequence that is 70% to 100%, e.g., 80% to 100%, including 85% to 100% identical to a homologous nucleotide sequence in one or more other saprophytes.

In some embodiments, saprophyte-specific primers are configured to amplify a nucleic acid product when nucleic acids containing the target nucleotide sequence from the saprophyte as well as non-fungal nucleic acids are present in the sample, and not to amplify a nucleic acid product when the nucleic acids from the saprophyte is absent from the sample and non-fungal nucleic acids are present in the sample. The non-fungal nucleic acids may include human genomic DNA and/or bacterial DNA. In certain embodiments, the saprophyte-specific primers have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, saprophyte-specific primers are designed to amplify a first nucleic acid product when the saprophyte-specific primers are used to perform PCR with template nucleic acids in a sample containing a first subset of saprophytes, and are designed to amplify a second nucleic acid product when the primers are used to perform PCR with template nucleic acids in a sample containing a second subset of saprophytes that is different from the first subset of saprophytes, where the first and second nucleic acid products are distinguishable. In some cases, saprophyte-specific primers are designed to amplify a first nucleic acid product when the saprophyte-specific primers are used to perform PCR with template nucleic acids in a sample containing a saprophyte, and non-saprophyte-specific primers are designed to amplify a second nucleic acid product when the non-saprophyte-specific primers are used to perform PCR with template nucleic acids in a sample containing the non-saprophyte targeted by the non-saprophyte-specific primers, where the first and second nucleic acid products are distinguishable.

Saprophyte secondary clade-specific primers may be designed to be used in the present method in a single reaction mixture that includes any convenient number of secondary clade-specific primers. In certain embodiments, a pair (e.g., forward and reverse primer pair) of saprophyte-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair being configured to amplify a different secondary clade-specific nucleotide sequence. In certain embodiments, a pair (e.g., forward and reverse primer pair) of saprophyte-specific primers is designed to be used in a single reaction mixture that includes 1 to 10 pairs, e.g. 1 to 8 pairs, 1 to 6 pairs, 1 to 5 pairs, including 1 to 4 pairs of secondary clade-specific primers, each pair being configured to amplify a different secondary clade-specific nucleotide sequence. In certain embodiments, the pair (e.g., forward and reverse primer pair) of saprophyte-specific primers is designed to be used in a single reaction mixture that includes a pair of yeast- and/or one or more pairs of dermatophyte secondary clade-specific primers. In some embodiments, one or more pairs, e.g., two or more, 3 or more, 4 or more, including 5 or more saprophyte secondary clade-specific primers are configured to be used in a single reaction mixture in the present method, where each pair of saprophyte secondary clade-specific primers in the reaction mixture is configured to amplify a secondary clade-specific nucleotide sequence for different saprophyte secondary clade members. In some embodiments, 1 to 8 pairs, e.g., 1 to 6 pairs, 1 to 5 pairs, 1 to 4 pairs, 2 to 5 pairs, including 2 to 4 pairs of saprophyte secondary clade-specific primers are configured to be used in a single reaction mixture in the present method, where each pair of saprophyte secondary clade-specific primers in the reaction mixture is configured to amplify a secondary clade-specific nucleotide sequence for different saprophyte secondary clade members.

The saprophyte-specific primers may be designed to target any suitable nucleotide sequence that has a high percentage of sequence identity among saprophytes and is divergent in non-saprophytes. In certain embodiments, the saprophyte-specific primers are configured to amplify a saprophyte-specific nucleotide sequence within a nuclear-encoded ribosomal RNA gene. In certain embodiments, the saprophyte-specific primers are configured to amplify a saprophyte-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the saprophyte-specific primers are configured to amplify a saprophyte-specific nucleotide sequence encoding an 18S ribosomal RNA, or a portion thereof, and/or an internal transcribed spacer, or a portion thereof, adjacent the nucleotide sequence encoding the 18S ribosomal RNA.

In certain embodiments, the saprophyte-specific primers are configured to amplify a nucleotide sequence that includes a sequence 70% or more, e.g., 80% or more, 90% or more, 95% or more, including 97% or more identical to a sequence set forth in one of FIGS. 30, 31, 32, 33, 34, 35, and 36. In certain embodiments, the saprophyte-specific primers are configured to amplify a nucleotide sequence 70% or more, e.g., 80% or more, 90% or more, 95% or more, including 97% or more identical to a sequence set forth in one of FIGS. 30, 31, 32, 33, 34, 35, and 36. In certain embodiments, the saprophyte-specific primers include one or more pairs of primers, each pair containing a primer that includes a nucleotide sequence 85% or more, e.g., 90% or more, 95% or more, 98% or more, including 99% or more identical to a sequence of the sequences set forth as SEQ ID NOs:20-26, or a primer sequence identified in one of FIGS. 30, 31, 32, 33, 34, 35, and 36. In certain embodiments, the saprophyte-specific primers include one or more pairs of primers, each pair containing a primer that includes a nucleotide sequence 85% or more, e.g., 90% or more, 95% or more, 98% or more, including 99% or more identical to the sequence set forth in one of SEQ ID NOs:20-26, or a primer sequence identified in one of FIGS. 30, 31, 32, 33, 34, 35, and 36. In certain embodiments, the saprophyte-specific primers include one or more pairs of primers, each pair containing a primer 85% or more, e.g., 90% or more, 95% or more, 98% or more, including 99% or more identical to the sequence set forth in one of SEQ ID NOs:20-26, or a primer sequence identified in one of FIGS. 30, 31, 32, 33, 34, 35, and 36.

Primer Design and Use in Assays

The dermatophyte-, yeast-, and saprophyte-specific primers and probes may be configured to generate and detect PCR amplification products that are distinguishable from each other when any two or more of a dermatophyte, a yeast, and a saprophyte are present in the sample. In certain embodiments dermatophyte-specific primers and probes are configured to amplify, detect and differentiate a dermatophyte-specific nucleic acid product, and yeast-specific primers are configured to amplify, detect, and differentiate a yeast-specific nucleic acid product, where the dermatophyte-specific nucleic acid product and yeast-specific nucleic acid product are distinguishable.

In certain embodiments yeast-specific primers and probes are configured to amplify, detect, and differentiate a yeast-specific nucleic acid product and saprophyte-specific primers are configured to amplify, detect and differentiate a saprophyte-specific nucleic acid product, where the yeast-specific nucleic acid product and saprophyte-specific nucleic acid product are distinguishable. In some cases, the yeast- and saprophyte-specific nucleic acid products are distinguishable by having distinct expected Tm range(s), as determined by a melt analysis.

A primer of the present disclosure may generally be 10 to 50 nucleotides (nt) long, e.g., 12 to 40 nt long, 15 to 30 nt long, including 15 to 25 nt long.

Primary Clade-Specific Primers and Probes

Aspects of the present disclosure include primary clade-specific primers and probes that are designed to amplify, detect, and differentiate target sequences within the genomes of primary clade members to produce nucleic acid products that distinguish one primary clade member from another primary clade member.

In certain embodiments, primary clade-specific primers are designed to amplify a nucleic acid product when the primers are used to perform PCR with template nucleic acids obtained from an organism that belongs to a primary clade member present in a sample, and designed not to amplify a nucleic acid product when the primary clade member is not present in the sample assayed. In certain embodiments, primary clade-specific primers are designed to amplify a nucleic acid product when the primers are used to perform PCR with template nucleic acids in a sample containing a target primary clade member, and designed not to amplify a nucleic acid product in a sample containing a non-target primary clade member but not the target primary clade member.

Primary clade-specific primers may be designed to be used in the present method in a single reaction mixture that includes any convenient number of primary clade-specific primers. In certain embodiments, a pair of primary clade-specific primers is designed to be used in a single reaction mixture that includes one or more pairs, e.g., two or more pairs, 3 or more pairs, 4 or more pairs, 5 or more pairs, including 6 or more pairs, and include 10 or fewer pairs, e.g., 8 or fewer pairs, 6 or fewer pairs, 5 or fewer pairs, including 4 or fewer pairs of primers, each pair in the reaction mixture being configured to amplify a different primary clade-specific nucleotide sequence. In certain embodiments, a pair of primary clade-specific primers is designed to be used in a single reaction mixture that includes 1 to 10 pairs, e.g. 1 to 5 pairs, including 1 to 4 pairs of primary clade-specific primers, each pair in the reaction mixture being configured to amplify a different primary clade-specific nucleotide sequence.

The primary clade-specific primers may be designed to target any suitable nucleotide sequence that has a high percentage of sequence identity among organisms that belong to a primary clade member and may be divergent in organisms that do not belong to the primary clade member. In certain embodiments, the primary clade-specific primers are configured to amplify a primary clade-specific nucleotide sequence within a nuclear-encoded ribosomal RNA gene. In certain embodiments, the primary clade-specific primers are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs; and/or a mitochondrial nucleotide sequence, including a nicotinamide adenine dinucleotide (NADH) dehydrogenase subunit gene or a putative reverse transcriptase gene, or portions thereof.

The primary clade member may be any suitable species and/or higher phylogenetic group of organisms that can be defined by one or more feature(s) of nucleic acids containing a nucleotide sequence associated with organisms that belong to the species or group, where the primary clade member belongs to a secondary clade member determined to be present using secondary clade-specific primers, as described herein.

Detection of Primary Clade Member within the Secondary Clade of Yeast

In some instances, the primary clade member belongs to the secondary yeast clade member, and may include, without limitation, the species *C. albicans, C. parapsilosis, C. glabrata, C. tropicalis, C. krusei, C. guilliermondii, C. haemulonii, C. lusitaiae, Cryptococcus* spp., *Trichosporon* spp. and *Malassezia pachydermatis*. Thus, in certain embodiments, primary clade-specific primers for the secondary yeast clade member include primers that are designed to amplify target sequences within the genome of a yeast to produce nucleic acid products that distinguish one yeast species from another yeast species. In some embodiments, primary clade-specific primers for the secondary yeast clade member include, without limitation, *C. albicans*-specific primers, *C. parapsilosis*-specific primers, *C. glabrata*-specific primers, *C. tropicalis*-specific primers, *C. krusei*-specific primers, *C. guilliermondii*-specific primers, *Cryptococcus* spp.-specific primers, *Trichosporon* spp.-specific primers, and *M. pachydermatis*-specific primers.

In certain embodiments, primary clade-specific primers and/or probes for a secondary yeast clade member, e.g., *C. albicans*-specific primers and/or probes, *C. parapsilosis*-specific primers, and/or probes, etc., are designed to amplify and detect a nucleic acid product when the primers are used to perform PCR with template nucleic acids obtained from an organism belonging to the primary clade member, e.g., *C. albicans, C. parapsilosis*, etc., that is present in a sample, and designed not to amplify a nucleic acid product when the primary clade member, e.g., *C. albicans, C. parapsilosis*, etc., is not present in the sample assayed. In certain embodiments, primary clade-specific primers primers and/or probes for a secondary yeast clade member are designed to amplify and detect a nucleic acid product when the primers are used to perform PCR with template nucleic acids in a sample containing a primary clade member and designed not to amplify and detect a nucleic acid product in a sample containing a non-primary clade member, e.g., non-*C. albicans*, non-*C. parapsilosis*, etc., but not containing the primary clade member. Thus, primary clade-specific primers and/or probes for a secondary yeast clade that specifically amplify and detect a nucleic acid product in a primary clade member may be designed to amplify and detect a nucleotide sequence that has low sequence identity in non-primary clade members.

In some embodiments, one or more primary clade-specific primers and/or probes for a secondary yeast clade member, e.g., *C. albicans*-specific primers, *C. parapsilosis*-specific primers, etc., are configured to amplify and detect a nucleic acid product when nucleic acids containing the target nucleotide sequence from the primary clade member, e.g., *C. albicans, C. parapsilosis*, etc., as well as non-fungal nucleic acids are present in the sample, and not to amplify and detect a nucleic acid product when the nucleic acids from the primary clade member is absent from the sample and non-fungal nucleic acids are present in the sample. The non-fungal nucleic acids may include human genomic DNA and/or bacterial DNA. In certain embodiments, the primary clade-specific primers for a secondary yeast clade member have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, first primary clade-specific primers and/or probes for a secondary yeast clade member, e.g., *C. albicans*-specific primers and/or probes, are designed to amplify and detect a first nucleic acid product when the first primary clade-specific primers and/or probes are used to perform PCR with template nucleic acids in a sample containing a first primary clade member, e.g., *C. albicans*, and second primary clade-specific primers and/or probes for a secondary yeast clade member, e.g., *C. parapsilosis*-specific primers and/or probes, are designed to amplify and detect a second nucleic acid product when the primers and/or probes are used to perform PCR with template nucleic acids in a sample containing a second primary clade member, e.g., *C. parapsilosis*, where the first and second nucleic acid products are distinguishable.

In certain embodiments, primary clade-specific primers and/or probes for a secondary yeast clade member are designed to amplify and detect a first nucleic acid product when the first primary clade-specific primers and/or probes are used to perform PCR with template nucleic acids in a sample containing a first primary clade member, and are designed to amplify and detect a second nucleic acid product when the primers and/or probes are used to perform PCR with template nucleic acids in a sample containing a second primary clade member, where the first and second nucleic acid products are distinguishable. The primary clade-specific primers and/or probes for a secondary yeast clade member, e.g., *C. albicans*-specific primers and/or probes, *C. parapsilosis*-specific primers and/or probes, etc., may be designed to target any suitable nucleotide sequence. In certain embodiments, the primary clade-specific primers and/or probes for a secondary yeast clade member are configured to amplify and detect a primary clade-specific nucleotide sequence within a nuclear-encoded ribosomal RNA gene. In certain embodiments, the primary clade-specific primers and/or probes for a secondary yeast clade member are configured to amplify and detect a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs.

In certain embodiments, the primary clade-specific primers and/or probes for a secondary yeast clade member are designed to amplify and detect a primary clade-specific nucleotide sequence encoding a mitochondrial NADH dehydrogenase subunit, or a portion thereof, or a mitochondrial putative reverse transcriptase gene, or a portion thereof.

In certain embodiments, *C. albicans*-specific primers and/or probes are designed to amplify and detect a nucleotide sequence that includes a sequence 90% or more, e.g., 95% or more, 98% or more, including 99% or more identical to the following sequence: GCTGGGTTTGGTGTT-GAGCAATACGACTTGGGTTTGCTTGAAA-GACGGTAGTGGTAA GGCGG-GATCGCTTTGACAATGGCTTAGGTCTACCAAAAACAT-TGCTTGCGGCGGTAA CGTCCACCACGTATATCTTCAAACTTTGACCT-CAAATCAGGTAGGACTACCCGC (SEQ ID NO: 88). In certain embodiments, *C. parapsilosis*-specific primers and/or probes are designed to amplify and detect a nucleotide sequence that includes a sequence 90% or more, e.g., 95% or more, 98% or more, including 99% or more identical to the following sequence:

```
                                       (SEQ ID NO: 89)
CTCGGGTTTGGTGTTGAGCGATACGCTGGGTTTGCTTGAAAGAAAGGCG
GAGTATAAACTAATGGATAGGTTTTTTCCACTCATTGGTACAAACTCCA
AAACTTCTTCCAAATTCGACCTCAAATCAGGTAGGACTACCCGC.
```

Detection of Primary Clade Member within the Secondary Clade of Dermatophyte

In some instances, the primary clade member belongs to the secondary dermatophyte clade member, and may include, without limitation, the genera/species *Trichophyton rubrum, T. mentagrophytes, Epidermophyton*, and *Microsporum*. Thus, in certain embodiments, primary clade-specific primers for the secondary dermatophyte clade member include primers that are designed to amplify target sequences within the genome of a dermatophyte to produce nucleic acid products that distinguish one dermatophyte genus/species from another dermatophyte genus/species. In some embodiments, primary clade-specific primers for the secondary dermatophyte clade member include, without limitation, *Trichophyton*-specific primers, *Epidermophyton*-specific primers and *Microsporum*-specific primers.

In certain embodiments, primary clade-specific primers for a secondary dermatophyte clade, e.g., *Trichophyton*-specific primers, *Epidermophyton*-specific primers and *Microsporum*-specific primers, etc., are designed to amplify a nucleic acid product when the primers are used to perform PCR with template nucleic acids obtained from an organism belonging to the primary clade member, e.g., *Trichophyton, Epidermophyton* and *Microsporum*, etc., that is present in a sample, and designed not to amplify a nucleic acid product when the primary clade member is not present in the sample assayed. In certain embodiments, primary clade-specific primers for a secondary dermatophyte clade member are designed to amplify a nucleic acid product when the primers are used to perform PCR with template nucleic acids in a sample containing a primary clade member and designed not to amplify a nucleic acid product in a sample containing a non-primary clade member, e.g., non-*Trichophyton*, non-*Epidermophyton*, non-*Microsporum*, etc., but not containing the primary clade member. Thus, primary clade-specific primers for a secondary dermatophyte clade member that specifically amplify a nucleic acid product in a primary clade member may be designed to amplify a nucleotide sequence that has low sequence identity in non-primary clade members.

In some embodiments, one or more primary clade-specific primers for a secondary dermatophyte clade member, e.g., *Trichophyton*-specific primers, *Epidermophyton*-specific primers and *Microsporum*-specific primers, etc., are configured to amplify a nucleic acid product when nucleic acids containing the target nucleotide sequence from the primary clade member, *Trichophyton*, *Epidermophyton* and *Microsporum*, etc., as well as non-fungal nucleic acids are present in the sample, and not to amplify a nucleic acid product when the nucleic acids from the primary clade member is absent from the sample and non-fungal nucleic acids are present in the sample. The non-fungal nucleic acids may include human genomic DNA and/or bacterial DNA. In certain embodiments, the primary clade-specific primers for a secondary dermatophyte clade member have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, a first primary clade-specific primers for a secondary dermatophyte clade member, e.g., *Epidermophyton*-specific primers, are designed to amplify a first nucleic acid product when the first primary clade-specific primers are used to perform PCR with template nucleic acids in a sample containing a first primary clade member, e.g., *Epidermophyton*, and a second primary clade-specific primers for a secondary dermatophyte clade member, e.g., *Microsporum*-specific primers, are designed to amplify a second nucleic acid product when the primers are used to perform PCR with template nucleic acids in a sample containing a second primary clade member, e.g., *Microsporum*, where the first and second nucleic acid products are distinguishable. In some cases, the first and second nucleic acid products are distinguishable by having distinct melting temperature (Tm) range(s), as determined by performing a melt analysis, described below, and/or by having distinct rates of amplification, as determined by a $C_t$ range.

In certain embodiments, primary clade-specific primers for a secondary dermatophyte clade member, e.g., *Trichophyton*-specific primers, are designed to amplify a first nucleic acid product when the first primary clade-specific primers are used to perform PCR with template nucleic acids in a sample containing a first primary clade member, e.g., *T. mentagrophytes*, and are designed to amplify a second nucleic acid product when the primers are used to perform PCR with template nucleic acids in a sample containing a second primary clade member, e.g., *T. rubrum*, where the first and second nucleic acid products are distinguishable. The primary clade-specific primers for a secondary dermatophyte clade member, e.g., *Trichophyton*-specific primers, *Epidermophyton*-specific primers and *Microsporum*-specific primers, etc., may be designed to target any suitable nucleotide sequence. In certain embodiments, the primary clade-specific primers for a secondary dermatophyte clade member are configured to amplify a primary clade-specific nucleotide sequence within a nuclear-encoded ribosomal RNA gene. In certain embodiments, the primary clade-specific primers for a secondary dermatophyte clade member are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the primary clade-specific primers for a secondary dermatophyte clade member are designed to amplify a primary clade-specific nucleotide sequence encoding an 18S ribosomal RNA, or a portion thereof, a 5.8S ribosomal RNA, or portion thereof, and/or an internal transcribed spacer (ITS), or a portion thereof, adjacent the nucleotide sequence encoding the 18S ribosomal RNA or the 5.8S ribosomal RNA. In certain embodiments, the primary clade-specific primers for a secondary dermatophyte clade member are designed to amplify a primary clade-specific nucleotide sequence encoding ITS1 or ITS2.

In certain embodiments, *Trichophyton*-specific primers are designed to amplify a nucleotide sequence that includes or has a sequence 90% or more, e.g., 95% or more, 98% or more, including 99% or more identical to one of the following sequences: GCGGGCCCTTCTGG-GAGCCTCGAGCCGGACCGCGCCCGCCGGAGGACA-GACACCAA GAAAAAATTCTCTGAAGAGCTGTCAGTCT-GAGCGTTTAGCAAGCACAATCAGTT, and GCCGCGCTCTCCCAG-GAGAGCCGTTCGGCGAGCCTCTCTT-TAGTGGCTAAACGCTGG ACCGCGCCCGCCG-GAGGACAGACGCAAAAAAATTCTTTCAGAAGAG-CTGTCAGTCT GAGC (SEQ ID NO: 90). In certain embodiments, *Epidermophyton*-specific primers are designed to amplify a nucleotide sequence that includes or has a sequence 90% or more, e.g., 95% or more, 98% or more, including 99% or more identical to the following sequence: CCTAGGCTGCAGTGTCGCTGCAGCGTCTCGGGG-GGGCCGTTCGGGGGATGGAGAAG GATGCCCCGGCGGGGTTGATCGCTCCCC-CACCCCTGGACAGCGCTCGCCGAAGGAG TGAT-TCTCAGAAATTCTACGAAATCTCCAT-AGGTGGTTCAGTCTGAGCGTT (SEQ ID NO: 91). In certain embodiments, *Microsporum*-specific primers are designed to amplify a nucleotide sequence that includes or has a sequence 90% or more, e.g., 95% or more, 98% or more, including 99% or more identical to one of the following sequences:

(SEQ ID NO: 92)
CGCCCATTCTTGTCTACTGACCCGGTTGCCTCGGCGGGCCGCGCCTGCT
GTGCTACAGCGGCCGTTCGGGGGGACGCCTGAGGGGGACTCTTGTTTC
CTAGGCCACGCCC,
and ACGCCCATTCTTGTCTATTTACCCAGTTGCCTCGGCGGGCCGCGCACTC
GTGCCGCGCCTCGAGGAGCCGTCCGGGGACAATCAACTCCCTGGATCGC
GCCCGCCGGAGGAGTGATTAAAATCCATGAATACTGTTCC.

Detection of Primary Clade Member within the Secondary Clade of Saprophyte

In certain embodiments, primary clade-specific primers for a secondary saprophyte clade are designed to amplify a nucleic acid product when the primers are used to perform PCR with template nucleic acids obtained from an organism belonging to the primary clade member, e.g., *Aspergillus, Penicillium, Paecilomyces, Fusarium, Acremonium, Scopulariopsis, Chaetomium, Curvularia, Alternaria, Mucor,*

*Scytalidium* and *Rhizopus*, etc., that is present in a sample, and designed not to amplify a nucleic acid product when the primary clade member is not present in the sample assayed. In certain embodiments, primary clade-specific primers for a secondary saprophyte clade member are designed to amplify a nucleic acid product when the primers are used to perform PCR with template nucleic acids in a sample containing a primary clade member and designed not to amplify a nucleic acid product in a sample containing a non-primary clade member, e.g., non-*Aspergillus*, non-*Penicillium*, non-*Paecilomyces*, non-*Fusarium*, non-*Acremonium*, non-*Scopulariopsis*, non-*Chaetomium*, non-*Curvularia*, non-*Alternaria*, non-*Mucor*, non-*Scytalidium* or non-*Rhizopus*, etc., but not containing the primary clade member. Thus, primary clade-specific primers for a secondary saprophyte clade member that specifically amplify a nucleic acid product in a primary clade member may be designed to amplify a nucleotide sequence that has low sequence identity in non-primary clade members.

In some embodiments, one or more primary clade-specific primers for a secondary saprophyte clade member are configured to amplify a nucleic acid product when nucleic acids containing the target nucleotide sequence from the primary clade member, e.g., *Aspergillus, Penicillium, Paecilomyces, Fusarium, Acremonium, Scopulariopsis, Chaetomium, Curvularia, Alternaria, Mucor, Scytalidium* and *Rhizopus*, etc., as well as non-fungal nucleic acids are present in the sample, and not to amplify a nucleic acid product when the nucleic acids from the primary clade member is absent from the sample and non-fungal nucleic acids are present in the sample. The non-fungal nucleic acids may include human genomic DNA and/or bacterial DNA. In certain embodiments, the primary clade-specific primers for a secondary saprophyte clade member have a sequence identity of 60% or less, e.g., 50% or less, 40% or less, including 30% or less, and may have a sequence identity of 1% or more, e.g., 5% or more, 10% or more, including 20% or more to nucleotide sequences in non-target organisms, such as human and bacterial genomic sequences.

In certain embodiments, a first primary clade-specific primers for a secondary saprophyte clade member are designed to amplify a first nucleic acid product when the first primary clade-specific primers are used to perform PCR with template nucleic acids in a sample containing a first primary clade member and a second primary clade-specific primers for a secondary saprophyte clade member are designed to amplify a second nucleic acid product when the primers are used to perform PCR with template nucleic acids in a sample containing a second primary clade member, where the first and second nucleic acid products are distinguishable. In certain embodiments, primary clade-specific primers for a secondary saprophyte clade member are designed to amplify a first nucleic acid product when the first primary clade-specific primers are used to perform PCR with template nucleic acids in a sample containing a first primary clade member, and are designed to amplify a second nucleic acid product when the primers are used to perform PCR with template nucleic acids in a sample containing a second primary clade member, where the first and second nucleic acid products are distinguishable.

The primary clade-specific primers for a secondary saprophyte clade member may be designed to target any suitable nucleotide sequence. In certain embodiments, the primary clade-specific primers for a secondary saprophyte clade member are configured to amplify a primary clade-specific nucleotide sequence within a nuclear-encoded ribosomal RNA gene. In certain embodiments, the primary clade-specific primers for a secondary saprophyte clade member are configured to amplify a primary clade-specific nucleotide sequence encoding: an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the primary clade-specific primers for a secondary saprophyte clade member are designed to amplify a primary clade-specific nucleotide sequence encoding an encoding an 18S ribosomal RNA, a 28S ribosomal RNA, a 5.8S ribosomal RNA, or portions thereof, and/or an internal transcribed spacer, or a portion thereof, adjacent the nucleotide sequence encoding the 18S, 28S and 5.8S ribosomal RNAs. In certain embodiments, the primary clade-specific primers for a secondary saprophyte clade member are designed to amplify a primary clade-specific nucleotide sequence encoding ITS 1 or ITS2.

In certain embodiments, Acremonium-specific primers are designed to amplify a nucleotide sequence that includes a sequence 90% or more, e.g., 95% or more, 98% or more, including 99% or more identical to the following sequence: CGTCATTT-CAACCCTCAGGACCCGTTCGCGGGACCTGGC-GTTGGGGATCAGCCTGCC CCTGGCGGCGGCTGGCCCTGAAATA-CAGTGGCGGTTCCCTCGCGAACTCCTCCGTGC AGTAATTAAACCTCTCGCGGCAGGATAGCGGTT-GAACCACGCCGTTAAACCCCCA CTTCT-CAAGGTTGACCTCAGATCAGGTAG (SEQ ID NO: 93). In certain embodiments, *Acremonium*-specific primers are designed to amplify a nucleotide sequence 90% or more, e.g., 95% or more, 98% or more, including 99% or more identical to the following sequence:

(SEQ ID NO: 94)
CGTCATTTCAACCCTCAGGACCCGTTCGCGGGACCTGGCGTTGGGGATC

AGCCTGCCCCTGGCGGCGGCTGGCCCTGAAATACAGTGGCGGTTCCCTC

GCGAACTCCTCCGTGCAGTAATTAAACCTCTCGCGGCAGGATAGCGGTT

GAACCACGCCGTTAAACCCCCCACTTCTCAAGGTTGACCTCAGATCAGG

TAG.

In certain embodiments, *Alternaria*-specific primers are designed to amplify a nucleotide sequence that includes a sequence 90% or more, e.g., 95% or more, 98% or more, including 99% or more identical to the following sequence: CGGCCTACTGGTTTCG-GAGCGCAGCACAAGTCGCACTCTC-TATCAGCAAAGGTCTAG CATCCATTAAGCCTTTTTT-CAACTTTTGACCTCGG (SEQ ID NO: 95). In certain embodiments, *Alternaria*-specific primers are designed to amplify a nucleotide sequence 90% or more, e.g., 95% or more, 98% or more, including 99% or more identical to the following sequence:

(SEQ ID NO: 96)
CGGCCTACTGGTTTCGGAGCGCAGCACAAGTCGCACTCTCTATCAGCAA
AGGTCTAGCATCCATTAAGCCTTTTTTCAACTTTTGACCTCGG.

In certain embodiments, *Curvularia*-specific primers are designed to amplify a nucleotide sequence that includes a sequence 90% or more, e.g., 95% or more, 98% or more, including 99% or more identical to the following sequence: CCGGCCTACTGGTTTCGCAGCGCAGCACAT- TTTTGCGCTTGCAATCAGCAAAAGAGG ACGGCAATCCATCAAGACTCCTTCT-CACGTTGACCTC (SEQ ID NO: 97). In certain embodiments, *Curvularia*-specific primers are designed to amplify a nucleotide sequence 90% or more, e.g., 95% or more, 98% or more, including 99% or more identical to the following sequence:

(SEQ ID NO: 98)
CCGGCCTACTGGTTTCGCAGCGCAGCACATTTTTGCGCTTGCAATCAGC
AAAAGAGGACGGCAATCCATCAAGACTCCTTCTCACGTTGACCTC.

In certain embodiments, *Scytalidium*-specific primers are designed to amplify a nucleotide sequence that includes a sequence 90% or more, e.g., 95% or more, 98% or more, including 99% or more identical to the following sequence: GGAAGTGGGTGCGGCCTCCCGGCCGCGCTTAAGA-TATAGTCGGGCCCCCAGCGAAA GCTGGGGGGTAAGTCACTGCGACGAGAGCCG (SEQ ID NO: 99). In certain embodiments, *Scytalidium*-specific primers are designed to amplify a nucleotide sequence 90% or more, e.g., 95% or more, 98% or more, including 99% or more identical to the following sequence:

(SEQ ID NO: 100)
GGAAGTGGGTGCGGCCTCCCGGCCGCGCTTAAGATATAGTCGGGCCCCA
GCGAAAGCTGGGGGGTAAGTCACTGCGACGAGAGCCG.

In certain embodiments, Aspergillus-specific primers are designed to amplify a nucleotide sequence that includes a sequence 90% or more, e.g., 95% or more, 98% or more, including 99% or more identical to the following sequence: AACCAACCGGGATTGCCTCAGTAACGGCGAGT-GAAGCGGCAAGAGCTCAAATTTGA AAGCTGGCTCCTTCGGGGTCCGCATTGTAAT-TTGCAGAGGATGCTTCGGGTGCGGCC CCTGTCTAAGTGCCCTGGAACG (SEQ ID NO: 101). In certain embodiments, *Aspergillus*-specific primers are designed to amplify a nucleotide sequence 90% or more, e.g., 95% or more, 98% or more, including 99% or more identical to the following sequence:

(SEQ ID NO: 102)
AACCAACCGGGATTGCCTCAGTAACGGCGAGTGAAGCGGCAAGAGCTCAA
ATTTGAAAGCTGGCTCCTTCGGGGTCCGCATTGTAATTTGCAGAGGATGC
TTCGGGTGCGGCCCCTGTCTAAGTGCCCTGGAACG.

In certain embodiments, *Fusarium*-specific primers are designed to amplify a nucleotide sequence that includes a sequence 90% or more, e.g., 95% or more, 98% or more, including 99% or more identical to one of the following sequences: GGAGGGATCATTACCGAGTTTA-CAACTCCCAAACCCCTGTGAACATACCACTTGTTG CCTCGGCG-GATCAGCCCGCTCCCGGTAAAACGGGACGGC-CCGCCAGAGGACCCCTA AACTCTGTTTC-TATATGTAACTTCTGAGTAAAACCATAAATAAAT-CAAAACTTTCA (SEQ ID NO: 103), and CTCAT-CAACCCTGTGAACATACCTAAAACGTTGCTTCGG-CGGGAACAGACGGCCCC GTAACAACGGGCCGCCCCCGCCAGAGGACCCC-TAACTCTGTTTCTATAATGTTTCTT CTGAGTAAACAAGCAAATAAATTAAAACTTTCA (SEQ ID NO: 104). In certain embodiments, *Fusarium*-specific primers are designed to amplify a nucleotide sequence 90% or more, e.g., 95% or more, 98% or more, including 99% or more identical to one of the following sequences:

(SEQ ID NO: 105)
GGAGGGATCATTACCGAGTTTACAACTCCCAAACCCCTGTGAACATACCA

CTTGTTGCCTCGGCGGATCAGCCCGCTCCCGGTAAAACGGGACGGCCCGC

CAGAGGACCCCTAAACTCTGTTTCTATATGTAACTTCTGAGTAAAACCAT

AAATAAATCAAAACTTTCA,
and (SEQ ID NO: 106)
CTCATCAACCCTGTGAACATACCTAAAACGTTGCTTCGGCGGGAACAGAC
GGCCCCGTAACAACGGGCCGCCCCCGCCAGAGGACCCCTAACTCTGTTTC
TATAATGTTTCTTCTGAGTAAACAAGCAAATAAATTAAAACTTTCA.

In certain embodiments, *Scopulariopsis*-specific primers are designed to amplify a nucleotide sequence that includes a sequence 90% or more, e.g., 95% or more, 98% or more, including 99% or more identical to the following sequence: CTGTCCGAGCGTCAT-TCTTCCCTCGAGCGCGGCTAGCCC-TACGGGGCCTGCCGTCG CCCGGTGTTGGGGCTC-TACGGGTGGGGCTCGTCCCCCCCGCAGTCCCCG-AAATGTAG TGGCGGTCCAGCCGCGGCGCCCCCTGCGTAGTA-GATCCTACATCTCGCATCGGGTC (SEQ ID NO: 107). In certain embodiments, *Scopulariopsis*-specific primers are designed to amplify a nucleotide sequence 90% or more, e.g., 95% or more, 98% or more, including 99% or more identical to the following sequence:

(SEQ ID NO: 108)
CTGTCCGAGCGTCATTTCTTCCCTCGAGCGCGGCTAGCCCTACGGGGCCT

GCCGTCGCCCGGTGTTGGGGCTCTACGGGTGGGGCTCGTCCCCCCCGCAG

TCCCCGAAATGTAGTGGCGGTCCAGCCGCGGCGCCCCCTGCGTAGTAGAT

CCTACATCTCGCATCGGGTC.

Compositions Containing Clade-Specific Primers

Also provided herein is a composition that includes clade-specific primers, e.g., primary clade-specific primers or secondary clade-specific primers, which compositions may find use generating, or may be a part of, a reaction mixture for carrying out a PCR reaction, e.g., a real-time PCR reaction, as described herein. The composition may include at least one primer pair (e.g., a forward and reverse primer pair) for amplifying a target nucleotide sequence specific for a primary clade member or a secondary clade member, as described above. In some embodiments, the composition includes two or more pairs, e.g., three or more pairs, 4 or more pairs, 5 or more pairs, including 6 or more pairs of primers, and in some cases may include 10 or fewer pairs, e.g., 9 or fewer pairs, 8 or fewer pairs, 7 or fewer pairs, including 6 or fewer pairs of primers, each primer pair configured to amplify a target nucleotide sequence specific for a primary clade member or a secondary clade member. In certain embodiments, the composition includes 2 pairs to 10 pairs, e.g., 2 pairs to 8 pairs, 2 pairs to 7 pairs, 2 pairs to 6 pairs, including 2 pairs to 5 pairs of primers, each primer pair configured to amplify a target nucleotide sequence specific for a primary clade member or a secondary clade member. In some embodiments, the composition includes suitable hydrolysis probe(s) as described herein.

The combination of primers present in the composition may be any suitable combination of primers, e.g., combination of primer pairs, for amplifying a target nucleotide sequence specific for a primary clade member or a secondary clade member, where the amplified products specific for the different clade members are distinguishable from each other, e.g., based on the $C_t$ of the amplification reaction and/or Tm of the amplified products, as described herein. In some embodiments, the composition includes a yeast secondary clade-specific primer pair and a dermatophyte secondary clade-specific primer pair, as described above, where amplification products of nucleotide sequences targeted by the yeast secondary clade-specific primer pair and those targeted by the dermatophyte secondary clade-specific primer pair are distinguishable from each other, e.g., based on the $C_t$ of the amplification reaction.

In certain embodiments, the composition includes a two or more pairs, e.g., three or more pairs, 4 or more pairs, 5 or more pairs, including 6 or more pairs of primers, and in some cases may include 10 or fewer pairs, e.g., 9 or fewer pairs, 8 or fewer pairs, 7 or fewer pairs, including 6 or fewer pairs of saprophyte secondary clade-specific primers, as described above, where amplification products of nucleotide sequences targeted by the primer pairs specific to different sets of saprophyte secondary clade members are distinguishable from each other by real-time PCR, e.g., based on the $C_t$ of the amplification reaction.

The present composition may include any other suitable components for storing, transporting and/or carrying out a PCR reaction with the clade-specific primers. The composition may contain a suitable medium, e.g., an aqueous medium. A suitable aqueous medium includes, without limitation, water, a buffer solution, etc. The buffer may be any suitable buffer for storage of primers and/or for carrying out a PCR reaction. The buffer may have any suitable pH, such as, without limitation, a pH of from 6.0 to 9.0, e.g., from 6.5 to 8.9, from 7.0 to 8.7, fom 7.5 to 8.6, including from 8.0 to 8.5. In some embodiments, the buffer is a Tris (tris(hydroxymethyl)aminomethane) buffer. In certain embodiments, the aqueous medium includes a chelator, such as a divalent cation chelator (e.g., ethylenediaminetetraacetic acid (EDTA)). In some embodiments, the aqueous medium includes a chelator (e.g., EDTA) and a buffer (e.g., Tris). Suitable buffers may be obtained from ThermoFisher.

The present composition may be substantially free of enzymes and compounds that degrade nucleic acids, such as nucleases. In some embodiments, the composition is substantially sterile.

In some embodiments, the composition includes, without limitation, a nucleic acid template, primers, one or more polymerases, nucleotides, etc., suitable for performing a PCR reaction to amplify a nucleotide sequence targeted by the clade-specific primers (i.e., targeted by the clade-specific primer pairs). The polymerase may be any suitable polymerase, including, without limitation, a thermostable DNA polymerase, such as Taq polymerase, and variants thereof (e.g., commercially available variants of thermostable DNA polymerases). In some embodiments, the composition includes a hybridization probe configured to specifically anneal to a nucleic acid that contains a nucleotide sequence that is amplified by the clade-specific primers. The hybridization probe may be a fluorescent hybridization probe that changes its fluorescence properties based on whether the probe is hybridized to a target nucleic acid (e.g., by positioning a fluorescent dye attached to the probe at a sufficient distance to a fluorescent DNA intercalating dye to induce Förster resonance energy transfer (FRET) between the attached dye and the intercalating dye). Thus, in some embodiments, the clade-specific hybridization probe includes a fluorescent functional group (e.g., fluorescent dye) covalently attached to the probe nucleic acid. The excitation and emission wavelengths of the attached fluorescent dye and the intercalating dye may be suitably configured to promote a measurable, distance-dependent interaction between the attached dye and the intercalating dye.

Methods

Methods of Detecting an Agent Causing Onychodystrophy

The number of primary clade members in the secondary clade member to which the agent causing onychodystrophy detected by the present methods belongs may be any suitable number that may be independently distinguished using the present methods, and may depend on, e.g., the sequence diversity of the target sequences amplified the primary clade-specific primers, the specificity of the primary clade-specific primers, the desired sensitivity and/or specificity of detection, complexity of the sample, etc. In some embodiments, the present method includes a secondary clade member includes one or more, e.g., two or more, three or more, 4 or more, 5 or more, including 7 or more primary clade members, and in some embodiments, includes 10 or less, e.g., 9 or less, 8 or less, 7 or less, including 5 or less primary clade members. In some embodiments, a secondary clade member includes 1 to 10, e.g., 2 to 9, 2 to 8, including 2 to 7 primary clade members.

In general, at least one of the plurality of secondary clade member includes two or more, e.g., 3 or more, 4 or more, 5 or more, 6 or more, 7 or more, 8 or more, and up to 10 primary clade members. In some embodiments, at least one of the plurality of secondary clade member includes 2 to 10, e.g., 2 to 9, 2 to 8, including 2 to 7 primary clade members. In some embodiments, each of the plurality of secondary clade members includes two or more, e.g., 3 or more, 4 or more, 5 or more, 6 or more, 7 or more, 8 or more, and up to 10 primary clade members. In some embodiments, each of the plurality of secondary clade members includes 2 to 10, e.g., 2 to 9, 2 to 8, including 2 to 7 primary clade members.

In certain embodiments, the dermatophyte secondary clade member includes 2 to 6, such as 2 to 5, or 2 to 4 primary clade members. In certain embodiments, the yeast secondary clade member includes 2 to 4, such as 2 to 3, or 2 primary clade members. In certain embodiments, the saprophyte secondary clade member includes 2 to 10, such as 2 to 9, 2 to 8, or 2 to 7 primary clade members.

The screening steps, 210, 230, and 310, 330, of the present method may be carried out in a single reaction mixture, or a plurality of reaction mixtures, as appropriate. An implementation of the present method may include using a first portion of a sample as a template for a PCR reaction to screen for a secondary clade member 210, 230, and using a second portion of the sample for which the presence of the secondary clade member is detected to screen for a primary clade member 310, 330 that belongs to the secondary clade member. In certain embodiments, the present method of detecting, in a sample, an agent causing onychodystrophy includes performing the screening step 210, 310 in a first reaction mixture containing a first set of secondary clade-specific primers and a second reaction mixture containing a second set of secondary clade-specific primers, where the first and second sets of secondary clade-specific primers are specific for different secondary clade members. The first and second reaction mixtures may each contain at least a portion of the sample that is being tested for the presence or absence of the agent causing onychodystrophy, and a first and second PCRs (e.g., real-time PCRs), respectively, may be carried out.

In some embodiments, the first set of secondary clade-specific primers is specific for a first set of secondary clade members, which set of secondary clade members includes one or more of dermatophytes, yeasts, and saprophytes, and the second set of secondary clade-specific primers is specific for a second set of secondary clade members, which set of secondary clade members includes one or more of dermatophytes, yeasts, and saprophytes, where the first and second sets are different sets. "Different," as used in reference to different sets of secondary clade members, is meant to indicate that the sets are at least non-overlapping. In some embodiments, the first set of secondary clade-specific primers is specific for a first set of secondary clade members, which set of secondary clade members includes dermatophytes and yeasts, and the second set of secondary clade-specific primers is specific for a second set of secondary clade members, which set of secondary clade members includes saprophytes. In certain embodiments, a set of secondary clade members that includes saprophytes includes two or more, e.g., 3 or more, 4 or more, including 5 or more, and includes 8 or fewer, e.g., 6 or fewer, 5 or fewer, including 4 or fewer saprophyte secondary clade members, where the saprophyte secondary clade members among the set are distinct from each other. In certain embodiments, a set of secondary clade members that includes saprophytes includes 2 to 8, e.g., 2 to 6, 2 to 5, including 2 to 4 saprophyte secondary clade members, where the saprophyte secondary clade members among the set are distinct from each other.

The screening 230, 330 using primary-clade specific primers, to determine which of the primary clade members of the secondary clade member identified in the earlier screening 210, 310 may be present in the sample, may be performed in one or more (e.g., 2 or more, three or more, four or more, etc.) reaction mixtures. In some cases, a single reaction mixture that includes primary-clade specific primers that distinguish between two or more, e.g., three or more, 4 or more, 5 or more, and in some cases, 10 or fewer, 8 or fewer, 7 or fewer, including 6 or fewer different primary clade members is used, where each primary clade member may be targeted by a specific pair of primary-clade specific primers. In certain embodiments, a single reaction mixture that includes primary-clade specific primers that distinguish between 2 to 10, e.g., 2 to 8, 2 to 6, 2 to 5, including 2 to 4 different primary clade members is used, where each primary clade member may be targeted by a specific pair of primary-clade specific primers.

Further aspects of the present disclosure include performing control reactions to enable proper interpretation of results of the PCR on samples. Control reactions may include a positive control, negative control, extraction/inhibition control and a reagent blank control. In some embodiments, a positive control, as described above, is run in parallel to the sample to determine whether the reaction conditions are sufficient to generate a positive result when the sample contains an agent causing onychodystrophy of interest. In some embodiments, a negative control, as described above, is run in parallel to the sample to confirm that positive results are not obtained, e.g., due to contamination of the sample and/or reagent during handling.

In some embodiments, a control is performed to confirm proper PCR amplification from samples that are subjected to cell lysis and nucleic acid extraction processes, as described below (Extraction/Inhibition control; EC/IC). In certain embodiments, EC/IC includes adding an amount of a known nucleic acid to a sample for which the presence or absence of an agent causing onychodystrophy is to be determined before the sample is processed to lyse cells and extract nucleic acids from the cells, preparing the sample to lyse cells and release cellular nucleic acids, and performing real-time PCR on the sample using primers that amplifies a nucleotide sequence contained in the known nucleic acid to detect the presence of the known nucleic acid. The known nucleic acid may be any suitable nucleic acid, and may be, e.g., a *Saccharomyces pombe*, citrate synthase gene.

In some embodiments, the present method includes performing a reagent blank control (RB). The RB control may include adding an amount of known nucleic acid to a sample that does not contain any other source of nucleic acids, and processing the sample in parallel to a sample for which the presence or absence of an agent causing onychodystrophy is to be determined, and performing real-time PCR on the sample using primers that amplifies a nucleotide sequence contained in the known nucleic acid to detect the presence of the known nucleic acid. In some embodiments, the RB sample may be used as a negative control by performing a real-time PCR on the RB sample using clade-specific primers.

The PCR reactions employed in the present disclosure may be performed using any convenient common PCR reagents, other than the template, probes, primers, and protocols. A PCR reaction mixture may contain any suitable ingredient for performing a PCR reaction, including, a nucleic acid template, primers, one or more polymerases, nucleotides, a buffer, etc. The PCR reaction may be a real-time PCR reaction. The real-time PCR may be carried out using any convenient reagent and equipment for performing real-time PCR.

The PCR cycle parameters may be any suitable set of cycle parameters for amplifying the nucleotide sequences targeted by the clade-specific primers, when the sample contains nucleic acids that include the target nucleotide sequences in detectable amounts. In some embodiments, the cycle parameters include a denaturing temperature in the range of 90 to 100° C., a denaturing time in the range of 10 to 45 seconds; an annealing temperature that may vary with the primers used in the reaction, and may be in the range of 50 to 75° C., and an annealing time of 10 to 45 seconds; and an extension temperature in the range of 60 to 75° C., and an extension time in the range of 30 to 120 seconds. The PCR cycle may include detection of amplification products in the reaction mixture by, e.g., detecting the level of fluorescence in the reaction mixture at the end of a cycle. The number of cycles may range from 18 to 45 cycles, such as 20 to 40 cycles. In certain embodiments, the number of cycles is from 30 cycles to 45 cycles, e.g., from 33 cycles to 38 cycles, including from 35 cycles to 37 cycles.

The template nucleic acid used in the real-time PCR of the present method may be DNA, e.g., genomic DNA, mitochondrial DNA, or may be RNA, e.g., mRNA. In certain embodiments, if the template nucleic acid is derived from mRNA, the method includes extracting RNA from the sample and subjecting the extracted RNA to a reverse transcriptase to generate a cDNA library, which may then be used as a template for the real-time PCR. Any suitable method may be used to generate a cDNA library.

In some embodiments, the present method further includes generating a report indicating the presence or absence of one or more onychomycotic fungi in a sample subjected to the screening steps, as described herein. In some embodiments, the report contains a list of secondary clade members tested, and indicates the presence or absence of the tested secondary clade members in the sample. In some embodiments, the report includes a list of primary clade members tested, and indicates the presence or absence of the tested primary clade members in the sample. The report may indicate the presence or absence of a yeast, dermatophyte, or a saprophyte in the sample, and may further indicate the presence or absence of a species that belongs to the secondary clade member for which the presence or absence was tested. The report may indicate the presence or absence of a yeast, dermatophyte, or a saprophyte in the sample, and may further indicate the presence or absence of the species or genera for which the presence or absence was tested.

The report may be provided in any suitable form, including, but not limited to, a report on a physical piece of paper, a report in digital form accessible by a user interface on a computer system (e.g., a web page, or an e-mail), an entry in a database of a patient's medical record, and/or a data file on a non-transient computer readable data-storage medium (e.g., a flash drive, hard drive, compact disc (CD), etc.).

Samples

The sample may be any suitable tissue in which the presence of an agent causing onychodystrophy is to be detected. In certain embodiments, the sample includes keratinous tissue, such as nail, skin, hair, etc. A nail sample may include a toenail, a fingernail, or portions thereof. In some embodiments, the sample includes bodily fluids, such as sweat, mucus, tears, saliva, etc.

In some embodiments, the sample includes nail clippings from one or more, e.g., 2 or more, 3 or more, 4 or more, 5 or more, including 8 or more fingernails and/or toenails, and includes nail clippings from 20 or less, e.g., 15 or less, 10 or less, 5 or less, including 3 or less fingernails. In some embodiments, the sample includes nail clippings from 1 to 20, e.g., 1 to 15, 1 to 10, 1 to 5, including 1 to 3 fingernails and/or toenails.

In some embodiments, the sample includes 0.1 mg or more, including 0.5 mg or more, 1 mg or more, 2 mg or more, 5 mg or more, 10 mg or more, 20 mg or more, 50 mg or more and includes 200 mg or less, including 150 mg or less, 100 mg or less, 80 mg or less, 50 mg or less, 20 mg or less, 10 mg or less, 5 mg or less, including lm g or less of nail clippings from one or more fingernails and/or toenails. In some embodiments, the sample includes nail clippings from one or more fingernails and/or toenails in the range of 0.1 to 200 mg, e.g., 0.5 to 100 mg, 0.5 to 20 mg, 0.5 to 10 mg, including 1 to 5 mg.

In some embodiments, the sample includes nucleic acids, e.g., DNA, at a concentration of 0.01 ng/µL or more, e.g., 0.05 ng/µL or more, 0.1 ng/µL or more, 1.0 ng/µL or more, 5.0 ng/µL or more, 10 ng/µL or more, including 50 ng/µL or more, and includes nucleic acids, e.g., DNA, at a concentration of 1,000 ng/µL or less, e.g., 500 ng/µL or less, 100 ng/µL or less, 50 ng/µL or less, 20 ng/µL or less, 10 ng/µL or less, 0.1 ng/µL or less, including 0.01 ng/µL or less. In some embodiments, the sample includes nucleic acids, e.g., DNA, at a concentration in the range of 0.01 ng/µL to 1,000 ng/µL, e.g., 0.01 ng/µL to 100 ng/µL, 0.1 ng/µL to 50 ng/µL, including 1 ng/µL to 20 ng/µL.

The sample may be labeled with an identifying label prior to analysis. In some embodiments, the identifying label may be a barcode label, or a radio-frequency identification (RFID) tag. The identifying label may encode information including the source of the sample (e.g., patient, clinic, hospital), the analysis performed (e.g., PCR, culture, histopathology), etc.

The sample may be prepared to lyse cells and release nucleic acids within cells into a solution using any suitable method, as described below. In some embodiments, the sample contains a suitable buffer for lysing cells, for stabilizing nucleic acids in the sample and/or for carrying out PCRs.

Method of Preparing a Sample

In certain embodiments, the present method includes preparing a sample, e.g., a nail sample, for screening by the method described herein. Preparing the sample may include treating the sample with mechanical, thermal, chemical and/or enzymatic methods of lysing cells and cellular compartments (e.g., plasma membrane, cell wall, nucleus, mitochondria, etc.) in the sample to release nucleic acids, e.g., DNA and/or RNA, into the bulk of the sample.

Any suitable method of mechanically lysing cells may be used. In some embodiments, mechanically lysing the cells includes, e.g., homogenizing, grinding, ultrasonicating or freezing the sample. In some embodiments, cells in the sample may be physically lysed by subjecting the sample to a blender, bead or ultrasonic homogenization, grinding by a mortar and pestle, French press, etc. Beads for homogenizing the sample may be, but are not limited to garnet, glass, ceramic, or steel beads. In some embodiments, the diameter of the beads is in the range of 0.05 mm to 5 mm, e.g., 0.1 mm to 4 mm, including 0.1 mm to 3 mm. The sample may be subjected to pulses of mechanical treatment, such as one or more, e.g., two or more, 3 or more, four or more pulses, and 8 or less, 6 or less, including 4 or less pulses. The pulse of a mechanical treatment may have a duration in the range of 10 to 60 seconds, e.g., 15 to 50 seconds, including 20 to 45 seconds.

Any suitable method of chemically lysing cells may be used. In some embodiments, chemical lysis methods include alkaline lysis, detergent lysis (e.g., sodium dodecyl sulfate (SDS)), solvent lysis (e.g., chloroform), etc. In one embodiment, chemically lysing cells involves use of a chaotropic agent, e.g., a chaotropic salt. Non-limiting examples of chaotropic agents include guanidinium isothiocyanate, guanidinium chloride, urea, thiourea, lithium perchlorate, lithium acetate, sodium iodide, phenol and others.

Any suitable method of enzymatically lysing cells may be used. In some embodiments, enzymatic lysis methods include treatment of the sample with protease, lipase, glycoside hydrolases, etc. In some embodiments, cells in the sample may be enzymatically lysed by subjecting the sample to proteinase K, trypsin, subtilisin, lyticase, lysozyme, collagenase, cellulase, glucanase, chitinase, pectinase, or amylase, etc.

Any suitable method of thermally lysing cells may be used. In some embodiments, the sample is subjected to a temperature of 50° C. or more, e.g., 60° C. or more, 70° C. or more, 80° C. or more, 90° C. or more, or 95° C. or more, and is subjected to a temperature of 100° C. or less, e.g., 98° C. or less, including 95° C. or less, to lyse the cells in the sample. In some embodiments, the sample is subjected to a temperature in the range of 50° C. to 100° C., e.g., 60° C. to 100° C., 70° C. to 100° C., 80° C. to 100° C., including 90° C. to 98° C., to lyse the cells in the sample. In some embodiments, the sample is subjected to heat for 5 to 60 minutes, e.g., 10 to 30 minutes, to lyse the cells. In certain embodiments, the sample is subjected to heat in the presence of a lysis buffer containing, e.g., enzymatic and/or chemical lysing agents.

In some embodiments, the preparing step includes subjecting a sample sequentially to two or more of mechanical, thermal, chemical and/or enzymatic methods of lysing cells, as described above. The order in which the sample is subjected to the methods of lysing cells may be any suitable order. In some embodiments, the sample is prepared by subjecting the sample to mechanical, enzymatic and thermal methods of lysing cells. In certain embodiments, the sample is prepared by subjecting the sample first to mechanical lysis, then to enzymatic lysis, and then to thermal lysis.

The preparing step may also include purifying the released nucleic acids after lysing the cells. The nucleic acids may be purified using any suitable method, including ethanol precipitation, and solid phase extraction by binding the nucleic acids to a spin column or a magnetic substrate, followed by elution. In some embodiments, nucleic acids released from lysed cells are used in the assay without purification.

Use of Assay to Facilitate Diagnosis and Selection of Therapy

The methods of the present disclosure find use in detecting an agent causing onychodystrophy in a sample to determine the presence of and/or the type of fungus at a site of infection, e.g., a nail infection, or a cutaneous region surrounding a nail. Determining the presence of a fungus, and, if present, identifying the type of fungus (e.g., yeast, dermatophyte, or saprophyte; and/or yeast genera/species or dermatophyte species) at the site suspected of a fungal infection can facilitate a medical professional in selection and/or administration of an antifungal medication that is more likely to provide a clinical benefit to the patient.

Thus, the present method finds use in diagnosing a nail infection in a patient, e.g., a human patient, suffering from a nail infection. The methods of the present disclosure thus may include obtaining a sample, e.g., a nail or other cutaneous sample associated with the nail, determining the presence or absence, in the sample, of an agent causing onychodystrophy and, if present, the type of fungus or bacteria, using an assay method as described herein, generating a report that indicates the presence or absence, in the patient sample, of one or more agent causing onychodystrophy and, optionally, if present, identifying the likely type of fungus or bacteria present in the infection, and, optionally, indicating suggested therapy(ies) for treatment of the infection based on the assay results.

The methods of the present disclosure can include selecting a therapy, e.g., an antifungal medication, based on the results of the assay. In some embodiments, the methods of the present disclosure can include administering a therapy, e.g., an antifungal medication, based on the results of the assay. Where the methods include selection and/or administration of an antifungal therapy, the therapy is selected according to the primary and/or secondary clade member detected. For example, where a yeast infection is detected, then the therapy selected is one most likely effective against yeast; where a primary member of a yeast secondary clade is detected, then the therapy selected can be one most likely effective against that primary clade member. Where a dermatophyte infection is detected, then the therapy selected is one most likely effective against a dermatophyte; where a primary member of a dermatophyte secondary clade is detected, then the therapy selected can be one most likely effective against that primary clade member. Where a saprophyte infection is detected, then the therapy selected is one most likely effective against a saprophyte. Where a *Pseudomonas aeruginosa* infection is detected, then the therapy selected is one most likely effective against *Pseudomonas aeruginosa*.

In some embodiments, the therapy includes administering a pharmaceutical compound. A pharmaceutical compound or drug suitable for treating onychomycosis may be administered using any suitable method. The pharmaceutical compound may be administered topically or systemically. In some embodiments, the pharmaceutical compound is administered orally or topically. An orally administered pharmaceutical compound for treating onychomycosis may include, without limitation, itraconazole, fluconazole, and/or terbinafine. A topically administered pharmaceutical compound for treating onychomycosis may include, without limitation, tavaborole, efinaconazole or ciclopirox. The pharmaceutical compound may be administered in any suitable dosage form, e.g., as a tablet, liquid, cream, emulsion, etc. and may be administered in conjunction with any suitable pharmaceutically acceptable carrier.

The therapy may also include providing a first pharmaceutical compound as a first line treatment of onychomycosis, and providing a second pharmaceutical compound as a second line treatment, and so on, depending on the outcome of each successive lines of treatment. Thus, in some embodiments, where a therapy is selected according to the primary and/or secondary clade member detected, the first and second lines of treatment may be selected according to the primary and/or secondary clade member detected. In some embodiments, where a therapy is selected according to the primary and/or secondary clade member detected, the first, second and third lines of treatment may be selected according to the primary and/or secondary clade member detected.

In some embodiments, where a yeast, e.g., a candida, is detected in a sample, the therapy may include administering a first line pharmaceutical compound that is itraconazole, a second line pharmaceutical compound that is fluconazole and/or a third line pharmaceutical compound that is terbinafine.

In some embodiments, where a dermatophyte is detected in a sample, the therapy may include administering a first line pharmaceutical compound that is terbinafine, a second line pharmaceutical compound that is fluconazole and/or a third line pharmaceutical compound that is itraconazole. In some embodiments, where a dermatophyte is detected in a sample, the therapy may include administering tavaborole or efinaconazole. In some embodiments, where *Trichophyton mentagrophytes* is detected in the sample, the therapy may include administering tavaborole or efinaconazole. In some embodiments, where *Trichophyton rubrum* is detected in the sample, the therapy may include administering tavaborole, efinaconazole or ciclopirox.

In some embodiments, where a saprophyte is detected in a sample, the therapy may include administering a first line pharmaceutical compound that is itraconazole, a second line pharmaceutical compound that is terbinafine and/or a third line pharmaceutical compound that is fluconazole. In some embodiments, where an *Acremonium* spp. is detected in the sample, the first line pharmaceutical compound may be terbinafine.

In some embodiments, where *Pseudomonas aeruginosa* is detected in a sample, the therapy may include administering a combination of an antipseudomonal beta-lactam (e.g., penicillin or cephalosporin) and an aminoglycoside. Carbapenems (eg, imipenem, meropenem) with antipseudomonal quinolones may be used in conjunction with an aminoglycoside. Antibiotics that may have activity against *P.aeruginosa* include, e.g., aminoglycosides (gentamicin, amikacin, and tobramycin); quinolones (ciprofloxacin and levofloxacin); cephalosporins (ceftazidime, cefepime, cefoperazone, cefpirome, and ceftobiprole); antipseudomonal penicillins (carboxypenicillins (carbenicillin and ticarcillin), and ureidopenicillins (mezlocillin, azlocillin, and piperacillin)); carbapenems (meropenem, imipenem, doripenem); polymyxins (polymyxin B and colistin); and monobactams (aztreonam)

Where the assay results indicate the absence of a fungal infection, then the therapy selected can be one that does not involve an antifungal medication, thereby avoiding administration of such drugs where such is not likely to provide a clinical benefit.

In some embodiments, the present method of detecting, in a sample, an agent causing onychodystrophy may be performed in conjunction with more conventional methods of diagnosing an infection, such as microscopy, histology and fungal culture methods. In some embodiments, microscopic visualization of fungal elements in a nail sample may include using potassium hydroxide (KOH) to clarify a thin section of a nail sample from a patient.

The present method of detecting, in a sample, an agent causing onychodystrophy can facilitate sensitive detection of, e.g., an onychomycotic infection, as well as identification of the nature of the infecting organism. In some embodiments, the screening step using secondary clade-specific primers detects the presence of an organism that belongs to a secondary clade member (e.g., a yeast secondary clade member, dermatophyte secondary clade member or a saprophyte secondary clade member) at a DNA copy number of the secondary clade member of 1 or more, e.g., 2 or more, 4 or more, 10 or more, 50 or more, 100 or more, 200 or more, 500 or more, 1,000 or more, 1,500 or more, 2,000 or more, including 2,500 or more, and detects the presence of the secondary clade member at a DNA copy number of the secondary clade member of 15,000 or less, e.g., 12,000 or less, 5,000 or less, 2,500 or less, 2,000 or less, 1,000 or less, 500 or less, 200 or less, including 100 or less, in a reaction mixture. In some embodiments, the screening step using secondary clade-specific primers detects the presence of an organism that belongs to a secondary clade member at a DNA copy number of the secondary clade member in the range of 1 to 15,000, including 2 to 12,000, 4 to 5,000, 1,000 to 15,000, 1,500 to 10,000, including 1,500 to 5,000, in a reaction mixture.

In some embodiments, the screening step using primary clade-specific primers detects the presence of an organism that belongs to a primary clade member (e.g., a yeast primary clade member, dermatophyte primary clade member, or a saprophyte primary clade member) at a DNA copy number of the primary clade member of 5 or more, e.g., 10 or more, 20 or more, 50 or more, 100 or more, 150 or more, 300 or more, 500 or more, 1,000 or more, 2,000 or more, including 5,000 or more, and detects the presence of the primary clade member at a DNA copy number of the primary clade member of 10,000 or less, e.g., 7,000 or less, 5,000 or less, 2,500 or less, 1,000 or less, 500 or less, 200 or less, including 100 or less, in a reaction mixture. In some embodiments, the screening step using primary clade-specific primers detects the presence of an organism that belongs to a primary clade member at a DNA copy number of the primary clade member in the range of 5 to 10,000, e.g., 5 to 5,000, 5 to 1,000, 5 to 200, 100 to 10,000, 150 to 7,000, 150 to 2,000, including 150 to 500, in a reaction mixture.

The limit of detection for detecting the presence of an organism that belongs to a secondary clade member in a sample by the present methods may in certain cases be 0.0001 ng or more, e.g., 0.0002 ng or more, 0.0004 ng or more, 0.001 ng or more, 0.002 ng or more, 0.004 ng or more, 0.01 ng or more, 0.02 ng or more, 0.04 ng or more, including 0.1 ng or more, and may in certain cases be 10 ng or less, e.g., 5 ng or less, 1 ng or less, 0.4 ng or less, 0.2 ng or less, 0.1 ng or less, 0.04 ng or less, 0.02 ng or less, including 0.01 ng or less, of DNA per reaction (e.g., PCR reaction). In certain embodiments, the limit of detection for detecting the presence of an organismt that belongs to a secondary clade member in a sample by the present methods may be 0.0001 ng to 10 ng, e.g., 0.0002 ng to 5 ng, 0.0004 ng to 5 ng, 0.0004 ng to 1 ng, including 0.0004 ng to 0.1 ng of DNA in a reaction mixture.

The limit of detection for detecting the presence of an organism that belongs to a primary clade member in a sample by the present method may in certain cases be 0.0001 ng or more, e.g., 0.0002 ng or more, 0.0004 ng or more, 0.001 ng or more, 0.002 ng or more, 0.004 ng or more, 0.01 ng or more, 0.02 ng or more, 0.04 ng or more, including 0.1 ng or more, and may in certain cases be 10 ng or less, e.g., 5 ng or less, 1 ng or less, 0.4 ng or less, 0.2 ng or less, 0.1 ng or less, 0.04 ng or less, 0.02 ng or less, including 0.01 ng or less, of DNA per reaction (e.g., PCR reaction). In certain embodiments, the limit of detection for detecting the presence of an organism that belongs to a primary clade member in a sample by the present methods may be 0.0001 ng to 10 ng, e.g., 0.0002 ng to 5 ng, 0.0004 ng to 5 ng, 0.0004 ng to 1 ng, including 0.0004 ng to 0.1 ng of DNA in a reaction mixture.

The limit of detection for detecting the presence of an organism that belongs to a secondary clade member (e.g., a yeast secondary clade member) in a sample by the present methods may in certain cases be 100 colony forming units (CFU) or more, e.g., 200 CFU or more, 500 CFU or more, including 1,000 CFU or more, and may in certain cases be 10,000 CFU or less, e.g., 5,000 CFU or less, 4,000 CFU or less, including 3,500 or less, of the secondar clade member per reaction (e.g., PCR reaction). In certain embodiments, the limit of detection for detecting the presence of an organism that belongs to a secondary clade member in a sample by the present methods may be 100 CFU to 10,000 CFU, e.g., 200 CFU to 5,000 CFU, 500 CFU to 5,000 CFU, including 1,000 CFU to 4,000 CFU of the secondar clade member in a reaction mixture.

The limit of detection for detecting the presence of an organism that belongs to a primary clade member (e.g., a yeast primary clade member) in a sample by the present method may in certain cases be 100 CFU or more, e.g., 200 CFU or more, 500 CFU or more, including 1,000 CFU or more, and may in certain cases be 10,000 CFU or less, e.g., 5,000 CFU or less, 4,000 CFU or less, including 3,500 or less, of the primary clade member per reaction (e.g., PCR reaction). In certain embodiments, the limit of detection for detecting a primary clade member in a sample by the present methods may be 100 CFU to 10,000 CFU, e.g., 200 CFU to 5,000 CFU, 500 CFU to 5,000 CFU, including 1,000 CFU to 4,000 CFU of the primary clade member in a reaction mixture.

The present method of detecting, in a sample, an agent causing onychodystrophy provides a reproducible method of detecting and/or identifying an onychomycotic infection. The method may be reproducible by producing substantially the same results when the method is repeated on different portions of the same sample multiple times, repeated on different samples containing the same target nucleotide sequence, and/or when the method is repeated by a different practitioner and/or different instrument using portions of the same sample. The assay may be reproducible when the assay is repeated 10 times or more, e.g., 12 times or more, 15 times or more, 18 times or more, 25 times or more, 30 times or more, including 50 times or more, and may be repeated 75 times or less, e.g., 65 times or less, 50 times or less, 40 times or less, 30 times or less, 25 times or less, 22 times or less, including 20 times or less. In some embodiments, the assay results are reproducible when the assay is repeated from 10 to 75 times, e.g., from 10 to 65 times, from 10 to 50 times, from 10 to 25 times, from 12 to 22 times, including 15 to 22 times.

The present method of detecting, in a sample, an agent causing onychodystrophy is an accurate detection method. Accuracy of detection can be measured by the concordance between the result of the present PCR method with the result of sequencing nucleic acids in the sample to determine the presence and the type, in a sample, of an agent causing onychodystrophy. In certain embodiments, the present PCR detection method has concordance with sequencing of 90% or more, e.g., 93% or more, including 95% or more.

In certain embodiments, the present method of detecting, in a sample, an agent causing onychodystrophy is a high-throughput method. In some embodiments, the method is a multiplexed method to determine the presence or absence of multiple onychomycotic fungi or multiple secondary clade members that contain onychomycotic fungi, as described above, in a single reaction mixture. In some embodiments, the present method determines the presence or absence of two or more, e.g., 3 or more, 4 or more, including 5 or more, and up to 6 secondary clade members in a single reaction mixture, by using a suitable number and combination of different secondary-clade specific primers, as described above, in the reaction mixture. In some embodiments, the present method determines the presence or absence of two or more, e.g., 3 or more, 4 or more, including 5 or more, and up to 6 primary clade members in a single reaction mixture, by using a suitable number and combination of different primary-clade specific primers, as described above, in the reaction mixture.

The present method of detecting, in a sample, an agent causing onychodystrophy can provide a more rapid detection method than conventional methods. For example, the turn-around time (e.g., the time between a sample is submitted for analysis and receiving the results of the analysis, e.g., receiving a report) of the present method for determining the presence or absence, in a sample, of an agent causing onychodystrophy can be 10 days or less, e.g., 7 days of less, 5 days or less, including 3 days or less, and may be 1 day or more, e.g., 2 days or more, including 3 days or more. In some embodiments, the turn-around time of the present method for determining, in a sample, the presence or absence of an agent causing onychodystrophy is in the range of 1 to 10 days, e.g., 1 to 7 days, 2 to 5 days, including 2 to 3 days. In some embodiments, the turn-around time of the present method for determining, in a sample, the presence or absence of an agent causing onychodystrophy is in the range of 12 to 24 hours.

Kits

Also provided herein is a kit that finds use in performing embodiments of the method of the present disclosure. The kit may include one or more primary clade-specific primer pairs specific for onychomycotic fungi, as described above, and a first and second sets of secondary clade-specific primer pairs, where the first set of secondary clade-specific primers is designed to determine the presence of one or more secondary clade members belonging to a first set of one or more secondary clade members, and the second set of secondary clade-specific primers are designed to determine the presence of one or more secondary clade members belonging to a second set of one or more secondary clade members, as described herein, and where the first and second sets of one or more secondary clade members are different sets. The secondary clade members may include a dermatophyte, a yeast, and a saprophyte. The kit may also include suitable hydrolysis probes as described herein.

The kit may contain additional components that find use in preparing the sample before performing the screening PCR reactions. In some embodiments, the kit contains a homogenization element (e.g., homogenization beads, a homogenizer, etc.), homogenization buffer and/or a lysis buffer.

The kit may also contain instructions for practicing the present method. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

1. A method of detecting, in a sample, an agent causing onychodystrophy, wherein the agent causing onychodystrophy belongs to a secondary clade member comprising one or more primary clade members, the method comprising:

i) screening a sample using at least a first and second set of secondary clade-specific primers to determine whether a secondary clade member among a plurality of secondary clade members is present or absent in the sample, wherein the plurality of secondary clade members comprises a dermatophyte, a yeast, and a saprophyte, wherein the screening comprises:

performing a first real time polymerase chain reaction (PCR) in a first reaction mixture using the first set of secondary clade-specific primers and a first hydrolysis probe specific for a DNA region amplified by the first set of secondary clade-specific primers, the first hydrolysis probe comprising a fluorescent reporter dye and a quencher; and performing a second real time PCR in a second reaction mixture using the second set of secondary clade-specific primers and a second hydrolysis probe specific for a DNA region amplified by the second set of secondary clade-specific primers, the second hydrolysis probe comprising a fluorescent reporter dye and a quencher; and ii) if the secondary clade member is determined to be present in the sample, performing a second screen of the sample to determine whether an an agent causing onychodystrophy is present or absent in the sample using primary clade-specific primers that are specific to a primary clade member that belongs to the secondary clade member, wherein the second screen comprises performing at least a third real time PCR in a third reaction mixture using the primary clade-specific primers and a third hydrolysis probe specific for a DNA region amplified by the primary clade-specific primers, the third hydrolysis probe comprising a fluorescent reporter dye and a quencher.

2. The method of 1, wherein the first real time PCR and the second real time PCR are performed in the same reaction mixture.

3. The method of 1 or 2, wherein the method comprises performing a fourth real time PCR in a fourth reaction mixture using *Pseudomonas aeruginosa*-specific primers and a fourth hydrolysis probe specific for a DNA region amplified by the *Pseudomonas aeruginosa*-specific primers, the fourth hydrolysis probe comprising a fluorescent reporter dye and a quencher, and wherein the method detects the presence or absence of *Pseudomonas aeruginosa* in the sample.

4. The method of 3, wherein the first real time PCR, the second real time PCR, and the fourth real time PCR are performed in the same reaction mixture.

5. The method of any one of 1-4, wherein the first and second sets of secondary clade-specific primers each comprise a primer pair that facilitate amplification of a secondary clade-specific nucleotide sequence within a nuclear-encoded ribosomal (rRNA) gene to facilitate production of amplification products encoding a secondary clade-specific nucleotide sequence within the nuclear-encoded rRNA gene.

6. The method of 5, wherein the amplification products comprise an amplification product for one or more of the following secondary clade-specific nucleotide sequence encoding:
an 18S ribosomal RNA (rRNA), or a portion thereof;
a 5.8S rRNA, or a portion thereof;
a 28S rRNA, or a portion thereof;
a portion of an internal transcribed spacer 1 (ITS1) adjacent the 18S rRNA;
a portion of an internal transcribed spacer 2 (ITS2) adjacent the 5.8S rRNA;
a portion of an internal transcribed spacer 2 (ITS2) adjacent the 28S rRNA;
a portion of an ITS1; and
a portion of an ITS2.

7. The method of 1, wherein the first set of one or more secondary clade-specific primers comprises one or more primer pairs that facilitate amplification of one or more nucleotide sequences 80% or more identical to a sequence selected from the group consisting of the sequences set forth in FIGS. 29-36, 37, 39, 41, 43, 45, and 47, and wherein the second set of one or more secondary clade-specific primers comprises one or more primer pairs that facilitate amplification of one or more nucleotide sequences 80% or more identical to a sequence selected from the group consisting of the sequence set forth in FIGS. 29-36, 37, 39, 41, 43, 45, and 47.

8. The method of 1, wherein the primary clade-specific primers comprise one or more primer pairs configured to amplify a primary clade-specific nucleotide sequence within a nuclear-encoded ribosomal RNA (rRNA) gene or a mitochondrial nucleotide sequence.

9. The method of 8, wherein the primary clade-specific nucleotide sequence encodes:
an 18S ribosomal RNA, or a portion thereof;
a 28S ribosomal RNA, or a portion thereof;
a 5.8S ribosomal RNA or a portion there of; and/or
an ITS, or a portion thereof, adjacent the 18S, 28S or 5.8S rRNA in the nuclear-encoded rRNA gene, and
wherein the mitochondrial nucleotide sequence encodes:
a nicotinamide adenine dinucleotide (NADH) dehydrogenase subunit gene, or a portion thereof, or
a putative reverse transcriptase gene, or a portion thereof.

10. The method of 1, wherein the primary clade-specific primers comprise one or more primer pairs configured to amplify a primary clade-specific nucleotide sequence encoding:
a 18S ribosomal RNA, or a portion thereof; and/or
an ITS, or a portion thereof, adjacent the 18S rRNA; or
a mitochondrial nucleotide sequence.

11. The method of 1, wherein the primary clade-specific primers comprise one or more primer pairs configured to amplify one or more nucleotide sequences 80% or more identical to a sequence selected from the group consisting of the sequences defined by the primer pairs set forth in each of FIGS. 50-72.

12. The method of 1, wherein the sample is obtained from a human subject.

13. The method of 1, wherein the method further comprises preparing the sample before the screening step i).

14. The method of 13, wherein the preparing step comprises releasing nucleic acids from a cellular compartment in the sample by subjecting the sample to mechanical, chemical, thermal and/or enzymatic treatments.

15. The method of any one of 1-14, wherein the first set of secondary clade-specific primers comprise a dermatophyte-specific forward primer comprising the sequence set forth as SEQ ID NO:1 and a dermatophyte-specific reverse primer comprising the sequence set forth as SEQ ID NO:2, and wherein the first hydrolysis probe comprises the sequence set forth as SEQ ID NO:3.

16. The method of any one of 1-15, wherein the second set of secondary clade-specific primers comprises (a) one or more yeast-specific forward primers comprising a sequence selected from SEQ ID NOs: 4-8 and a yeast-specific reverse primer comprising a sequence as set forth as SEQ ID NO:9, and wherein the second hydrolysis probe comprises a sequence selected from SEQ ID NOs: 10-13; and/or (b) a yeast-specific forward primer comprising the sequence set forth as SEQ ID NO:14 and a yeast-specific reverse primer comprising the sequence set forth as SEQ ID NO:15, and wherein the second hydrolysis probe comprises a sequence as set forth as SEQ ID NO:16.

17. The method of any one of 1-16, wherein an extraction control/inhibition control EC/IC is added to the sample prior to i), and wherein the first and/or second real time PCR utilizes ECIC forward and reverse primers comprising the sequences set forth as SEQ ID NO:17 and 18, respectively, and wherein the first and/or second real time PCR utilizes an ECIC hydrolysis probe comprising the sequence set forth as SEQ ID NO:19.

18. The method of any one of 1-17, wherein the first and/or second set of secondary clade-specific primers comprise one or more saprophyte-specific forward primers comprising a sequence selected from SEQ ID NOs:20, 23, and 25; and one or more saprophyte-specific reverse primers comprising a sequence selected from SEQ ID NOs:21, 22, 24, and 26; and wherein the first or second hydrolysis probe comprises a sequence selected from SEQ ID NOs: 27-31.

19. The method of any one of 3-18, wherein the *Pseudomonas aeruginosa*-specific primers comprise primers designed to facilitate amplification of a portion of the gyrA gene.

20. The method of 19, wherein the *Pseudomonas aeruginosa*-specific primers comprise a forward primer comprising the sequence set forth as SEQ ID NO:32 and a reverse primer comprising the sequence set forth as SEQ ID NO:33, and wherein the fourth hydrolysis probe comprises a sequence as set forth as SEQ ID NO:34.

21. The method of any one of 1-16 and 18-20, wherein an extraction control/inhibition control EC/IC is added to the sample prior to i), and wherein the fourth real time PCR utilizes ECIC forward and reverse primers comprising the sequences set forth as SEQ ID NO:17 and 18, respectively, and wherein the first and/or second real time PCR utilizes an ECIC hydrolysis probe comprising the sequence set forth as SEQ ID NO:19.

22. The method of any one of 1-21, wherein the primary clade-specific primers comprise primers specific for *Microsporum*.

23. The method of 22, wherein the primers specific for *Microsporum* comprise a forward primer comprising the sequence set forth as SEQ ID NO:35 and a reverse primer comprising the sequence set forth as SEQ ID NO:36, and wherein the third hydrolysis probe comprises the sequence set forth as SEQ ID NO:39.

24. The method of 22 or 23, wherein the primers specific for *Microsporum* comprise a forward primer comprising the sequence set forth as SEQ ID NO:37 and a reverse primer comprising the sequence set forth as SEQ ID NO:38, and wherein the third hydrolysis probe comprises the sequence set forth as SEQ ID NO:40.

25. The method of any one of 1-24, wherein the primary clade-specific primers comprise primers specific for *Epidermophyton*.

26. The method of 25, wherein the primers specific for *Epidermophyton* comprise a forward primer comprising the sequence set forth as SEQ ID NO:41 and a reverse primer comprising the sequence set forth as SEQ ID NO:42, and wherein the third hydrolysis probe comprises the sequence set forth as SEQ ID NO:43.

27. The method of any one of 1-26, wherein the primary clade-specific primers comprise primers specific for *T. mentagrophytes*.

28. The method of 25, wherein the primers specific for *T. mentagrophytes* comprise a forward primer comprising the sequence set forth as SEQ ID NO:44 and a reverse primer comprising the sequence set forth as SEQ ID NO:45, and wherein the third hydrolysis probe comprises the sequence set forth as SEQ ID NO:46.

29. The method of any one of 1-28, wherein the primary clade-specific primers comprise primers specific for *T. rubrum*.

30. The method of 29, wherein the primers specific for *T. rubrum* comprise a forward primer comprising the sequence set forth as SEQ ID NO:47 and a reverse primer comprising the sequence set forth as SEQ ID NO:48, and wherein the third hydrolysis probe comprises the sequence set forth as SEQ ID NO:49.

31. The method of any one of 1-30, wherein the primary clade-specific primers comprise primers specific for *Alternaria*.

32. The method of 31, wherein the primers specific for *Alternaria* comprise a forward primer comprising the sequence set forth as SEQ ID NO:50 and a reverse primer comprising the sequence set forth as SEQ ID NO:51, and wherein the third hydrolysis probe comprises the sequence set forth as SEQ ID NO:52.

33. The method of any one of 1-32, wherein the primary clade-specific primers comprise primers specific for *Fusarium*.

34. The method of 33, wherein the primers specific for *Fusarium* comprise a forward primer selected from a forward primer comprising the sequence set forth as SEQ ID NO:53 and a forward primer comprising the sequence set forth as SEQ ID NO:54; and a reverse primer comprising the sequence set forth as SEQ ID NO:55, and wherein the third hydrolysis probe comprises the sequence set forth as SEQ ID NO:56.

35. The method of any one of 1-34, wherein the primary clade-specific primers comprise primers specific for *Scopulariopsis*.

36. The method of 35, wherein the primers specific for *Scopulariopsis* comprise a forward primer comprising the sequence set forth as SEQ ID NO:57 and a reverse primer comprising the sequence set forth as SEQ ID NO:58, and wherein the third hydrolysis probe comprises the sequence set forth as SEQ ID NO:59.

37. The method of any one of 1-36, wherein the primary clade-specific primers comprise primers specific for *Scytalidium*.

38. The method of 37, wherein the primers specific for *Scytalidium* comprise a forward primer comprising the sequence set forth as SEQ ID NO:25 and a reverse primer comprising the sequence set forth as SEQ ID NO:26, and wherein the third hydrolysis probe comprises the sequence set forth as SEQ ID NO:27.

39. The method of any one of 1-38, wherein the primary clade-specific primers comprise primers specific for *Curvularia*.

40. The method of 39, wherein the primers specific for *Curvularia* comprise a forward primer comprising the sequence set forth as SEQ ID NO:60 and a reverse primer comprising the sequence set forth as SEQ ID NO:61, and wherein the third hydrolysis probe comprises the sequence set forth as SEQ ID NO:62.

41. The method of any one of 1-40, wherein the primary clade-specific primers comprise primers specific for *Acremonium*.

42. The method of 41, wherein the primers specific for *Acremonium* comprise a forward primer comprising the sequence set forth as SEQ ID NO:63 and a reverse primer comprising the sequence set forth as SEQ ID NO:64, and wherein the third hydrolysis probe comprises the sequence set forth as SEQ ID NO:65.

43. The method of any one of 1-42, wherein the primary clade-specific primers comprise primers specific for *Aspergillus*.

44. The method of 43, wherein the primers specific for *Aspergillus* comprise a forward primer comprising the sequence set forth as SEQ ID NO:66 and a reverse primer comprising the sequence set forth as SEQ ID NO:67, and wherein the third hydrolysis probe comprises the sequence set forth as SEQ ID NO:68.

45. The method of any one of 1-44, wherein the primary clade-specific primers comprise primers specific for one or more of *Candida albicans, C. parapsilosis*, and *C. tropicalis*.
46. The method of 45, wherein the primers specific for one or more of *Candida albicans, C. parapsilosis*, and *C. tropicalis* comprise a forward primer selected from a forward primer comprising the sequence set forth as SEQ ID NO:69 and a forward primer comprising the sequence set forth as SEQ ID NO:71; and a reverse primer comprising the sequence set forth as SEQ ID NO:70, wherein the third hydrolysis probe comprises one or more hydrolysis probes selected from the group consisting of hydrolysis probes comprising the sequence set forth in one of SEQ ID NOs:72, 73 and 74.
47. The method of any one of 1-46, wherein the primary clade-specific primers comprise primers specific for Trichosporon.
48. The method of 47, wherein the primers specific for *Trichosporon* comprise a forward primer comprising the sequence set forth as SEQ ID NO:76 and a reverse primer comprising the sequence set forth as SEQ ID NO:77, wherein the third hydrolysis probe comprises one or more hydrolysis probes selected from hydrolysis probes comprising the sequence set forth in one of SEQ ID NOs:78 and 79.
49. The method of any one of 1-48, wherein the primary clade-specific primers comprise primers specific for one or more of *Candida guillermondii* and *Cryptococcus*.
50. The method of 49, wherein the primers specific for one or more of *Candida guillermondii* and *Cryptococcus* comprise a forward primer selected from one more of a forward primer comprising the sequence set forth as SEQ ID NO:71 and a forward primer comprising the sequence set forth as SEQ ID NO:79, and a reverse primer comprising the sequence set forth as SEQ ID NO:70, wherein the third hydrolysis probe comprises one or more hydrolysis probes selected from the group consisting of hydrolysis probes comprising the sequence set forth in one of SEQ ID NOs:80-83.
51. The method of any one of 1-50, wherein the primary clade-specific primers comprise primers specific for *Malassezia*.
52. The method of 51, wherein the primers specific for *Malassezia* comprise a forward primer comprising the sequence set forth as SEQ ID NO:84; and one or more reverse primers selected from a reverse primer comprising the sequence set forth as SEQ ID NO:85 and a reverse primer comprising the sequence set forth as SEQ ID NO:86, wherein the third hydrolysis probe comprises the sequence set forth as SEQ ID NOs:87.
53. A method of detecting a yeast and/or a dermatophyte in a sample, the method comprising:
    i) screening a sample using at least a first set of yeast-specific primers and at least first set of dermatophyte-specific primers to determine whether a yeast and/or dermatophyte is present or absent in the sample, wherein the screening comprises:
        performing a first real time polymerase chain reaction (PCR) in a first reaction mixture using the first set of yeast-specific primers and a first hydrolysis probe specific for a DNA region amplified by the first set of yeast-specific primers, the first hydrolysis probe comprising a fluorescent reporter dye and a quencher; and
        performing a second real time PCR in a second reaction mixture using the first set of dermatophyte-specific primers and a second hydrolysis probe specific for a DNA region amplified by the first set of dermatophyte-specific primers, the second hydrolysis probe comprising a fluorescent reporter dye and a quencher; and
    ii) if the yeast and/or dermatophyte is determined to be present in the sample, performing a second screen of the sample to determine whether a genus and/or species of the yeast and/or dermatophyte is present or absent in the sample using yeast and/or dermatophyte genus and/or species-specific primers, wherein the second screen comprises performing at least a third real time PCR in a third reaction mixture using the yeast and/or dermatophyte genus and/or species-specific primers and a third hydrolysis probe specific for a DNA region amplified by the yeast and/or dermatophyte genus and/or species-specific primers, the third hydrolysis probe comprising a fluorescent reporter dye and a quencher.
54. The method of 53, wherein the first real time PCR and the second real time PCR are performed in the same reaction mixture.
55. The method of 53 or 54, wherein the first set of dermatophyte-specific primers comprise a dermatophyte-specific forward primer comprising the sequence set forth as SEQ ID NO:1 and a dermatophyte-specific reverse primer comprising the sequence set forth as SEQ ID NO:2, and wherein the first hydrolysis probe comprises the sequence set forth as SEQ ID NO:3.
56. The method of any one of 53-55, wherein the first set of yeast-specific primers comprises (a) one or more yeast-specific forward primers comprising a sequence selected from SEQ ID NOs: 4-8 and a yeast-specific reverse primer comprising a sequence as set forth as SEQ ID NO:9, and wherein the second hydrolysis probe comprises a sequence selected from SEQ ID NOs:10-13; and/or (b) a yeast-specific forward primer comprising the sequence set forth as SEQ ID NO:14 and a yeast-specific reverse primer comprising the sequence set forth as SEQ ID NO:15, and wherein the second hydrolysis probe comprises a sequence as set forth as SEQ ID NO:16.
57. The method of any one of 53-56, wherein an extraction control/inhibition control EC/IC is added to the sample prior to i), and wherein the first and/or second real time PCR utilizes ECIC forward and reverse primers comprising the sequences set forth as SEQ ID NO:17 and 18, respectively, and wherein the first and/or second real time PCR utilizes an ECIC hydrolysis probe comprising the sequence set forth as SEQ ID NO:19.
58. The method of any one of 53-57 wherein the dermatophyte genus and/or species-specific comprise primers specific for *Microsporum*.
59. The method of 58, wherein the primers specific for *Microsporum* comprise a forward primer comprising the sequence set forth as SEQ ID NO:35 and a reverse primer comprising the sequence set forth as SEQ ID NO:36, and wherein the third hydrolysis probe comprises the sequence set forth as SEQ ID NO:39.
60. The method of 58 or 59, wherein the primers specific for *Microsporum* comprise a forward primer comprising the sequence set forth as SEQ ID NO:37 and a reverse primer comprising the sequence set forth as SEQ ID NO:38, and wherein the third hydrolysis probe comprises the sequence set forth as SEQ ID NO:40.
61. The method of any one of 53-60, wherein the dermatophyte genus and/or species-specific primers primers comprise primers specific for *Epidermophyton*.
62. The method of 61, wherein the primers specific for *Epidermophyton* comprise a forward primer comprising the sequence set forth as SEQ ID NO:41 and a reverse primer comprising the sequence set forth as SEQ ID NO:42, and wherein the third hydrolysis probe comprises the sequence set forth as SEQ ID NO:43.

63. The method of any one of 53-62, wherein the dermatophyte genus and/or species-specific primers comprise primers specific for *T. mentagrophytes*.

64. The method of 63, wherein the primers specific for *T. mentagrophytes* comprise a forward primer comprising the sequence set forth as SEQ ID NO:44 and a reverse primer comprising the sequence set forth as SEQ ID NO:45, and wherein the third hydrolysis probe comprises the sequence set forth as SEQ ID NO:46.

65. The method of any one of 53-64, wherein the dermatophyte genus and/or species-specific primers comprise primers specific for *T. rubrum*.

66. The method of 65, wherein the primers specific for *T. rubrum* comprise a forward primer comprising the sequence set forth as SEQ ID NO:47 and a reverse primer comprising the sequence set forth as SEQ ID NO:48, and wherein the third hydrolysis probe comprises the sequence set forth as SEQ ID NO:49.

67. The method of any one of 53-66, wherein the yeast genus and/or species-specific primers comprise primers specific for one or more of *Candida albicans, C. parapsilosis*, and *C. tropicalis*.

68. The method of 67, wherein the primers specific for one or more of *Candida albicans, C. parapsilosis*, and *C. tropicalis* comprise a forward primer selected from a forward primer comprising the sequence set forth as SEQ ID NO:69 and a forward primer comprising the sequence set forth as SEQ ID NO:71; and a reverse primer comprising the sequence set forth as SEQ ID NO:70, wherein the third hydrolysis probe comprises one or more hydrolysis probes selected from the group consisting of hydrolysis probes comprising the sequence set forth in one of SEQ ID NOs:72, 73 and 74.

69. The method of any one of 53-68, wherein the yeast genus and/or species-specific primers comprise primers specific for *Trichosporon*.

70. The method of 69, wherein the primers specific for *Trichosporon* comprise a forward primer comprising the sequence set forth as SEQ ID NO:76 and a reverse primer comprising the sequence set forth as SEQ ID NO:77, wherein the third hydrolysis probe comprises one or more hydrolysis probes selected from hydrolysis probes comprising the sequence set forth in one of SEQ ID NOs:78 and 79.

71. The method of any one of 53-70, wherein the yeast genus and/or species-specific primers comprise primers specific for one or more of *Candida guillermondii* and *Cryptococcus*.

72. The method of 71, wherein the primers specific for one or more of *Candida guillermondii* and *Cryptococcus* comprise a forward primer selected from one more of a forward primer comprising the sequence set forth as SEQ ID NO:71 and a forward primer comprising the sequence set forth as SEQ ID NO:79, and a reverse primer comprising the sequence set forth as SEQ ID NO:70, wherein the third hydrolysis probe comprises one or more hydrolysis probes selected from the group consisting of hydrolysis probes comprising the sequence set forth in one of SEQ ID NOs:80-83.

73. The method of any one of 53-72, wherein the yeast genus and/or species-specific primers comprise primers specific for *Malassezia*.

74. The method of 73, wherein the primers specific for *Malassezia* comprise a forward primer comprising the sequence set forth as SEQ ID NO:84; and one or more reverse primers selected from a reverse primer comprising the sequence set forth as SEQ ID NO:85 and a reverse primer comprising the sequence set forth as SEQ ID NO:86, wherein the third hydrolysis probe comprises the sequence set forth as SEQ ID NOs:87.

75. A method of detecting a saprophyte and/or *Pseudomonas aeruginosa* in a sample, the method comprising:
   i) screening a sample using at least a first set of saprophyte-specific primers and at least first set of *Pseudomonas aeruginosa*-specific primers to determine whether a saprophyte and/or *Pseudomonas aeruginosa* is present or absent in the sample, wherein the screening comprises:
      performing a first real time polymerase chain reaction (PCR) in a first reaction mixture using the first set of saprophyte-specific primers and a first hydrolysis probe specific for a DNA region amplified by the first set of saprophyte-specific primers, the first hydrolysis probe comprising a fluorescent reporter dye and a quencher; and
      performing a second real time PCR in a second reaction mixture using the first set of *Pseudomonas aeruginosa*-specific primers and a second hydrolysis probe specific for a DNA region amplified by the first set of *Pseudomonas aeruginosa*-specific primers, the second hydrolysis probe comprising a fluorescent reporter dye and a quencher; and
   ii) if the saprophyte is determined to be present in the sample, performing a second screen of the sample to determine whether a genus and/or species of the saprophyte is present or absent in the sample using saprophyte genus and/or species-specific primers, wherein the second screen comprises performing at least a third real time PCR in a third reaction mixture using the saprophyte genus and/or species-specific primers and a third hydrolysis probe specific for a DNA region amplified by the saprophyte genus and/or species-specific primers, the third hydrolysis probe comprising a fluorescent reporter dye and a quencher.

76. The method of 75, wherein the first real time PCR and the second real time PCR are performed in the same reaction mixture.

77. The method of 75 or 76, wherein the saprophyte-specific primers comprise one or more saprophyte-specific forward primers comprising a sequence selected from SEQ ID NOs:20, 23, and 25; and one or more saprophyte-specific reverse primers comprising a sequence selected from SEQ ID NOs:21, 22, 24, and 26; and wherein the first or second hydrolysis probe comprises a sequence selected from SEQ ID NOs:27-31.

78. The method of any one of 75-77, wherein the saprophyte genus and/or species-specific primers comprise primers specific for *Alternaria*.

79. The method of 78, wherein the primers specific for *Alternaria* comprise a forward primer comprising the sequence set forth as SEQ ID NO:50 and a reverse primer comprising the sequence set forth as SEQ ID NO:51, and wherein the third hydrolysis probe comprises the sequence set forth as SEQ ID NO:52.

80. The method of any one of 75-79, wherein the saprophyte genus and/or species-specific primers comprise primers specific for *Fusarium*.

81. The method of 80, wherein the primers specific for *Fusarium* comprise a forward primer selected from a forward primer comprising the sequence set forth as SEQ ID NO:53 and a forward primer comprising the sequence set forth as SEQ ID NO:54; and a reverse primer comprising the sequence set forth as SEQ ID NO:55, and wherein the third hydrolysis probe comprises the sequence set forth as SEQ ID NO:56.

82. The method of any one of 75-81, wherein the saprophyte genus and/or species-specific primers comprise primers specific for *Scopulariopsis*.

83. The method of 82, wherein the primers specific for *Scopulariopsis* comprise a forward primer comprising the sequence set forth as SEQ ID NO:57 and a reverse primer comprising the sequence set forth as SEQ ID NO:58, and wherein the third hydrolysis probe comprises the sequence set forth as SEQ ID NO:59.

84. The method of any one of 75-83, wherein the saprophyte genus and/or species-specific primers comprise primers specific for *Scytalidium*.

85. The method of 84, wherein the primers specific for *Scytalidium* comprise a forward primer comprising the sequence set forth as SEQ ID NO:25 and a reverse primer comprising the sequence set forth as SEQ ID NO:26, and wherein the third hydrolysis probe comprises the sequence set forth as SEQ ID NO:27.

86. The method of any one of 75-85, wherein the saprophyte genus and/or species-specific primers comprise primers specific for *Curvularia*.

87. The method of 86, wherein the primers specific for *Curvularia* comprise a forward primer comprising the sequence set forth as SEQ ID NO:60 and a reverse primer comprising the sequence set forth as SEQ ID NO:61, and wherein the third hydrolysis probe comprises the sequence set forth as SEQ ID NO:62.

88. The method of any one of 75-87, wherein the saprophyte genus and/or species-specific primers comprise primers specific for *Acremonium*.

89. The method of 88, wherein the primers specific for *Acremonium* comprise a forward primer comprising the sequence set forth as SEQ ID NO:63 and a reverse primer comprising the sequence set forth as SEQ ID NO:64, and wherein the third hydrolysis probe comprises the sequence set forth as SEQ ID NO:65.

90. The method of any one of 75-89, wherein the saprophyte genus and/or species-specific primers comprise primers specific for *Aspergillus*.

91. The method of 90, wherein the primers specific for *Aspergillus* comprise a forward primer comprising the sequence set forth as SEQ ID NO:66 and a reverse primer comprising the sequence set forth as SEQ ID NO:67, and wherein the third hydrolysis probe comprises the sequence set forth as SEQ ID NO:68.

92. The method of any one of 75-91, wherein the *Pseudomonas aeruginosa*-specific primers comprise primers designed to facilitate amplification of a portion of the gyrA gene.

93. The method of 92, wherein the *Pseudomonas aeruginosa*-specific primers comprise a forward primer comprising the sequence set forth as SEQ ID NO:32 and a reverse primer comprising the sequence set forth as SEQ ID NO:33, and wherein the second hydrolysis probe comprises a sequence as set forth as SEQ ID NO:34.

94. The method of any one of 75-93, wherein an extraction control/inhibition control EC/IC is added to the sample prior to i), and wherein the first, second, and/or third real time PCR utilizes ECIC forward and reverse primers comprising the sequences set forth as SEQ ID NO:17 and 18, respectively, and wherein the first, second, and/or third real time PCR utilizes an ECIC hydrolysis probe comprising the sequence set forth as SEQ ID NO:19.

95. A screening method, wherein the method of any one of 53-74 and the method of 75-94 are performed on the same sample.

96. A kit for identifying, in a sample, an agent causing onychodystrophy, comprising the primers and hydrolysis probes of any one of 1-95.

97. The kit of 96, wherein the kit further comprises a homogenization and/or lysis buffer.

98. The kit of 96 or 97, wherein the kit further comprises a sample homogenization element configured to mechanically lyse the sample.

99. A composition comprising the primers and hydrolysis probes of any one of 1-95.

100. The composition of 99, further comprising a buffer.

101. The composition of 99 or 100, further comprising a thermostable DNA polymerase.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

I. PROCEDURES

A. Procedure Summary
1. Specimen Collection
   a. Dry nail clippings were collected and transported at ambient temperature using a sealed bag or other sterile container with a tightly fitting cap.
   b. Specimens were transported for receipt at BakoDx within four days of collection.
2. Specimen Grossing
   a. The gross description for all specimens was recorded, to include the source, number of fragments, size and shape of submitted specimens.
   b. Following gross analysis, the nail samples were minced aseptically and portions of each were submitted and processed for histological analysis, PCR analysis and bacterial culture.
3. Descriptions of Controls (CTLs)
   a. Extraction Control/Inhibition Control (EC/IC): EC/IC was used as an extraction control. Plasmid containing a fragment of the *Saccharomyces pombe* citrate synthase gene was added to each sample prior to cell lysis and DNA purification.
   b. Reagent Blank (RB): RB was used as a Negative Extraction Control. RBs were processed with each extraction batch and included in the PCR analysis. Each RB included EC/IC template DNA and results were used to monitor for potential contamination introduced during the extraction process.

c. PCR Positive Control (CTL): Positive controls for each target were included in each run. A series of eight plasmid constructs containing targets for each probe in the assays were constructed and used as the source of positive control DNA.

d. No template control (NTC): The NTC was used as a Reagent Contamination Control. NTC was included for each PCR Master Mix preparation, where molecular grade water is included with no nucleic acid template. NTC samples were used as a control to monitor for potential contamination.

4. DNA Extraction and Purification
   a. Minced nail samples were physically disrupted using ceramic bead homogenization.
   b. EC/IC was added and samples were treated with detergent-based lysis buffer and digested with Proteinase K.
   c. DNA was purified from the lysate and concentrated using the Mag-Bind® Plant DNA DS Kit (Omega Bio-tek) on an automated platform prior to PCR analysis.

5. Polymerase Chain Reaction (PCR)
   a. Real-Time PCR was then performed with fluorescently labeled (TaqMan®) probes to detect the presence of target organisms. Amplication reactions were performed using Platinum II Taq Hot-Start DNA polymerase (Thermofisher) in PCR reaction amplified on the QuantStudio-6 PCR machine (Thermofisher). Screen primers were designed to specifically amplify DNA from 3 categories of fungal organisms: yeast, dermatophytes and saprophytes and one bacterium, *Pseudomonas aeruginosa*. Reflex primers were designed to specifically amplify organisms at the genus and/or species level.
   b. The PCR set up for testing of clinical specimens was as follows:

| Reagent | Volume for 1 reaction | Volume for 91 reactions (1 plate) |
| --- | --- | --- |
| 3.5X MM | 2.9 μL | 312 μL |
| 50X Primer/Probe mix | 0.2 μL | 21.8 μL |
| MGW water | 4.9 μL | 539.8 μL |
| Final MM Reaction Volume | 8 μL | 873.6 μL |
| DNA sample | 2 μL | 2 μL per sample | c. The OIAD Screen Assay includes two separate PCR reactions:
      i. The OIAD Screen Rxn1 detects yeast and dermatophyte organisms and EC/IC
      ii. The OIAD Screen Rxn2 detects saprophytes and Pseudomonas aeruginosa organisms and EC/IC
   d. The OIAD Reflex Assays include of five separate PCR reactions:
      i. The OIAD Reflex Dermatophyte Rxn—detects *Trichophyton rubrum* complex, *Trichophyton mentagrophytes* complex, *Epidermophyton* spp., and *Microsproum* spp.
      ii. The OIAD Reflex Saprophyte Rxn1 detects *Alternaria* spp., *Fusarium* spp., *Scopulariopsis* spp., and *Scytalidium* spp.
      iii. The OIAD Reflex Saprophyte Rxn2—detectes *Acremonium* spp., *Aspergillus* spp., and *Curvularia* spp.
      iv. The OIAD Reflex Yeast Rxn1 detects *Candida albicans, Candida parapsilosis, Candida tropicalis*, and *Trichosporon* spp.
      v. The OIAD Reflex Yeast Rxn2 detects *Candida guilliermondii, Cryptococcus* spp., and *Malassezia* spp.

6. Results Interpretation
   a. A target is determined to be positive in the sample according to $C_t$ and delta Rn cutoff values established in this validation. If all fungal targets are negative and *Pseudomonas aeruginosa* is positive or negative, the testing is complete. If there are one or more classes of fungi determined to be positive, then the OIAD Reflex Assay/s is performed.
   b. The interpretive algorithm considers the $C_t$ values and the delta Rn values to determine if reactions are positive or negative. The EC/IC control is used in each sample to prevent false negative results.
      i. A valid sample has either a "Detected" value for at least one target and/or a valid EC/IC target value.
      ii. A "Detected" result is generated for a target whose $C_t$ value is below the established cutoff and the delta Rn at cycle 40 is above the established cutoff value.
      iii. A "Not Detected" result is generated for a target when the amplification does not reach the threshold value or the $C_t$ is above the established cutoff for that target and delta Rn is below the cutoff for that target at cycle 40, and there is a valid EC/IC target value. Samples negative for all targets are evaluated for successful EC/IC performance before a "Not Detected" interpretation was rendered.
      iv. An "Indeterminate" result is generated for any sample with no positive targets and no valid EC/IC target value.
   c. The results interpretation is automated. Life Technologies' QuantStudio™ 6 Flex Software is used for data acquisition, at 40 cycles of amplification. Data generated by the QuantStudio™ 6 Flex Software, together with Bako-developed data analysis software engine (PCREngine) assessed the validity of the assay controls, the EC/IC for each sample, and generated results for each sample.

II. EXAMPLE 1

Verification and Validation Overview

A. OIAD Screen and Reflex Assays Verification Study Summary
1. OIAD Screen Assay Specificity Studies Summary
   All assays were tested for reactivity against 1 ng genomic DNA from 54 specificity/inclusivity organisms including 13 yeast, 9 dermatophytes, 5 bacteria, 25 saprophytes and 2 controls. Human genomic DNA and plasmid based ECIC controls were tested at 4 ng and 0.0001 ng.
   a) OIAD Screen Assay—Dermatophytes:
      i. All intended dermatophyte targets were amplified by the assay.
      ii. The dermatophye screen assay correctly did not amplify on 13 yeast, 24 saprophytes and 5 bacteria
      iii. The dermatophye screen assay showed no cross reactivity to any organism tested.

b) OIAD Screen Assay—Saprophyte:
  i. All intended saprophyte targets were amplified by the assay.
  ii. The saprophyte screen assay correctly did not amplify on 13 yeast, 9 dermatophytes and 5 bacteria
  iii. The saprophyte screen assay showed no cross reactivity to any organisms tested.
c) OIAD Screen Assay—Dermatophytes:
  iv. All intended dermatophyte targets were amplified by the assay.
  v. The dermatophye screen assay correctly did not amplify on 13 yeast, 24 saprophytes and 5 bacteria
  vi. The dermatophye screen assay showed no cross reactivity to any organism tested.
d) OIAD Screen Assay—Saprophyte:
  iv. All intended saprophyte targets were amplified by the assay.
  v. The saprophyte screen assay correctly did not amplify on 13 yeast, 9 dermatophytes and 5 bacteria
  vi. The saprophyte screen assay showed no cross reactivity to any organisms tested.
e) OIAD Screen Assay—Yeast:
  i. All intended yeast targets were amplified by the assay.
  ii. The yeast screen assay correctly did not amplify on 9 dermatophytes, 25 saprophytes and 5 bacteria
  iii. The yeast screen assay showed no cross reactivity to any organism tested.
f) OIAD Screen Assay—*Pseudomonas aeruginosa*:
  i. The intended *Pseudomonas aeruginosa* target was amplified by the assay.
  ii. The *Pseudomonas aeruginosa* assay correctly did not amplify any of the 53 non-targeted organisms.
  iii. The *Pseudomonas aeruginosa* assay did not show any cross reactivity to any organisms tested.
g) No cross reactivity or interference detected with human genome DNA or the ECIC control.
h) No detectable signal or interference in Reagent Blank and No Template Controls.
2. OIAD Reflex Assays Specificity Studies Summary
  All assays were tested for reactivity against 1 ng genomic DNA from 54 specificity/inclusivity organisms including 13 yeast, 9 dermatophytes, 5 bacteria, 25 saprophytes and 2 controls. Exceptions was human genomic DNA used at 4 ng and ECIC at 0.0001 ng per reaction. Note: ECIC is present in the extracted sample and the cross-reactivity was tested also on OIAD Reflex Assays.
  a) OIAD Reflex Dermatophyte Rxn:
    i. All the intended dermatophyte targets were amplified by the assay.
    ii. The dermatophyte reflex assay correctly did not amplify on 11 yeast, 1 dermatophyte, 25 saprophytes and 5 bacteria.
    iii. No cross-reactivity found based on established assay cut-off values.
  b) OIAD Reflex Saprophyte Rxn1 and Rxn2:
    i. All intended saprophyte targets were amplified by the assay.
    ii. The saprophyte reflex assay correctly did not amplify on 12 yeast, 8 dermatophytes, 9 saprophytes and 5 bacteria.
    iii. No cross-reactivity found based on established assay cut-off values.
  c) OIAD Reflex Yeast Rxn1 and Rxn2:
    i. All intended yeast targets were amplified by the assay.
    ii. The yeast reflex assay correctly did not amplify on 5 yeast, 8 dermatophytes, 25 saprophytes and 5 bacteria.
    iii. No cross-reactivity found based on established assay cut-off values.
  d) No cross reactivity or interference detected with human genomic DNA or the ECIC control.
  e) No detectable signal or interference in Reagent Blank and No Template Controls.
3. OIAD Screen Assay Sensitivity Studies Summary
  Replicates of purified DNA (dermatophytes or saprophytes) or cultured cells (yeast or *Pseudomonas aeruginosa*) was spiked into nail matrix across a 10-fold dynamic range of DNA concentrations (1 ng-0.00001 ng) and tested by the OIAD Screen Assay. The lowest concentration where all replicates were detected was determined. Results indicated,
    a. Limit of detection concentration for OIAD Screen Assay—Dermatophyte was 0.0001-0.00001ng/reaction
    b. Limit of detection concentration for OIAD Screen Assay—Saprophyte was 0.001-0.00001ng/reaction
    c. Limit of detection concentration for OIAD Screen Assay—Yeast was 400-2100 CFU/extraction.
    d. Limit of detection concentration for OIAD Screen Assay—*Pseudomonas aeruginosa* was 3445 CFU/extraction.
4. OIAD Reflex Assays Sensitivity Studies Summary
  Replicates of purified DNA (dermatophytes or saprophytes) or cultured cells (yeast) was spiked into nail matrix across a 10-fold dynamic range of DNA concentrations (1 ng-0.00001 ng) and tested by the OIAD Reflex Assays. The lowest concentration where all replicates were detected was determined.
    a. Limit of detection concentration for OIAD Reflex Assays—Dermatophytes was 0.0001-0.00001 ng/reaction
    b. Limit of detection concentration for OIAD Reflex Assays—Saprophytes was 0.001-0.0001 ng/reaction
    c. Limit of detection concentration for OIAD Reflex Assays—Yeast was 50-492 CFU/extraction
5. OIAD Screen Assay Intraday Repeatability/Interday Reproducibility Studies Summary
  Replicates of 3 levels of DNA (saprophytes or dermatophytes) or 3 levels of cultured cells (yeast or Pseudomonas aeruginosa) determined from the LoD study were spiked into human nail matrix and tested by the OIAD Screen Assay on the same day (intraday) and across 4 different days (interday). Results are reported as % CV of the $C_t$. All replicates reported are positive and within the established cut off values.
    a. OIAD Screen Assay—Dermatophytes intraday repeatability ranged from 0.65-4.2% CV, while the interday reproducibility ranged from 1.31-10.67% CV.
    b. OIAD Screen Assay—Saprophytes intraday repeatability ranged from 0.23-7.92% CV, while the interday reproducibility ranged from 1.75-5.89% CV.

c. OIAD Screen Assay—Yeast intraday repeatability ranged from 0.97-5.06% CV, while the interday reproducibility ranged from 2.57-8.48% CV.
d. OIAD Screen Assay—*Pseudomonas aeruginosa* intraday repeatability ranged from 1.25-2.41% CV, while the interday reproducibility ranged from 2.4-4.19% CV.
6. OIAD Reflex Assays Intraday Repeatability/Interday Reproducibility Studies Summary
Replicates of 3 levels of DNA (saprophytes and dermatophytes) or 3 levels of cultured cells (yeast and *Pseudomonas aeruginosa*) determined from the LoD study were spiked into human nail matrix and tested by the Onychodystrophy Reflex PCR assay on the same day (intraday) and across 4 different days (interday). Results are reported as % CV of the Ct. All replicates reported are positive and within the established cut off values.
a. OIAD Reflex Assays—Dermatophytes intraday repeatability ranged from 0.9-6.76% CV, while the interday reproducibility ranged from 10.9-5.42% CV.
b. OIAD Reflex Assays—Saprophytes intraday repeatability ranged from 0.73-5.73% CV, while the interday reproducibility ranged from 1.70-7.32% CV.
c. OIAD Reflex Assays—Yeast intraday repeatability ranged from 0.67-5.89% CV, while the interday reproducibility ranged from 2.72-5.88% CV.

B. OIAD Screen and Reflex Assays Validation Study Summary

A total of 802 clinical samples were included in the accuracy studies, with an additional 364 contrived samples, bringing the total number of tested samples to 1166. The overall accuracy was assessed by comparison of the OIAD Screen Assay results to the reference method. The reference method consisted of routine histological staining with Periodic Acid-Schiff (PAS) and/or Gomori Methenamine Silver (GMS). Overall accuracy for *Pseudomonas aeruginosa* was assessed using microbial culture as the reference. All discordant samples were resolved by Sanger sequencing using a different PCR amplicon than used for the OIAD Screen Assay.

Samples positive for fungus by the OIAD Screen Assay were analyzed using the OIAD Reflex Assays. Results were compared to the reference reflex method which consisted of Sanger sequencing using a different PCR amplicon than the OIAD Reflex Assay. Dermatophyte ID was used as an additional reference for OIAD Reflex Assay—Dermatophyte validation, described generally in U.S. Patent Application Publication No. US-2017-0029906-A1, the disclosure of which is incorporated by reference herein.

Overall accuracy and independent correlation results for dermatophytes, saprophytes, yeast and *Pseudomonas aeruginosa* were calculated for the OIAD Screen Assay. Total concordance values of the OIAD Screen Assay with the Reference assay (PAS/GMS) are shown.
OIAD Screen Assay results indicated the following:
a. Overall concordance with the reference method was 88%; concordance was 93% following discordant resolution by sequencing.
b. Concordance for Dermatophytes with the reference method was 90%; concordance was 98% following discordant resolution by sequencing.
c. Concordance for Saprophytes with the reference method was 90%; concordance was 95% following discordant resolution by sequencing.
d. Concordance for Yeast with the reference method was 93%; concordance was 98% following discordant resolution by sequencing.
e. Concordance for Pseudomonas aeruginosa with the reference method was 65%; concordance was 100% following discordant resolution by sequencing.

Correlation results for dermatophytes, saprophytes and yeast organisms were calculated for the test OIAD Reflex Assays. Total concordance values of the test OIAD Reflex Assay with Reference assay (OIAD Screen Assay/Sanger Sequencing) are shown.
OIAD Reflex Assay—Dermatophytes results indicated the following:
a. Concordance for *Trichophyton rubrum* with the reference method was 98%
b. Concordance for *Trichophyton mentagrophytes* with the reference method was 99%
c. Concordance for *Epidermophyton* spp. with the reference method was 100%
d. Concordance for *Microsporum* spp. with the reference method was 100%
OIAD Reflex Assay—Saprophytes results indicated the following:
a. Concordance for *Alternaria* spp. with the reference method was 97%
b. Concordance for *Fusarium* spp. with the reference method was 97%
c. Concordance for *Scopulariopsis* spp. with the reference method was 98%
d. Concordance for *Scytalidium* spp. with the reference method was 98%
e. Concordance for *Acremonium* spp. with the reference method was 99%
f. Concordance for *Aspergillus* spp. with the reference method was 96%
g. Concordance for *Curvularia* spp. with the reference method was 100%
OIAD Reflex Assay—Yeast results indicated the following:
a. Concordance for *Candida albicans* with the reference method was 99%
b. Concordance for *Candida parapsilosis* with the reference method was 98%
c. Concordance for *Candida tropicalis* with the reference method was 99%
d. Concordance for *Trichosporon* spp. with the reference method was 98%
e. Concordance for *Candida guilliermondii* with the reference method was 97%
f. Concordance for *Cryptococcus* spp. with the reference method was 99%
g. Concordance for *Malassezia* spp with the reference method was 92%

C. OIAD Verification and Validation Conclusions

The results of the verification study show that the analytical performance of the OIAD Assay is highly sensitive, specific and reproducible. Furthermore, the validation studies demonstrate performance consistent with that of the literature compared to the gold standard histological staining techniques (PAS/GMS) for fungal identification and microbiological culture for *Pseudomonas aeruginosa* identification. In addition, the validation identifies several clear advantages of the PCR assay when compared to current gold standard methods including a faster turn around time of 24 hours compared to 2-3 days, higher sensitivity and the ability to identify genus and species. Accuracy of PCR results was confirmed by Sanger sequencing.

Finally, the results reported by the OIAD assay are in line with that reported in the literature.

TABLE 9

Prevalence range of causative agents of onychodystrophy in OIAD Assay compared to literature reports

| Class | % Positive Reported Range, literature* | % Positive in the OIAD Assay† |
|---|---|---|
| Dermatophytes | 18.8 to 100 | 56 |
| Saprophytes | 0 to 51.6 | 35 |
| Yeasts | 2.7 to 64.1 | 20 |
| *Pseudomonas aeruginosa* | 4-7 | 5.2 |

*% positive of culture confirmed cases
†% positive of PCR confirmed cases

III. EXAMPLE 2

Verification Study Results

A. OIAD Screen Assay
1. Specificity and Inclusivity Studies
   a. Design
      i. All assays were tested for specificity/inclusivity against 54 separate organisms including 13 yeast, 9 dermatophytes, 5 bacteria, 25 saprophytes and 2 controls (Table 8).
      i. The identities of DNA isolated from in-house cultures were previously confirmed by DNA sequencing. Organisms not isolated from in house culture included *Aspergiluus flavus* (ATCC #204304D-2), *Trichophyton mentagrophytes* (ATCC #9533D-2), *Malassezia restricta* (ATCC #MYA-4611D-5), *Candida albicans* (ATCC #MYA-2876D-5), *Candida tropicalis* (ATCC #66029D-5), *Candida parapsilosis* (ATCC #22019D-5), *Candida guilliermondii* (ATCC #6260D-5), *Candida lusitaniae* (ATCC #42720D-5), *Cryptococcus neoformans* (ATCC #208821D-2), human genomic DNA (Promega, cat #G3041), and ECIC (synthetic plasmid DNA from Genscript).
      ii. Each organism was tested at 1 ng/reaction except for human genomic DNA (HugDNA) tested at 4ng/reaction and ECIC plasmid DNA tested at 0.0001 ng/reaction.
   b. Results (see Table 10)
      i. OIAD Screen Assay—Dermatophyte: All nine dermatophytes were identified as dermatophytes. Correctly, no amplification was observed with the dermatophyte assay against 45 non-targeted organisms.
      ii. OIAD Screen Assay—Saprophyte: All twenty-six saprophytes were identified as saprophytes. Correctly, no amplification was observed with the saprophyte assay against 28 non-targeted organisms.
      iii. OIAD Screen Assay—Yeast: All thirteen yeasts were identified as yeast. Correctly, no amplification was observed with the yeast assay against 41 non-targeted organisms.
      iv. OIAD Screen Assay—*Pseudomonas aeruginosa*: The *Pseudomonas aeruginosa* sample was identified as *Pseudomonas aeruginosa*. Correctly, no amplification was observed with the assay against 53 non-targeted organisms.

TABLE 10

Results of Specificty and Inclusivity testing with OIAD Screen Assay

| | | OIAD Screen Assay | | | |
|---|---|---|---|---|---|
| Organism | Category | Yeast | Derma-tophyte | Sapro-phyte | *Pseudomonas aeruginosa* |
| *Candida albicans* | Yeast | POS | ND | ND | ND |
| *Candida parapsilosis* | Yeast | POS | ND | ND | ND |
| *Candida tropicalis* | Yeast | POS | ND | ND | ND |
| *Trichosporon asahii* | Yeast | POS | ND | ND | ND |
| *Candida guilliermondii* | Yeast | POS | ND | ND | ND |
| *Candida carribica* | Yeast | POS | ND | ND | ND |
| *Cryptococcus* | Yeast | POS | ND | ND | ND |
| *Malassezia glabosa* | Yeast | POS | ND | ND | ND |
| *Malassezia restricta* | Yeast | POS | ND | ND | ND |
| *Malassezia sympodialis* | Yeast | POS | ND | ND | ND |
| *Malassezia furfur* | Yeast | POS | ND | ND | ND |
| *Candida lusitaniae* | Yeast | POS | ND | ND | ND |
| *Candida krusei* | Yeast | POS | ND | ND | ND |
| *Epidermophyton* | Dermatophyte | ND | POS | ND | ND |
| *Microsporum audouinii* | Dermatophyte | ND | POS | ND | ND |
| *Microsporum gypsium* | Dermatophyte | ND | POS | ND | ND |
| *Microsporum canis* | Dermatophyte | ND | POS | ND | ND |
| *Trichophyton mentagrophytes* | Dermatophyte | ND | POS | ND | ND |
| *Trichophyton rubrum* | Dermatophyte | ND | POS | ND | ND |
| *Trichophyton tonsurans* | Dermatophyte | ND | POS | ND | ND |
| *Trichophyton verrucosum* | Dermatophyte | ND | POS | ND | ND |
| *Trichophyton violaceum* | Dermatophyte | ND | POS | ND | ND |
| *Pseudomonas aeruginosa* | Bacteria | ND | ND | ND | POS |
| *Proteus mirabilis* | Bacteria | ND | ND | ND | ND |
| *Serratia marcescens* | Bacteria | ND | ND | ND | ND |
| *Staphylococcus aureus* | Bacteria | ND | ND | ND | ND |
| *Streptococcus pyogenes* | Bacteria | ND | ND | ND | ND |
| *Acremonium* | Saprophyte | ND | ND | POS | ND |
| *Alternaria* | Saprophyte | ND | ND | POS | ND |
| *Aspergillus flavus* | Saprophyte | ND | ND | POS | ND |
| *Aspergillus nishimurae* | Saprophyte | ND | ND | POS | ND |
| *Aspergillus ochraceus* | Saprophyte | ND | ND | POS | ND |
| *Aspergillus sydowii* | Saprophyte | ND | ND | POS | ND |
| *Aspergillus versicolor* | Saprophyte | ND | ND | POS | ND |
| *Aspergillus sclerotiorum* | Saprophyte | ND | ND | POS | ND |
| *Aspergillus oryzae* | Saprophyte | ND | ND | POS | ND |

TABLE 10-continued

Results of Specificty and Inclusivity testing with OIAD Screen Assay

| | | OIAD Screen Assay | | | |
|---|---|---|---|---|---|
| Organism | Category | Yeast | Derma-tophyte | Sapro-phyte | *Pseudomonas aeruginosa* |
| *Chaetomium* | Saprophyte | ND | ND | POS | ND |
| *Cladosporium* | Saprophyte | ND | ND | POS | ND |
| *Curvularia* | Saprophyte | ND | ND | POS | ND |
| *Epicoccum* | Saprophyte | ND | ND | POS | ND |
| *Fusarium oxysporum* | Saprophyte | ND | ND | POS | ND |
| *Fusarium solani* | Saprophyte | ND | ND | POS | ND |
| *Mucor* | Saprophyte | ND | ND | POS | ND |
| *Paecilomyces* | Saprophyte | ND | ND | POS | ND |
| *Penicillium polonicum* | Saprophyte | ND | ND | POS | ND |
| *Penicillium citrinum* | Saprophyte | ND | ND | POS | ND |
| *Penicillium chrysogenum* | Saprophyte | ND | ND | POS | ND |
| *Rhizopus* | Saprophyte | ND | ND | POS | ND |
| *Scopulariopsis* | Saprophyte | ND | ND | POS | ND |
| *Scytalidium* | Saprophyte | ND | ND | POS | ND |
| *Nigrospora* | Saprophyte | ND | ND | POS | ND |
| *Chrysosporium* | Saprophyte* | ND | POS | POS | ND |
| HugDNA | Control | ND | ND | ND | ND |
| ECIC DNA | Control | ND | ND | ND | ND |

POS, detected or amplified by the assay;
ND, not detected by the assay
*Closely related to Dermatophyte fungi[38, 39].

1. Analytical Sensitivity Studies
   a. Design
      i. OIAD Screen Assay—Saprophytes and Dermatophytes: Multiple replicates of purified DNA spiked into nail matrix across a DNA concentration range of 1 ng to 0.00001 ng were tested. The lowest concentration where all replicates were detected was determined.
      ii. OIAD Screen Assay—Yeast and *Pseudomonas aeruginosa*: Fresh Yeasts or *Pseudomonas aeruginosa* were suspended in saline and their concentration were initially estimated by the McFarland method and finally determined colony formation units (CFU). For each microorganism, multiple concentrations were spiked, extracted and tested to determine the assay sensitivity. The lowest concentration where all replicates were detected was determined.
      iii. Detailed sensitivity study data is presented in FIGS. 75 and 76.
   b. Results
      i. OIAD Screen Assay—Dermatophyte results are shown in Table 11. Results indicated Dermatophytes can be detected down to 0.001 ng/reaction or lower.
      ii. OIAD Screen Assay—Saprophytes results are shown in Table 11. Results indicated Saprophytes can be detected down to 0.001 ng/reaction or lower.
      iii. OIAD Screen Assay—Yeast results are shown in Table 11. Results indicated Yeasts can be detected down to $2.1 \times 10e^4$ CFU/extraction or lower.
      iv. OIAD Screen Assay—*Pseudomonas aeruginosa* results are shown in Table 11. Results indicated *Pseudomonas aeruginosa* can be detected down to 3445 CFU/extraction or lower.

TABLE 11

OIAD Screen Assay Sensitivity Summary Table

| Assay | Organism Used for Sensitivity Study | LoD | Units |
|---|---|---|---|
| Dermatophyte | *Trichophyton mentagrophytes* | 0.00001 | ng DNA/extraction |
| | *Trichophyton rubrum* | 0.00001 | ng DNA/extraction |
| | *Epidermophyton* | 0.00001 | ng DNA/extraction |
| | *Microsporum canis* | 0.0001 | ng DNA/extraction |
| Saprophyte | *Acremonium* | 0.0001 | ng DNA/extraction |
| | *Alternaria* | 0.001 | ng DNA/extraction |
| | *Aspergillus* | 0.00001 | ng DNA/extraction |
| | *Curvularia* | 0.0001 | ng DNA/extraction |
| | *Fusarium* | 0.0001 | ng DNA/extraction |
| | *Scopulariopsis* | 0.0001 | ng DNA/extraction |
| | *Scytalidium* | 0.001 | ng DNA/extraction |
| Yeast | *Candida albicans* | 1200 | CFU/extraction |
| | *Candia parapsilosis* | 5919 | CFU/extraction |
| | *Candida tropicalis* | 400 | CFU/extraction |
| | *Trichosporon asahii* | 520 | CFU/extraction |
| | *Candida guilliermondii* | 3936 | CFU/extraction |
| | *Cryptococcus neoformans* | 1856 | CFU/extraction |
| | *Malassezia furfur* | 21000 | CFU/extraction |
| *Pseudomonas* | *Pseudomonas aeruginosa* | 3445 | CFU/extraction |

2. Precision Studies
   a. Design
      i. Saprophytes and Dermatophytes: Replicates of 3 levels of DNA determined from the sensitivity study were spiked into human nail matrix and tested by the Onychodystrophy Screen PCR assay.
      ii. Yeast and *Pseudomonas aeruginosa*: Cultured cells were spiked into human nail matrix at 3 levels determined from the sensitivity study and tested by the OIAD Screen Assay.
      iii. Intraday/repeatability: Three concentrations were extracted and run in triplicate on the same day through the Onychodystrophy screen assay.
      iv. Interday/reproducibility: Three concentrations were extracted and run in replicates on different days across three different lots of reagents, two independent operators, two different extraction instruments, two different PCR setup instruments, and six different PCR instruments.
      v. Results are reported as % CV of the Ct. All replicates reported are positive and within the established cut off values except where indicated.
   b. Results
      i. OIAD Screen Assay—Dermatophyte results are shown in Tables 12 and 14. The repeatability is 4.2% CV or lower; the reproducibility is 10.67% CV or lower.
      ii. OIAD Screen Assay—Saprophyte results are shown in Tables 12 and 14. The repeatability is 5.66% CV or lower; the reproducibility is 5.89% CV or lower.
      iii. OIAD Screen Assay—Yeast results are shown in Tables 13 and 15. The repeatability is 5.06% CV or lower; the reproducibility is 8.08% CV or lower.
      iv. OIAD Screen Assay—*Pseudomonas aeruginosa* results are shown in Tables 13 and 15. The repeatability is 2.4% CV or lower; the reproducibility is 4.19% CV or lower.

TABLE 12

OIAD Screen Assay - Dermatophyte and Saprophyte Intraday/Repeatability

| | Sample | ng DNA/ extraction | Agreement w/ expected result | Average Ct | SD | CV (%) |
|---|---|---|---|---|---|---|
| Dermatophyte | Trichophyton mentagrophytes | 2 | 3/3 | 100% | 24.94 | 0.28 | 1.13 |
| | | 0.4 | 3/3 | 100% | 27.11 | 0.18 | 0.65 |
| | | 0.08 | 3/3 | 100% | 29.90 | 0.46 | 1.55 |
| | Trichophyton rubrum | 2 | 3/3 | 100% | 24.70 | 0.38 | 1.54 |
| | | 0.4 | 3/3 | 100% | 27.36 | 0.32 | 1.16 |
| | | 0.08 | 3/3 | 100% | 29.11 | 0.23 | 0.78 |
| | Epidermophyton | 2 | 3/3 | 100% | 25.67 | 0.22 | 0.85 |
| | | 0.4 | 3/3 | 100% | 27.89 | 1.17 | 4.20 |
| | | 0.08 | 3/3 | 100% | 29.75 | 0.57 | 1.93 |
| | Microsporum | 2 | 3/3 | 100% | 26.83 | 0.74 | 2.76 |
| | | 0.4 | 3/3 | 100% | 29.11 | 0.40 | 1.36 |
| | | 0.08 | 3/3 | 100% | 32.09 | 0.91 | 2.84 |
| Saprophyte | Acremonium | 2 | 3/3 | 100% | 27.88 | 0.39 | 1.41 |
| | | 0.4 | 3/3 | 100% | 31.58 | 0.18 | 0.58 |
| | | 0.08 | 3/3 | 100% | 33.59 | 0.08 | 0.23 |
| | Alternaria | 2 | 3/3 | 100% | 26.38 | 0.44 | 1.68 |
| | | 0.4 | 3/3 | 100% | 28.71 | 0.80 | 2.80 |
| | | 0.08 | 3/3 | 100% | 30.60 | 0.87 | 2.83 |
| | Aspergillus | 2 | 3/3 | 100% | 24.59 | 0.40 | 1.62 |
| | | 0.4 | 3/3 | 100% | 27.66 | 0.61 | 2.19 |
| | | 0.08 | 3/3 | 100% | 30.19 | 0.78 | 2.59 |
| | Curvularia | 2 | 3/3 | 100% | 25.80 | 0.35 | 1.37 |
| | | 0.4 | 3/3 | 100% | 27.77 | 0.06 | 0.23 |
| | | 0.08 | 3/3 | 100% | 29.72 | 0.33 | 1.10 |
| | Fusarium | 2 | 3/3 | 100% | 31.52 | 0.42 | 1.33 |
| | | 0.4 | 3/3 | 100% | 33.30 | 0.69 | 2.08 |
| | | 0.08 | 3/3 | 100% | 36.39 | 2.88 | 7.92 |
| | Scopulariopsis | 1 | 3/3 | 100% | 25.24 | 1.43 | 5.66 |
| | | 0.2 | 3/3 | 100% | 27.36 | 0.29 | 1.08 |
| | | 0.04 | 3/3 | 100% | 29.61 | 0.29 | 0.99 |
| | Scytalidium | 1 | 3/3 | 100% | 31.66 | 0.73 | 2.30 |
| | | 0.2 | 3/3 | 100% | 33.25 | 1.35 | 4.05 |
| | | 0.04 | 3/3 | 100% | 37.31 | 1.73 | 4.64 |

TABLE 13

OIAD Screen Assay - Yeast and *Pseudomonas aeruginosa* Intraday/Repeatability

| | Sample | CFU/ extraction | Agreement w/ expected result | Average CT | SD | CV (%) |
|---|---|---|---|---|---|---|
| Yeast | Candida albicans | 4439 | 3/3 | 100% | 28.9 | 0.35 | 1.21 |
| | | 10358 | 3/3 | 100% | 29.17 | 0.64 | 2.2 |
| | | 24170 | 3/3 | 100% | 26.91 | 0.42 | 1.56 |
| | Candida parapsilosis | 5919 | 3/3 | 100% | 30.34 | 0.4 | 1.33 |
| | | 13810 | 3/3 | 100% | 29.01 | 0.04 | 0.15 |
| | | 32224 | 3/3 | 100% | 27.79 | 1 | 3.61 |
| | Candida tropicalis | 1078 | 3/3 | 100% | 29.79 | 0.81 | 2.72 |
| | | 2515 | 3/3 | 100% | 29.56 | 1.5 | 5.06 |
| | | 5867 | 3/3 | 100% | 28 | 0.71 | 2.54 |
| | Trichosporon | 2402 | 3/3 | 100% | 29.01 | 0.31 | 1.07 |
| | | 5604 | 3/3 | 100% | 27.99 | 0.94 | 3.36 |
| | | 13076 | 3/3 | 100% | 27.2 | 0.69 | 2.54 |
| | Candida guilliermondii | 10026 | 3/3 | 100% | 31.13 | 0.37 | 1.17 |
| | | 23393 | 3/3 | 100% | 29.68 | 0.4 | 1.35 |
| | | 54584 | 3/3 | 100% | 28.23 | 0.96 | 3.41 |
| | Cryptococcus | 4426 | 3/3 | 100% | 30.55 | 0.7 | 2.28 |
| | | 10327 | 3/3 | 100% | 29.49 | 0.51 | 1.73 |
| | | 24096 | 3/3 | 100% | 27.96 | 0.27 | 0.97 |
| | Malassezia furfur | 7433 | 3/3 | 100% | 31.09 | 0.43 | 1.38 |
| | | 17344 | 3/3 | 100% | 28.95 | 0.84 | 2.89 |
| | | 40470 | 3/3 | 100% | 27.29 | 0.57 | 2.1 |
| P. aeruginosa | Pseudomonas aeruginosa | 3445 | 3/3 | 100% | 36.52 | 0.46 | 1.25 |
| | | 6891 | 3/3 | 100% | 35.42 | 0.86 | 2.44 |
| | | 13781 | 3/3 | 100% | 34.57 | 0.72 | 2.08 |

TABLE 14

OIAD Screen Assay - Dermatophyte and Saprophyte Interday/Reproducibility

| | Sample | ng DNA/ extraction | Agreement w/ expected result | | Average CT | SD | CV (%) |
|---|---|---|---|---|---|---|---|
| Dermatophyte | Trichophyton mentagrophytes | 2 | 9/9 | 100% | 25.62 | 1.55 | 6.06 |
| | | 0.4 | 8/8* | 100% | 27.02 | 0.76 | 2.80 |
| | | 0.08 | 9/9 | 100% | 29.43 | 0.81 | 2.74 |
| | Trichophyton rubrum | 2 | 9/9 | 100% | 25.15 | 1.45 | 5.78 |
| | | 0.4 | 9/9 | 100% | 27.47 | 0.99 | 3.59 |
| | | 0.08 | 9/9 | 100% | 29.29 | 0.38 | 1.31 |
| | Epidermophyton | 2 | 9/9 | 100% | 25.27 | 1.21 | 4.81 |
| | | 0.4 | 9/9 | 100% | 28.15 | 3.00 | 10.67 |
| | | 0.08 | 7/9** | 78% | 29.55 | 1.77 | 6.00 |
| | Microsporum | 2 | 9/9 | 100% | 26.96 | 1.00 | 3.72 |
| | | 0.4 | 9/9 | 100% | 29.40 | 1.48 | 5.04 |
| | | 0.08 | 9/9 | 100% | 31.81 | 1.37 | 4.32 |
| Saprophyte | Acremonium | 2 | 8/8* | 100% | 27.56 | 1.12 | 4.08 |
| | | 0.4 | 9/9 | 100% | 30.64 | 0.80 | 2.60 |
| | | 0.08 | 9/9 | 100% | 32.64 | 1.00 | 3.06 |
| | Alternaria | 2 | 9/9 | 100% | 25.79 | 0.86 | 3.33 |
| | | 0.4 | 9/9 | 100% | 27.92 | 0.92 | 3.29 |
| | | 0.08 | 9/9 | 100% | 30.20 | 0.63 | 2.08 |
| | Aspergillus | 2 | 9/9 | 100% | 24.01 | 0.54 | 2.24 |
| | | 0.4 | 9/9 | 100% | 26.84 | 0.91 | 3.39 |
| | | 0.08 | 9/9 | 100% | 29.06 | 0.96 | 3.32 |
| | Curvularia | 2 | 8/8* | 100% | 24.89 | 0.90 | 3.60 |
| | | 0.4 | 6/7** | 86% | 27.04 | 1.07 | 3.97 |
| | | 0.08 | 8/8* | 100% | 29.40 | 0.51 | 1.75 |
| | Fusarium | 2 | 9/9 | 100% | 30.63 | 0.99 | 3.24 |
| | | 0.4 | 9/9 | 100% | 33.10 | 0.65 | 1.97 |
| | | 0.08 | 9/9 | 100% | 34.88 | 2.05 | 5.89 |
| | Scopulariopsis | 1 | 9/9 | 100% | 25.57 | 0.84 | 3.29 |
| | | 0.2 | 9/9 | 100% | 26.86 | 0.67 | 2.50 |
| | | 0.04 | 9/9 | 100% | 28.67 | 1.00 | 3.49 |
| | Scytalidium | 1 | 9/9 | 100% | 30.28 | 1.46 | 4.84 |
| | | 0.2 | 9/9 | 100% | 32.72 | 1.35 | 4.14 |
| | | 0.04 | 9/9 | 100% | 36.11 | 1.02 | 2.82 |

*Note: Extraction failures were taken out from the analysis.
**Note: Extraction failures were taken out from the analysis. Missed amplification considered in the analysis.

TABLE 15

OIAD Screen Assay - Yeast and *Pseudomonas aeruginosa* Interday/Reproducibility

| | Sample | CFU/ extraction | Agreement w/ expected result | | Average CT | SD | CV (%) |
|---|---|---|---|---|---|---|---|
| Yeast | Candida albicans | 4439 | 11/12 | 92% | 30.96 | 2.46 | 7.95 |
| | | 10358 | 12/12 | 100% | 29.72 | 0.88 | 2.97 |
| | | 24170 | 12/12 | 100% | 27.75 | 0.79 | 2.85 |
| | Candida parapsilosis | 5919 | 11/12 | 100% | 32.07 | 2.4 | 7.49 |
| | | 13810 | 12/12 | 100% | 29.7 | 1.38 | 4.64 |
| | | 32224 | 12/12 | 100% | 28.61 | 1.85 | 6.46 |
| | Candida tropicalis | 1078 | 9/12 | 75% | 31 | 2.16 | 6.98 |
| | | 2515 | 12/12 | 100% | 30.61 | 2.6 | 8.48 |
| | | 5867 | 12/12 | 100% | 28.46 | 1.62 | 5.71 |
| | Trichosporon | 2402 | 12/12 | 100% | 30.78 | 2.54 | 8.25 |
| | | 5604 | 12/12 | 100% | 28.74 | 1.92 | 6.67 |
| | | 13076 | 12/12 | 100% | 28.9 | 1.97 | 6.82 |
| | Candida guilliermondii | 10026 | 12/12 | 100% | 31.12 | 1.64 | 5.26 |
| | | 23393 | 12/12 | 100% | 29.2 | 1.24 | 4.24 |
| | | 54584 | 12/12 | 100% | 27.58 | 1.33 | 4.81 |
| | Cryptococcus | 4426 | 12/12 | 100% | 32.97 | 2.51 | 7.61 |
| | | 10327 | 12/12 | 100% | 30.58 | 0.78 | 2.57 |
| | | 24096 | 12/12 | 100% | 29.07 | 0.97 | 3.33 |
| | Malassezia furfur | 7433 | 12/12 | 100% | 32.44 | 2.08 | 6.41 |
| | | 17344 | 12/12 | 100% | 29.91 | 1.53 | 5.12 |
| | | 40470 | 11/11 | 100% | 28.68 | 1.48 | 5.15 |
| P. aeruginosa | Pseudomonas aeruginosa | 3445 | 11/11 | 100% | 37.24 | 0.89 | 2.4 |
| | | 6891 | 12/12 | 100% | 35.88 | 0.9 | 2.5 |
| | | 13781 | 12/12 | 100% | 34.34 | 1.44 | 4.19 |

B. OIAD Reflex Assays
1. Specificity and Inclusivity Studies
   a. Design
      i. All assays were tested for specificity/inclusivity against 52 separate organisms including 13 yeast, 9 dermatophytes, 5 bacteria, 25 saprophytes and 2 controls (Tables 16-18).
      ii. Each organism was tested at 1 ng/reaction except for human genomic DNA (HugDNA) tested at 4ng/reaction and ECIC plasmid DNA tested at 0.0001 ng/reaction.
      iii. The identities of DNA isolated from in-house cultures were previously confirmed by DNA sequencing. Organisms not isolated from in house culture included *Aspergiluus flavus* (ATCC #204304D-2), *Trichophyton mentagrophytes* (ATCC #9533D-2), *Malassezia restricta* (ATCC #MYA-4611D-5), *Candida albicans* (ATCC #MYA-2876D-5), *Candida tropicalis* (ATCC #66029D-5), *Candida parapsilosis* (ATCC #22019D-5), *C. guilliermondii* (ATCC #6260D-5), *Candida lusitaniae* (ATCC #42720D-5), *Cryptococcus neoformans* (ATCC #208821D-2), human genomic DNA (Promega, cat #G3041), and ECIC (synthetic plasmid DNA from Genscript).
   b. Results
      i. Dermatophyte detection. The assay correctly detected *Trichophyton rubrum* complex, *Trichophyton mentatgrophytes* complex, *Epidermophyton* and *Microsporum*. Cross reactivity was not observed (Table 16) based on the established assay cut-off values as indicated in FIG. 74.

TABLE 16

OIAD Reflex Assay-Dermatophyte Specificity and Inclusivity Study Results

| | OIAD Reflex Assay-Dermatophyte Rxn | | | |
|---|---|---|---|---|
| Organism | Trichophyton mentagrophytes | Trichophyton rubrum | Epidermophyton | Microsporum |
| Candida albicans | ND | ND | ND | ND |
| Candida parapsilosis | ND | ND | ND | ND |
| Candida tropicalis | ND | ND | ND | ND |
| Trichosporon asahii | ND | ND | ND | ND |
| Candida guilliermondii | ND | ND | ND | ND |
| Candida carribica | ND | ND | ND | ND |
| Cryptococcus | ND | ND | ND | ND |
| Malassezia globosa | ND | ND | ND | ND |
| Malassezia restricta | ND | ND | ND | ND |
| Malassezia sympodialis | ND | ND | ND | ND |
| Malassezia furfur | ND | ND | ND | ND |
| Candida lusitaniae | ND | ND | ND | ND |
| Candida krusei | ND | ND | ND | ND |
| Epidermophyton | ND | ND | POS | ND |
| Microsporum audouinii | ND | ND | ND | POS |
| Microsporum gypsium | ND | ND | ND | POS |
| Microsporum canis | ND | ND | ND | POS |
| Trichophyton mentagrophytes | POS | ND | ND | ND |
| Trichophyton rubrum | ND | POS | ND | ND |
| Trichophyton tonsurans (part of T mentagrophytes complex) | POS | ND | ND | ND |
| Trichophyton verrucosum | ND | ND | ND | ND |
| Trichophyton violaceum (T rubrum complex) | ND | POS | ND | ND |
| Pseudomonas aeruginosa | ND | ND | ND | ND |
| Proteus mirabilis | ND | ND | ND | ND |
| Serratia marcescens | ND | ND | ND | ND |
| Staphylococcus aureus | ND | ND | ND | ND |
| Streptococcus pyogenes | ND | ND | ND | ND |
| Acremonium | ND | ND | ND | ND |
| Alternaria | ND | ND | ND | ND |
| Aspergillus flavus | ND | ND | ND | ND |
| Aspergillus nishimurae | ND | ND | ND | ND |
| Aspergillus ochraceus | ND | ND | ND | ND |
| Aspergillus sydowii | ND | ND | ND | ND |
| Aspergillus versicolor | ND | ND | ND | ND |
| Aspergillus sclerotiorum | ND | ND | ND | ND |
| Aspergillus oryzae | ND | ND | ND | ND |
| Chaetomium | ND | ND | ND | ND |
| Cladosporium | ND | ND | ND | ND |
| Curvularia | ND | ND | ND | ND |
| Epicoccum | ND | ND | ND | ND |
| Fusarium oxysporum | ND | ND | ND | ND |
| Fusarium solani | ND | ND | ND | ND |
| Mucor | ND | ND | ND | ND |
| Paecilomyces | ND | ND | ND | ND |
| Penicillium polonicum | ND | ND | ND | ND |
| Penicillium citrinum | ND | ND | ND | ND |
| Penicillium chrysogenum | ND | ND | ND | ND |
| Rhizopus | ND | ND | ND | ND |
| Scopulariopsis | ND | ND | ND | ND |
| Scytalidium | ND | ND | ND | ND |
| Nigrospora | ND | ND | ND | ND |
| Chrysosporium | ND | ND | ND | ND |
| HugDNA | ND | ND | ND | ND |
| ECIC DNA | ND | ND | ND | ND |

ND-None detected based on established assay cut-off values (see Cut off value FIG. 74)
POS-Positive Signal ii. Saprophyte detection. The assay correctly detected *Acremonium, Alternaria, Aspergillus, Curvularia, Fusarium, Scopulariopsis* and *Scytalidium*. Cross reactivity was not observed (Table 17) based on the established assay cut-off values as indicated in FIG. 74.

TABLE 17

OIAD Reflex Assay - Saprophyte Specificity and Inclusivity Study Results

| | OIAD Reflex Saprophyte Rxn1 and Rxn2 | | | | | | |
|---|---|---|---|---|---|---|---|
| Organism | Acremonium | Alternaria | Aspergillus | Curvularia | Fusarium | Scopulariopsis | Scytalidium |
| Candida albicans | ND | ND | ND | ND | ND | ND | ND |
| Candida parapsilosis | ND | ND | ND | ND | ND | ND | ND |
| Candida tropicalis | ND | ND | ND | ND | ND | ND | ND |
| Trichosporon asahii | ND | ND | ND | ND | ND | ND | ND |
| Candida guilliermondii | ND | ND | ND | ND | ND | ND | ND |
| Candida carribica | ND | ND | ND | ND | ND | ND | ND |
| Cryptococcus | ND | ND | ND | ND | ND | ND | ND |
| Malassezia glabosa | ND | ND | ND | ND | ND | ND | ND |
| Malassezia restricta | ND | ND | ND | ND | ND | ND | ND |
| Malassezia sympodialis | ND | ND | ND | ND | ND | ND | ND |
| Malassezia furfur | ND | ND | ND | ND | ND | ND | ND |
| Candida lusitaniae | ND | ND | ND | ND | ND | ND | ND |
| Candida krusei | ND | ND | ND | ND | ND | ND | ND |
| Epidermophyton | ND | ND | ND | ND | ND | ND | ND |
| Microsporum audouinii | ND | ND | ND | ND | ND | ND | ND |
| Microsporum gypsium | ND | ND | ND | ND | ND | ND | ND |
| Microsporum canis | ND | ND | ND | ND | ND | ND | ND |
| Trichophyton mentagrophytes | ND | ND | ND | ND | ND | ND | ND |
| Trichophyton rubrum | ND | ND | ND | ND | ND | ND | ND |
| Trichophyton tonsurans | ND | ND | ND | ND | ND | ND | ND |
| Trichophyton verrucosum | ND | ND | ND | ND | ND | ND | ND |
| Trichophyton violaceum | ND | ND | ND | ND | ND | ND | ND |
| Pseudomonas aeruginosa | ND | ND | ND | ND | ND | ND | ND |
| Proteus mirabilis | ND | ND | ND | ND | ND | ND | ND |
| Serratia marcescens | ND | ND | ND | ND | ND | ND | ND |
| Staphylococcus aureus | ND | ND | ND | ND | ND | ND | ND |
| Streptococcus pyogenes | ND | ND | ND | ND | ND | ND | ND |
| Acremonium | POS | ND | ND | ND | ND | ND | ND |
| Alternaria | ND | POS | ND | ND | ND | ND | ND |
| Aspergillus flavus | POS | ND | POS | ND | ND | ND | ND |
| Aspergillus nishimurae | ND | ND | POS | ND | ND | ND | ND |
| Aspergillus ochraceus | ND | ND | POS | ND | ND | ND | ND |
| Aspergillus sydowii | ND | ND | POS | ND | ND | ND | ND |
| Aspergillus versicolor | ND | ND | POS | ND | ND | ND | ND |
| Aspergillus sclerotiorum | ND | ND | POS | ND | ND | ND | ND |
| Aspergillus oryzae | ND | ND | POS | ND | ND | ND | ND |
| Chaetomium | ND | ND | ND | ND | ND | ND | ND |
| Cladosporium | ND | ND | ND | ND | ND | ND | ND |
| Curvularia | ND | ND | ND | POS | ND | ND | ND |
| Epicoccum | ND | ND | ND | ND | ND | ND | ND |
| Fusarium oxysporum | ND | ND | ND | ND | POS | ND | ND |
| Fusarium solani | ND | ND | ND | ND | POS | ND | ND |
| Mucor | ND | ND | ND | ND | ND | ND | ND |
| Paecilomyces | ND | ND | ND | ND | ND | ND | ND |
| Penicillium polonicum | ND | ND | ND | ND | ND | ND | ND |
| Penicillium citrinum | ND | ND | ND | ND | ND | ND | ND |
| Penicillium chrysogenum | ND | ND | ND | ND | ND | ND | ND |
| Rhizopus | ND | ND | ND | ND | ND | ND | ND |
| Scopulariopsis | ND | ND | ND | ND | ND | POS | ND |
| Scytalidium | ND | ND | ND | ND | ND | ND | POS |
| Nigrospora | ND | ND | ND | ND | ND | ND | ND |
| Chrysosporium | ND | ND | ND | ND | ND | ND | ND |
| HugDNA | ND | ND | ND | ND | ND | ND | ND |
| ECIC DNA | ND | ND | ND | ND | ND | ND | ND |

ND- None detected based on assay cut-off values (see Cut off value FIG. 74)
POS - Positive Signal iii. Yeast detection. The assay correctly detected *Candida albicans, Candida parapsilosis, Candida tropicalis, Candida guilliermondii, Trichosporon asahii, Cryptococcus* and *Malassezia*. Cross reactivity was not observed (Table 18) based on the established assay cut-off values as indicated in FIG. 74.

TABLE 18

OIAD Reflex Assay - Yeast Specificity and Inclusivity Study Results

OIAD Reflex Assay - Yeasts Rx1 and Rxn2

| Organism | Candida albicans | Candida parapsilosis | Candida. tropicalis | Trichosporon | Candida guilliermondii | Cryptococcus | Malassezia furfur |
|---|---|---|---|---|---|---|---|
| Candida albicans | POS | ND | ND | ND | ND | ND | ND |
| Candida parapsilosis | ND | POS | ND | ND | ND | ND | ND |
| Candida tropicalis | ND | ND | POS | ND | ND | ND | ND |
| Trichosporon asahii | ND | ND | ND | POS | ND | ND | ND |
| Candida guilliermondii | ND | ND | ND | ND | POS | ND | ND |
| Candida carribica | ND | ND | ND | ND | ND | ND | ND |
| Cryptococcus | ND | ND | ND | ND | ND | POS | ND |
| Malassezia glabosa | ND | ND | ND | ND | ND | ND | ND |
| Malassezia restricta | ND | ND | ND | ND | ND | ND | ND |
| Malassezia sympodialis | ND | ND | ND | ND | ND | ND | ND |
| Malassezia furfur | ND | ND | ND | ND | ND | ND | POS |
| Candida lusitaniae | ND | ND | ND | ND | ND | ND | ND |
| Candida krusei | ND | ND | ND | ND | ND | ND | ND |
| Epidermophyton | ND | ND | ND | ND | ND | ND | ND |
| Microsporum audouinii | ND | ND | ND | ND | ND | ND | ND |
| Microsporum gypsium | ND | ND | ND | ND | ND | ND | ND |
| Microsporum canis | ND | ND | ND | ND | ND | ND | ND |
| Trichophyton mentagrophytes | ND | ND | ND | ND | ND | ND | ND |
| Trichophyton rubrum | ND | ND | ND | ND | ND | ND | ND |
| Trichophyton tonsurans | ND | ND | ND | ND | ND | ND | ND |
| Trichophyton verrucosum | ND | ND | ND | ND | ND | ND | ND |
| Trichophyton violaceum | ND | ND | ND | ND | ND | ND | ND |
| Pseudomonas aeruginosa | ND | ND | ND | ND | ND | ND | ND |
| Proteus mirabilis | ND | ND | ND | ND | ND | ND | ND |
| Serratia marcescens | ND | ND | ND | ND | ND | ND | ND |
| Staphylococcus aureus | ND | ND | ND | ND | ND | ND | ND |
| Streptococcus pyogenes | ND | ND | ND | ND | ND | ND | ND |
| Acremonium | ND | ND | ND | ND | ND | ND | ND |
| Alternaria | ND | ND | ND | ND | ND | ND | ND |
| Aspergillus flavus | ND | ND | ND | ND | ND | ND | ND |
| Aspergillus nishimurae | ND | ND | ND | ND | ND | ND | ND |
| Aspergillus ochraceus | ND | ND | ND | ND | ND | ND | ND |
| Aspergillus sydowii | ND | ND | ND | ND | ND | ND | ND |
| Aspergillus versicolor | ND | ND | ND | ND | ND | ND | ND |

TABLE 18-continued

OIAD Reflex Assay - Yeast Specificity and Inclusivity Study Results

OIAD Reflex Assay - Yeasts Rx1 and Rxn2

| Organism | Candida albicans | Candida parapsilosis | Candida. tropicalis | Trichosporon | Candida guilliermondii | Cryptococcus | Malassezia furfur |
|---|---|---|---|---|---|---|---|
| Aspergillus sclerotiorum | ND | ND | ND | ND | ND | ND | ND |
| Aspergillus oryzae | ND | ND | ND | ND | ND | ND | ND |
| Chaetomium | ND | ND | ND | ND | ND | ND | ND |
| Cladosporium | ND | ND | ND | ND | ND | ND | ND |
| Curvularia | ND | ND | ND | ND | ND | ND | ND |
| Epicoccum | ND | ND | ND | ND | ND | ND | ND |
| Fusarium oxysporum | ND | ND | ND | ND | ND | ND | ND |
| Fusarium solani | ND | ND | ND | ND | ND | ND | ND |
| Mucor | ND | ND | ND | ND | ND | ND | ND |
| Paecilomyces | ND | ND | ND | ND | ND | ND | ND |
| Penicillium polonicum | ND | ND | ND | ND | ND | ND | ND |
| Penicillium citrinum | ND | ND | ND | ND | ND | ND | ND |
| Penicillium chrysogenum | ND | ND | ND | ND | ND | ND | ND |
| Rhizopus | ND | ND | ND | ND | ND | ND | ND |
| Scopulariopsis | ND | ND | ND | ND | ND | ND | ND |
| Scytalidium | ND | ND | ND | ND | ND | ND | ND |
| Nigrospora | ND | ND | ND | ND | ND | ND | ND |
| Chrysosporium | ND | ND | ND | ND | ND | ND | ND |
| HugDNA | ND | ND | ND | ND | ND | ND | ND |
| ECIC DNA | ND | ND | ND | ND | ND | ND | ND |

ND- None detected based on assay cut-off values (see Cut off value FIG. 74)
POS - Positive Signal 2. Analytical Sensitivity Studies
   a. Design
      i. Saprophytes and Dermatophytes: Multiple replicates of purified DNA spiked into nail matrix across DNA concentration range of 1 ng to 0.00001 ng were tested. The lowest concentration where all replicates were detected was determined.
      ii. Yeast and *Pseudomonas aeruginosa*: Fresh Yeasts culture cells were suspended in saline and their concentration were initially estimated by McFarland method and finally determined by colony formation. For each microorganism, serial dilutions were extracted and were tested to determine the range of assay sensitivity for each microorganisms. The lowest concentration where all replicates were detected was determined.
      iii. Detailed results are shown in FIGS. 75 and 76
   b. Results
      i. Summary Dermatophyte results are shown in Table 19. Dermatophytes can be detected down to 0.0001 ng/extraction or lower.
      ii. Summary Saprophytes results are shown in Table 19. Saprohytes can be detected down to 0.001 ng/extraction or lower.
      iii. Summary Yeast results are shown in Table 19. Yeasts can be detected down to 492 CFU/extraction or lower.

TABLE 19

OIAD Reflex Assays Summary LoD Table

| Assay | Organism | LoD | Units |
|---|---|---|---|
| Dermatophyte | T mentarophytes | 0.00001 | ng DNA/extraction |
|  | T rubrum | 0.00001 | ng DNA/extraction |
|  | Epidermophyton | 0.00001 | ng DNA/extraction |
|  | M canis | 0.0001 | ng DNA/extraction |
| Saprophyte | Acremonium | 0.001 | ng DNA/extraction |
|  | Alternaria | 0.0001 | ng DNA/extraction |
|  | Aspergillus | 0.001 | ng DNA/extraction |
|  | Curvularia | 0.0001 | ng DNA/extraction |
|  | Fusarium | 0.001 | ng DNA/extraction |
|  | Scopulariopsis | 0.001 | ng DNA/extraction |
|  | Scytalidium | 0.001 | ng DNA/extraction |
| Yeast | C. albicans | 75 | CFU/extraction |
|  | C. parapsilosis | 466 | CFU/extraction |
|  | C. tropicalis | 50 | CFU/extraction |
|  | Trichosporon asahii | 32.5 | CFU/extraction |
|  | C. guilliermondii | 492 | CFU/extraction |
|  | Cryptococcus neoformans | 232 | CFU/extraction |
|  | Malassezia futfur | 210 | CFU/extraction |

3. Precision
   a. Design
      i. Saprophytes and Dermatophytes: Replicates of 3 levels of DNA determined from the sensitivity study were spiked into human nail matrix and tested by the Onychodystrophy Reflex PCR assay.
      ii. Yeast: Cultured cells were spiked into human nail matrix at 3 levels determined from the sensitivity study and tested by the Onychodystrophy Reflex PCR assay.
      iii. Intraday/repeatability: Three concentrations were extracted and run in triplicate on the same day through the Onychodystrophy reflex assay.

iv. Interday/reproducibility: Three concentrations were extracted and run in triplicate on three to four different days through the OIAD Reflex Assays across three different lots of reagents, two independent operators, two different extraction instruments, two different PCR setup instruments, and six different PCR instruments.

v. Results are reported as % CV of the Ct. All replicates reported are positive and within the established cut off values except where indicated.

b. Results
  i. Dermatophyte results are shown in Tables 20 and 22. The repeatability is 6.76% CV or lower; the reproducibility is 5.42% CV or lower.
  ii. Saprophyte results are shown in Tables 20 and 22. The repeatability is 5.93% CV or lower; the reproducibility is 5.93% CV or lower.
  iii. Yeast results are shown in Tables 21 and 23. The repeatability is 5.89% CV or lower; the reproducibility is 5.88% CV or lower.

TABLE 20

OIAD Reflex Assay- Dermatophyte and Saprophyte Intraday/Repeatability

| | Sample | ng DNA/extraction | Agreement w/ expected result | | Average CT | SD | CV (%) |
|---|---|---|---|---|---|---|---|
| Dermatophyte | T mentag | 2 | 3/3 | 100% | 26.94 | 1.80 | 6.70 |
| | | 0.4 | 3/3 | 100% | 27.35 | 1.04 | 3.79 |
| | | 0.08 | 3/3 | 100% | 29.48 | 0.74 | 2.51 |
| | T rubrum | 2 | 3/3 | 100% | 28.76 | 1.35 | 4.70 |
| | | 0.4 | 3/3 | 100% | 30.40 | 1.46 | 4.80 |
| | | 0.08 | 3/3 | 100% | 31.25 | 0.28 | 0.90 |
| | Epidermophyton | 2 | 3/3 | 100% | 24.83 | 1.68 | 6.76 |
| | | 0.4 | 3/3 | 100% | 28.22 | 1.61 | 5.71 |
| | | 0.08 | 3/3 | 100% | 31.06 | 0.92 | 2.96 |
| | Microsporum | 2 | 3/3 | 100% | 28.71 | 0.76 | 2.64 |
| | | 0.4 | 3/3 | 100% | 31.31 | 1.09 | 3.48 |
| | | 0.08 | 3/3 | 100% | 32.01 | 0.49 | 1.54 |
| Saprophyte | Acremonium | 2 | 3/3 | 100% | 26.75 | 0.89 | 3.32 |
| | | 0.4 | 3/3 | 100% | 30.25 | 0.89 | 2.94 |
| | | 0.08 | 3/3 | 100% | 32.34 | 1.06 | 3.28 |
| | Alternaria | 2 | 3/3 | 100% | 22.73 | 0.89 | 3.92 |
| | | 0.4 | 3/3 | 100% | 24.45 | 0.91 | 3.70 |
| | | 0.08 | 3/3 | 100% | 27.30 | 0.81 | 2.95 |
| | Aspergillus | 2 | 3/3 | 100% | 28.98 | 0.47 | 1.61 |
| | | 0.4 | 3/3 | 100% | 31.05 | 1.12 | 3.62 |
| | | 0.08 | 3/3 | 100% | 33.27 | 0.54 | 1.61 |
| | Curvularia | 2 | 3/3 | 100% | 28.97 | 0.70 | 2.41 |
| | | 0.4 | 3/3 | 100% | 31.21 | 0.94 | 3.00 |
| | | 0.08 | 3/3 | 100% | 34.65 | 0.59 | 1.70 |
| | Fusarium | 2 | 3/3 | 100% | 32.80 | 1.74 | 5.30 |
| | | 0.4 | 3/3 | 100% | 35.74 | 0.34 | 0.96 |
| | | 0.08 | 3/3 | 100% | 37.55 | 2.23 | 5.93 |
| | Scopulariopsis | 1 | 3/3 | 100% | 30.31 | 0.72 | 2.38 |
| | | 0.2 | 3/3 | 100% | 28.51 | 0.49 | 1.72 |
| | | 0.04 | 3/3 | 100% | 30.47 | 0.22 | 0.73 |
| | Scytalidium | 1 | 3/3 | 100% | 29.10 | 1.38 | 4.76 |
| | | 0.2 | 3/3 | 100% | 31.74 | 1.32 | 4.16 |
| | | 0.04 | 3/3 | 100% | 35.31 | 0.38 | 1.08 |

TABLE 21

OIAD Reflex Assay- Yeast Intraday/Repeatability

| | Sample | CFU/extraction | Agreement w/ expected result | | Average CT | SD | CV (%) |
|---|---|---|---|---|---|---|---|
| Yeast | C. albicans | 349 | 3/3 | 100% | 32.98 | 1.18 | 3.59 |
| | | 815 | 3/3 | 100% | 32.16 | 0.66 | 2.05 |
| | | 1903 | 3/3 | 100% | 30.01 | 0.84 | 2.81 |
| | C. parapsilosis | 466 | 3/3 | 100% | 34.03 | 1.07 | 3.15 |
| | | 1087 | 3/3 | 100% | 32.6 | 0.35 | 1.07 |
| | | 2537 | 3/3 | 100% | 31.37 | 0.77 | 2.44 |
| | C. tropicalis | 85 | 3/3 | 100% | 32.51 | 1.36 | 4.17 |
| | | 198 | 3/3 | 100% | 31.92 | 0.21 | 0.67 |
| | | 462 | 3/3 | 100% | 30.72 | 0.47 | 1.52 |
| | Trichosporon | 189 | 3/3 | 100% | 31.9 | 0.51 | 1.6 |
| | | 441 | 3/3 | 100% | 29.74 | 0.91 | 3.07 |
| | | 1029 | 3/3 | 100% | 28.82 | 0.33 | 1.14 |
| | C. guilliermondii | 789 | 3/3 | 100% | 33.7 | 0.36 | 1.05 |
| | | 1841 | 3/3 | 100% | 32.28 | 0.5 | 1.56 |
| | | 4297 | 3/3 | 100% | 30.96 | 1.82 | 5.89 |
| | Cryptococcus | 348 | 3/3 | 100% | 33.69 | 0.61 | 1.81 |
| | | 813 | 3/3 | 100% | 31.54 | 0.44 | 1.41 |
| | | 1897 | 3/3 | 100% | 31.33 | 0.52 | 1.67 |

TABLE 21-continued

OIAD Reflex Assay- Yeast Intraday/Repeatability

| Sample | CFU/extraction | Agreement w/ expected result | Average CT | SD | CV (%) |
|---|---|---|---|---|---|
| M. furfur | 585 | 3/3 100% | 32.23 | 0.71 | 2.21 |
|  | 1365 | 3/3 100% | 29.96 | 0.86 | 2.87 |
|  | 3186 | 3/3 100% | 29.34 | 0.92 | 3.15 |

TABLE 22

OIAD Reflex Assay- Dermatophyte and Saprophyte Interday/Reproducibility

|  | Sample | ng/extraction | Agreement w/ expected result | Average CT | SD | CV (%) |
|---|---|---|---|---|---|---|
| Dermatophyte | Trichophyton mentagrophytes | 2 | 9/9 100% | 25.82 | 1.39 | 5.38 |
|  |  | 0.4 | 8/8* 100% | 27.03 | 0.68 | 2.52 |
|  |  | 0.08 | 9/9 100% | 29.48 | 0.74 | 2.51 |
|  | Trichophyton rubrum | 2 | 9/9 100% | 27.22 | 1.40 | 5.13 |
|  |  | 0.4 | 9/9 100% | 29.52 | 1.06 | 3.59 |
|  |  | 0.08 | 9/9 100% | 31.25 | 0.28 | 0.90 |
|  | Epidermophyton | 2 | 9/9 100% | 24.99 | 1.13 | 4.52 |
|  |  | 0.4 | 9/9 100% | 27.06 | 1.47 | 5.42 |
|  |  | 0.08 | 9/9 100% | 31.06 | 0.92 | 2.96 |
|  | Microsporum | 2 | 9/9 100% | 28.16 | 1.22 | 4.33 |
|  |  | 0.4 | 9/9 100% | 30.54 | 0.98 | 3.22 |
|  |  | 0.08 | 9/9 100% | 32.01 | 0.49 | 1.54 |
| Saprophyte | Acremonium | 2 | 8/8* 100% | 26.47 | 1.07 | 4.05 |
|  |  | 0.4 | 9/9 100% | 30.27 | 0.57 | 1.88 |
|  |  | 0.08 | 9/9 100% | 32.34 | 1.06 | 3.28 |
|  | Alternaria | 2 | 9/9 100% | 22.73 | 0.54 | 2.37 |
|  |  | 0.4 | 9/9 100% | 24.83 | 0.67 | 2.71 |
|  |  | 0.08 | 9/9 100% | 27.30 | 0.81 | 2.95 |
|  | Aspergillus | 2 | 9/9 100% | 29.26 | 0.81 | 2.78 |
|  |  | 0.4 | 9/9 100% | 32.01 | 1.04 | 3.25 |
|  |  | 0.08 | 9/9 100% | 33.27 | 0.54 | 1.61 |
|  | Curvularia | 2 | 8/8* 100% | 30.99 | 1.78 | 5.75 |
|  |  | 0.4 | 6/7** 86% | 32.45 | 1.47 | 4.55 |
|  |  | 0.08 | 6/6* 100% | 34.65 | 0.59 | 1.70 |
|  | Fusarium | 2 | 9/9 100% | 32.91 | 1.07 | 3.26 |
|  |  | 0.4 | 9/9 100% | 35.43 | 0.63 | 1.77 |
|  |  | 0.08 | 9/9 100% | 37.55 | 2.23 | 5.93 |
|  | Scopulariopsis | 1 | 9/9 100% | 28.92 | 2.12 | 7.32 |
|  |  | 0.2 | 9/9 100% | 29.23 | 1.31 | 4.48 |
|  |  | 0.04 | 9/9 100% | 31.62 | 1.57 | 4.96 |
|  | Scytalidium | 1 | 9/9 100% | 29.96 | 1.20 | 3.99 |
|  |  | 0.2 | 9/9 100% | 31.77 | 1.31 | 4.12 |
|  |  | 0.04 | 9/9 100% | 34.90 | 1.08 | 3.11 |

*Note: Extraction failures were taken out from the analysis.
**Note: Extraction failures were taken out from the analysis. Missed amplification considered in the analysis.

TABLE 23

OIAD Reflex Assay- Yeast Interday/Reproducibility

|  | Sample | CFU/extraction | Agreement w/ expected result | Average CT | SD | CV (%) |
|---|---|---|---|---|---|---|
| Yeast | Candida albicans | 349 | 12/12 100% | 33.09 | 1.06 | 3.19 |
|  |  | 815 | 12/12 100% | 32.18 | 1.05 | 3.27 |
|  |  | 1903 | 12/12 100% | 30.54 | 1.11 | 3.62 |
|  | Candida parapsilosis | 466 | 12/12 100% | 34.66 | 1.54 | 4.45 |
|  |  | 1087 | 12/12 100% | 33.77 | 1.26 | 3.74 |
|  |  | 2537 | 12/12 100% | 32.67 | 1.53 | 4.68 |
|  | Candida tropicalis | 85 | 12/12 100% | 33.88 | 1.99 | 5.88 |
|  |  | 198 | 12/12 100% | 32.98 | 1.86 | 5.65 |
|  |  | 462 | 12/12 100% | 31.72 | 1.63 | 5.15 |
|  | Trichosporon | 189 | 12/12 100% | 32.27 | 1.37 | 4.25 |
|  |  | 441 | 12/12 100% | 30.68 | 1.22 | 3.99 |
|  |  | 1029 | 12/12 100% | 29.63 | 1.52 | 5.13 |
|  | Candida guilliermondii | 789 | 12/12 100% | 33.95 | 1.45 | 4.28 |
|  |  | 1841 | 12/12 100% | 32.96 | 1.69 | 5.12 |
|  |  | 4297 | 12/12 100% | 31.55 | 1.74 | 5.53 |

TABLE 23-continued

OIAD Reflex Assay- Yeast Interday/Reproducibility

| Sample | CFU/extraction | Agreement w/ expected result | | Average CT | SD | CV (%) |
|---|---|---|---|---|---|---|
| Cryptococcus | 348 | 12/12 | 100% | 34.61 | 0.94 | 2.72 |
| | 813 | 12/12 | 100% | 33.3 | 1.29 | 3.87 |
| | 1897 | 12/12 | 100% | 31.85 | 0.81 | 2.55 |
| Malassezia | 585 | 12/12 | 100% | 32.41 | 1.26 | 3.89 |
| furfur | 1365 | 12/12 | 100% | 30.94 | 1.54 | 4.97 |
| | 3186 | 12/12 | 100% | 29.79 | 0.84 | 2.82 |

IV. EXAMPLE 3

Validation Results

A. OIAD Screen Assay Concordance with Reference Method a. Design
  i. The clinical performance of the OIAD Screen Assay fungal targets was assessed using histopathology as the reference method on 802 clinical samples. In addition, 364 contrived and sequence verified samples were also used in the analysis for a total of 1166 samples.
  ii. The clinical performance of the OIAD Screen Assay-*Pseudomonas aeruginosa* was assessed using microbiological culture as the reference method. Due to the lack of availability of sufficient sample remaining for culture from the original 802 clinical samples, an additional 113 samples were analyzed via the OIAD Screen assay compared to microbiological culture.
  iii. Sanger sequencing was used to resolve discordant results on clinical samples. For all contrived samples the reference method was Sanger sequencing for each sample. Results are reported as overall, and broken out for each class of organism (dermatophyte, saprophyte, yeast and *Pseudomonas aeruginosa*). Values in parentheses are that following discordant resolution by sequencing.

b. OIAD Screen Assay Overall Results (Table 24).
  i. Results of the OIAD Screen Assay versus histopathology demonstrated an overall 88% accuracy, 93% clinical sensitivity and 75% clinical specificity.
  ii. Sixty-two Reference positive, OIAD Screen negative samples were analyzed by Sanger sequencing and results indicated
    a. Thirty were positive for fungus
    b. Six failed sequencing
    c. Twenty-six had insufficient sample available
  iii. Eighty-two Reference negative, OIAD Screen positive samples were analyzed by Sanger Sequencing and results indicated
    a. Fifty-eight were positive for fungus
    b. Twenty-four had insufficient sample available

TABLE 24

Results of the OIAD Screen Assay compared to the Reference assay

| | OIAD Screen + | OIAD Screen − | Total | | |
|---|---|---|---|---|---|
| Reference + | 780 (838) | 62 (62) | 842 (917) | Accuracy | 88% (93%) |
| Reference − | 82 (24) | 242 (242) | 324 (249) | Sensitivity | 93% (93%) |
| Total | 862 (862) | 304 (304) | 1166 | Specificity | 75% (91%) |

Values in paraenthesis are that following discordant resolution by sequencing c. OIAD Screen Assay—Dermatophyte Results (Table 25).
  i. Results of the OIAD Screen Assay—Dermatophyte versus histopathology demonstrated a 90% accuracy, 93% clinical sensitivity and 89% clinical specificity.
  ii. Eighteen Reference positive, OIAD Screen Assay-Dermatophyte negative samples were analyzed by Sanger sequencing and results indicated:
    a. Two were positive for dermatophyte
    b. Five were positive for yeast
    c. Eight were positive for saprophyte
    d. Three failed sequencing
  iii. Ninty-eight Reference negative, OIAD Screen Assay—Dermatophyte positive samples were analyzed by Sanger sequencing and results indicated:
    a. Eighty were positive for dermatophyte
    b. Four were positive for yeast
    c. Four were positive for saprophyte
    d. Four failed sequencing
    e. Six had insufficient sample available

TABLE 25

Results of the OIAD Screen Assay-Dermatophyte compared to the Reference assay

| | OIAD Screen Dermatophyte + | OIAD Screen Dermatophyte − | Total | | |
|---|---|---|---|---|---|
| Reference + | 249 (329) | 18 (5) | 267 (334) | Accuracy | 90% (98%) |
| Reference − | 98 (18) | 801 (814) | 899 (832) | Sensitivity | 93% (99%) |
| Total | 347 (347) | 819 (819) | 1166 | Specificity | 89% (98%) |

Values in paraenthesis are that following discordant resolution by sequencing d. OIAD Screen Assay—Saprophyte Results (Table 26).
  i. Results of the OIAD Screen Assay-Saprophyte versus histopathology demonstrated a 90% accuracy, 86% clinical sensitivity, and 91% clinical specificity.
  ii. Thirty-four Reference positive, OIAD Screen Assay—Saprophyte negative samples were analyzed by Sanger sequecning and results indicated:

a. Eight were positive for yeast
b. Seventeen were positive for saprophyte
c. Three failed sequencing
d. Six had insufficient sample available
iii. Eighty-two Reference negative, OIAD Screen Assay-Saprophyte positive samples were analyzed by Sanger Sequencing and results indicated:
a. Two were positive for dermatophyte
b. Seven were positive for yeast
c. Forty-seven were positive for saprophyte
d. Two failed sequencing
e. Twenty-four had insufficient sample available

TABLE 26

Results of the OIAD Screen Assay-Saprophyte compared to the Reference assay

|  | OIAD Screen Saprophyte + | OIAD Screen Saprophyte − | Total |  |  |
|---|---|---|---|---|---|
| Reference + | 212 (259) | 34 (26) | 246 (285) | Accuracy | 90% (95%) |
| Reference − | 82 (35) | 838 (846) | 920 (881) | Sensitivity | 86% (91%) |
| Total | 294 (294) | 872 (872) | 1166 | Specificity | 91% (96%) |

Values in paraenthesis are that following discordant resolution by sequencing e. OIAD Screen Assay—Yeast Results (Table 27).
  i. Results of the OIAD Screen Assay—Yeast versus histopathology demonstrated a 93% accuracy, 98% clinical sensitivity, and 92% clinical specificity.
  ii. Four Reference positive, OIAD Screen Assay-Yeast negative samples were analyzed by Sanger sequencing and results indicated:
    a. Two were positive for saprophyte
    b. Two failed sequencing
  iii. Seventy-six Reference negative, OIAD Screen Assay-Yeast positive samples were analyzed by Sanger Sequencing and results indicated:
    a. Five were positive for dermatophyte
    b. Forty-nine were positive for yeast
    c. Seventeen were positive for saprophyte
    d. One failed sequencing
    e. Four had insufficient sample available

TABLE 27

Results of the OIAD Screen Assay-Yeast compared to the Reference assay

|  | OD Screen Yeast + | OD Screen Yeast − | Total |  |  |
|---|---|---|---|---|---|
| Reference + | 196 (245) | 4 (2) | 200 (247) | Accuracy | 93% (98%) |
| Reference − | 76 (27) | 890 (892) | 966 (919) | Sensitivity | 98% (99%) |
| Total | 272 (272) | 894 (894) | 1166 | Specificity | 92% (97%) |

Values in paraenthesis are that following discordant resolution by sequencing f. OIAD Screen Assay—*Pseudomonas aeruginosa* Results (Table 28).
  ii. Results of the OIAD Screen Assay—*Pseudomonas aeruginosa* versus microbiological culture demonstrated a 65% accuracy, 63% clinical sensitivity, and 65% clinical specificity.
  iv. Seven Reference positive, OIAD Screen Assay-*Pseudomonas aeruginosa* negative samples were analyzed by Sanger sequecning and determined to be negative.
  v. Thirty-three Reference negative, OIAD Screen Assay-*Pseudomonas aeruginosa* positive samples were analyzed by Sanger Sequencing and results and were determined to be positive.

TABLE 28

Results of the OIAD Screen Assay-*Pseudomonas aeruginosa* compared to the Reference assay

|  | OIAD Screen P. aerugionosa + | OIAD Screen P. aeruginosa − | Total |  |  |
|---|---|---|---|---|---|
| Reference + | 12 (45) | 7 (0) | 19 (45) | Accuracy | 65% (100%) |
| Reference − | 33 (0) | 61 (68) | 94 (68) | Sensitivity | 63% (100%) |
| Total | 45 | 68 | 113 | Specificity | 65% (100%) |

Values in paraenthesis are that following discordant resolution by sequencing

B. OIAD Reflex Assay Concordance with Reference Method
  a. Design
    The clinical performance of the OIAD Reflex assays were assessed using Sanger sequencing as the reference method on OIAD Screen positive samples. For dermatophytes, an additional reference method used was the Dermataophyte ID by PCR assay, described generally in U.S. Patent Application Publication No. US-2017-0029906-A1, the disclosure of which is incorporated by reference herein.
  b. Yeast OD Reflex PCR Results (Tables 29-35)

TABLE 29

OIAD Reflex Assay-*C. albicans* vs OIAD Screen Assay and Sequencing

|  | OIAD Reflex C. albicans + | OIAD Reflex C. albicans − | Total |  |  |
|---|---|---|---|---|---|
| Reference + | 31 | 1 | 32 | Accuracy | 99% |
| Reference − | 1 | 177 | 178 | Sensitivity | 97% |
| Total | 32 | 178 | 210 | Specificity | 99% |

TABLE 30

OIAD Reflex Assay-*C. parapsilosis* vs OIAD Screen Assay and Sequencing

|  | OIAD Reflex C. parapsilosis + | OIAD Reflex C. parapsilosis − | Total |  |  |
|---|---|---|---|---|---|
| Reference + | 41 | 0 | 41 | Accuracy | 98% |
| Reference − | 5 | 164 | 169 | Sensitivity | 100% |
| Total | 46 | 164 | 210 | Specificity | 97% |

TABLE 31

OIAD Reflex Assay-*C. tropicalis* vs OIAD Screen Assay and Sequencing

|  | OIAD Reflex C. tropicalis + | OIAD Reflex C. tropicalis − | Total |  |  |
|---|---|---|---|---|---|
| Reference + | 30 | 0 | 30 | Accuracy | 99% |
| Reference − | 2 | 178 | 180 | Sensitivity | 100% |
| Total | 32 | 178 | 210 | Specificity | 99% |

TABLE 32

OIAD Reflex Assay-*Trichosporon* vs OD Screen PCR/Sequencing

|  | OIAD Reflex *Trichosporon*+ | OIAD Reflex *Trichosporon*− | Total |  |  |
|---|---|---|---|---|---|
| Reference+ | 30 | 0 | 30 | Accuracy | 98% |
| Reference− | 4 | 176 | 180 | Sensitivity | 100% |
| Total | 34 | 176 | 210 | Specificity | 98% |

TABLE 33

OIAD Reflex Assay-*C. guilliermondii* vs OIAD Screen Assay and Sequencing

|  | OIAD Reflex *C. guilliermondii*+ | OIAD Reflex *C. guilliermondii*− | Total |  |  |
|---|---|---|---|---|---|
| Reference+ | 32 | 0 | 32 | Accuracy | 97% |
| Reference− | 5 | 155 | 160 | Sensitivity | 100% |
| Total | 37 | 155 | 192 | Specificity | 97% |

TABLE 34

OIAD Reflex Assay-*Cryptococcus* vs OIAD Screen Assay and Sequencing

|  | OIAD Reflex *Cryptococcus*+ | OIAD Reflex *Cryptococcus*− | Total |  |  |
|---|---|---|---|---|---|
| Reference+ | 30 | 1 | 31 | Accuracy | 99% |
| Reference− | 1 | 160 | 161 | Sensitivity | 97% |
| Total | 31 | 161 | 192 | Specificity | 99% |

TABLE 35

OIAD Reflex Assay- *Malassezia* vs OIAD Screen Assay and Sequencing

|  | OIAD Reflex *Malassezia*+ | OIAD Reflex *Malassezia*− | Total |  |  |
|---|---|---|---|---|---|
| Reference+ | 28 | 3 | 31 | Accuracy | 92% |
| Reference− | 13 | 148 | 161 | Sensitivity | 90% |
| Total | 41 | 151 | 192 | Specificity | 92% | c. Dermatophyte OD Reflex PCR results (Tables 36-39)

TABLE 36

OIAD Reflex Assay- *T. rubrum* vs OIAD Screen Assay and Sequencing

|  | OIAD Reflex *T. rubrum*+ | OIAD Reflex *T. rubrum*− | Total |  |  |
|---|---|---|---|---|---|
| Reference+ | 220 | 5 | 225 | Accuracy | 98% |
| Reference− | 2 | 113 | 115 | Sensitivity | 98% |
| Total | 222 | 118 | 340 | Specificity | 98% |

TABLE 37

OIAD Reflex Assay- *T. mentagrophytes* vs OIAD Screen Assay and Sequencing

|  | OIAD Reflex *T. mentagrophytes*+ | OIAD Reflex *T. mentagrophytes*− | Total |  |  |
|---|---|---|---|---|---|
| Reference+ | 36 | 0 | 36 | Accuracy | 99% |
| Reference− | 2 | 302 | 304 | Sensitivity | 100% |
| Total | 38 | 302 | 340 | Specificity | 99% |

TABLE 38

OIAD Reflex Assay- *Epidermophylon* vs OIAD Screen Assay and Sequencing

|  | OIAD Reflex *Epidermophyton*+ | OIAD Reflex *Epidermophyton*− | Total |  |  |
|---|---|---|---|---|---|
| Reference+ | 30 | 0 | 30 | Accuracy | 100% |
| Reference− | 1 | 309 | 310 | Sensitivity | 100% |
| Total | 31 | 309 | 340 | Specificity | 100% |

TABLE 39

OIAD Reflex Assay- *Microsporum* vs OIAD Screen Assay and Sequencing

|  | OIAD Reflex *Microsporum*+ | OIAD Reflex *Microsporum*− | Total |  |  |
|---|---|---|---|---|---|
| Reference+ | 28 | 0 | 28 | Accuracy | 100% |
| Reference− | 0 | 312 | 312 | Sensitivity | 100% |
| Total | 28 | 312 | 340 | Specificity | 100% | e. Saprophyte Reflex results (Tables 40-46)

TABLE 40

OIAD Reflex Assay- *Alternaria* vs OIAD Screen Assay and Sequencing

|  | OIAD Reflex *Alternaria*+ | OIAD Reflex *Alternaria*– | Total |  |  |
|---|---|---|---|---|---|
| Reference+ | 32 | 3 | 35 | Accuracy | 97% |
| Reference– | 5 | 268 | 273 | Sensitivity | 91% |
| Total | 37 | 271 | 308 | Specificity | 98% |

TABLE 41

OIAD Reflex Assay- *Fusarium* vs OIAD Screen Assay and Sequencing

|  | OIAD Reflex *Fusarium*+ | OIAD Reflex *Fusarium*– | Total |  |  |
|---|---|---|---|---|---|
| Reference+ | 32 | 4 | 36 | Accuracy | 97% |
| Reference– | 5 | 267 | 272 | Sensitivity | 89% |
| Total | 37 | 271 | 308 | Specificity | 98% |

TABLE 42

OIAD Reflex Assay- *Scopulariopsis* vs OIAD Screen Assay and Sequencing

|  | OIAD Reflex *Scopulariopsis*+ | OIAD Reflex *Scopulariopsis*– | Total |  |  |
|---|---|---|---|---|---|
| Reference+ | 45 | 0 | 45 | Accuracy | 98% |
| Reference– | 6 | 257 | 263 | Sensitivity | 100% |
| Total | 51 | 257 | 308 | Specificity | 98% |

TABLE 43

OIAD Reflex Assay- *Scytalidium* vs OIAD Screen Assay and Sequencing

|  | OIAD Reflex *Scytalidium*+ | OIAD Reflex *Scytalidium*– | Total |  |  |
|---|---|---|---|---|---|
| Reference+ | 50 | 0 | 50 | Accuracy | 98% |
| Reference– | 6 | 252 | 258 | Sensitivity | 100% |
| Total | 58 | 252 | 308 | Specificity | 98% |

TABLE 44

OIAD Reflex Assay-*Acremonium* vs OIAD Screen Assay and Sequencing

|  | OIAD Reflex *Acremonium*+ | OIAD Reflex *Acremonium*– | Total |  |  |
|---|---|---|---|---|---|
| Reference+ | 33 | 0 | 33 | Accuracy | 99% |
| Reference– | 2 | 193 | 195 | Sensitivity | 100% |
| Total | 35 | 193 | 228 | Specificity | 99% |

TABLE 45

OIAD Reflex Assay- *Aspergillus* vs OIAD Screen Assay and Sequencing

|  | OIAD Reflex *Aspergillus*+ | OIAD Reflex *Aspergillus*– | Total |  |  |
|---|---|---|---|---|---|
| Reference+ | 47 | 5 | 52 | Accuracy | 96% |
| Reference– | 4 | 172 | 176 | Sensitivity | 90% |
| Total | 51 | 177 | 228 | Specificity | 98% |

TABLE 46

OIAD Reflex Assay- *Curvularia* vs OIAD Screen Assay and Sequencing

|  | OIAD Reflex *Curvularia*+ | OIAD Reflex *Curvularia*– | Total |  |  |
|---|---|---|---|---|---|
| Reference+ | 27 | 1 | 28 | Accuracy | 100% |
| Reference– | 0 | 200 | 200 | Sensitivity | 96% |
| Total | 27 | 201 | 228 | Specificity | 100% |

REFERENCES

1. Barak, O., A. Asarch, and T. Horn, *PAS is optimal for diagnosing onychomycosis*. J Cutan Pathol, 2010. 37(10): p. 1038-40.
2. Baudraz-Rosselet, F., et al., *Onychomycosis insensitive to systemic terbinafine and azole treatments reveals non-dermatophyte moulds as infectious agents*. Dermatology, 2010. 220(2): p. 164-8.
3. Blake, N., et al., *A Retrospective Review of Diagnostic Testing for Onychomycosis of the Foot*. J Am Podiatr Med Assoc, 2015. 105(6): p. 503-8.
4. Borman, A. M., et al., *Analysis of the dermatophyte species isolated in the British Isles between* 1980 *and* 2005 *and review of worldwide dermatophyte trends over the last three decades*. Med Mycol, 2007. 45(2): p. 131-41.
5. Bristow, I. R. and M. C. Spruce, *Fungal foot infection, cellulitis and diabetes: a review*. Diabet Med, 2009. 26(5): p. 548-51.
6. Chandran, N. S., et al., *Complementary role of a polymerase chain reaction test in the diagnosis of onychomycosis*. Australas J Dermatol, 2013. 54(2): p. 105-8.

7. D'Agata, E., *Pseudomonas aeruginosa*, in *Principles and Practice of Infectious Diseases*, D. R. Bennett J E, Blaser M J, Editor. 2015, Elsevier, Saunders.
8. D'Hue, Z., S. M. Perkins, and S. D. Billings, *GMS is superior to PAS for diagnosis of onychomycosis*. J Cutan Pathol, 2008. 35(8): p. 745-7.
9. Dhib, I., et al., *Multiplex PCR assay for the detection of common dermatophyte nail infections*. Mycoses, 2014. 57(1): p. 19-26.
10. Elewski, B. E., *Onychomycosis: pathogenesis, diagnosis, and management*. Clin Microbiol Rev, 1998. 11(3): p. 415-29.
11. Emam, S. M., *Real-time PCR: A rapid and sensitive method for diagnosis of dermatophyte induced onychomycosis, a comparative study*. 2016. 52(Issue 1): p. 83-90.
12. Farwa, U., et al., *Non-dermatophyte moulds as pathogens of onychomycosis*. J Coll Physicians Surg Pak, 2011. 21(10): p. 597-600.
13. Gupta, A. K., et al., *Systematic review of nondermatophyte mold onychomycosis: diagnosis, clinical types, epidemiology, and treatment*. J Am Acad Dermatol, 2012. 66(3): p. 494-502.
14. Gupta, A. K., K. A. Foley, and S. G. Versteeg, *New Antifungal Agents and New Formulations Against Dermatophytes*. Mycopathologia, 2017. 182(1-2): p. 127-141.
15. Gupta, A. K., et al., *The prevalence of unsuspected onychomycosis and its causative organisms in a multicentre Canadian sample of 30 000 patients visiting physicians' offices*. J Eur Acad Dermatol Venereol, 2016. 30(9): p. 1567-72.
16. Haghani, I., et al., *Comparison of diagnostic methods in the evaluation of onychomycosis*. Mycopathologia, 2013. 175(3-4): p. 315-21.
17. Hwang, S. M., M. K. Suh, and G. Y. Ha, *Onychomycosis due to nondermatophytic molds*. Ann Dermatol, 2012. 24(2): p. 175-80.
18. Jo Siu, W. J., et al., *Comparison of in vitro antifungal activities of efinaconazole and currently available antifungal agents against a variety of pathogenic fungi associated with onychomycosis*. Antimicrob Agents Chemother, 2013. 57(4): p. 1610-6.
19. Kizny Gordon, A., et al., *Clinical application of a molecular assay for the detection of dermatophytosis and a novel non-invasive sampling technique*. Pathology, 2016. 48(7): p. 720-726.
20. Litz, C. E. and R. Z. Cavagnolo, *Polymerase chain reaction in the diagnosis of onychomycosis: a large, single-institute study*. Br J Dermatol, 2010. 163(3): p. 511-4.
21. Mehlig, L., et al., *Clinical evaluation of a novel commercial multiplex-based PCR diagnostic test for differential diagnosis of dermatomycoses*. Mycoses, 2014. 57(1): p. 27-34.
22. Morales-Cardona, C. A., et al., *Non-dermatophyte mould onychomycosis: a clinical and epidemiological study at a dermatology referral centre in Bogota, Colombia*. Mycoses, 2014. 57(5): p. 284-93.
23. Nenoff, P., U. Paasch, and W. Handrick, [*Infections of finger and toe nails due to fungi and bacteria*]. Hautarzt, 2014. 65(4): p. 337-48.
24. Oppel, T. and H. C. Korting, *Onychodystrophy and its management*. Ger Med Sci, 2003. 1: p. Doc02.
25. Petinataud, D., et al., *Optimising the diagnostic strategy for onychomycosis from sample collection to FUNGAL identification evaluation of a diagnostic kit for real-time PCR*. Mycoses, 2016. 59(5): p. 304-11.
26. Piraccini, B. M. and A. Alessandrini, *Onychomycosis: A Review*. J Fungi (Basel), 2015. 1(1): p. 30-43.
27. Queller, J. N. and N. Bhatia, *The Dermatologist's Approach to Onychomycosis*. J Fungi (Basel), 2015. 1(2): p. 173-184.
28. Reza Kermanshahi, T. and R. Rhatigan, *Comparison between PAS and GMS stains for the diagnosis of onychomycosis*. J Cutan Pathol, 2010. 37(10): p. 1041-4.
29. Shenoy, M. M., et al., *Comparison of potassium hydroxide mount and mycological culture with histopathologic examination using periodic acid-Schiff staining of the nail clippings in the diagnosis of onychomycosis*. Indian J Dermatol Venereol Leprol, 2008. 74(3): p. 226-9.
30. Spiliopoulou, A., et al., *Evaluation of a commercial PCR test for the diagnosis of dermatophyte nail infections*. J Med Microbiol, 2015. 64(Pt 1): p. 25-31.
31. Tosti A, P. B., *Nail disorders*, in *Dermatology*, S. J. Bolognia J L, Cerroni L, Editor. 2018, Elsevier. p. 1207-1208.
32. Velasquez-Agudelo, V. and J. A. Cardona-Arias, *Meta-analysis of the utility of culture, biopsy, and direct KOH examination for the diagnosis of onychomycosis*. BMC Infect Dis, 2017. 17(1): p. 166.
33. Westerberg, D. P. and M. J. Voyack, *Onychomycosis: Current trends in diagnosis and treatment*. Am Fam Physician, 2013. 88(11): p. 762-70.
34. Muller S, Ebnother M, Itin, P. 2014. Green nail syndrome (*Pseudomonas aeruginosa* nail infection): Two cases successfully treated with topical Nadifloxacin, an Acne medication. Case Report Dermatology. 6(20). 180-184.
35. Gupta, A. K., G. Gupta, H. C. Jain, C. W. Lynde, K. A. Foley, D. Daigle, E. A. Cooper and R. C. Summerbell (2016). "The prevalence of unsuspected onychomycosis and its causative organisms in a multicentre Canadian sample of 30 000 patients visiting physicians' offices." J Eur Acad Dermatol Venereol 30(9): 1567-1572.
36. Summerbell, R. C., E. Cooper, U. Bunn, F. Jamieson and A. K. Gupta (2005). "Onychomycosis: a critical study of techniques and criteria for confirming the etiologic significance of nondermatophytes." Med Mycol 43(1): 39-59.
37. Luk, N. M., M. Hui, T. S. Cheng, L. S. Tang and K. M. Ho (2012). "Evaluation of PCR for the diagnosis of dermatophytes in nail specimens from patients with suspected onychomycosis." Clin Exp Dermatol 37(3): 230-234.
38. G. Sybren de Hoog, Dukik K, Monod M, Packeu A, Stubbe D, et. al. (2017) "Toward a Novel Multilocus Phylogenetic Taxonomy for the Dermatophytes". Mycopathologica 182:5-31.
39. Chrysosporium. Mycology Online. The University of Adelaide. https://mycology(dot)adelaide(dot)edu.au/descriptions/hyphomycetes/chrysosporium/40.
40. Ghannoum, M. A., R. A. Hajjeh, R. Scher, N. Konnikov, A. K. Gupta, R. Summerbell, S. Sullivan, R. Daniel, P. Krusinski, P. Fleckman, P. Rich, R. Odom, R. Aly, D. Pariser, M. Zaiac, G. Rebell, J. Lesher, B. Gerlach, G. F. Ponce-De-Leon, A. Ghannoum, J. Warner, N. Isham and B. Elewski (2000). "A large-scale North American study of fungal isolates from nails: the frequency of onychomycosis, fungal distribution, and antifungal susceptibility patterns." J Am Acad Dermatol 43(4): 641-648.
41. Gupta, A. K., H. C. Jain, C. W. Lynde, P. Macdonald, E. A. Cooper and R. C. Summerbell (2000). "Prevalence and epidemiology of onychomycosis in patients visiting physicians' offices: a multicenter canadian survey of 15,000 patients." *J Am Acad Dermatol* 43(2 Pt 1): 244-248.

42. Gupta, A. K., H. C. Jain, C. W. Lynde, G. N. Watteel and R. C. Summerbell (1997). "Prevalence and epidemiology of unsuspected onychomycosis in patients visiting dermatologists' offices in Ontario, Canada—a multicenter survey of 2001 patients." *Int J Dermatol* 36(10): 783-787.
43. Verification and Validation Study Report for Bako Pseudomonas aeruginosa Assay. Approved by Bako Medical Director on Jul. 10, 2018.
44. Sigurgeirsson, B. and R. Baran (2014). "The prevalence of onychomycosis in the global population: a literature study." *J Eur Acad Dermatol Venereol* 28(11): 1480-1491.

While aspects of the present disclosure have been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method of detecting, in a sample, an agent causing onychodystrophy, wherein the agent causing onychodystrophy belongs to a secondary clade member comprising one or more primary clade members, the method comprising:

i) screening a sample using at least a first and second set of secondary clade-specific primers to determine whether a secondary clade member among a plurality of secondary clade members is present or absent in the sample, wherein the plurality of secondary clade members comprises a dermatophyte, a yeast, and a saprophyte, wherein the screening comprises:
performing a first real time polymerase chain reaction (PCR) in a first reaction mixture using the first set of secondary clade-specific primers and a first hydrolysis probe specific for a DNA region amplified by the first set of secondary clade-specific primers, the first hydrolysis probe comprising a fluorescent reporter dye and a quencher; and
performing a second real time PCR in a second reaction mixture using the second set of secondary clade-specific primers and a second hydrolysis probe specific for a DNA region amplified by the second set of secondary clade-specific primers, the second hydrolysis probe comprising a fluorescent reporter dye and a quencher; and ii) performing a second screen of the sample to determine whether an agent causing onychodystrophy is present or absent in the sample using primary clade-specific primers that are specific to a primary clade member that belongs to the secondary clade member, wherein the second screen comprises performing at least a third real time PCR in a third reaction mixture using the primary clade-specific primers and a third hydrolysis probe specific for a DNA region amplified by the primary clade-specific primers, the third hydrolysis probe comprising a fluorescent reporter dye and a quencher
wherein the first set of one or more secondary clade-specific primers comprises one or more primer pairs that facilitate amplification of one or more nucleotide sequences 80% or more identical to a sequence selected from the group consisting of SEQ ID NOS. 203-211, 213, 215-219 and 221, and wherein the second set of one or more secondary clade-specific primers comprises one or more primer pairs that facilitate amplification of one or more nucleotide sequences 80% or more identical to a sequence selected from the group consisting of the sequence of SEQ ID NOS. 203-211, 213, 215-219 and 221.

2. The method of claim 1, wherein the first real time PCR and the second real time PCR are performed in the same reaction mixture.

3. The method of claim 1, wherein the method comprises performing a fourth real time PCR in a fourth reaction mixture using *Pseudomonas aeruginosa*-specific primers and a fourth hydrolysis probe specific for a DNA region amplified by the *Pseudomonas aeruginosa*-specific primers, the fourth hydrolysis probe comprising a fluorescent reporter dye and a quencher, and wherein the method detects the presence or absence of *Pseudomonas aeruginosa* in the sample.

4. The method of claim 3, wherein the first real time PCR, the second real time PCR, and the fourth real time PCR are performed in the same reaction mixture.

5. The method of claim 1, wherein the first and second sets of secondary clade-specific primers each comprise a primer pair that facilitate amplification of a secondary clade-specific nucleotide sequence within a nuclear-encoded ribosomal (rRNA) gene to facilitate production of amplification products encoding a secondary clade-specific nucleotide sequence within the nuclear-encoded rRNA gene.

6. The method of claim 5, wherein the amplification products comprise an amplification product for one or more of the following secondary clade-specific nucleotide sequence encoding:
an 18S ribosomal RNA (rRNA), or a portion thereof;
a 5.8S rRNA, or a portion thereof;
a 28S rRNA, or a portion thereof;
a portion of an ITS1; and
a portion of an ITS2.

7. The method of claim 1, wherein the primary clade-specific primers comprise one or more primer pairs configured to amplify a primary clade-specific nucleotide sequence within a nuclear-encoded ribosomal RNA (rRNA) gene or a mitochondrial nucleotide sequence.

8. The method of claim 7, wherein the primary clade-specific nucleotide sequence encodes:
an 18S ribosomal RNA, or a portion thereof;
a 28S ribosomal RNA, or a portion thereof;
a 5.8S ribosomal RNA or a portion there of; and/or
an ITS, or a portion thereof, adjacent the 18S, 28S or 5.8S rRNA in the nuclear-encoded rRNA gene, and
wherein the mitochondrial nucleotide sequence encodes:
a nicotinamide adenine dinucleotide (NADH) dehydrogenase subunit gene, or a portion thereof, or
a putative reverse transcriptase gene, or a portion thereof.

9. The method of claim 1, wherein the primary clade-specific primers comprise one or more primer pairs configured to amplify a primary clade-specific nucleotide sequence encoding:
a 18S ribosomal RNA, or a portion thereof; and/or
an ITS, or a portion thereof, adjacent the 18S rRNA; or
a mitochondrial nucleotide sequence.

10. A method of detecting a yeast and/or a dermatophyte in a sample, the method comprising:
i) screening a sample using at least a first set of yeast-specific primers and at least first set of dermatophyte-specific primers to determine whether a yeast and/or dermatophyte is present or absent in the sample, wherein the screening comprises:
performing a first real time polymerase chain reaction (PCR) in a first reaction mixture using the first set of yeast-specific primers and a first hydrolysis probe specific for a DNA region amplified by the first set of yeast-specific primers, the first hydrolysis probe comprising a fluorescent reporter dye and a quencher; and
performing a second real time PCR in a second reaction mixture using the first set of dermatophyte-specific primers and a second hydrolysis probe specific for a DNA region amplified by the first set of dermatophyte-specific primers, the second hydrolysis probe comprising a fluorescent reporter dye and a quencher; and
ii) if the yeast and/or dermatophyte is determined to be present in the sample, performing a second screen of the sample to determine whether a genus and/or species of the yeast and/or dermatophyte is present or absent in the sample using yeast and/or dermatophyte genus and/or species-specific primers, wherein the second screen comprises performing at least a third real time PCR in a third reaction mixture using the yeast and/or dermatophyte genus and/or species-specific primers and a third hydrolysis probe specific for a DNA region amplified by the yeast and/or dermatophyte genus and/or species-specific primers, the third hydrolysis probe comprising a fluorescent reporter dye and a quencher
wherein the first set of dermatophyte-specific primers comprise a dermatophyte-specific forward primer comprising the sequence of SEQ ID NO:1 and a dermatophyte-specific reverse primer comprising the sequence of SEQ ID NO:2, and wherein the first hydrolysis probe comprises the sequence of SEQ ID NO:3.

11. The method of claim 10, wherein the first real time PCR and the second real time PCR are performed in the same reaction mixture.

12. The method of claim 10, wherein the first set of yeast-specific primers comprises (a) one or more yeast-specific forward primers comprising a sequence selected from SEQ ID NOs: 4-8 and a yeast-specific reverse primer comprising a sequence of SEQ ID NO:9, and wherein the second hydrolysis probe comprises a sequence selected from SEQ ID NOs:10-13; and/or (b) a yeast-specific forward primer comprising the sequence of SEQ ID NO:14 and a yeast-specific reverse primer comprising the sequence of SEQ ID NO:15, and wherein the second hydrolysis probe comprises a sequence of SEQ ID NO:16.

13. The method of claim 10, wherein an extraction control/inhibition control EC/IC is added to the sample prior to i), and wherein the first and/or second real time PCR utilizes ECIC forward and reverse primers comprising the sequences of SEQ ID NO:17 and 18, respectively, and wherein the first and/or second real time PCR utilizes an ECIC hydrolysis probe comprising the sequence of SEQ ID NO:19.

14. A method of detecting a saprophyte and/or *Pseudomonas aeruginosa* in a sample, the method comprising:
i) screening a sample using at least a first set of saprophyte-specific primers and at least first set of

*Pseudomonas aeruginosa*-specific primers to determine whether a saprophyte and/or *Pseudomonas aeruginosa* is present or absent in the sample, wherein the screening comprises:

performing a first real time polymerase chain reaction (PCR) in a first reaction mixture using the first set of saprophyte-specific primers and a first hydrolysis probe specific for a DNA region amplified by the first set of saprophyte-specific primers, the first hydrolysis probe comprising a fluorescent reporter dye and a quencher; and performing a second real time PCR in a second reaction mixture using the first set of *Pseudomonas aeruginosa*-specific primers and a second hydrolysis probe specific for a DNA region amplified by the first set of *Pseudomonas aeruginosa*-specific primers, the second hydrolysis probe comprising a fluorescent reporter dye and a quencher; and ii) if the saprophyte is determined to be present in the sample, performing a second screen of the sample to determine whether a genus and/or species of the saprophyte is present or absent in the sample using saprophyte genus and/or species-specific primers, wherein the second screen comprises performing at least a third real time PCR in a third reaction mixture using the saprophyte genus and/or species-specific primers and a third hydrolysis probe specific for a DNA region amplified by the saprophyte genus and/or species-specific primers, the third hydrolysis probe comprising a fluorescent reporter dye and a quencher, wherein the saprophyte-specific primers comprise one or more saprophyte-specific forward primers comprising a sequence selected from SEQ ID NOs:20, 23, and 25; and one or more saprophyte-specific reverse primers comprising a sequence selected from SEQ ID NOs:21, 22, 24, and 26; and wherein the first or second hydrolysis probe comprises a sequence selected from SEQ ID NOs:27-31.

15. The method of claim 14, wherein the first real time PCR and the second real time PCR are performed in the same reaction mixture.

16. The method of any one of claim 14, wherein the saprophyte genus and/or species-specific primers comprise primers specific for *Alternaria*.

17. The method of claim 16, wherein the primers specific for *Alternaria* comprise a forward primer comprising the sequence of SEQ ID NO:50 and a reverse primer comprising the sequence of SEQ ID NO:51, and wherein the third hydrolysis probe comprises the sequence of SEQ ID NO:52.

* * * * *